(12) United States Patent
Flynn et al.

(10) Patent No.: US 11,766,481 B2
(45) Date of Patent: Sep. 26, 2023

(54) GLYCAN MODIFIED SHORT INTERFERING RNA

(71) Applicants: GanNA Bio, Inc., Cambridge, MA (US); The Children's Medical Center Corporation, Boston, MA (US); Beth Israel Deaconess Medical Center, Inc., Boston, MA (US); The Board of Trustees of the Leland Stanford Junior University, Stanford, CA (US)

(72) Inventors: Ryan A. Flynn, Brookline, MA (US); Brian Goodman, Boston, MA (US); Ciaran Lawlor, Milton, MA (US); Namita Bisaria, Somerville, MA (US); Richard D. Cummings, Brookline, MA (US); Mohui Wei, Boston, MA (US); Carolyn R. Bertozzi, Menlo Park, CA (US)

(73) Assignees: GanNA Bio, Inc., Cambridge, MA (US); The Children's Medical Center, Boston, MA (US)

( * ) Notice: Subject to any disclaimer, the term of this patent is extended or adjusted under 35 U.S.C. 154(b) by 0 days.

(21) Appl. No.: 17/825,737

(22) Filed: May 26, 2022

(65) Prior Publication Data
US 2022/0387607 A1    Dec. 8, 2022

Related U.S. Application Data

(63) Continuation of application No. PCT/US2022/026117, filed on Apr. 25, 2022.
(Continued)

(51) Int. Cl.
A61K 47/61    (2017.01)

(52) U.S. Cl.
CPC .................................. *A61K 47/61* (2017.08)

(58) Field of Classification Search
CPC ............................ A61K 47/61; A61K 47/549
See application file for complete search history.

(56) References Cited

U.S. PATENT DOCUMENTS

| 5,795,958 A | 8/1998 | Rao et al. |
| 9,796,756 B2 | 10/2017 | Hadwiger et al. |

(Continued)

FOREIGN PATENT DOCUMENTS

| EP | 3498724 A1 | 6/2019 |
| WO | 2009073809 A2 | 6/2009 |

(Continued)

OTHER PUBLICATIONS

Huang , Preclinical and Clinical Advances of GalNac-Decorated Nucleic Acid Therapeutics, Molecular Therapy: Nucleic Acids, vol. 6 (Year: 2016).*

(Continued)

*Primary Examiner* — Carlos A Azpuru
(74) *Attorney, Agent, or Firm* — Hogan Lovells US LLP

(57) ABSTRACT

The present disclosure relates to glycan-modified nucleic acids, including short interfering RNA molecules. The glycan-modified nucleic acids include an oligosaccharide moiety that is bond to the nucleic acid and that contains a multiple antennary complex type N-glycan. The disclosure also relates to pharmaceutical compositions containing such glycan-modified nucleic acids, and methods for making and using such glycan-modified nucleic acids.

30 Claims, 51 Drawing Sheets

Specification includes a Sequence Listing.

Related U.S. Application Data

(60) Provisional application No. 63/189,492, filed on May 17, 2021, provisional application No. 63/188,930, filed on May 14, 2021, provisional application No. 63/179,065, filed on Apr. 23, 2021.

(56) References Cited

U.S. PATENT DOCUMENTS

| | | |
|---|---|---|
| 2015/0246133 A1 | 9/2015 | Tellers et al. |
| 2015/0283256 A1 | 10/2015 | Wakefield et al. |
| 2016/0102120 A1 | 4/2016 | Hadwiger et al. |
| 2016/0333364 A1* | 11/2016 | Carrell ............... C12N 15/8218 |
| 2017/0253875 A1 | 9/2017 | Rozema et al. |
| 2019/0192674 A1 | 6/2019 | Uehara et al. |
| 2019/0256849 A1 | 8/2019 | Li et al. |
| 2021/0009994 A1 | 1/2021 | Godron et al. |
| 2021/0189394 A1 | 6/2021 | Rozema et al. |
| 2022/0372476 A1 | 11/2022 | Khvorova et al. |

FOREIGN PATENT DOCUMENTS

| | | |
|---|---|---|
| WO | 2011/156690 A2 | 12/2011 |
| WO | 2013166155 A1 | 11/2013 |
| WO | 2016100812 A1 | 6/2016 |
| WO | 2019089561 A1 | 5/2019 |
| WO | 2020072922 A1 | 4/2020 |
| WO | 2021055892 A1 | 3/2021 |

OTHER PUBLICATIONS

Brown, "We Do GalNAc and So Can You!" Dicerna Pharmaceuticals, AsiaTIDES (2016), 22 pgs.

Brown, et al., "Investigating the pharmacodynamic durability of GalNAc-siRNA conjugates", Nucleic Acid Research, vol. 48, No. 21, (2020), pp. 11827-11844.

Cunha, et al., "Biotechnological Evolutoin of siRNA Molecules: From Bench Tool to the Refined Drug", Pharmaceuticals, vol. 15, No. 5, (2022), pp. 1-21.

Serrano-Sevilla, et al., "Natural Polysaccharides for siRNA Delivery: Nanocarriers Based on Chitosan, Hyaluronic Acid, and Their Derivatives", Molecules, vol. 24, No. 14, (2019), pp. 1-34.

Springer, et al., "GalNAc-siRNA Conjugates: Leading the Way for Delivery of RNAi Therapeutics", Nucleic Acid Therapeutics, vol. 28, No. 3, (2018), pp. 109-118.

Weingärtner et. al., "Less is More: Novel Hepatocyte-Targeted siRNA Conjugates for Treatment of Liver-Related Disorders", Molecular Therapy Nucleic Acicles, vol. 10, (2020), pp. 242-250.

Sewing, et al., "GalNAc Conjugation Attenuates the Cytotoxicity of Antisense Oligonucleotide Drugs in Renal Tubular Cells", Molecular Therapy Nucleic Acids, vol. 14, (2019) pp. 67-79.

Tanowitz, et al., "Asialoglycoprotein receptor 1 mediates productive uptake of N-acetylgalactosamine-conjugated and unconjugated phosphorothioate antisense oligonucleotides into liver hepatocytes", Nucleic Acids Research, vol. 45, No. 21, (2017), pp. 12388-12400.

Harumoto, et al., "Enhancement of Gene Knockdown on CD22-Expressing Cells by Chemically Modified Glycan Ligand-siRNA Conjugates", ACS Publications, vol. 17, No. 2, (2022), pp. 292-298.

Uehara et al., "Targeted delivery to macrophages and dentritic cells by chemically modified mannose ligand-conjugated siRNA", Nucleic Acids Research, (2022), vol. 50, No. 9, pp. 4840-4859.

Flynn, et al., "Mammalian Y RNAs are modified at discrete guanosine residues with N-glycans", bioRxiv preprint doi: https://doi.org/10.1101/787614, (2019), pp. 1-31.

Anderluh, et al., "Emerging glyco-based strategies to steer immune responses", The FEBS Journa, vol. 288, No. 16, (2021), pp. 4746-4772.

Becer et al., "Click Chemistry beyond Metal-Catalyzed Cycloaddition", Angew. Chem. Int. Ed (2009), 48, pp. 4009-4908.

Flynn, et al., "Small RNAs are modified with N-glycans and displayed on the surface of living cells", Cell vol. 184, No. 12, (2021), pp. 3109-3124.

Kubota et al., "Expanding the Scope of RNA Metabolic Labeling with Vinyl Nucleosides and Inverse Electron-Demand Diels-Alder Chemistry", ACS Chem Biol. (2019), 14(8), pp. 1698-1707.

Lenza et al., "Current Status on Therapeutic Molecules Targeting Siglec Receptors", Cells, Vo;. 9, No. 12, (2020), pp. 1-19.

Paunovska et al., "Drug delivery systems for RNA therapeutics", Nature Reviews Genetics, vol. 23, (2022), pp. 265-280.

Raposo et al., "Human Lectins, Their Carbohydraft Affinities and Where to Find Them", Biomolecules, vol. 11, No. 2, (2021), pp. 188-215.

Riboldi et al., "Human C-type Lectin Domain Family 4, Member C(CLEC4C/BDCA-2/CD303) is a Receptor for Asialo-galactosyl-oligosaccharides", J. Biol. Chem., vol. 286, No. 41, (2011), pp. 35329-35333.

Sharma et al., "Novel Cluster and Monomer-Based GalNAc Structures Induce Effective Uptake of SiRNAs in Vitro and in Vivo", Bioconjugate Chem, vol. 29, (2018), pp. 2478-2488.

Smith et al., "The clinical impact of glycobiology: targeting selectins, Siglecs and mammalian glycans", Nature Reviews, vol. 20, (2021), pp. 217-243.

Gao et al., "Differential recognition of oligomannose isomers by glycan-binding proteins involved in innate and adaptive immunity", Sci Adv., (2021), vol. No. 24, pp. 1-25.

Zhang et al., "Genetic Programming of Macrophages to Perfrom Anti-Tumor Functions using Targeted Mma Nanocarriers", Nature Communications, vol. 10, No. 3974, (2019), pp. 1-16.

Zatsepin, et al., "Synthesis and applications of oligonucleotide-carbohydrate conjugates", Chemistry & Biodiversity, vol. 1, No. 10, (2004), pp. 1401-1417.

Novoa, et al., "DNA display of glycoconjugates to emulate oligomeric interactions of glycans", Beilstein Journal of Organic Chemistry, vol. 11, (2015), pp. 707-719.

Mäkilä, et al., "Synthesis of multi-galactose-conjugated 2'-O-methyl oligoribonucleotides and their in vivo imaging with positron emission tomography", Bioorganic & Medicinal Chemistry, Elsevier, Amsterdam, NL, vol. 22, No. 24, (2014), pp. 6806-6813.

Maklakova, et al., "A new approach to the synthesis of ligands of asialoglycoprotein receptor for targeted delivery of oligonucleotides to hepatocytes", Russian Chemical Bulletin, vol. 64, No. 7, (2015), pp. 1655-1662.

Spinelli, et al., "Glycoclusters on oligonucleotide and PNA scaffolds: synthesis and applications", Chemical Society Reviews, vol. 42, No. 11, (2013), pp. 4557-4573.

Yan, et al., "Glycotargeting to improve cellular delivery efficiency of nucleic acids", Glycoconjugate Journal, vol. 24, No. 2-3, (2007), pp. 107-123.

Invitation to Pay Additional Fees and, where applicable, Protest Fee dated Jul. 15, 2022 in PCT/US2022/026117 filed Apr. 25, 2022.

Sago, et al., "High-throughput in vivo screen of functional mRNA delivery identified nanoparticles for endothelial cell gene editing," Proceedings of the National Academy of Sciences, vol. 115, No. 42, (2018), pp. E9944-E9952.

Dahlman et al., "Barcoded nanoparticles for high throughput in vivo discovery of targeted therapeutics," Proceedings of the National Academy of Sciences, vol. 114, No. 8, (2017), pp. 2060-2065.

Witzigmann et al., "Lipid nanoparticle technology for therapeutic gene regulation in the liver," Advanced Drug Delivery Reviews, Elsevier, Amsterdam, NL, vol. 159, (2020), pp. 344-363.

Gan et al., "Naoparticles containing constrained phospholipds delivery mRNA to liver immune cells in vivo without targeting ligands," Bioengineering & Translation Medicine, vol. 5, No. 3, (2020), pp. 1-11.

Qiu et al., "Lipid nanoparticle-mediated codelivery of Cas9 mrNA and single-guide RNA achieves liver-specific in vivo genome editing of Angpt13," Proceedings of the National Academy of Sciences, vol. 188, No. 10, 2021).

Hou et al., "Lipid nanoparticles for mRNA delivery", Nature Reviews Materials, (2021), pp. 2058-8427.

Notification of Transmittal of the International Search Report and the Written Opinion of the International Searching Authority, or the Declaration, dated Nov. 23, 2022 in PCT/US2022/040462.

(56) References Cited

OTHER PUBLICATIONS

Notification of Transmittal of the International Search Report and the Written Opinion of the International Searching Authority, or the Declaration, dated Dec. 16, 2022 in PCT/US2022/076342.
Bojar et al., "A Useful Guide to Lectin Binding: Machine-Learning Directed Annotation of 57 Unique Lectin Specificities," ACS Chem. Biol., (2022), vol. 17, pp. 2993-3012.
Schnaar et al., "Glycobiology simplified: diverse roles of glycan recognition in inflammation," Journal of Leukocyte Biology, vol. 99, (2016), pp. 825-838.
Li, et al., "Core Fucosylation of IgG B Cell Receptor Is Required for Antigen Recognition and Antibody Production," J Immunol., (2015), 194 (6), pp. 2596-2606.
Taylor et al., "Structural insights into what glycan arrays tell us about how glycan-binding proteins interact with ligands", Glycobiology, vol. 19, No. 11, (2009), pp. 1155-1162.
Cummings et al., "Essential of Glycobiology [Internet], 4th edition," National Library of Medicine, (2022), 17 pages, https://www.ncbi.nlm.nih.gov/books/NBK579967.

\* cited by examiner

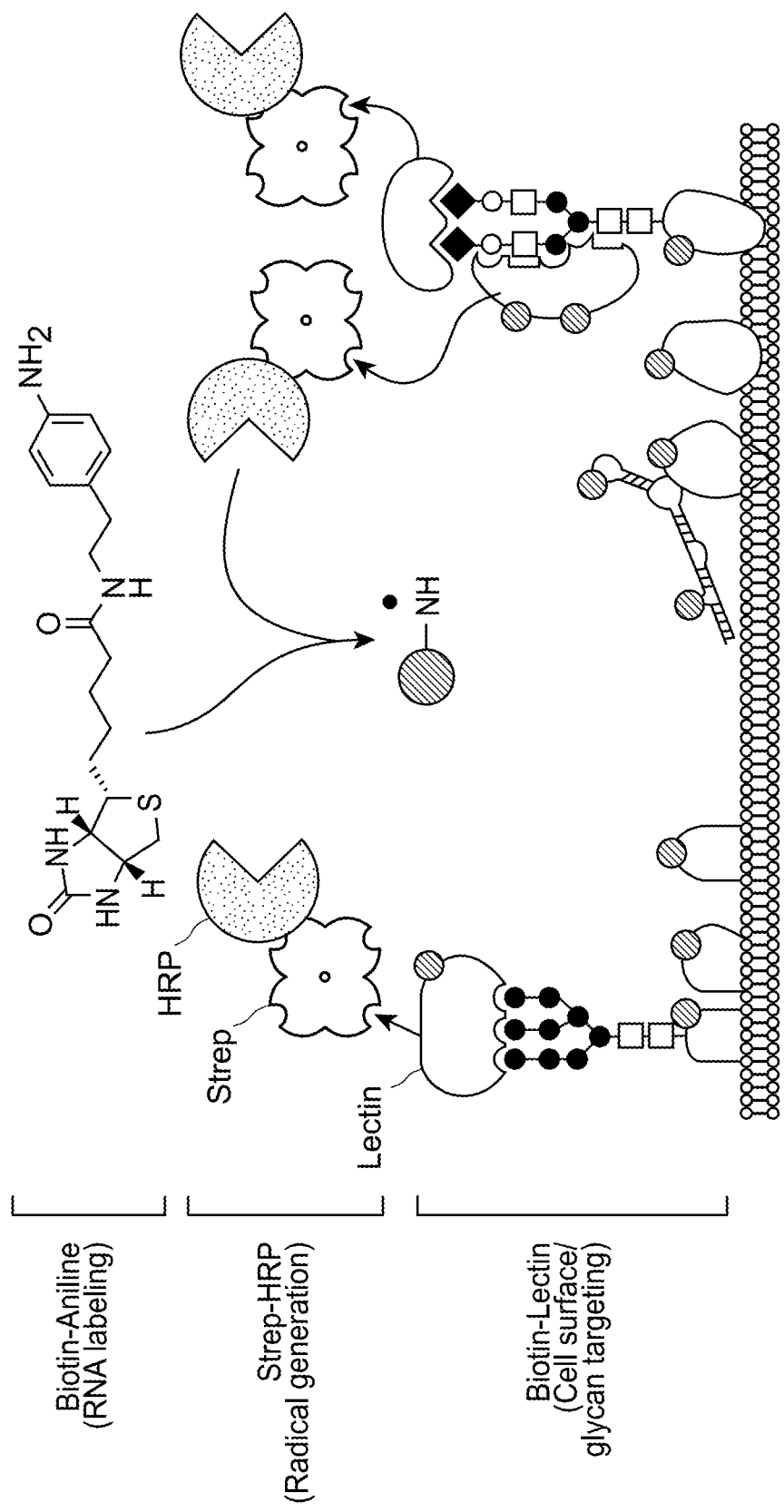

*HeLa RNA glycans*

Putative structures based on *glycan composition*

GLYCAN MODIFIED SHORT INTERFERING RNA

RELATED APPLICATIONS

The present application is a continuation of International Application No. PCT/US2022/026117, filed on Apr. 25, 2022, which claims the benefit of U.S. Provisional Application No. 63/179,065, filed on Apr. 23, 2021, U.S. Provisional Application No. 63/188,930 filed on May 14, 2021, and U.S. Provisional Application No. 63/189,492, filed on May 17, 2021, each of which are incorporated by reference in their entireties.

GOVERNMENT SUPPORT

This invention was made with government support under grant number R24 GM137763 awarded by the National Institutes of Health. The government has certain rights in the invention.

REFERENCE TO A SEQUENCE LISTING

This application contains a Sequence Listing in computer readable form. The computer readable form is incorporated herein by reference. Said ASCII copy, created on Apr. 22, 2022, is named 772233_202320_SL.txt and is 16,179 bytes in size.

FIELD OF THE INVENTION

The present disclosure relates to glyconucleic acids, such as glycoRNA and glycoDNA described herein. Provided are glycosylated ribonucleic acid (glycoRNA)-related methods and compositions.

BACKGROUND

Glycans are polymers of monosaccharides (single sugar molecules) that have been shown to regulate a wide array of critical biological processes, ranging from cell-cell contacts to host-pathogen interactions, and even the organization of multicellular organisms (See e.g., Varki and Gagneux, 2015). Glycans particularly regulate essential cellular functions in the context of cell surface events and are present in the cells of all living things (See e.g., Varki and Gagneux, 2015). Glycans regulate a myriad of essential cellular functions, especially in the context of cell surface events. For instance, complex glycans facilitate the folding and purposeful trafficking of proteins and lipids for secretion or membrane presentation. Thus, many fundamental processes such as embryogenesis, host-pathogen recognition and tumor-immune interactions rely on glycosylation. Glycans are present in every cell studied to date across the kingdoms of life, and in mammals are composed of roughly 10 monomeric carbohydrate units. Glycans can comprise fucose linked to GlcNAc residues at the core of the glycan or on the arms of the glycan. Sialic acid residues may be found at the terminal ends of glycans. In addition, some glycans are bisecting type N-glycans.

RNA represents another biopolymer that all living things require. RNA is canonically made up of four bases, but post-transcriptional modifications (PTMs) can dramatically expand the chemical diversity of RNA. So far, greater than 100 PTMs having been identified (See e.g., Frye et. al, 2018; Machnicka et. al, 2013; Nachtergaele, 2016). The use of non-canonical or non-natural nucleotides further adds to the chemical diversity of RNA. In addition to being messengers, RNAs can function as scaffolds, molecular decoys, enzymes, and network regulators across the nucleus and cytosol (See e.g., Cech and Steitz, 2014; Sharp, 2009; Wang and Chang, 2011).

DNA is another biopolymer central to all known forms of life. DNA provides organisms with the instructions it needs to carry out functions for development, survival, and reproduction.

RNA and DNA are both nucleic acids, though they have several differences. The bases they are canonically limited to differ. They also contain different sugars. DNA is traditionally confined to the nucleus of a cell, but RNA is capable of leaving the nucleus.

There remains a need for therapeutic methods of and compositions for delivering nucleic acids to specific cells in the body of a subject.

SUMMARY

The disclosure relates to novel conjugates between asparagine-linked (N-linked) glycans and nucleic acids (DNA, RNA) linked, e.g., via biorthogonal click chemistry. It is important to develop such novel conjugates, which may modulate the biophysical properties of the conjugates, for example, modulate the stability of the nucleic acids in biological systems (e.g., serum) and/or modulate delivery of the nucleic acids (e.g., targeted delivery to specific membranes, organelles). In one aspect, the present disclosure provides a pharmaceutical composition comprising a modified RNA comprising a glycan moiety. In some embodiments, the pharmaceutical composition comprises a modified RNA comprising a glycan moiety comprising at least 6 monosaccharides. In some embodiments, the pharmaceutical composition further comprises a pharmaceutically acceptable carrier. The pharmaceutical composition can comprise a glyconucleic acid comprising a nucleic acid and at least one glycan moiety comprising at least 6 monosaccharides conjugated to the nucleic acid, and a pharmaceutically acceptable carrier. The glycan moiety can comprise at least 8 monosaccharides. The glycan moiety can comprise at least 10 monosaccharides. The glycan moiety can comprise an N-linked glycan or an O-linked glycan.

The glycan moiety can comprise a bi-antennary glycan. The bi-antennary glycan can comprise a first terminal residue and a second terminal residue. The glycan moiety can comprise a tri-antennary glycan. The tri-antennary glycan can comprise a first terminal residue, a second terminal residue and a third terminal residue.

In some embodiments, the glycan moiety comprises sialic acid, fucose, or a combination thereof. In some embodiments, the glycan moiety comprises GlcNAc, mannose, galactose, sialic acid, fucose, or a combination thereof. At least one of the first terminal residue, the second terminal residue and the third terminal residue, if present, can comprise sialic acid. At least one of the first terminal residue, the second terminal residue and the third terminal residue, if present, can comprise fucose. At least one of the first terminal residue, the second terminal residue and the third terminal residue, if present, can comprise GlcNAc. At least one of the first terminal residue, the second terminal residue and the third terminal residue, if present, can comprise mannose. At least one of the first terminal residue, the second terminal residue and the third terminal residue, if present, can comprise NeuNAc. At least one of the first terminal residue, the second terminal residue and the third terminal residue, if present, can comprise galactose.

The nucleic acid of the pharmaceutical composition can be an RNA. The nucleic acid of the pharmaceutical composition can be an siRNA. The nucleic acid of the pharmaceutical composition can be an mRNA. The nucleic acid of the pharmaceutical composition can be a circular RNA. The nucleic acid of the pharmaceutical composition can be a guide RNA. The nucleic acid of the pharmaceutical composition can be an aptamer RNA. The nucleic acid of the pharmaceutical composition can be an DNA.

The at least one glycan moiety can comprise a compound of Table 2A or 2B. The modified nucleic acid can comprise a nucleic acid of Table 1. The at least one glycan moiety can be conjugated to the modified nucleic acid via a click-chemistry reaction. The nucleic acid can be conjugated to the glycan via a linker group covalently bound to a terminus of the nucleic acid. The nucleic acid can be conjugated to the glycan via a linker covalently bound to a chemically modified nucleotide in the middle of the nucleic acid. The nucleic acid can be conjugated to the glycan via a linker covalently bound to a chemically modified nucleotide that is not located at the 3' terminal or the 5' terminal of the nucleic acid. The nucleic acid can be conjugated to the glycan via a chemical handle inserted between two nucleotides of the nucleic acid. In embodiments, the two nucleotides do not include nucleotides at the 3' terminal or the 5' terminal of the nucleic acid.

In another aspect, provided herein are compounds of Formula (I):

A-L-B  (I), or a salt, co-crystal, tautomer, stereoisomer, solvate, hydrate, polymorph, or an isotopically enriched derivative thereof, wherein:

A is a nucleic acid of deoxyribonucleic acid (DNA) or ribonucleic acid (RNA) comprising a first click-chemistry handle;

B is an asparagine-linked glycan (N-glycan) comprising a second click-chemistry handle; and L comprises a linker formed by a biorthogonal click chemistry reaction between the first click-chemistry handle and the second click-chemistry handle.

Also provided herein are methods of preparing a compound of Formula (I), the method comprising reacting nucleic acid A, comprising a first click-chemistry handle with compound B, which is an asparagine-linked glycan (N-glycan) comprising a second click-chemistry handle; wherein the reaction of the first step is carried out under biorthogonal click chemistry conditions.

The glyconucleic acid compound can have Formula (I): A-L-B (I), or a salt, co-crystal, tautomer, stereoisomer, solvate, hydrate, polymorph, or an isotopically enriched derivative thereof, wherein: A is a nucleic acid comprising a first click-chemistry handle; B is an asparagine-linked glycan (N-glycan) comprising a second click-chemistry handle; and L comprises a linker formed by a biorthogonal click chemistry reaction between the first click-chemistry handle and the second click-chemistry handle. A can be an RNA comprising a first click-chemistry handle. A can be an siRNA comprising a first click-chemistry handle. A can be an mRNA comprising a first click-chemistry handle. A can be a circular RNA comprising a first click-chemistry handle. A can be a DNA comprising a first click-chemistry handle.

A can comprise a first click-chemistry handle selected from those listed in Table 4 under "Reagent A", and B can comprise a second click-chemistry handle selected from those listed in Table 4 under "Reagent B". A can comprise a first click-chemistry handle selected from those listed in Table 4 under "Reagent B", and B can comprise a second click-chemistry handle selected from those listed in Table 4 under "Reagent A". B can be an asparagine linked glycan comprising a bi-antennary glycan, wherein the bi-antennary glycan comprises a first terminal residue and a second terminal residue. B can be an asparagine linked glycan comprising a tri-antennary glycan, wherein the tri-antennary glycan comprises a first terminal residue, a second terminal residue and a third terminal residue.

At least one of the first terminal residue, the second terminal residue and the third terminal residue, if present, can comprise sialic acid. At least one of the first terminal residue, the second terminal residue and the third terminal residue, if present, can comprise fucose. At least one of the first terminal residue, the second terminal residue and the third terminal residue, if present, can comprise GlcNAc. At least one of the first terminal residue, the second terminal residue and the third terminal residue, if present, can comprise mannose. At least one of the first terminal residue, the second terminal residue and the third terminal residue, if present, can comprise NeuNAc. At least one of the first terminal residue, the second terminal residue and the third terminal residue, if present, can comprise galactose.

The disclosure also relates to methods of treating a disease or condition comprising administering to a subject in need thereof a therapeutically effective amount of the pharmaceutical composition disclosed herein or the glyconucleic acid disclosed herein. The disease or condition can be selected from an inflammation disorder, an autoimmune disease, a cancer, a metabolic disease, a clotting disease, an anti-clotting disease, an allergy, a viral disease, and a microbial infection. In embodiments, the disease or condition is inflammation. In embodiments, the disease or condition is cancer. In embodiments, the disease or condition is an autoimmune disease. In embodiments, the disease or condition is an IgE-mediated allergy. In embodiments, the disease or condition is systemic lupus erythematosus. In embodiments, the disease or condition is a microbial infection. In embodiments, the disease or condition is a viral infection. In embodiments, the disease or condition is a metabolic disease.

In another aspect, provided are glycosylated ribonucleic acid (glycoRNA)-related methods and compositions. In certain aspects, provided are methods for reducing interaction between glycan binding protein (GBP)-expressing cells and cells displaying cell surface glycosylated ribonucleic acids (glycoRNAs). In some embodiments, such methods comprise contacting the GBP-expressing cells and/or the cells displaying cell surface glycoRNAs with an agent that binds the GBP and/or cell surface glycoRNAs such that interaction between the GBP-expressing cells and the cells displaying cell surface glycoRNAs is reduced. Such methods may be performed in vitro, in vivo or ex vivo. Also provided are conjugates, fusion proteins and compositions that find use, e.g., in practicing the methods of the present disclosure. Methods of targeting an agent to GBP-expressing cells, and methods of assessing a biological sample for glycoRNAs are also provided.

The disclosure further relates to methods for reducing interaction between glycan binding protein (GBP)-expressing cells and cells displaying cell surface glycosylated ribonucleic acids (glycoRNAs), comprising: contacting the GBP-expressing cells with soluble glycoRNAs which bind to GBP expressed on the surface of the GBP-expressing cells, in an amount effective to reduce interaction between the GBP-expressing cells and the cells displaying cell surface glycoRNAs.

The soluble glycoRNAs can comprise RNAs from the Y RNA family. The soluble glycoRNAs can comprise Y5 RNAs. The soluble glycoRNAs can comprise snoRNAs, tRNAs, snRNAs, rRNAs, or any combination thereof. The soluble glycoRNAs can comprise soluble sialylated RNAs. The soluble sialylated RNAs can comprise Neu5Ac, Neu5Gc, or a combination thereof. The soluble glycoRNAs are conjugated to one or more agents. The one or more agents can comprise a therapeutic agent. The one or more agents comprise a detectable label. The GBPs comprise sialic acid-binding immunoglobulin-like lectins (Siglecs). The Siglecs can comprise Siglec-11. The Siglecs can comprise Siglec-14. The GBPs can comprise C-type lectins. The GBPs can comprise galectins. The GBPs can comprise selectins.

BRIEF DESCRIPTION OF THE DRAWINGS

FIG. 1A is a schematic of an RNA extraction protocol. Ac$_4$ManNAz=peracetylated N-azidoacetylmannosamine. Prot.K=proteinase K. DBCO=dibenzocyclooctyne. FIG. 1B is an RNA blotting of RNA from HeLa cells treated with 100 µM Ac$_4$ManNAz for the indicated amount of time. After RNA purification, Ac$_4$ManNAz was conjugated to DBCO-biotin, visualized with Streptavidin-IR800 (Strep), and imaged on an infrared scanner. Before RNA transfer to the membrane, total RNA was stained and imaged with SYBR Gold (Sybr) to interrogate quality and loading. All subsequent blots were prepared in this manner, and Ac$_4$ManNAz is always used at 100 µM. The regions where glycoRNAs are present and non-specific labeling (*) is noted. FIG. 1C is an RNA Blot of Ac$_4$ManNAz-labeled HeLa RNA treated in vitro with Turbo DNase or RNase cocktail (A/T1)+/−SUPERaseIn (RNase inhibitor). FIG. 1D is an RNA Blot of murine RNA after in vivo Ac$_4$ManNAz delivery via intraperitoneal injection on indicated days at 300 mg Ac$_4$ManNAz/kg/day. RNA from the liver and spleen were analyzed. Mock (m) mice were injected with DMSO only. RNase treatment was performed on extracted RNA.

FIG. 2A is a blot of total or poly-adenylated (poly-A) enriched RNA from HeLa cells treated with Ac$_4$ManNAz. FIG. 2B is a blot of total RNA from HeLa cells treated with Ac$_4$ManNAz after differential precipitation fractionation using silica-based columns. FIG. 2C is a blotting of total RNA from H9 human embryonic stem cells (H9) treated with Ac$_4$ManNAz after sucrose density gradient (15-30% sucrose) fractionation. An input profile is displayed to the right of the gradient. FIG. 2D is a scatter plot analysis Ac$_4$ManNAz-enriched RNAs purified from the small RNA fractions of FIG. 2C from HeLa and H9 cells. Reads mapping to snRNA, snoRNAs, and Y RNAs are shown. Significance scores ($-\log_{10}$(adjusted p-value)) are overlaid for HeLa cells as the size of each datapoint and for H9 cells as the color of each datapoint. FIG. 2E is a representative blot of total RNA from wild-type (WT) or Y5 knockout (KO) 293T cells treated with Ac$_4$ManNAz. The inset graph in FIG. 2E shows quantification of the blot in FIG. 2E from biological triplicates. P value calculated by a paired, two-tailed t-test.

FIG. 3A is a blotting of RNA from HeLa cells treated with 1.75 mM 9-azido sialic acid for indicated times. FIG. 3B is a blotting of Ac$_4$ManNAz-labeled HeLa cell RNA treated with *Vibrio cholerae* (VC) Sialidase or Heat-inactivated Sialidase (VC-Sialidase-HI). FIG. 3C is a blotting of RNA from HeLa cells treated with Ac$_4$ManNAz and the indicated concentrations of P-3F$_{AX}$-Neu5Ac. FIG. 3D Unlabeled total RNA from H9 cells was isolated, reacted with the indicated enzyme (no enzymes, RNase cocktail, or Sialidase treatment), cleaned up to remove cleaved metabolites, and processed with the fluorogenic 1,2-diamino-4,5-methylenedioxybenzene (DMB) probe. HPLC analysis quantified the presence and abundance of specific sialic acids. The inset image in FIG. 3D is an Sybr gel image of the total RNA for each condition. The main sialic acid peaks are #2 and 3. The identity of peak 1 is unknown, but it is RNase sensitive. FIG. 3E is a graph showing quantification of DMB results from FIG. 3D from 4188, H9, and HeLa cells from four biological replicates.

FIG. 4A is a blotting of RNA from ldlD CHO cells labeled with Ac$_4$ManNAz, Galactose (Gal, 10 µM), N-acetylgalactosamine (GalNAc, 100 µM), or all for 24 hours. FIG. 4B is a blotting of RNA from HeLa cells treated with Ac$_4$ManNAz and indicated concentrations of NGI-1, an inhibitor of OST, for 24 hours. FIG. 4C is a blotting as in FIG. 4B but with the indicated concentrations of Kifunensine. FIG. 4D is a graph quantifying Ac$_4$ManNAz signal after treatment of Ac$_4$ManNAz-labeled HeLa cell RNA with the indicated enzymes in vitro each for 1 hour at 37° C. in biological triplicate. FIG. 4E is a schematic of the method used to release glycans from RNA samples and subsequently purify free glycans for mass spectrometry analysis. FIG. 4F is an unsupervised clustering analysis of glycans (rows) released from peptide and RNA fractions (columns) of 293, H9, or HeLa cells via PNGaseF cleavage. Glycans had to be found biological replicates of at least one of the six samples to be included. FIG. 4G is a principal component analysis plot of peptide- and RNA PNGaseF-release glycans. FIG. 4H is a set of bar plots of the fraction of glycans containing fucose or sialic acid modifications which were released from peptides or RNA samples. Numbers on the horizontal axis are the absolute numbers of glycans found with each of the modifications from a given dataset.

FIGS. 5A-5G are images and graphs illustrating that glycoRNAs are on the external surface of living cells. FIG. 5A is a blotting of RNA and proteins after subcellular fractionation designed to robustly purify nuclei. Non-nuclear proteins GAPDH and β-Tubulin and nuclear Histone 3 lysine 4 trimethylation (H3K4me3) are visualized by western blot. FIG. 5B is a blotting of RNA and proteins after subcellular fractionation designed to separate soluble cytosol from membranous organelles. Membrane proteins RPN1, Sec63, and soluble β-Tubulin are visualized by western blot. FIG. 5C is a blotting of RNA from HeLa cells labeled with 100 µM Ac$_4$ManNAz for 24 hours and then expose to fresh media containing 100 µM Ac$_4$ManNAz with or without 150 nM VC-Sia for 60 minutes at 37° C. FIG. 5D is a graph quantifying the experiment shown in FIG. 5C across biological triplicates and from 293T or K562 cells treated in the same manner. P-value calculated by a paired, two-tailed t-test. FIG. 5E is a schematic of the Lectin-based proximity labeling of RNA on cell surfaces. Living cells are stained with a biotinylated lectin that recruits streptavidin-HRP which is in turn able to generate nitrene radicals from biotin-aniline after the addition of hydrogen peroxide. RNA from these cells is then extracted and analyzed for biotin labeling which reveals if that RNA was in proximity to the lectin. FIG. 5F is a blotting of total RNA samples generated as described in FIG. 5E. Lanes 5 and 6 were processed in vitro (after purifying RNA) with RNase Cocktail or VC-Sia to demonstrate any sensitivity of the biotin-aniline signal to these enzymes. FIG. 5G is a blotting of total RNA samples similar to the experiment reported in FIG. 5F, however cells were first lysed in a hypotonic buffer, destroying cellular membranes which are normally impermeable to nitrene radicals. Labeling of rRNA is evident here while not in FIG. 5F.

FIG. 6A is a cartoon model of a glycoRNA on the cells surface depicted with two glycans identified in the PNGaseF release experiment. Prediction locations of binding for the anti-dsRNA antibody (J2) and Siglec-Fc proteins are highlighted. FIG. 6B is a FACS analysis of single HeLa cells pre-treated with the indicated enzymes or inhibitors and then stained with the J2 antibody. Gated region (orange) indicates the population shifted towards high J2 binding. FIG. 6C is a FACS analysis of single HeLa cells pre-treated with the OST inhibitor NGI-1 for 12 hours at the indicated concentrations. Dashed vertical line denotes a J2-high population and for each sample the fraction of cells within this region are shown as a percentage. FIG. 6D is a FACS analysis of single HeLa cells pre-treated with RNase then stained with the indicated Siglec-Fc reagents.

FIG. 8A shows that nucleic acids can vary in backbone composition and length and location of the modified nucleotide. FIG. 8A shows a reaction between a short (20 nt) nucleic acid with a 3' terminal alkyne modification is depicted, and a glycan containing a terminal azide (glycan with simple oligosaccharides (<10 sugars) to more complex glycan structures that are functionalized with fucose (triangle) and sialic acid (diamonds)). Multiple glycans are shown in FIG. 8A, but in the CuAAC reactions a single modified nucleic acid species are reacted with a single glycan species. FIG. 8B shows an example of a modified nucleotide with an alkyne moiety, 3' 5-Octadiynyl dU.

FIG. 9 shows that glycan modifications can be placed at the terminal 5', 3' ends or internally, as shown for the mRNA, aptamer, and circRNA depictions.

FIG. 10A shows the types and concentrations of the azido-N-glycans used in Example 10: A2G0-Asn-N3 (G-28) (50 nmol); 2,3SA2-A2G2-Asn-N3 (G-35) (50 nmol), A2G2-Asn-N3 (G-29) (50 nmol), and 2,6SA2-A2G2-Asn-N3 (G-30) (50 nmol). FIG. 10B shows the MALDI-MS spectra for G-28. FIG. 10C shows the MALDI-MS spectra for G-29. FIG. 10D shows the MALDI-MS spectra for G-35. FIG. 10E shows the MALDI-MS spectra for G-30.

FIG. 11 shows new shifted bands that correspond to N-glycan-RNA or N-glycan-DNA-coupled conjugates that were produced.

FIG. 13A shows relative expression of Cy5 signal in human CD14+ monocytes following 4 hr incubation with glycoRNAs relative to X-3/I-4 duplex of GlycoRNA. FIG. 13B shows relative expression of Cy5 signal in human CD3+ T cells following 4 hr incubation with glycoRNAs. FIG. 13C shows relative expression of Cy5 signal in human CD3+ T cells following 4 hr incubation with glycoRNAs.

FIG. 15A shows relative expression of Cy5 signal in HepG2 cells with glycoRNA duplexes R-1/I-1, R-2/I-1, R-3/I-1, R-4/I-1, R-5/I-1, and R-6/I-1, relative to X-3/I-4 at 10 nM concentration following 4 hr incubation. FIG. 15B shows relative expression of Cy5 signal in HepG2 cells with glycoRNA duplexes R-1/I-1, R-2/I-1, R-3/I-1, R-4/I-1, R-5/I-1, and R-6/I-1, relative to X-3/I-4 at 100 nM concentration following 4 hr incubation.

FIG. 16A: R-1/I-1; FIG. 16B: R-2/I-1; FIG. 16C: R-3/I-1; FIG. 16D: R-4/I-1; FIG. 16E: R-5/I-1; FIG. 16F: R-6/I-1.

DETAILED DESCRIPTION

Figure 1A:
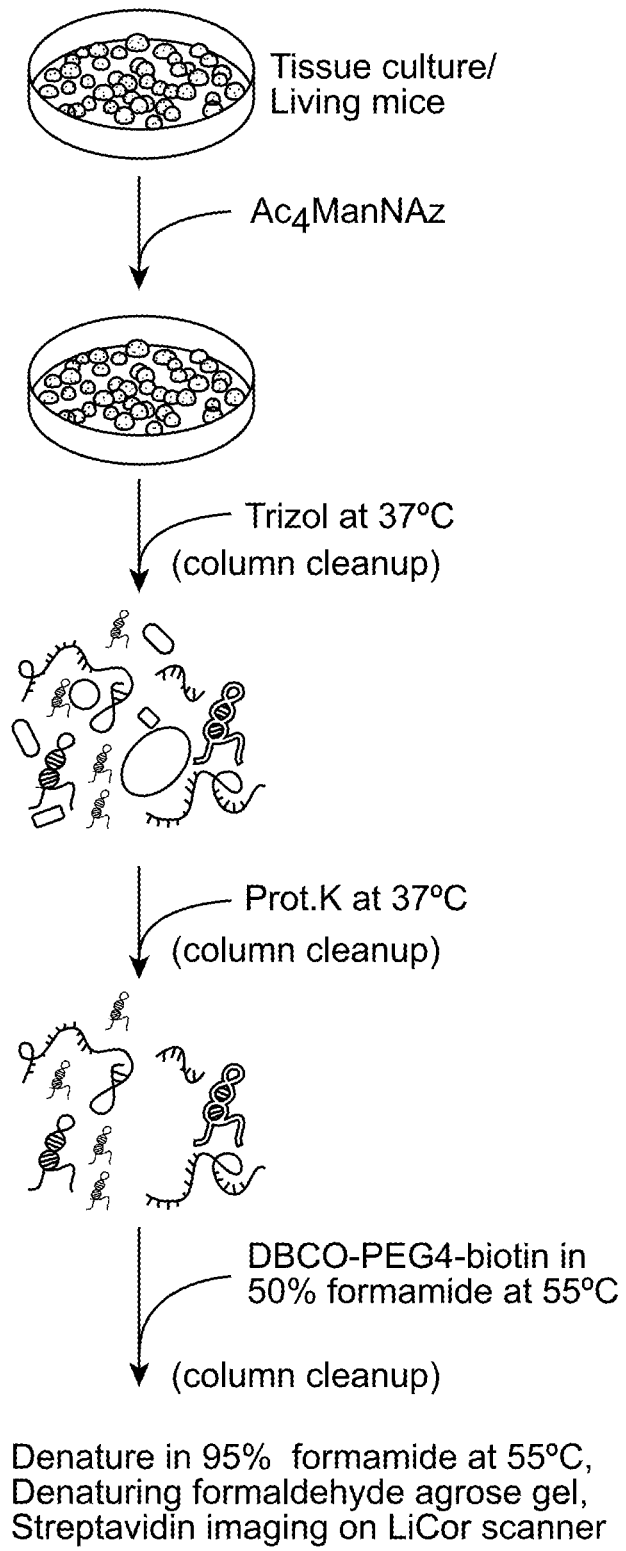
FIGS. 1A-1D are a schematic and blot images showing that Ac$_4$ManNAz, a glycan reporter, incorporates into mammalian cellular RNA.

In one aspect, the present disclosure provides a pharmaceutical composition comprising a modified nucleic acid comprising a glycan moiety. In some embodiments, the pharmaceutical composition further comprises a pharmaceutically acceptable carrier. Glycans modify lipids and proteins to mediate inter- and intramolecular interactions across all domains of life. RNA is not thought to be a major target of naturally occurring glycosylation. Surprisingly demonstrated herein is that mammals use RNA as a third scaffold for glycosylation. Using a battery of chemical and biochemical approaches, it was found that conserved small noncoding RNAs bear sialylated glycans. These "glycoRNAs" were present in multiple cell types and mammalian species, in cultured cells, and in vivo. GlycoRNA assembly depends on canonical N-glycan biosynthetic machinery and results in structures enriched in sialic acid and fucose. Analysis of living cells revealed that the majority of glycoRNAs were present on the cell surface and can interact with anti-dsRNA antibodies and members of the Siglec receptor family. Collectively, these findings point to an expanded role for RNA in extracellular biology.

Using synthetic chemistry or enzymatic processes, glycans can be attached to either RNA or DNA to form a glyconucleic acid, such as glycoRNA or glycoDNA. Specifically, the glycans that attach to RNA or DNA contain at least 1 monosaccharide. In other embodiments, the glycans that attach to RNA or DNA contain at least 10 monosaccharides. Preferably, the glycans that attach to RNA or DNA contain at least 6 monosaccharides. Preferably, the glycans that attach to RNA or DNA contain at least 10 monosaccharides. By attaching glycans to RNA or DNA, a more stable biophysical material can be created. Glycans can facilitate targeting RNA to a cell population, and a cell can be targeted with or without internalization. Endogenous mammalian glycoRNA glycans appear to be structurally unique to those found on proteins (Flynn et. al, 2019). There can be different compositions of glycans, including fucosylated, sialylated, and asialylated glycans. The majority of natural cellular glycoRNAs present on the cell surface, and the RNA species are small, highly conserved RNAs.

The glycoconjugates of nucleic acids, such as linear or circular DNA and RNA provide several advantages. In particular, the glycoconjugates can be administered to target delivery to desired organs or cell types without the need to use additional delivery vehicles, such as lipid nanoparticles (LNPs). Selectivity for certain organs and cell types can be provided by selecting an appropriate array of glycans for conjugation to the nucleic acid. The glycoconjugated nucleic acids, in particular RNA, are also more stable than unglycated nucleic acids.

With glycoconjugates of nucleic acids, such as RNA, cell targeting can be performed, and potentially endosomal escape. Known targeting moieties such as triple N-Acetylgalactosamine (GalNac), three chemically linked monosaccharides, can facilitate targeting the RNA to a cell population such as the liver and eventually allowing internalization. Glycans can also target a cell without internalization. Glycoconjugates, including glycoRNA, can localize to the cell surface directly. Once a glycoRNA reaches the cell, the glycoconjugate can then bind to glycoreceptors on a cell surface and activate cellular signal transduction. For example, binding of a Siglec cell surface receptor by a glycoRNA could lead to activation of the Immunoreceptor tyrosine-based inhibitory (ITIM) domain of the Siglec protein, causing cell suppression. A glycoRNA can also be delivered into a cell. Glycans on circular RNA (circRNA) or mRNA can create a more stable biophysical material, which could be useful for stability or packing into a lipid nanoparticle (LNP), among other things.

A glycan can be conjugated to biomolecules, including RNA, such as linear mRNA, circular mRNA, siRNA, miRNA and the like, or DNA, including linear DNA or circular DNA. In addition, glycan composition can be modified with various monosaccharide enzymatically through the use of glycosyltransferases (See e.g., Van Delft et. al, 2015). Moreover, glycan orientation to create programmable binding interfaces for glycan receptors can be defined using an RNA that forms a particular structure and includes modified nucleotides in particular places.

After a glyconucleic acid, such as glycoRNA and glycoDNA, has been created, it can be formulated for administration into the body by any desired methods such as parenteral administration, such as intravenous injection (IV), intramuscular injection, intrathecal injection, intraperitoneal injection, subcutaneous injection, or injection into a desired organ or tissue (e.g., intravitreal injection), topical application, or nasal or oral inhalation, for example following aerosolization. The glycoRNA can be packed into an LNP, or it can be naked. Small RNA therapeutics may work better when using naked RNA since long RNA can be destroyed by a single cut. For large naked RNA, local application may be best for systemic delivery.

Definitions

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); Worthington Enzyme Manual, Worthington Biochemical Corp., Freehold, N.J.; *Handbook of Biochemistry: Section A Proteins*, Vol I, CRC Press (1976); Handbook of Biochemistry: Section A Proteins, *Vol II*, CRC Press (1976); *Essentials of Glycobiology*, Cold Spring Harbor Laboratory Press (1999).

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and compositions. The upper and lower limits of these smaller ranges may independently be included in the smaller ranges and are also encompassed within the methods and compositions, subject to any specifically excluded limit in the stated range. Where the stated range includes one or both of the limits, ranges excluding either or both of those included limits are also included in the methods and compositions.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications, patents and other references mentioned herein are hereby incorporated by reference in their entireties.

The following terms, unless otherwise indicated, shall be understood to have the following meanings:

Throughout this specification and claims, the word "comprise" or variations such as "comprises" or "comprising", will be understood to imply the inclusion of a stated integer or group of integers but not the exclusion of any other integer or group of integers.

As used herein, the term terms "glycosylated nucleic acid" and "glyconucleic acid" should be understood to refer to a modified nucleic acid comprising a glycan moiety, as described and disclosed herein. As used herein, the terms "glycosylated ribonucleic acid" and "glycoRNA" should be understood to refer to a modified ribonucleic acid comprising a glycan moiety, as described and disclosed herein. As used herein, the terms "glycosylated deoxyribonucleic acid" and "glycoDNA" should be understood to refer to a modified deoxyribonucleic acid comprising a glycan moiety, as described and disclosed herein.

As used herein, the term "polymer" refers to a substance composed of natural or synthetic monomers, such as ribonucleotides.

As used herein, the term "moiety" refers to a molecule. For instance, a "carbohydrate moiety" or an "oligosaccharide moiety" generally refers to a glycan composition.

A "modified sequence" is a nucleic acid molecule that includes at least one difference from a naturally-occurring nucleic acid molecule. A modified sequence includes all exogenous modified and unmodified heterologous sequences (i.e., sequences derived from an organism or cell other than that harboring the modified sequence) as well as endogenous genes, operons, coding sequences, or non-coding sequences, that have been modified, mutated, or that include deletions or insertions as compared to a naturally-occurring sequence. Such sequences also include all sequences, regardless of origin, that are linked to an inducible promoter or to another control sequence with which they are not naturally associated. Such sequences further include all sequences that can be used to down-regulate or knock out expression of an endogenous gene. These include anti-sense molecules, RNAi molecules, constructs for producing homologous recombination, cre-lox constructs, and the like.

The term "polynucleotide" or "nucleic acid molecule" or "nucleotide sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, and as an example for all sequences described herein under the general format "SEQ ID NO:", "nucleic acid comprising SEQ ID NO: 1" refers to a nucleic acid, at least a portion of which has either (i) the sequence of SEQ ID NO: 1, or (ii) a sequence complementary to SEQ ID NO: 1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

As used herein, an "isolated" composition (e.g., glycoligand) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The nucleic acids (also referred to as polynucleotides) of this present invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "downregulate," as in "downregulating a signal," means the process whereby the level of target gene expression prior to and following contact with the glycoligand can be compared, e.g., on an mRNA or protein level. If it is determined that the amount of RNA or protein expressed from the target gene is lower following contact with the glyco-ligand, then it can be concluded that the glyco-ligand downregulates target gene expression. The level of target RNA or protein in the cell can be determined by any method desired. For example, the level of target RNA can be determined by Northern blot analysis, reverse transcription coupled with polymerase chain reaction (RT-PCR), or RNAse protection assay. The level of protein can be determined, for example, by Western blot analysis.

"Operatively linked" or "operably linked" expression control sequences refers to a linkage in which the expression control sequence is contiguous with the gene of interest to control the gene of interest, as well as expression control sequences that act in trans or at a distance to control the gene of interest. The term is also used herein with respect to a glycan moiety conjugated to a synthetic scaffold domain as described herein.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof, domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

As used herein, the term "monosaccharide" refers to a carbohydrate molecule that cannot be hydrolyzed into two or more simpler carbohydrates. Examples of monosaccharides include, but are not limited to, GlcNAc, mannose, fucose, glucose, fructose and galactose.

The term "N-linked glycan" or "N-glycans" refers to a N-linked oligosaccharide structures, that are covalently bound to a nitrogen atom, optionally via an amide bond, optionally as an N-glycan conjugated at an asparagine or arginine residue via an N-acetylglucosamine residue on the glycan generally via glycosyltransferase. These "N-linked glycosylation sites" occur in the peptide primary structure containing, for example, the canonical amino acid sequence asparagine-X-serine/threonine, where X is any amino acid residue except proline and aspartic acid. "N-linked glycans" refer to N-linked oligosaccharide structures. The N-glycans can be attached to proteins or scaffolds, which can be manipulated further in vitro or in vivo. Common N-linked glycans typically include complex, hybrid, high-mannose, branched, and multiple antennary structures. The term "N-linked type" with respect to a glycan can refer to a scaffold having an attached N-acetylglucosamine (GlcNAc) residue linked to the amide nitrogen of an asparagine residue (N-linked) on the protein or scaffold, that is similar or even identical to those produced in humans.

"O-glycans" or "O-linked glycans" refer to O-linked oligosaccharide structures. The O-glycans can be attached to proteins or scaffolds, which can be manipulated further in vitro or in vivo. Common O-GalNAc core structures typically include Core 1, Core 2 and poly-N-acetyllactosamine (LacNAc) structures. In some embodiments, the O-linked oligosaccharide are covalently bound via an oxygen atom on a serine residue. The term "O-linked type" with respect to glycans can refer to conjugates having an attached N-acetylgalactosamine (GalNAc) residue linked to the oxygen atom of a serine or threonine residue on the protein or scaffold, that is similar or even identical to those produced in humans.

The term "glycan" refers to oligosaccharide structures— the predominant oligosaccharide structures found on glycoproteins include glucose (Glu), galactose (Gal), mannose (Man), fucose (Fuc), N-acetylgalactosamine (GalNAc), N-acetylglucosamine (GlcNAc), N-acetylgalactosamine (GalNAc), and sialic acid (e.g., N-acetyl-neuraminic acid (NeuAc or NANA). Hexoses (Hex), categorized as monosaccharides with 6 carbon atoms, such as glucose, galactose, mannose, are not readily discernable via mass spectrometry and may also be present. N-glycans differ with respect to the number of branches ("antennae" or "arms") comprising peripheral sugars (e.g., GlcNAc, galactose, fucose and sialic acid) that are added to the "triamannosyl core." The term "triamannosyl core", also referred to as "M3", "M3GN2", the "triamannose core", the "pentasaccharide core" or the "paucimannose core" reflects Man3GlcNAc2 oligosaccharide structure where the Manα1,3 arm and the Manα1,6 arm extends from the di-GlcNAc structure (GlcNAc2): β1,4GlcNAc-β1,4GlcNAc. N-glycans are classified according to their branched constituents (e.g., high-mannose, complex or hybrid).

A "high-mannose" type N-glycan comprises four or more mannose residues on the di-GlcNAc oligosaccharide structure. "M9" reflects Man9GlcNAc2. "M5" reflects Man5GlcNAc2.

A "hybrid" type N-glycan has at least one GlcNAc residue on the terminal end of the α1,3 mannose (Man α1,3) arm of the trimannose core and zero or more mannoses on the α1,6 mannose (Man α1,3) arm of the trimannose core. An example of a hybrid glycan is GlcNAcMan3GlcNAc2.

A "complex" type N-glycan typically has at least one GlcNAc residue attached to the Manα1,3 arm and at least one GlcNAc attached to the Manα1,6 arm of the trimannose core (sometimes referred to as "G0" or "G0F" fucosylated). Complex N-glycans may also have galactose or N-acetylgalactosamine residues ("G2" or "G2F" fucosylated) that are optionally modified with sialic acid ("G2S2" or "G2FS2" fucosylated) or derivatives (e.g., "Neu" refers to neuraminic acid and "Ac" refers to acetyl). Complex N-glycans may also have intrachain substitutions comprising "bisecting" GlcNAc and core fucose. Complex N-glycans may also have multiple antennae on the trimannose core, often referred to as "multiple antennary glycans" or also termed "multi-branched glycans," which can be tri-antennary, tetra-antennary, or penta-antennary glycans.

As used herein, the term "predominantly" or variations such as "the predominant" or "which is predominant" will be understood to mean the glycan species as measured that has the highest mole percent (%) of total N-glycans after the glyco-ligand has been removed (e.g., treated with PNGase and the glycans released) and are analyzed by mass spectroscopy, for example, MALDI-TOF MS. In other words, the phrase "predominantly" is defined as an individual entity, such as a specific glycoform, present in greater mole percent than any other individual entity. For example, if a composition consists of species A in 40 mole percent, species B in 35 mole percent and species C in 25 mole percent, the composition comprises predominantly species A. The term "enriched", "uniform", "homogenous" and "consisting essentially of" are also synonymous with "predominant" in reference to one or more glycans.

The mole % of N-glycans as measured by MALDI-TOF-MS in positive mode refers to mole % saccharide transfer with respect to mole % total N-glycans. Certain cation adducts such as K+ and Na+ are normally associated with the peaks eluted increasing the mass of the N-glycans by the molecular mass of the respective adducts.

By "effective amount" or "therapeutically effective amount" is meant a dosage sufficient to produce a desired result, e.g., an amount sufficient to effect beneficial or desired (including preventative and/or therapeutic) results, such as a reduction in a symptom of a medical condition (e.g., cancer, an infectious disease, an immune-mediated disorder (e.g., an autoimmune disorder, an inflammatory disorder), etc.) as compared to a control. With respect to cancer, in some embodiments, the therapeutically effective amount is sufficient to slow the growth of a tumor, reduce the size of a tumor, and/or the like. An effective amount can be administered in one or more administrations.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$ alkyl"). In some embodiments, a heteroalkyl group is a saturated group having 1 to 18 carbon atoms and 1 or more heteroatoms within the parent chain ("hetero$C_{1-18}$ alkyl"). In some embodiments, a heteroalkyl group is a saturated group having 1 to 16 carbon atoms and 1 or more heteroatoms within the parent chain ("hetero$C_{1-16}$ alkyl"). In some embodiments, a heteroalkyl group is a saturated group having 1 to 14 carbon atoms and 1 or more heteroatoms within the parent chain ("hetero$C_{1-14}$ alkyl"). In some embodiments, a heteroalkyl group is a saturated group having 1 to 12 carbon atoms and 1 or more heteroatoms within the parent chain ("hetero$C_{1-12}$ alkyl"). In some embodiments, a heteroalkyl group is a saturated group having 1 to 10 carbon atoms and 1 or more heteroatoms within the parent chain ("hetero$C_{1-10}$alkyl"). In some embodiments, a heteroalkyl group is a saturated group having 1 to 8 carbon atoms and 1 or more heteroatoms within the parent chain ("hetero$C_{1-8}$alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-20}$ alkyl. In certain embodiments, the heteroalkyl group is an unsubstituted heteroC$_{1-10}$alkyl. In certain embodiments, the heteroalkyl group is a substituted heteroC$_{1-20}$ alkyl. In certain embodiments, the heteroalkyl group is an unsubstituted heteroC$_{1-10}$alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

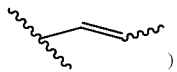
)

may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetra-hydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. The disclosure is not intended to be limited in any manner by the exemplary substituents described herein.

When substituted, exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, NR$^{bb}$C(=O)N(R$^{bb}$)$_2$, —C(=NR$^{bb}$)R$^{aa}$, —C(=NR$^{bb}$)OR$^{aa}$, OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^b$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X, —OP(OR$^{cc}$)$_2$, —OP(OR$^{cc}$)$_3$$^+$X, —OP(R$^{cc}$)$_4$, —OP(OR$^{cc}$)$_4$, —B(R$^{aa}$)$_2$, —B(OR$^{cc}$)$_2$, —BR$^{aa}$(OR), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^d$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R)$_3$$^+$X$^-$, —N(OR$^{ee}$)R$^{ee}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ee}$C(=O)R$^{ee}$, —NR$^{ff}$CO$_2$R$^{ee}$, —NR$^{ee}$C(=O)N(R$^{ff}$)$_2$, —C(=NR$^{ff}$)OR$^{ee}$, —OC(=NR$^{ee}$)R$^{ee}$, —OC(=NR$^{ff}$)OR$^{ee}$, —C(=NR$^{ee}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ee}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl and 5-10 membered heteroaryl, or two R$^f$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$ ($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(=NH)NH($C_{1-6}$ alkyl), —OC(=NH)$NH_2$, —NHC(=NH)N($C_{1-6}$ alkyl)$_2$, —NHC(=NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2$($C_{1-6}$ alkyl), —$SO_2$O($C_{1-6}$ alkyl), —$OSO_2$($C_{1-6}$ alkyl), —SO($C_{1-6}$ alkyl), —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

Before the methods and compositions of the present disclosure are described in greater detail, it is to be understood that the methods and compositions are not limited to particular embodiments described, as such may, of course, vary. It is also to be understood that the terminology used herein is for the purpose of describing particular embodiments only, and is not intended to be limiting, since the scope of the methods and compositions will be limited only by the appended claims.

Unless otherwise defined, all technical and scientific terms used herein have the same meaning as commonly understood by one of ordinary skill in the art to which this present invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

It is appreciated that certain features of the methods and compositions, which are, for clarity, described in the context of separate embodiments, may also be provided in combination in a single embodiment. Conversely, various features of the methods and compositions, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and compositions and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

As used herein, the term "salt" refers to any and all salts, and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphor sulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and N+(C1-4 alkyl)4 salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R×0.5 H2O)), and polyhydrates (x is a number greater than 1, e.g., dihydrates (R×2 H2O) and hexahydrates (R×6 H2O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "co-crystal" refers to a crystalline structure comprising at least two different components (e.g., a compound disclosed herein and an acid), wherein each of the components is independently an atom, ion, or molecule. In certain embodiments, none of the components is a solvent. In certain embodiments, at least one of the components is a solvent. A co-crystal of a compound disclosed herein and an acid is different from a salt formed from a compound disclosed herein and the acid. In the salt, a compound disclosed herein is complexed with the acid in a way that proton transfer (e.g., a complete proton transfer) from the acid to a compound disclosed herein easily occurs at room temperature. In the co-crystal, however, a compound disclosed herein is complexed with the acid in a way that proton transfer from the acid to a compound disclosed herein does not easily occur at room temperature. In certain embodiments, in the co-crystal, there is no proton transfer from the acid to a compound disclosed herein. In certain embodiments, in the co-crystal, there is partial proton transfer from the acid to a compound disclosed herein. Co-crystals may be useful to improve the properties (e.g., solubility, stability, and ease of formulation) of a compound disclosed herein.

The term "isotopes" refers to variants of a particular chemical element such that, while all isotopes of a given element share the same number of protons in each atom of the element, those isotopes differ in the number of neutrons.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal. A "patient" refers to a human subject in need of treatment of a disease.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

Nucleic Acid Features

As described elsewhere herein, the present disclosure provides a pharmaceutical composition comprising a modified nucleic acid comprising a glycan moiety. As used herein, the term "modified nucleic acid" refers to a nucleic acid that has been chemically altered in one or more ways, as compared to a naturally occurring nucleic acid.

In some embodiments, the modified nucleic acid is modified to allow for conjugation of the nucleic acid to the glycan moiety. In some embodiments, the modified nucleic acid comprises a non-nucleotide chemical handle that enables conjugation of the nucleic acid to the glycan moiety. In some embodiments, the modified nucleic acid comprises a click-chemistry handle, allowing for conjugation with a glycan moiety comprising a second click-chemistry handle. In some embodiments, the modified nucleic acid comprises a click-chemistry handle attached to a base of a nucleotide. In some embodiments wherein the modified nucleic acid comprises a linear nucleic acid, the modified nucleic acid comprises a click-chemistry handle attached to a terminus of the polynucleotide chain. In some embodiments, the modified nucleic acid comprises a click-chemistry handle attached to the backbone of the nucleic acid.

In some embodiments, the modified nucleic acid is modified in such a way that results in increased stability of the nucleic acid, as compared to an analogous naturally occurring version of the nucleic acid. In some embodiments, the present disclosure contemplates any and all sugar, backbone and base modifications known in the art for generating a modified nucleic acid having increased stability as compared to a comparable unmodified nucleic acid. In some embodiments, the modified nucleic acid comprises at least one chemical modification described in Ochoa, et al., Molecules 2020, 25(20), 4659, which is incorporated by reference herein in its entirety. For example, the modified nucleic acid can comprise at least one modification described by Ochoa, et al. in FIG. 1 and Table 1 disclosed therein.

In some embodiments, the modified nucleic acid is an siRNA comprising a modified backbone.

In some embodiments, the modified nucleic acid is modified in such a way that minimizes immune response. For example, the modified nucleic acid can be a modified mRNA, comprising one or more chemical alterations that result in a lessened immunogenic response upon administration to a subject, as compared to a non-modified mRNA.

In some embodiments, the modified nucleic acid is a circular RNA, wherein the circular RNA is modified as compared to a naturally occurring RNA by being self-ligated, thereby lacking a cap or tail. In some embodiments, the modified nucleic acid is a capped RNA, whereby the 5' and/or 3' ends are capped by a chemical alteration.

In some embodiments, the modified nucleic acid comprises non-naturally occurring nucleotides. Examples of modified nucleotides (such as non-naturally occurring nucleotides) include, but are not limited to, diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In some embodiments, the modified nucleic acid comprises at least one non-naturally occurring nucleotide. In some embodiments, at least about 10%, about 20%, about 30%, about 40%, about 50%, about 60%, about 70%, about 80%, about 90%, or about 95% of the bases are modified, so as to be non-naturally occurring. In some embodiments, about 100%, or all of the bases are modified.

In some embodiments, the modified nucleic acid comprises a modification to at least one phosphate group. In some embodiments, at least one of the phosphate linkages are phosphorothioates.

In some embodiments, the modified nucleic acid comprises a modification to at least one sugar group. In some embodiments, the modified nucleic acid comprises at least one 2-fluororibose. In some embodiments, the modified nucleic acid comprises at least one 2-methoxyribose.

In some embodiments, the modified nucleic acid does not comprise any non-natural nucleotides. For example, the modified nucleic acid comprises a nucleic acid portion that only comprises naturally occurring nucleotides, and the modified nucleic acid is only modified in that the nucleic acid portion is conjugated to a glycan moiety.

In some embodiments, the modified nucleic acid comprises a modified RNA or a modified DNA.

In some embodiments, the pharmaceutical composition comprises a modified nucleic acid that is a modified naked nucleic acid. As used herein, the term "naked" refers to a modified nucleic acid that is not formulated with a nanoparticle, such as but not limited to a lipid nanoparticle.

In some embodiments, the modified nucleic acid comprises about 15, about 20, about 25, about 30, about 50, about 100, about 500, about 1000, about 1500, about 2000, about 2500, about 3000, about 4000, about 5000, about 6000, about 7000, about 8000, about 9000, or about 10000 nucleotides or any values and ranges therebetween. In some embodiments, the modified nucleic acid comprises at least about 15, at least about 20, at least about 25, at least about 30, at least about 50, at least about 100, at least about 500, at least about 1000, at least about 1500, at least about 2000, at least about 2500, at least about 3000, at least about 4000, at least about 5000, at least about 6000, at least about 7000, at least about 8000, at least about 9000, or at least about 10000 nucleotides. In some embodiments, the modified nucleic acid comprises more than 10000 nucleotides. In some embodiments, the modified nucleic acid comprises fewer than about 15, fewer than about 20, fewer than about 25, fewer than about 30, fewer than about 50, fewer than about 100, fewer than about 500, fewer than about 1000, fewer than about 1500, fewer than about 2000, fewer than about 2500, fewer than about 3000, fewer than about 4000, fewer than about 5000, fewer than about 6000, fewer than about 7000, fewer than about 8000, fewer than about 9000, or fewer than about 10000 nucleotides.

In some embodiments, the modified nucleic acid comprises one or more non-naturally occurring nucleotides. In some embodiments, the modified nucleic acid comprises one or more non-naturally occurring nucleotides, or modified nucleotides, that are modified such that they can form a covalent linkage between the modified nucleic acid and the glycan moiety. The one or more modified nucleotides that allow for conjugation to the glycan moiety can occur at any position in the nucleic acid. In certain embodiments, the number of nucleotides modified with a glycan varies. In certain embodiments, the number of nucleotides modified with a glycan is 1. In other embodiments, the number of nucleotides modified with a glycan range anywhere from 1 nucleotide modified with a glycan to all nucleotides modified with a glycan. In other embodiments, the number of nucleotides modified with a glycan range anywhere from 1 nucleotide modified with a glycan to all nucleotides modified with a glycan, and any ranges and individual values therebetween. In certain embodiments, the number of nucleotides modified with a glycan is 2. In certain embodiments, the number of nucleotides modified with a glycan is 3. In certain embodiments, the number of nucleotides modified with a glycan is 5. In certain embodiments, the number of nucleotides modified with a glycan is 10. In some embodiments, the modified nucleic acid comprises at least one chemically modified nitrogenous base. In some embodiments, the modified nucleic acid comprises two, three, four, five or more chemically modified nitrogenous bases.

In some embodiments, the modified nucleic acid comprises a modified RNA. In any embodiment described herein, throughout the entirety of the present disclosure, where such an embodiment refers to a modified nucleic acid, the embodiment is to be understood as also being applicable to a modified RNA. The modified RNA can be all hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, viral satellite RNA, circular RNA, naked RNA, extracellular RNA (exRNA), small cajal body-specific RNA (scaRNA), Xist RNA, or HOTAIR RNA. In some embodiments, the modified nucleic acid comprises a modified RNA comprising a microRNA binding moiety. In some embodiments, the modified RNA comprises a sequence encoding a polypeptide. In some embodiments, the modified RNA is a modified naked RNA. In some embodiments, the modified RNA is a linear RNA. In some embodiments, the modified RNA is a circular RNA. In some embodiments, the modified RNA is an mRNA. In some embodiments, the modified RNA is an miRNA.

In some embodiments, the glycoRNA comprises a sequence encoding a chimeric antigen receptor. The chimeric antigen receptor can comprise an antigen-binding domain, a transmembrane domain, and an intracellular domain. In some embodiments, the antigen-binding protein comprises an antigen-binding domain, a transmembrane domain, and an intracellular signaling domain. In some embodiments, the antigen-binding domain is linked to the transmembrane domain, which is linked to the intracellular signaling domain to produce a chimeric antigen receptor. In some embodiments, the antigen-binding domain binds to a tumor antigen, a tolerogen, or a pathogen antigen, or the antigen is a tumor antigen, or a pathogen antigen. In some embodiments, the antigen-binding domain is an antibody or antibody fragment thereof (e.g., scFv, Fv, Fab, dAb). In some embodiments, the antigen binding domain is a bispecific antibody. In some embodiments, the bispecific antibody has first immunoglobulin variable domain that binds a first epitope and a second immunoglobulin variable domain that binds a second epitope. In some embodiments, the first epitope and the second epitope are the same. In some embodiments, the first epitope and the second epitope are different.

In some embodiments, the transmembrane domain links the binding domain and the intracellular signaling domain. In some embodiments, the transmembrane domain is a hinge protein (e.g., immungloubuline hinge), a polypeptide linker (e.g., GS linker), a KIR2DS2 hinge, a CD8a hinge, or a spacer.

In some embodiments, the intracellular signaling domain comprises at least a portion of a T-cell signaling molecule. In some embodiments, the intracellular signaling domain comprises an immunoreceptor tyrosine-based activation motif. In some embodiments, the intracellular signaling domain comprises at least a portion of CD3zeta, common FcRgamma (FCER1G), Fc gamma R1la, FcRbeta (Fc Epsilon Rib), CD3 gamma, CD3delta, CD3epsilon, CD79a, CD79b, DAP10, DAP12, or any combination thereof. In some embodiments, the intracellular signaling domain further comprises a costimulatory intracellular signaling domain.

In some embodiments, the costimulatory intracellular signaling domain comprises at least one or more of a TNF receptor protein, immunoglobulin-like protein, a cytokine receptor, an integrin, a signaling lymphocytic activation molecule, or an activating NK cell receptor protein. In some embodiments, the costimulatory intracellular signaling domain comprises at least one or more of CD27, CD28, 4-1BB, OX40, GITR, CD30, CD40, PD-1, ICOS, BAFFR, HVEM, ICAM-1, LFA-1, CD2, CDS, CD7, CD287, LIGHT, NKG2C, NKG2D, SLAMF7, NKp80, NKp30, NKp44, NKp46, CD160, CD19, CD4, CD8alpha, CD8beta, IL2R beta, IL2R gamma, IL7R alpha, ITGA4, VLA1, CD49a, IA4, CD49D, ITGA6, VLA6, CD49f, ITGAD, CD103, ITGAL, ITGAM, ITGAX, ITGB1, CD29, ITGB2, CD18, ITGB7, TNFR2, TRAN CE/TRANKL, CD226, SLAMF4, CD84, CD96, CEACAMI, CRTAM, CD229, CD 160, PSGL1, CD100, CD69, SLAMF6, SLAMF1, SLAMF8, CD162, LTBR, LAT, GADS, SLP-76, PAG/Cbp, CD19a, B37-H-3, or a ligand that binds to CD83.

In some embodiments, the modified nucleic acid comprises a modified DNA. In any embodiment described herein, throughout the entirety of the present disclosure, where such an embodiment refers to a modified nucleic acid, the embodiment is to be understood as also being applicable to a modified DNA. In some embodiments, the modified DNA is a modified naked DNA. In some embodiments, the modified DNA is a linear DNA. In some embodiments, the modified DNA is a circular DNA.

In some embodiments, the modified nucleic acid comprises a nucleotide sequence selected from those described in Table 1. The modified nucleic acid described in table 1 can comprise an optional base modification, an optional sugar modification and/or an optional phosphate modification. In table 1, the term "pos." refers to the nucleic acid position.

TABLE 1

Exemplary Nucleic Acids

| Ref# | Sequence | SEQ ID NO | Optional Base Modification | Optional Sugar Modification | Optional Phosphate Modification |
|---|---|---|---|---|---|
| I-1 | UUUCGAAUCAAUCCAACAGUAGC | 3 | None | Pos. 1: 2-OMe Ribose<br>Pos. 2: 2-Fluororibose<br>Pos. 3: 2-OMe Ribose<br>Pos. 4: 2-Fluororibose<br>Pos. 5: 2-OMe Ribose<br>Pos. 6: 2-Fluororibose<br>Pos. 7: 2-OMe Ribose<br>Pos. 8: 2-Fluororibose<br>Pos. 9: 2-OMe Ribose<br>Pos. 10: 2-Fluororibose<br>Pos. 11: 2-OMe Ribose<br>Pos. 12: 2-OMe Ribose<br>Pos. 13: 2-OMe Ribose<br>Pos. 14: 2-Fluororibose<br>Pos. 15: 2-OMe Ribose<br>Pos. 16: 2-Fluororibose<br>Pos. 17: 2-OMe Ribose<br>Pos. 18: 2-Fluororibose<br>Pos. 19: 2-OMe Ribose<br>Pos. 20: 2-Fluororibose<br>Pos. 21: 2-OMe Ribose:<br>Pos. 22: 2-OMe Ribose:<br>Pos. 23: 2-OMe Ribose | Pos. 1: Phosphorothioate linkage<br>Pos. 2: Phosphorothioate linkage<br>Pos. 3: Phosphate (standard)<br>Pos. 4: Phosphate (standard)<br>Pos. 5: Phosphate (standard)<br>Pos. 6: Phosphate (standard)<br>Pos. 7: Phosphate (standard)<br>Pos. 8: Phosphate (standard)<br>Pos. 9: Phosphate (standard)<br>Pos. 10: Phosphate (standard)<br>Pos. 11: Phosphate (standard)<br>Pos. 12: Phosphate (standard)<br>Pos. 13: Phosphate (standard)<br>Pos. 14: Phosphate (standard)<br>Pos. 15: Phosphate (standard)<br>Pos. 16: Phosphate (standard)<br>Pos. 17: Phosphate (standard)<br>Pos. 18: Phosphate (standard)<br>Pos. 19: Phosphate (standard)<br>Pos. 20: Phosphate (standard)<br>Pos. 21: Phosphorothioate linkage<br>Pos. 22: Phosphorothioate linkage<br>Pos. 23: Phosphate (standard) |
| I-2 | UACUGUUGGAUUGAUUCGAAA | 4 | 5': Cy5<br>3' DBCO | Pos. 1: 2-Fluororibose<br>Pos. 2: 2-OMe Ribose<br>Pos. 3: 2-Fluororibose<br>Pos. 4: 2-OMe Ribose<br>Pos. 5: 2-Fluororibose<br>Pos. 6: 2-OMe Ribose<br>Pos. 7: 2-Fluororibose<br>Pos. 8: 2-OMe Ribose<br>Pos. 9: 2-Fluororibose<br>Pos. 10: 2-Fluororibose<br>Pos. 11: 2-Fluororibose<br>Pos. 12: 2-OMe Ribose<br>Pos. 13: 2-Fluororibose<br>Pos. 14: 2-OMe Ribose<br>Pos. 15: 2-Fluororibose<br>Pos. 16: 2-OMe Ribose<br>Pos. 17: 2-Fluororibose<br>Pos. 18: 2-OMe Ribose<br>Pos. 19: 2-Fluororibose<br>Pos. 20: 2-OMe Ribose<br>Pos. 21: 2-Fluororibose | Pos. 1: Phosphorothioate linkage<br>Pos. 2: Phosphorothioate linkage<br>Pos. 3: Phosphate (standard)<br>Pos. 4: Phosphate (standard)<br>Pos. 5: Phosphate (standard)<br>Pos. 6: Phosphate (standard)<br>Pos. 7: Phosphate (standard)<br>Pos. 8: Phosphate (standard)<br>Pos. 9: Phosphate (standard)<br>Pos. 10: Phosphate (standard)<br>Pos. 11: Phosphate (standard)<br>Pos. 12: Phosphate (standard)<br>Pos. 13: Phosphate (standard)<br>Pos. 14: Phosphate (standard)<br>Pos. 15: Phosphate (standard)<br>Pos. 16: Phosphate (standard)<br>Pos. 17: Phosphate (standard)<br>Pos. 18: Phosphate (standard)<br>Pos. 19: Phosphate (standard)<br>Pos. 20: Phosphate (standard)<br>Pos. 21: Phosphate (standard) |
| I-3 | UACUGUUGGAUUGAUUCGAAA | 5 | 5' None<br>3' DBCO | Pos. 1: 2-Fluororibose:<br>Pos. 2: 2-OMe Ribose<br>Pos. 3: 2-Fluororibose<br>Pos. 4: 2-OMe Ribose<br>Pos. 5: 2-Fluororibose<br>Pos. 6: 2-OMe Ribose<br>Pos. 7: 2-Fluororibose<br>Pos. 8: 2-OMe Ribose<br>Pos. 9: 2-Fluororibose<br>Pos. 10: 2-Fluororibose<br>Pos. 11: 2-Fluororibose<br>Pos. 12: 2-OMe Ribose<br>Pos. 13: 2-Fluororibose<br>Pos. 14: 2-OMe Ribose<br>Pos. 15: 2-Fluororibose<br>Pos. 16: 2-OMe Ribose<br>Pos. 17: 2-Fluororibose<br>Pos. 18: 2-OMe Ribose<br>Pos. 19: 2-Fluororibose<br>Pos. 20: 2-OMe Ribose<br>Pos. 21: 2-Fluororibose | Pos. 1: Phosphorothioate linkage<br>Pos. 2: Phosphorothioate linkage<br>Pos. 3: Phosphate (standard)<br>Pos. 4: Phosphate (standard)<br>Pos. 5: Phosphate (standard)<br>Pos. 6: Phosphate (standard)<br>Pos. 7: Phosphate (standard)<br>Pos. 8: Phosphate (standard)<br>Pos. 9: Phosphate (standard)<br>Pos. 10: Phosphate (standard)<br>Pos. 11: Phosphate (standard)<br>Pos. 12: Phosphate (standard)<br>Pos. 13: Phosphate (standard)<br>Pos. 14: Phosphate (standard)<br>Pos. 15: Phosphate (standard)<br>Pos. 16: Phosphate (standard)<br>Pos. 17: Phosphate (standard)<br>Pos. 18: Phosphate (standard)<br>Pos. 19: Phosphate (standard)<br>Pos. 20: Phosphate (standard)<br>Pos. 21: Phosphate (standard) |
| I-4 | UUCGAAUCAAUCCAACAGUAGC | 6 | None | Pos. 1: 2-Fluororibose<br>Pos. 2: 2-OMe Ribose<br>Pos. 3: 2-Fluororibose<br>Pos. 4: 2-OMe Ribose<br>Pos. 5: 2-Fluororibose<br>Pos. 6: 2-OMe Ribose | Pos. 1: Phosphorothioate linkage<br>Pos. 2: Phosphate (standard)<br>Pos. 3: Phosphate (standard)<br>Pos. 4: Phosphate (standard)<br>Pos. 5: Phosphate (standard)<br>Pos. 6: Phosphate (standard) |

TABLE 1-continued

Exemplary Nucleic Acids

| Ref# | Sequence | SEQ ID NO | Optional Base Modification | Optional Sugar Modification | Optional Phosphate Modification |
|---|---|---|---|---|---|
| | | | | Pos. 7: 2-Fluororibose | Pos. 7: Phosphate (standard) |
| | | | | Pos. 8: 2-OMe Ribose | Pos. 8: Phosphate (standard) |
| | | | | Pos. 9: 2-Fluororibose | Pos. 9: Phosphate (standard) |
| | | | | Pos. 10: 2-OMe Ribose | Pos. 10: Phosphate (standard) |
| | | | | Pos. 11: 2-OMe Ribose | Pos. 11: Phosphate (standard) |
| | | | | Pos. 12: 2-OMe Ribose | Pos. 12: Phosphate (standard) |
| | | | | Pos. 13: 2-Fluororibose | Pos. 13: Phosphate (standard) |
| | | | | Pos. 14: 2-OMe Ribose | Pos. 14: Phosphate (standard) |
| | | | | Pos. 15: 2-Fluororibose | Pos. 15: Phosphate (standard) |
| | | | | Pos. 16: 2-OMe Ribose | Pos. 16: Phosphate (standard) |
| | | | | Pos. 17: 2-Fluororibose | Pos. 17: Phosphate (standard) |
| | | | | Pos. 18: 2-OMe Ribose | Pos. 18: Phosphate (standard) |
| | | | | Pos. 19: 2-Fluororibose | Pos. 19: Phosphate (standard) |
| | | | | Pos. 20: 2-OMe Ribose: | Pos. 20: Phosphorothioate linkage |
| | | | | Pos. 21: 2-OMe Ribose: | Pos. 21: Phosphorothioate linkage |
| | | | | Pos. 22: 2-OMe Ribose | |
| I-5 | UACUGUU GGAUUGA UUCGAAA | 7 | 5': (Cy5Lumi-Mal)(SHC6) 3': (NHC6)(DBCO-C6NHS) | Pos. 1: 2-Fluororibose Pos. 2: 2-OMe Ribose Pos. 3: 2-Fluororibose Pos. 4: 2-OMe Ribose Pos. 5: 2-Fluororibose Pos. 6: 2-OMe Ribose Pos. 7: 2-Fluororibose Pos. 8: 2-OMe Ribose Pos. 9: 2-Fluororibose Pos. 10: 2-Fluororibose Pos. 11: 2-Fluororibose Pos. 12: 2-OMe Ribose Pos. 13: 2-Fluororibose Pos. 14: 2-OMe Ribose Pos. 15: 2-Fluororibose Pos. 16: 2-OMe Ribose Pos. 17: 2-Fluororibose Pos. 18: 2-OMe Ribose Pos. 19: 2-Fluororibose Pos. 20: 2-OMe Ribose Pos. 21: 2-Fluororibose | Pos. 1: Phosphorothioate linkage Pos. 2: Phosphorothioate linkage Pos. 3: Phosphate (standard) Pos. 4: Phosphate (standard) Pos. 5: Phosphate (standard) Pos. 6: Phosphate (standard) Pos. 7: Phosphate (standard) Pos. 8: Phosphate (standard) Pos. 9: Phosphate (standard) Pos. 10: Phosphate (standard) Pos. 11: Phosphate (standard) Pos. 12: Phosphate (standard) Pos. 13: Phosphate (standard) Pos. 14: Phosphate (standard) Pos. 15: Phosphate (standard) Pos. 16: Phosphate (standard) Pos. 17: Phosphate (standard) Pos. 18: Phosphate (standard) Pos. 19: Phosphate (standard) Pos. 20: Phosphate (standard) Pos. 21: Phosphate (standard) |
| I-6 | UACUGUU GGAUUGA UUCGAAA | 8 | 5' None 3' 3': (NHC6)(DBCO-C6NHS) | Pos. 1: 2-Fluororibose Pos. 2: 2-OMe Ribose Pos. 3: 2-Fluororibose Pos. 4: 2-OMe Ribose Pos. 5: 2-Fluororibose Pos. 6: 2-OMe Ribose Pos. 7: 2-Fluororibose Pos. 8: 2-OMe Ribose Pos. 9: 2-Fluororibose Pos. 10: 2-Fluororibose Pos. 11: 2-Fluororibose Pos. 12: 2-OMe Ribose Pos. 13: 2-Fluororibose Pos. 14: 2-OMe Ribose Pos. 15: 2-Fluororibose Pos. 16: 2-OMe Ribose Pos. 17: 2-Fluororibose Pos. 18: 2-OMe Ribose Pos. 19: 2-Fluororibose Pos. 20: 2-OMe Ribose Pos. 21: 2-Fluororibose | Pos. 1: Phosphorothioate linkage Pos. 2: Phosphorothioate linkage Pos. 3: Phosphate (standard) Pos. 4: Phosphate (standard) Pos. 5: Phosphate (standard) Pos. 6: Phosphate (standard) Pos. 7: Phosphate (standard) Pos. 8: Phosphate (standard) Pos. 9: Phosphate (standard) Pos. 10: Phosphate (standard) Pos. 11: Phosphate (standard) Pos. 12: Phosphate (standard) Pos. 13: Phosphate (standard) Pos. 14: Phosphate (standard) Pos. 15: Phosphate (standard) Pos. 16: Phosphate (standard) Pos. 17: Phosphate (standard) Pos. 18: Phosphate (standard) Pos. 19: Phosphate (standard) Pos. 20: Phosphate (standard) Pos. 21: Phosphate (standard) |
| I-7 | UACUGUU GGAUUGA UUCGAAA | 9 | 5': (Cy5Lumi-Mal)(SHC6) 3': None | Pos. 1: 2-Fluororibose Pos. 2: 2-OMe Ribose Pos. 3: 2-Fluororibose Pos. 4: 2-OMe Ribose Pos. 5: 2-Fluororibose Pos. 6: 2-OMe Ribose Pos. 7: 2-Fluororibose Pos. 8: 2-OMe Ribose Pos. 9: 2-Fluororibose Pos. 10: 2-Fluororibose Pos. 11: 2-Fluororibose Pos. 12: 2-OMe Ribose Pos. 13: 2-Fluororibose | Pos. 1: Phosphorothioate linkage Pos. 2: Phosphorothioate linkage Pos. 3: Phosphate (standard) Pos. 4: Phosphate (standard) Pos. 5: Phosphate (standard) Pos. 6: Phosphate (standard) Pos. 7: Phosphate (standard) Pos. 8: Phosphate (standard) Pos. 9: Phosphate (standard) Pos. 10: Phosphate (standard) Pos. 11: Phosphate (standard) Pos. 12: Phosphate (standard) Pos. 13: Phosphate (standard) |

TABLE 1-continued

Exemplary Nucleic Acids

| Ref# | Sequence | SEQ ID NO | Optional Base Modification | Optional Sugar Modification | Optional Phosphate Modification |
|---|---|---|---|---|---|
| | | | | Pos. 14: 2-OMe Ribose | Pos. 14: Phosphate (standard) |
| | | | | Pos. 15: 2-Fluororibose | Pos. 15: Phosphate (standard) |
| | | | | Pos. 16: 2-OMe Ribose | Pos. 16: Phosphate (standard) |
| | | | | Pos. 17: 2-Fluororibose | Pos. 17: Phosphate (standard) |
| | | | | Pos. 18: 2-OMe Ribose | Pos. 18: Phosphate (standard) |
| | | | | Pos. 19: 2-Fluororibose | Pos. 19: Phosphate (standard) |
| | | | | Pos. 20: 2-OMe Ribose | Pos. 20: Phosphate (standard) |
| | | | | Pos. 21: 2-Fluororibose | Pos. 21: Phosphate (standard) |
| Formula (I) | 5'-GGC TGG TCC GAG TGC AGT GGT GTT TAC AAC TAA TTG ATC ACA ACC AGT TAC AGA TTT CT/ i5OctdU/ TGT TCC TTC TCC ACT CCC ACT GCT TCA CTT GAC TAG CCT T-3' | 1 | | | |
| Formula (I) | AGUUGGT CCGAGUG UUGUGGG UUAUUGU UAAGUU/ i5OctdU/ AUUUAACA UUGUCU CCCCCCA CAACCGC GCUUGAC UAGCUUG CUG | 2 | | | |

In some embodiments, the modified nucleic acid comprises a nucleotide having a sequence with at least about 70% sequence identity, at least about 75% sequence identity, at least about 80% sequence identity, at least about 85% sequence identity, at least about 90% sequence identity, at least about 91% sequence identity, at least 92% sequence identity, at least about 93% sequence identity, at least about 94% sequence identity, at least 95% sequence identity, about 96% sequence identity, about 97% sequence identity, at least 98% sequence identity, at least about 9900 sequence identity or greater to a sequence selected from those in Table 1.

Glycan Features

As described elsewhere herein, the present disclosure provides a pharmaceutical composition comprising a modified nucleic acid comprising a glycan moiety. In some embodiments, the glycan moiety comprises at least one monosaccharide. In some embodiments, the glycan moiety comprises at least two monosaccharides. In some embodiments, the glycan moiety comprises at least three monosaccharides. In some embodiments, the glycan moiety comprises at least four monosaccharides. In some embodiments, the glycan moiety comprises at least five monosaccharides. In some embodiments, the glycan moiety comprises at least six monosaccharides. In some embodiments, the glycan moiety comprises at least seven monosaccharides. In some embodiments, the glycan moiety comprises at least eight monosaccharides. In some embodiments, the glycan moiety comprises at least nine monosaccharides. In some embodiments, the glycan moiety comprises at least ten monosaccharides. The glycan moiety can comprise at least about 11, 12, 13, 14, 15, 16, 17, 18, 19, 20, 21, 22, 23, 24, 25, 26, 27, 28, 29, 30 or more monosaccharides. In certain embodiments, the number of sugars per glycan on a modified nucleic acid varies. In certain embodiments, the number of sugars per glycan on a modified nucleic acid is 1, 2, 3, 4, 5, 6, 7, 8, 9, 10, or more than 10. In certain embodiments, at least one or all of the glycans on the modified nucleic acid contains at least about 10 sugar residues. In certain embodiments, at least one or all of the glycans on the modified nucleic acid contains at least about 9 sugar residues. In certain preferred embodiments, at least one or all of the glycans on the modified nucleic acid contains at least about 6 sugar residues.

In some embodiments, the glycan moiety comprises GlcNAc, mannose, galactose, sialic acid, and fucose, or a combination thereof. In some embodiments, the glycan moiety comprises sialic acid, fucose, or a combination thereof. In some embodiments, the glycan moiety comprises sialic acid. In some embodiments, the glycan moiety comprises fucose. In some embodiments, the glycan moiety comprises mannose. In some embodiments, the glycan moiety comprises GlcNAc (N-Acetylglucosamine). In some embodiments, the glycan moiety comprises galactose. In some embodiments, the glycan moiety comprises a fucose linked to a GlcNAc residue.

In some embodiments, the glycan moiety comprises a bi-antennary glycan, wherein the bi-antennary glycan comprises a first terminal residue and a second terminal residue. In some embodiments, at least one of the first terminal residue or second terminal residue of the bi-antennary glycan comprises sialic acid. In some embodiments, at least one of the first terminal residue or second terminal residue of the bi-antennary glycan comprises a sialic acid residue comprising one or more poly-sialic acid terminal modifications. In some embodiments, at least one of the first terminal residue or second terminal residue of the bi-antennary glycan comprises fucose. In some embodiments, one of the first terminal residue or second terminal residue of the bi-antennary glycan comprises fucose and the other comprises sialic acid.

In some embodiments, the glycan moiety comprises a tri-antennary glycan, wherein the tri-antennary glycan comprises a first terminal residue, a second terminal residue, and a third terminal residue. In some embodiments, at least one of the first terminal residue, the second terminal residue or the third terminal residue of the tri-antennary glycan comprises sialic acid. In some embodiments, at least one of the first terminal residue, the second terminal residue or the third terminal residue of the tri-antennary glycan comprises a sialic acid residue comprising one or more poly-sialic acid terminal modifications. In some embodiments, at least one of the first terminal residue, or the second terminal residue of the tri-antennary glycan comprises fucose. In some embodiments, at least one of the first terminal residue, the second terminal residue or the third terminal residue of the tri-antennary glycan comprises sialic acid, and at least one of the remaining terminal residues comprises fucose.

In some embodiments wherein the glycan moiety comprises a bi-antennary glycan or a tri-antennary glycan, the glycan comprises a fucose linked to a GlcNAc residue in a core or a base region of the glycan. In some embodiments wherein the glycan moiety comprises a bi-antennary glycan or a tri-antennary glycan, the glycan comprises a fucose linked to a GlcNAc residue in a tree, branch or arm region of the glycan.

In some embodiments, the glycan moiety comprises a bisecting glycan. In some embodiments, the glycan moiety comprises a bi-antennary glycan comprising a GlcNAc moiety bound to the monosaccharide that links the two branches of the bi-antennary glycan, thereby forming a bisecting glycan.

In some embodiments, the glycan moiety is an N-linked glycan, such that the glycan is conjugated to the modified nucleic acid through a nitrogen atom.

In some embodiments, the glycan moiety comprises a glycan comprising a N-acetylglucosamine (GlcNAc) at the non-reducing terminus, further comprising a conjugation handle covalently bonded to the non-reducing end terminal GlcNAc. As used herein, the terms "non-reducing end terminal GlcNAc" and "GlcNAc at the non-reducing terminus" refer to a GlcNAc monosaccharide residue that is a part of a glycan moiety and forms a terminus of said glycan. As an illustrative example, in Exemplary Glycan G-1, the "GlcNAc(b1-" at the end of the IUPAC name is the non-reducing end terminal GlcNAc:
GlcNAc(b1-2)Man(a1-3)[GlcNAc(b1-2)Man(a1-6)]Man(b1-4)GlcNAc(b1-4)[Fuc(a1-6)]GlcNAc(b1-

In some embodiments, the glycan moiety comprises a glycan comprising a GlcNAc at the non-reducing terminus, further comprising an asparagine residue covalently bound to the non-reducing end terminal GlcNAc of the glycan. In some embodiments, the asparagine residue is covalently bound to the non-reducing end terminal GlcNAc of the glycan, as shown:

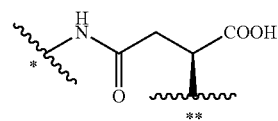

wherein, * indicates the point of attachment to the non-reducing end terminal GlcNAc of the glycan and ** indicates the point of attachment to the modified RNA, or a linker group attached to the modified RNA.

In some embodiments, the asparagine residue is covalently bound to the non-reducing end terminal GlcNAc as shown:

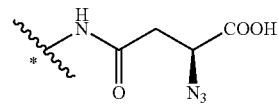

wherein, * indicates the point of attachment to the non-reducing end terminal GlcNAc of the glycan.

In some embodiments, the glycan moiety comprises a glycan comprising a GlcNAc at the non-reducing terminus, further comprising an arginine residue covalently bound to the non-reducing end terminal GlcNAc. In some embodiments, the glycan moiety comprises a glycan comprising a GlcNAc at the non-reducing terminus, further comprising an azide click chemistry handle covalently bound to the non-reducing end terminal GlcNAc, either directly or through a linker group. In some embodiments, the linker group bridging the non-reducing end terminal GlcNAc and the azide comprises one or more polyethylene glycol units. In some embodiments, the linker group bridging the non-reducing end terminal GlcNAc and the azide comprises 1-10 PEG units. In some embodiments, the linker group bridging the non-reducing end terminal GlcNAc and the azide comprises one PEG unit. In some embodiments, the linker group bridging the non-reducing end terminal GlcNAc and the azide comprises two PEG units. In some embodiments, the linker group bridging the non-reducing end terminal GlcNAc and the azide comprises three PEG units. In some embodiments, the linker group bridging the non-reducing end terminal GlcNAc and the azide comprises four PEG units. In some embodiments, the linker group bridging the non-reducing end terminal GlcNAc and the azide comprises five PEG units.

In some embodiments, the linker group bridging the non-reducing end terminal GlcNAc and the azide comprises one or more peptide residues.

In some embodiments, the glycan moiety comprises a glycan comprising a GlcNAc at the non-reducing terminus, further comprising a conjugation handle covalently bonded to the non-reducing end terminal GlcNAc, wherein the conjugation handle comprises aminooxy-PEG3-azide:

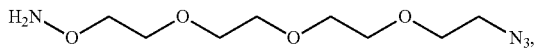

or as it relates to the glyconucleic acid conjugate as a whole, the product of a click-chemistry reaction between aminooxy-PEG3-azide and an alkyne moiety attached to the nucleic acid portion of the glyconucleic acid conjugate.

In some embodiments, the glycan moiety comprises a glycan comprising a GlcNAc at the non-reducing terminus, further comprising aminooxy-PEG3-azide covalently bound to the non-reducing end terminal GlcNAc as shown:

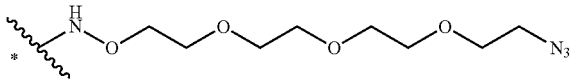

wherein, * indicates the point of attachment to the non-reducing end terminal GlcNAc of the glycan.

In some embodiments, the glycan moiety comprises a glycan comprising a GlcNAc at the non-reducing terminus, further comprising a linker covalently bound to the non-reducing end terminal GlcNAc as shown:

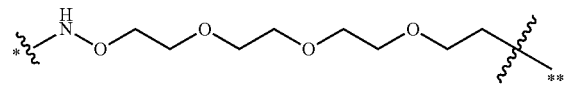

wherein, * indicates the point of attachment to the non-reducing end terminal GlcNAc of the glycan and ** indicates the point of attachment to the modified RNA, or a linker group attached to the modified RNA.

Figure 7A:
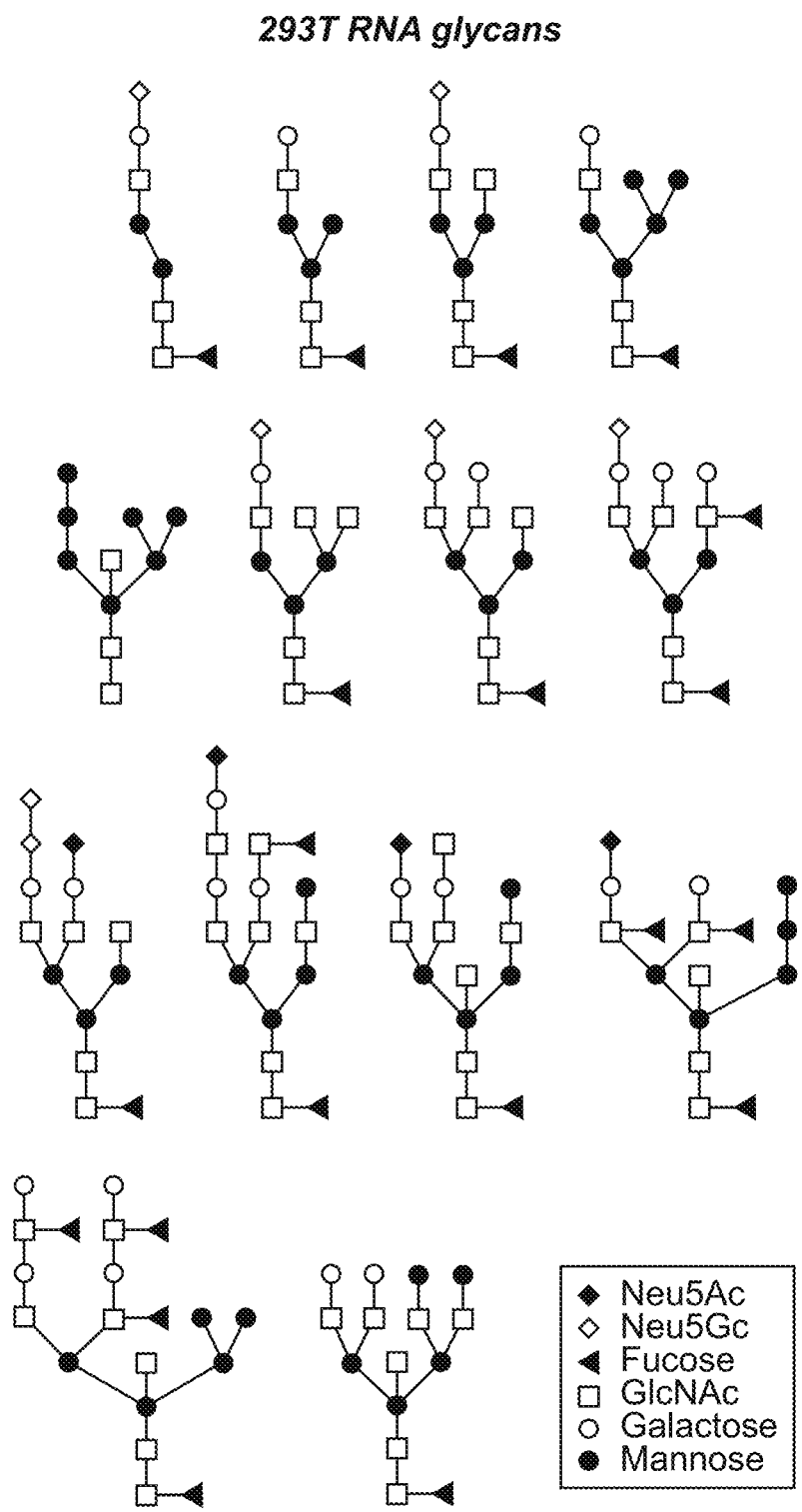
FIGS. 7A-7C are structures of exemplary glycan moieties. In certain embodiments, the glyconucleic acid of the present disclosure comprises a glycan moiety depicted in FIGS. 7A-7C.
Figure 7B:
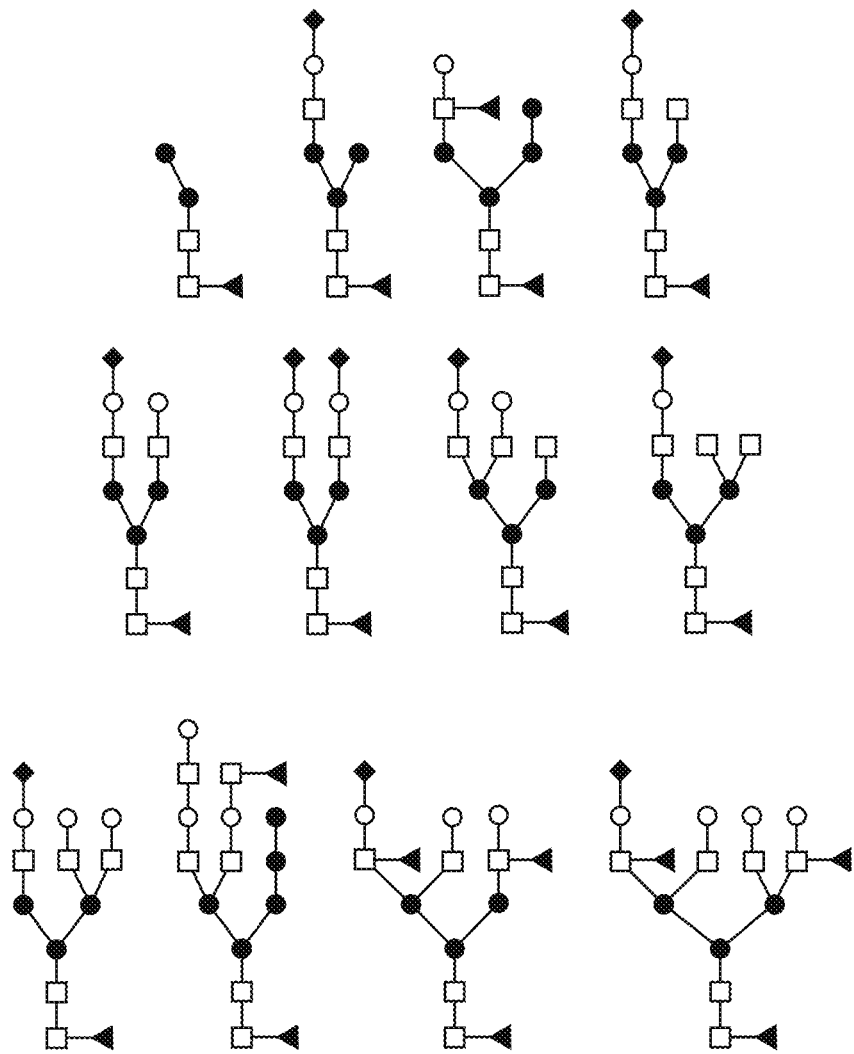
Figure 7C:
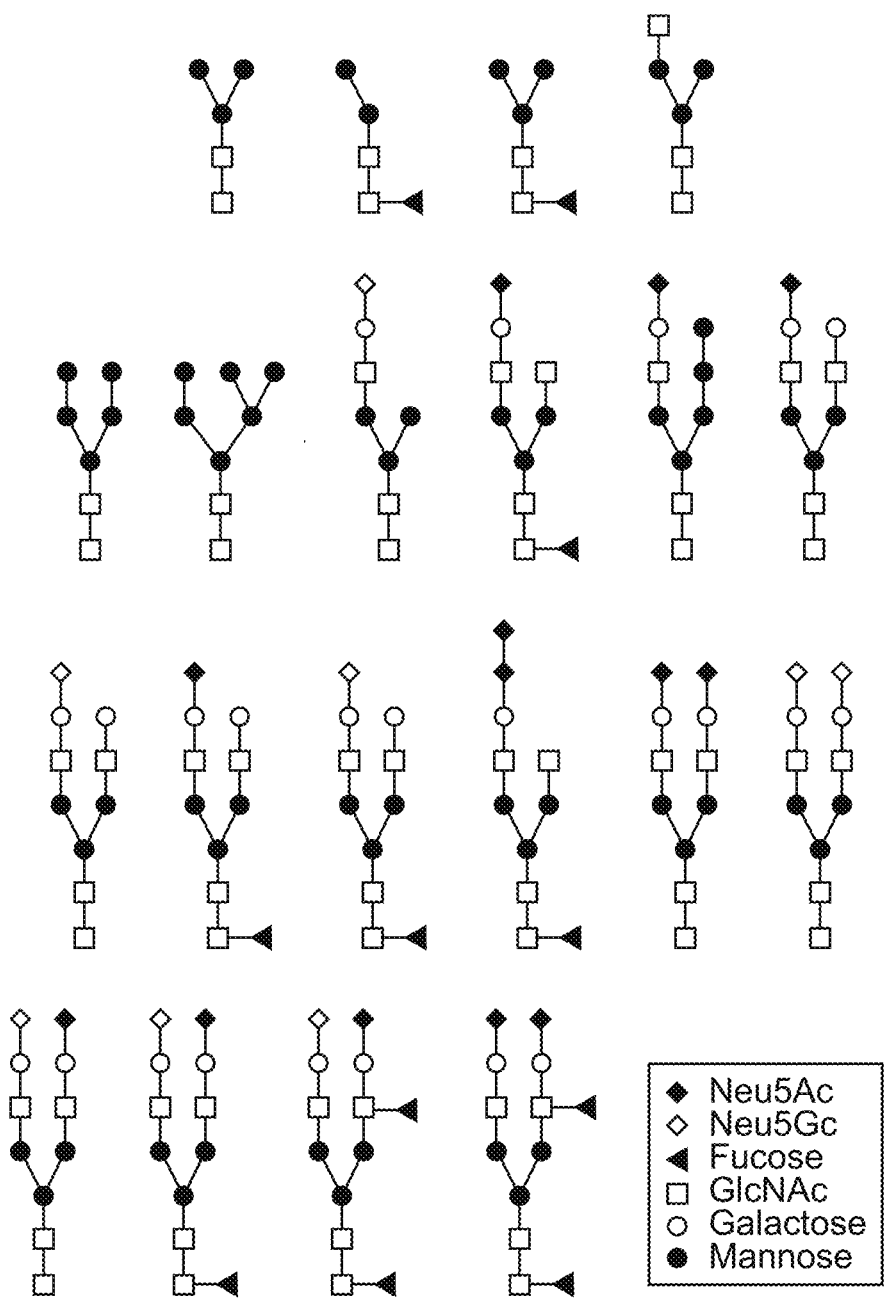
Figure 7C:
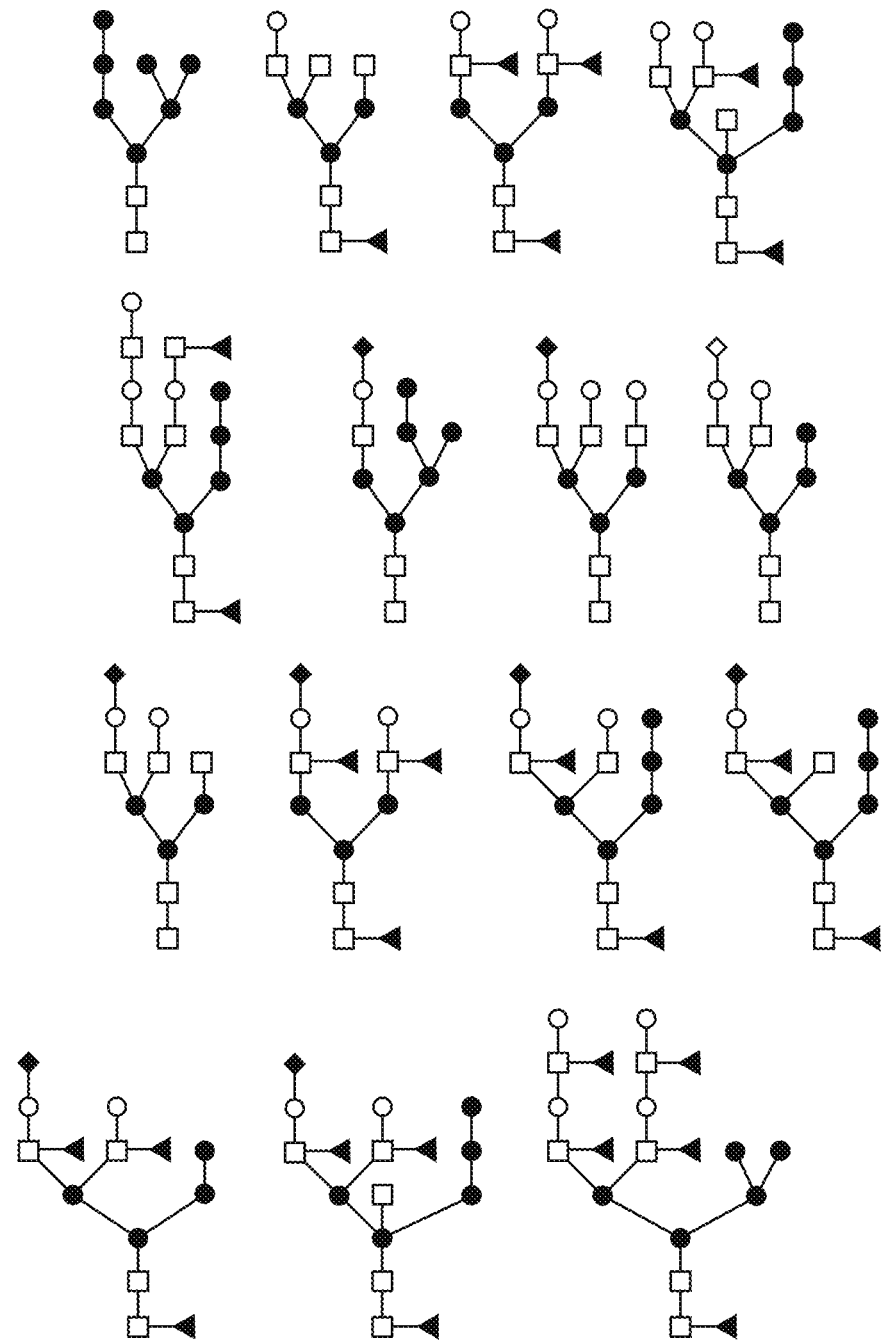
Figure 7C:
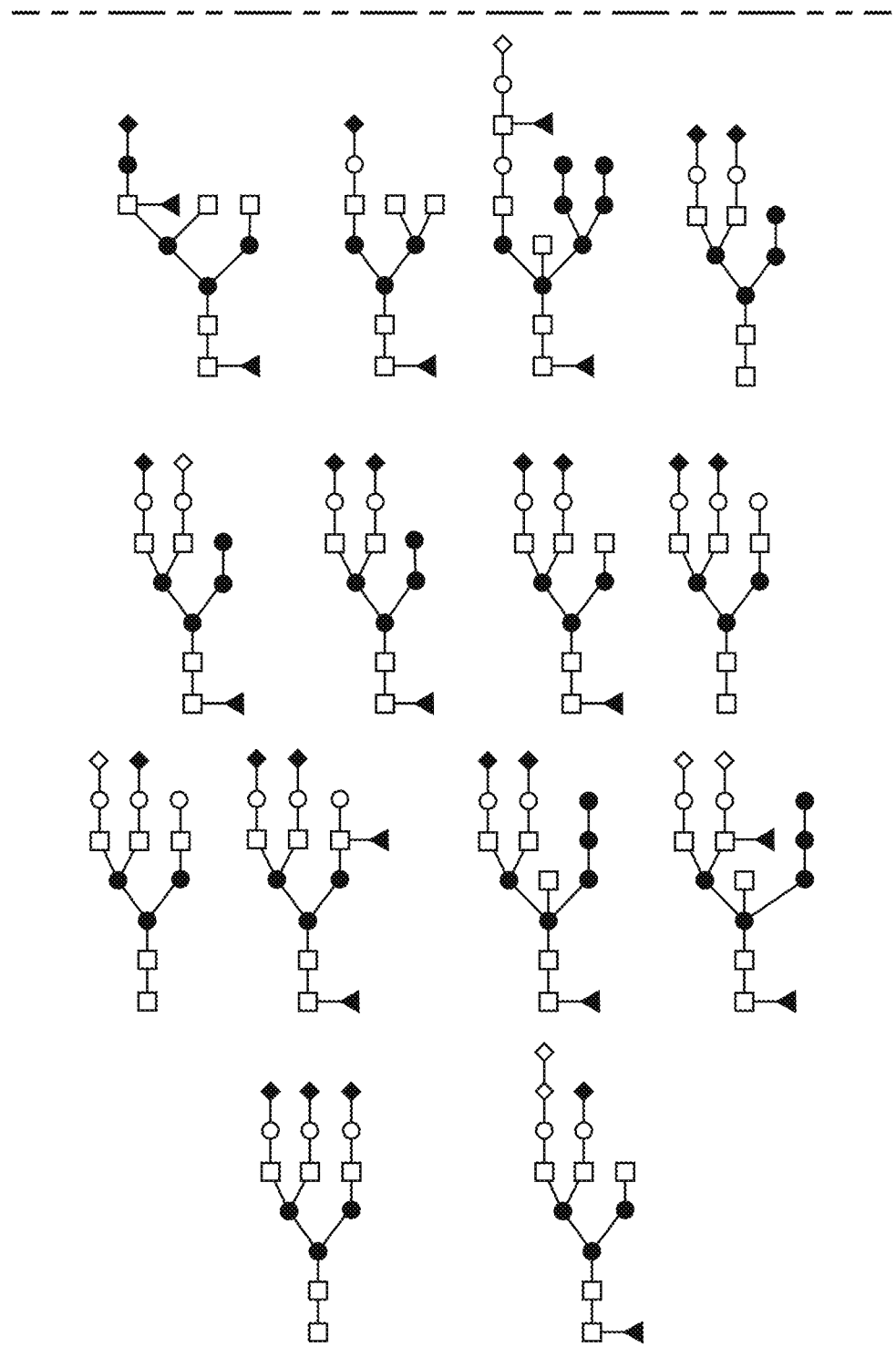
Figure 8A:
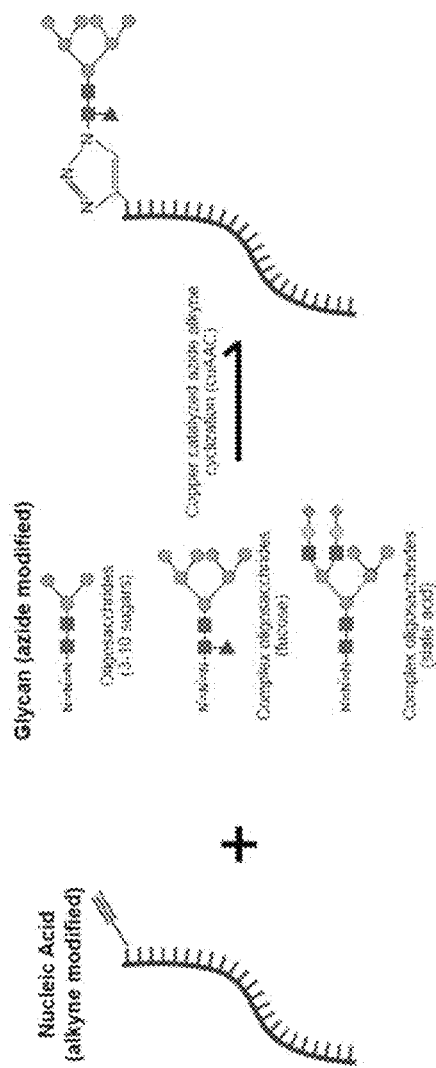
FIGS. 8A-8B show schematics of copper-catalyzed alkyne-azide cycloaddition (CuAAC) reactions between alkyne modified nucleic acids and azide-glycans.
Figure 8B:
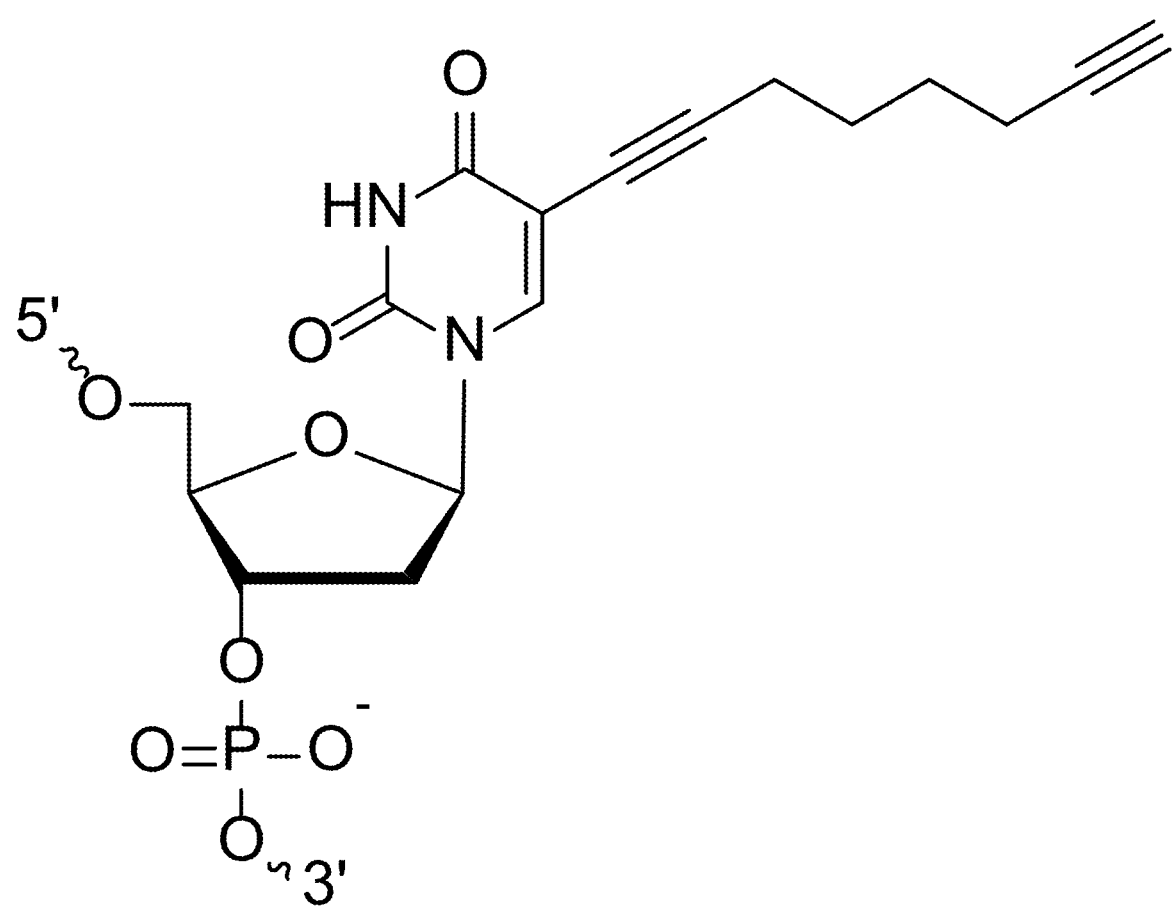

In some embodiments, the glycan moiety comprises a glycan selected from those depicted in FIGS. 7A-7C. In some embodiments, the glycan moiety comprises a glycan selected from those depicted in FIG. 7A. In some embodiments, the glycan moiety comprises a glycan selected from those depicted in FIG. 7B. In some embodiments, the glycan moiety comprises a glycan selected from those depicted in FIG. 7C.

In some embodiments, the glycan moiety comprises a glycan selected from those described in Table 2A:

TABLE 2A

Exemplary Glycans

| Ref # | IUPAC name |
|---|---|
| G-1 | GlcNAc(b1-2)Man(a1-3)[GlcNAc(b1-2)Man(a1-6)]Man(b1-4)GlcNAc(b1-4)[Fuc(a1-6)]GlcNAc(b1- |
| G-2 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)[Fuc(a1-6)]GlcNAc(b1- |
| G-3 | Man(a1-3)[Man(a1-6)]Man(b1-4)GlcNAc(b1-4)GlcNAc(b1- |
| G-4 | Gal(b1-4)GlcNAc(b1-2)Man(a1-3)[Gal(b1-4)GlcNAc(b1-2)Man(a1-6)][GlcNAc(b1-4)]Man(b1-4)GlcNAc(b1-4)GlcNAc(b1- |
| G-5 | NeuNAc(a2-3)Gal(b1-4)GlcNAc(b1-2)Man(a1-3)[NeuNAc(a2-3)Gal(b1-4)GlcNAc(b1-2)Man(a1-6)]Man(b1-4)GlcNAc(b1-4)GlcNAc(b1- |
| G-6 | Man(b1-4)GlcNAc(b1-4)GlcNAc(b1- |
| G-7 | Man(a1-6)[Man(a1-3)]Man(a1-6)[Man(a1-3)]Man(b1-4)GlcNAc(b1-4)GlcNAc(b1- |
| G-8 | GlcNAc(b1-2)Man(a1-3)[GlcNAc(b1-2)Man(a1-6)]Man(b1-4)GlcNAc(b1-4)GlcNAc(b1- |
| G-9 | Gal(b1-4)GlcNAc(b1-2)Man(a1-3)[Gal(b1-4)GlcNAc(b1-2)Man(a1-6)]Man(b1-4)GlcNAc(b1-4)GlcNAc(b1- |
| G-10 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)GlcNAc(b1- |
| G-11 | Gal(b1-4)GlcNAc(b1-2)Man(a1-3)[Gal(b1-4)GlcNAc(b1-2)Man(a1-6)]Man(b1-4)GlcNAc(b1-4)[Fuc(a1-6)]GlcNAc(b1- |
| G-34 | Neu5Ac(a2-3)Gal(b1-4)GlcNAc(b1-2)Man(a1-3)[Neu5Ac(a2-3)Gal(b1-4)GlcNAc(b1-2)Man(a1-6)]Man(b1-4)GlcNAc(b1-4)GlcNAc(b1- |

In some embodiments, the glycan moiety is or comprises a glycan that differs from a glycan recited in Table 2A by the replacement of a single monosaccharide. In some embodiments, the glycan moiety is or comprises a glycan that differs from a glycan recited in Table 2A by the replacement of two monosaccharides. As a non-limiting example, the glycan moiety can comprise a glycan recited in Table 2A, wherein a mannose is replaced by a galactose (or vice versa), but otherwise the rest of the glycan moiety remains the same.

In some embodiments, the glycan moiety comprises a glycan described in Table 2A, further comprising a conjugation handle covalently bonded to the non-reducing end terminal GlcNAc.

In some embodiments, the glycan moiety comprises a glycan described in Table 2A, further comprising an asparagine residue covalently bound to the non-reducing end terminal GlcNAc. In some embodiments, the glycan moiety comprises a glycan illustrated in any one of glycan described in Table 2A, further comprising an asparagine residue covalently bound to the non-reducing end terminal GlcNAc as shown:

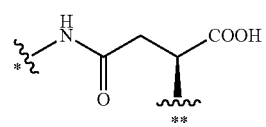

wherein, * indicates the point of attachment to the non-reducing end terminal GlcNAc of the glycan and ** indicates the point of attachment to the modified RNA, or a linker group attached to the modified RNA.

In some embodiments, the glycan moiety comprises a glycan described in Table 2A, further comprising an asparagine residue covalently bound to the non-reducing end terminal GlcNAc as shown:

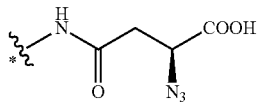

wherein, * indicates the point of attachment to the non-reducing end terminal GlcNAc of the glycan.

In some embodiments, the glycan moiety comprises a glycan described in Table 2A, further comprising an arginine residue covalently bound to the non-reducing end terminal GlcNAc. In some embodiments, the glycan moiety comprises a glycan described in Table 2A, further comprising an azide click chemistry handle covalently bound to the non-reducing end terminal GlcNAc, either directly or through a linker group. In some embodiments, the linker group bridging the non-reducing end terminal GlcNAc and the azide comprises one or more peptide residues. In some embodiments, the linker group bridging the non-reducing end terminal GlcNAc and the azide comprises one or more polyethylene glycol (PEG) units. In some embodiments, the linker group bridging the non-reducing end terminal GlcNAc and the azide comprises 1-10 PEG units. In some embodiments, the linker group bridging the non-reducing end terminal GlcNAc and the azide comprises one PEG unit. In some embodiments, the linker group bridging the non-reducing end terminal GlcNAc and the azide comprises two PEG units. In some embodiments, the linker group bridging the non-reducing end terminal GlcNAc and the azide comprises three PEG units. In some embodiments, the linker group bridging the non-reducing end terminal GlcNAc and the azide comprises four PEG units. In some embodiments, the linker group bridging the non-reducing end terminal GlcNAc and the azide comprises five PEG units.

In some embodiments, the glycan moiety comprises a glycan described in Table 2A, further comprising a conjugation handle covalently bonded to the non-reducing end terminal GlcNAc, wherein the conjugation handle comprises aminooxy-PEG3-azide:

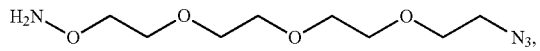

or as it relates to the glyconucleic acid conjugate as a whole, the product of a click-chemistry reaction between aminooxy-PEG3-azide and an alkyne moiety attached to the nucleic acid portion of the glyconucleic acid conjugate.

In some embodiments, the glycan moiety comprises a glycan described in Table 2A, further comprising aminooxy-PEG3-azide covalently bound to the non-reducing end terminal GlcNAc as shown:

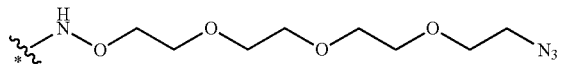

wherein, * indicates the point of attachment to the non-reducing end terminal GlcNAc of the glycan.

In some embodiments, the glycan moiety comprises a glycan described in Table 2A, further comprising a linker covalently bound to the non-reducing end terminal GlcNAc as shown:

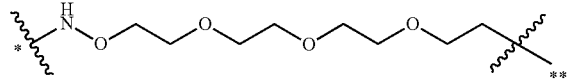

wherein, * indicates the point of attachment to the non-reducing end terminal GlcNAc of the glycan and ** indicates the point of attachment to the modified RNA, or a linker group attached to the modified RNA.

In some embodiments, the glycan moiety comprises an azide functionalized glycan selected from those described in Table 2B:

TABLE 2B

Exemplary Modified Glycans

| Ref # | IUPAC name |
|---|---|
| G-12 | Man(a1-3)[Man(a1-6)]Man(b1-4)GlcNAc(b1-4)GlcNAc(b1-Aminooxy-PEG3-Azide |
| G-13 | Gal(b1-4)GlcNAc(b1-2)Man(a1-3)[Gal(b1-4)GlcNAc(b1-2)Man(a1-6)][GlcNAc(b1-4)]Man(b1-4)GlcNAc(b1-4)GlcNAc(b1-Aminooxy-PEG3-Azide |
| G-14 | NeuNAc(a2-3)Gal(b1-4)GlcNAc(b1-2)Man(a1-3)[NeuNAc(a2-3)Gal(b1-4)GlcNAc(b1-2)Man(a1-6)]Man(b1-4)GlcNAc(b1-4)GlcNAc(b1-Aminooxy-PEG3-Azide |
| G-15 | Man(b1-4)GlcNAc(b1-4)GlcNAc(b1-Aminooxy-PEG3-Azide |
| G-16 | Man(a1-6)[Man(a1-3)]Man(a1-6)[Man(a1-3)]Man(b1-4)GlcNAc(b1-4)GlcNAc(b1-Aminooxy-PEG3-Azide |
| G-17 | GlcNAc(b1-2)Man(a1-3)[GlcNAc(b1-2)Man(a1-6)]Man(b1-4)GlcNAc(b1-4)GlcNAc(b1-Aminooxy-PEG3-Azide |
| G-18 | Gal(b1-4)GlcNAc(b1-2)Man(a1-3)[Gal(b1-4)GlcNAc(b1-2)Man(a1-6)]Man(b1-4)GlcNAc(b1-4)GlcNAc(b1-Aminooxy-PEG3-Azide |
| G-19 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)GlcNAc(b1-Aminooxy-PEG3-Azide |
| G-20 | Gal(b1-4)GlcNAc(b1-2)Man(a1-3)[Gal(b1-4)GlcNAc(b1-2)Man(a1-6)]Man(b1-4)GlcNAc(b1-4)[Fuc(a1-6)]GlcNAc(b1-Aminooxy-PEG3-Azide |
| G-21 | GlcNAc(b1-2)Man(a1-3)[GlcNAc(b1-2)Man(a1-6)]Man(b1-4)GlcNAc(b1-4)[Fuc(a1-6)]GlcNAc(b1-Aminooxy-PEG3-Azide |
| G-22 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)[Fuc(a1-6)]GlcNAc(b1-Aminooxy-PEG3-Azide |

TABLE 2B-continued

Exemplary Modified Glycans

| Ref # | IUPAC name |
|---|---|
| G-23 | Man(a1-3)[Man(a1-6)]Man(b1-4)GlcNAc(b1-4)GlcNAc(b1-Asn-Azide |
| G-24 | Gal(b1-4)GlcNAc(b1-2)Man(a1-3)[Gal(b1-4)GlcNAc(b1-2)Man(a1-6)][GlcNAc(b1-4)]Man(b1-4)GlcNAc(b1-4)GlcNAc(b1-Asn-Azide |
| G-25 | NeuNAc(a2-3)Gal(b1-4)GlcNAc(b1-2)Man(a1-3)[NeuNAc(a2-3)Gal(b1-4)GlcNAc(b1-2)Man(a1-6)]Man(b1-4)GlcNAc(b1-4)GlcNAc(b1-Asn-Azide |
| G-26 | Man(b1-4)GlcNAc(b1-4)GlcNAc(b1-Asn-Azide |
| G-27 | Man(a1-6)[Man(a1-3)]Man(a1-6)[Man(a1-3)]Man(b1-4)GlcNAc(b1-4)GlcNAc(b1-Asn-Azide |
| G-28 | GlcNAc(b1-2)Man(a1-3)[GlcNAc(b1-2)Man(a1-6)]Man(b1-4)GlcNAc(b1-4)GlcNAc(b1-Asn-Azide |
| G-29 | Gal(b1-4)GlcNAc(b1-2)Man(a1-3)[Gal(b1-4)GlcNAc(b1-2)Man(a1-6)]Man(b1-4)GlcNAc(b1-4)GlcNAc(b1-Asn-Azide |
| G-30 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)GlcNAc(b1-Asn-Azide |
| G-31 | GlcNAc(b1-2)Man(a1-3)[GlcNAc(b1-2)Man(a1-6)]Man(b1-4)GlcNAc(b1-4)[Fuc(a1-6)]GlcNAc(b1-Asn-Azide |
| G-32 | Gal(b1-4)GlcNAc(b1-2)Man(a1-3)[Gal(b1-4)GlcNAc(b1-2)Man(a1-6)]Man(b1-4)GlcNAc(b1-4)[Fuc(a1-6)]GlcNAc(b1-Asn-Azide |
| G-33 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)[Fuc(a1-6)]GlcNAc(b1-Asn-Azide |
| G-35 | Neu5Ac(a2-3)Gal(b1-4)GlcNAc(b1-2)Man(a1-3)[Neu5Ac(a2-3)Gal(b1-4)GlcNAc(b1-2)Man(a1-6)]Man(b1-4)GlcNAc(b1-4)GlcNAc(b1-Asn-Azide |
| G-36 | Neu5Ac(a2-3)Gal(b1-4)GlcNAc(b1-2)Man(a1-3)[Neu5Ac(a2-3)Gal(b1-4)GlcNAc(b1-2)Man(a1-6)]Man(b1-4)GlcNAc(b1-4)GlcNAc(b1-Aminooxy-PEG3-Azide |

Glycan—Nucleic Acid Conjugation Features

As described above, in one aspect, the present disclosure provides a glyconucleic acid comprising: i) a modified nucleic acid; and ii) at least one glycan moiety conjugated to the modified nucleic acid.

In some embodiments, the modified nucleic acid is conjugated to the glycan moiety through a nitrogen atom. In some embodiments, the modified nucleic acid is conjugated to the glycan moiety through an amide bond. In some embodiments, the glycan moiety is an N-linked glycan, wherein the glycan is attached through an amide nitrogen of an asparagine or an arginine residue via an N-acetylglucosamine residue.

In some embodiments, the modified nucleic acid is conjugated to the glycan via a click-chemistry reaction. In some embodiments, the modified nucleic acid portion comprises a first click-chemistry handle and the glycan portion comprises a second click chemistry handle, such that the modified nucleic acid portion and glycan portion are covalently linked by a chemical moiety formed by the click-chemistry reaction between the first and second handles. In some embodiments, the modified nucleic acid portion comprises an alkyne handle and the glycan portion comprises an azide handle, such that the modified nucleic acid portion and glycan portion are covalently linked by a chemical moiety formed by the click-chemistry reaction between the azide handle and the alkyne handle. In some embodiments, the modified nucleic acid portion comprises an alkyne handle and the glycan portion comprises an azide handle, such that the modified nucleic acid portion and glycan portion are covalently linked by a triazole formed by the click-chemistry reaction between the azide handle and the alkyne handle. In some embodiments, the modified nucleic acid portion comprises an azide handle and the glycan portion comprises an alkyne handle, such that the modified nucleic acid portion and glycan portion are covalently linked by a chemical moiety formed by the click-chemistry reaction between the azide handle and the alkyne handle. In some embodiments, the modified nucleic acid portion comprises an azide handle and the glycan portion comprises an alkyne handle, such that the modified nucleic acid portion and glycan portion are covalently linked by a triazole formed by the click-chemistry reaction between the azide handle and the alkyne handle.

In some embodiments, the modified nucleic acid portion comprises a modification of a ribose, such that the ribose is modified with an azide moiety capable of undergoing a click-chemistry reaction. In some embodiments, the modified nucleic acid portion comprises a modification of a ribose, such that the ribose is modified with an alkyne moiety capable of undergoing a click-chemistry reaction. In some embodiments, the ribose is modified at a position selected from 2'OH, 3'OH, and 5'OH.

In some embodiments, the non-reducing end of the glycan portion comprises an azide moiety capable of undergoing a click-chemistry reaction. In some embodiments, the non-reducing end of the glycan portion comprises an alkyne moiety capable of undergoing a click-chemistry reaction.

In some embodiments, the modified nucleic acid is conjugated to the glycan via a strong non-covalent interaction. In some embodiments, the modified nucleic acid is conjugated to the glycan via a high affinity biotin/streptavidin interaction. In some embodiments, the modified nucleic acid comprises a biotin moiety and the glycan comprises a streptavidin moiety, such that the biotin and streptavidin moieties interact. In some embodiments, the modified nucleic acid comprises a streptavidin moiety and the glycan comprises a biotin moiety, such that the biotin and streptavidin moieties interact.

In some embodiments, the modified nucleic acid is conjugated to the glycan via a linker group covalently bound to a terminus of the modified nucleic acid. In some embodiments, the modified nucleic acid is conjugated to the glycan via a linker covalently bound to a chemically modified nucleotide in the middle of the polynucleotide. In some embodiments, the modified nucleic acid is conjugated to the glycan via a chemical handle inserted between two nucleotides in the middle of the polynucleotide.

In some embodiments, the modified nucleic acid comprises a cleavable linker between the nucleic acid and glycan moiety. In some embodiments, the cleavable linker is a pH dependent cleavable bond. In some embodiments, the cleavable linker is a disulfide bond. In some embodiments, the cleavable linker is a peptide cleavage site. In some embodiments, the cleavable linker is a cit-val linker.

In some embodiments, the modified nucleic acid is conjugated to two or more glycan moieties. In some embodiments, the two or more glycan moieties are different glycan moieties. In some embodiments, the nucleic acid comprises a nucleotide modified with orthogonal modifications that allow for coupling to two more chemically distinct glycans. For example, the nucleic acid can be modified with two or more distinct conjugation handles, allowing for selective conjugation to two or more chemically distinct glycans, wherein each of glycan comprises a different complimentary conjugation handle.

In some embodiments, the modified nucleic acid is conjugated to the one or more glycans through a bioorthogonal reaction. In some embodiments, the bioorthogonal reaction is a bioorthogonal click-chemistry reaction. In some embodiments, the bioorthogonal reaction comprises a strain-promoted azide-alkyne cycloaddition. In some embodiments, the bioorthogonal reaction comprises the reaction of transcyclooctene and a tetrazine.

Exemplary Glycan—Nucleic Acid Conjugates

In one aspect, the present disclosure provides compounds of Formula (I):

A-L-B (I), or a salt, co-crystal, tautomer, stereoisomer, solvate, hydrate, polymorph, or an isotopically enriched derivative thereof, wherein:

A is a nucleic acid of deoxyribonucleic acid (DNA) or ribonucleic acid (RNA) comprising a first click-chemistry handle;

B is an asparagine-linked glycan (N-glycan) comprising a second click-chemistry handle; and L comprises a linker formed by a biorthogonal click chemistry reaction between the first click-chemistry handle and the second click-chemistry handle.

In certain embodiments of Formula (I), A is a nucleic acid of deoxyribonucleic acid (DNA) or ribonucleic acid (RNA); B is an asparagine-linked glycan (N-glycan); and L comprises a linker. In certain embodiments, L is any linker as defined herein.

In certain embodiments of Formula (I), A is a nucleic acid of deoxyribonucleic acid (DNA) or ribonucleic acid (RNA); B is an asparagine-linked glycan (N-glycan); and L comprises a linker formed by a biorthogonal click chemistry reaction between a first click-chemistry handle and a second click-chemistry handle.

In certain embodiments of Formula (I), A is a nucleic acid of deoxyribonucleic acid (DNA) or ribonucleic acid (RNA); B is an asparagine-linked glycan (N-glycan); and L comprises a linker formed by a biorthogonal click chemistry reaction between a first click-chemistry handle and a second click-chemistry handle, wherein the first click-chemistry handle was attached to A prior to the click chemistry reaction and the second click-chemistry handle was attached to B prior to the click chemistry reaction.

In certain embodiments, in Formula (I), A is DNA (e.g., comprising a first click-chemistry handle). In certain embodiments, in Formula (I), A is an antisense oligonucleotide (ASO). In certain embodiments, in Formula (I), A is an antisense oligonucleotide (ASO) (e.g., comprising a first click-chemistry handle). In certain embodiments, in Formula (I), A is single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, in Formula (I), A is single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA; comprising a first click-chemistry handle. In certain embodiments, in Formula (I), A is DNA which comprises the sequence:

```
                                       (SEQ ID NO: 1)
5'-GGC TGG TCC GAG TGC AGT GGT GTT TAC AAC TAA

TTG ATC ACA ACC AGT TAC AGA TTT CT/i5OctdU/TGT

TCC TTC TCC ACT CCC ACT GCT TCA CTT GAC TAG CCT

T-3'.
```

In certain embodiments, A has a sequence with at least 70% sequence identity, at least 75% sequence identity, at least 80% sequence identity, at least 85% sequence identity, or at least 90% sequence identity, at least 92% sequence identity, at least 95% sequence identity, or at least 98% sequence identity to the full-length sequence of SEQ ID NO: 1. In certain embodiments, A has a sequence with at least 80% sequence identity to the full-length sequence of SEQ ID NO: 1.

In certain embodiments, in Formula (I), A is RNA, comprising a first click-chemistry handle. In certain embodiments, in Formula (I), A is small interfering RNA (siRNA). In certain embodiments, in Formula (I), A is small interfering RNA (siRNA), comprising a first click-chemistry handle. In certain embodiments, in Formula (I), A is siRNA comprising a modification (e.g., at the 2' position). In certain embodiments, in Formula (I), A is siRNA comprising a modification selected from the group consisting of a 2'OMe modification, a fluorine modification (e.g., at the 2' position), a phosphorothioate modification. In certain embodiments, in Formula (I), A is siRNA comprising a modification selected from the group consisting of a 2'OMe modification, a fluorine modification, a phosphorothioate modification, which also comprises a first click-chemistry handle. In certain embodiments, in Formula (I), A is mRNA. In certain embodiments, in Formula (I), A is mRNA, comprising a first click-chemistry handle. In certain embodiments, in Formula (I), A is guideRNA. In certain embodiments, in Formula (I), A is guideRNA, comprising a first click-chemistry handle. In certain embodiments, in Formula (I), A is circular RNA (circRNA). In certain embodiments, in Formula (I), A is circular RNA (circRNA), comprising a first click-chemistry handle. In certain embodiments, in Formula (I), A is aptamer RNA. In certain embodiments, in Formula (I), A is aptamer RNA, comprising a first click-chemistry handle. In certain embodiments, in Formula (I), A is single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, in Formula (I), A is single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA, comprising a first click-chemistry handle. In certain embodiments, A has a sequence with at least 70% sequence identity, at least 75% sequence identity, at least 80% sequence identity, at least 85% sequence identity, at least 90% sequence identity, at least 92% sequence identity, at least 95% sequence identity, or at least 98% sequence identity to the full-length sequence of:

```
                                           (SEQ ID NO: 2)
AGUUGGUCCGAGUGUUGUGGGUUAUUGUUAAGUU/i5OctdU/
AUUUAACAUUGUCUCCCCCCACAACCGCGCUUGACUAGCUUGCUG.
```

In certain embodiments, A has a sequence with at least 80% sequence identity to the full-length sequence of SEQ ID NO: 2. In certain embodiments, in Formula (I), A is RNA which comprises SEQ ID NO: 2.

In certain embodiments, in Formula (I), L comprises a linker formed by a biorthogonal click chemistry reaction (e.g., copper-catalyzed azide-alkyne cyclization (CuAAC), strain-promoted azide-alkyne cycloaddition (SPAAC), transcyclooctyne (TCO)-tetrazine ligation, transcyclooctene-tetrazine ligation, alkene-tetrazine ligation, cross-linking between a primary amine and a N-hydroxysuccinimide ester (NHS ester), a transcyclooctyne-azide coupling, or a cyclopropane-azide coupling, azide-Staudinger ligation). In certain embodiments, in Formula (I), L comprises a linker formed by a biorthogonal click chemistry reaction (e.g., copper-catalyzed azide-alkyne cyclization (CuAAC), strain-promoted azide-alkyne cycloaddition (SPAAC), transcyclooctyne (TCO)-tetrazine ligation, transcyclooctene-tetrazine ligation, cross-linking between a primary amine and a N-hydroxysuccinimide ester (NHS ester), a transcyclooctyne-azide coupling, or a cyclopropene-azide coupling, azide-Staudinger ligation). In certain embodiments, in Formula (I), L comprises a linker formed by a biorthogonal click chemistry reaction between a first click-chemistry handle and a second click-chemistry handle. In certain embodiments, in Formula (I), L comprises a linker formed by a biorthogonal click chemistry reaction between a first click-chemistry handle and a second click-chemistry handle shown in Table 3 or 4 below. In certain embodiments, in Formula (I), L comprises a linker formed by a click chemistry reaction that is a copper-catalyzed azide-alkyne cyclization (CuAAC). In certain embodiments, in Formula (I), L comprises a linker formed by a click chemistry reaction that is a copper-free reaction. In certain embodiments, in Formula (I), L comprises a linker formed by a click chemistry reaction that is a strain-promoted azide-alkyne cycloaddition (SPAAC), a transcyclooctyne (TCO)-tetrazine ligation, transcyclooctene-tetrazine ligation, an azide-Staudinger ligation, a cross-linking between a primary amine and a N-hydroxysuccinimide ester (NHS ester), a transcyclooctyne-azide coupling, or a cyclopropane-azide coupling. In certain embodiments, in Formula (I), L comprises a linker formed by a click chemistry reaction that is a strain-promoted azide-alkyne cycloaddition (SPAAC). In certain embodiments, in Formula (I), L comprises a linker formed by a click chemistry reaction that is a transcyclooctyne (TCO)-tetrazine ligation or transcyclooctene-tetrazine ligation. In certain embodiments, in Formula (I), L comprises a linker formed by a click chemistry reaction that is a transcyclooctyne (TCO)-tetrazine ligation. In certain embodiments, in Formula (I), L comprises a linker formed by a click chemistry reaction that is transcyclooctene-tetrazine ligation. In certain embodiments, in Formula (I), L comprises a linker formed by a click chemistry reaction that is an azide-Staudinger ligation, a cross-linking between a primary amine and a N-hydroxysuccinimide ester (NHS ester), a transcyclooctyne-azide coupling, or a cyclopropane-azide coupling. In certain embodiments, in Formula (I), L comprises a linker formed by a click chemistry reaction that is an azide-Staudinger ligation. In certain embodiments, in Formula (I), L comprises a linker formed by a click chemistry reaction that is a cross-linking between a primary amine and a N-hydroxysuccinimide ester (NHS ester). In certain embodiments, in Formula (I), L comprises a linker formed by a click chemistry reaction that is a transcyclooctyne-azide coupling. In certain embodiments, in Formula (I), L comprises a linker formed by a click chemistry reaction that is a cyclopropane-azide coupling.

A click chemistry handle or click-chemistry handle can be a reactant, or a reactive group, that can partake in a click chemistry reaction. For example, a strained alkyne, e.g., a cyclooctyne, is a click chemistry handle, since it can partake in a strain-promoted cycloaddition. In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles (click-chemistry handle 1 and click-chemistry handle 2) suitable for use according to some aspects of this invention are described herein, for example, in Tables 3 and 4. Other suitable click chemistry handles are known to those of skill in the art. For two molecules to be conjugated via click chemistry, the click chemistry handles of the molecules are reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to, those described in Table 3:

TABLE 3

Exemplary Click Chemistry Handles and Reactions

| Scheme | Reaction name |
|---|---|
| terminal Alkyne + azide → triazole | 1,3-dipolar cycloaddition |
| strained Alkyne (cyclooctyne) + azide → fused triazole | Strain-promoted cycloaddition |
| diene + dienophile → cyclohexene | Diels-Alder reaction |
| R—SH (thiol) + alkene → R—S-CH2-CH2-R1 | Thiol-ene reaction |

Table 3 provides examples of click chemistry handles and reactions. R, R1, and R2 may represent any molecule comprising a sortase recognition motif. In some embodiments, each occurrence of R, R1, and R2 is independently RR-LPXT-[X]$_y$—, or -[X]$_y$-LPXT-RR, wherein each occurrence of X independently represents any amino acid residue, each occurrence of y is an integer between 0 and 10, inclusive, and each occurrence of RR independently represents a protein or an agent (e.g., a protein, peptide, a detectable label, a binding agent, a small molecule, etc.), and, optionally, an additional linker.

In some embodiments, click chemistry handles are used that can react to form covalent bonds in the absence of a metal catalyst. Such click chemistry handles are well known to those of skill in the art and include the click chemistry handles described in Becer, Hoogenboom, and Schubert, Click Chemistry beyond Metal-Catalyzed Cycloaddition, Angewandte Chemie International Edition (2009) 48: 4900-4908. See Table 4 below.

TABLE 4

Exemplary Click Chemistry Handles and Reactions

| | Reagent A | Reagent B | Mechanism | Notes on reaction |
|---|---|---|---|---|
| 0 | Azide | Alkyne | Cu-catalyzed [3 + 2] azide-alkyne cycloaddition (CuAAC) | 2 h at 60° C. in H$_2$O |
| 1 | Azide | Cyclooctyne | Strain-promoted [3 + 2] azide-alkyne cycloaddition (SPAAC) | 1 h at RT |
| 2 | Azide | Activated alkyne | [3 + 2] Huisgen cycloaddition | 4 h at 50° C. |
| 3 | Azide | Electron-deficient alkyne | [3 + 2] cycloaddition | 12 h at RT in H$_2$O |
| 4 | Azide | Aryne | [3 + 2] cycloaddition | 4 h at RT in THF with crown ether or 24 h at RT in CH$_3$CN |
| 5 | Tetrazine | Alkene | Diels-Alder retro-[4 + 2] cycloaddition | 40 min at 25° C. (100% yield); N$_2$ is the only by-product |

TABLE 4-continued

Exemplary Click Chemistry Handles and Reactions

| | Reagent A | Reagent B | Mechanism | Notes on reaction |
|---|---|---|---|---|
| 6 | Tetrazole | Alkene | 1,3-dipolar cycloaddition (photoclick) | Few min UV irradiation and then overnight at 4° C. |
| 7 | Dithioester | Diene | Hetero-Diels-Alder cycloaddition | 10 min at RT |
| 8 | Anthracene | Maleimide | [4 + 2] Diels-Alder reaction | 2 days at reflux in toluene |
| 9 | Thiol | Alkene | Radical addition (thio click) | 30 min UV (Quantitative conv.) or 24 h UV irradiation (>96%) |
| 10 | Thiol | Enone | Michael addition | 24 h at RT in CH$_3$CN |
| 11 | Thiol | Maleimide | Michael addition | 1 h at 40° C. in THF or 16 at RT in dioxane |
| 12 | Thiol | Para-fluoro | Nucleophilic substitution | Overnight at RT in DMF or 60 min at 40° C. in DMF |
| 13 | Amine | Para-fluoro | Nucleophilic substitution | 20 min MW at 95° C. in NMP as solvent |

RT = room temperature,
DMF = N.N-dimethylformamide,
NMP = N-methylpyrolidone,
THF = tetrahydrofuran,
CH$_3$CN = acetonitrile In certain embodiments, A comprises the first click-chemistry handle that is an alkyne. In certain embodiments, A comprises the first click-chemistry handle that is an alkyne, for example, wherein the alkyne comprises structure:

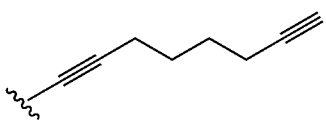

In certain embodiments, the nucleic acid A comprises the first click-chemistry handle that is an alkyne attached to a base of the nucleic acid. In certain embodiments, A comprises the structure:

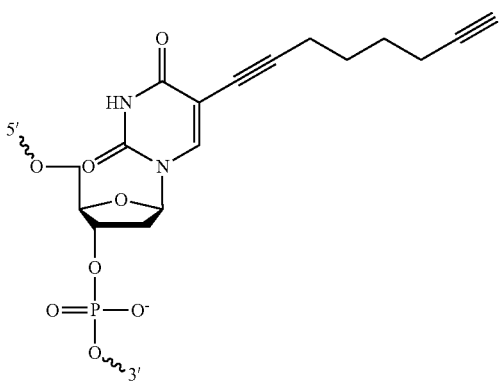

(5-Octadiynyl dU, aka i5OctdU), and A is RNA or DNA. In certain embodiments, A comprises the first click-chemistry handle that is an alkene (vinyl) and B comprises a second click-chemistry handle that is a tetrazine. In certain embodiments, A comprises the first click-chemistry handle that is an alkene (vinyl) (e.g., in FIGS. 2B and/or 2C in Kubota et al.) in Kubota et al., "Expanding the Scope of RNA Metabolic Labeling with Vinyl Nucleosides and Inverse Electron-Demand Diels-Alder Chemistry." ACS Chemical Biology vol. 14, 8 (2019): 1698-1707, incorporated herein by reference. In certain embodiments, A comprises the first click-chemistry handle that is an alkene (vinyl) (e.g., in FIGS. 2B and/or 2C in Kubota et al.) and a second click-chemistry handle that is a tetrazine (e.g., in FIG. 3A Kubota et al.) from Kubota et al., "Expanding the Scope of RNA Metabolic Labeling with Vinyl Nucleosides and Inverse Electron-Demand Diels-Alder Chemistry." ACS Chemical Biology vol. 14, 8 (2019): 1698-1707, incorporated herein by reference. In certain embodiments, A comprises the first click-chemistry handle that is an alkene, wherein A comprises

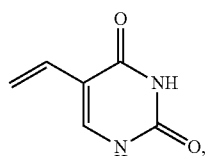
(5-VU,1)

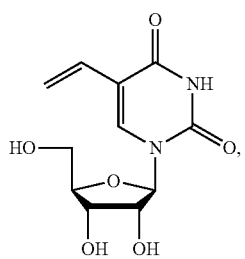
(5-VU)

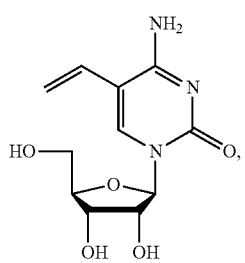
(5-VC)

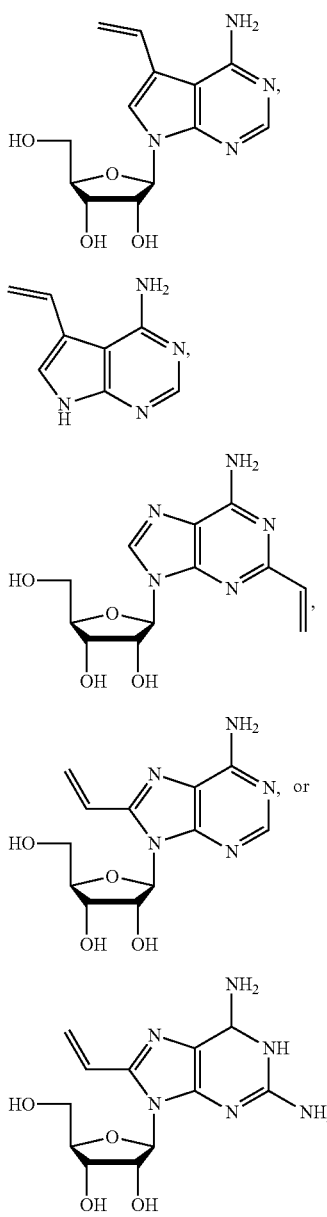

In certain embodiments, L is or comprises substituted or unsubstituted alkylene, alknylene, substituted or unsubstituted alkenylene, substituted or unsubstituted heteroalkylene, substituted or unsubstituted carbocyclylene, substituted or unsubstituted heterocyclylene, substituted or unsubstituted arylene, substituted or unsubstituted heteroarylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, —OC(=O)N(R$^A$)—, —S(O)$_2$NR$^A$—, —NR$^A$S(O)$_2$—, or a combination thereof, and each R$^A$ is independently hydrogen or substituted or unsubstituted alkyl.

In certain embodiments, L is or comprises a substituted or unsubstituted alkylene, alknylene, substituted or unsubstituted heteroalkylene, substituted or unsubstituted carbocyclylene, substituted or unsubstituted heterocyclylene, substituted or unsubstituted arylene, substituted or unsubstituted heteroarylene, —O—, —N(R$^A$)—, —S—, or a combination thereof, and each R$^A$ is independently hydrogen or substituted or unsubstituted alkyl.

In certain embodiments, L is or comprises a substituted or unsubstituted alkylene, alknylene, substituted or unsubstituted heteroalkylene, substituted or unsubstituted carbocyclylene, substituted or unsubstituted heterocyclylene, substituted or unsubstituted arylene, substituted or unsubstituted heteroarylene, —O—, or a combination thereof.

In certain embodiments, L is or comprises a substituted or unsubstituted alkylene, alknylene, substituted or unsubstituted carbocyclylene, substituted or unsubstituted heterocyclylene, substituted or unsubstituted arylene, substituted or unsubstituted heteroarylene, —O—, or a combination thereof.

In certain embodiments, L is or comprises a combination of alknylene, substituted or unsubstituted alkylene, and substituted or unsubstituted heteroarylene, In certain embodiments, L is or comprises a combination of alknylene, unsubstituted alkylene, and unsubstituted heteroarylene, In certain embodiments, L is or comprises a substituted or unsubstituted heteroarylene. In certain embodiments, L is or comprises a substituted or unsubstituted 5-6 membered heteroarylene. In certain embodiments, L is or comprises a substituted or unsubstituted 5-6 membered heteroarylene having 2-3 nitrogen atoms in the heteroaryl ring. In certain embodiments, L is or comprises substituted or unsubstituted 5-membered heteroarylene having 2-3 nitrogen atoms in the heteroaryl ring. In certain embodiments, L is or comprises a substituted or unsubstituted triazole.

In certain embodiments, L comprises a substituted or unsubstituted heterocyclylene. In certain embodiments, L comprises a substituted or unsubstituted heterocyclylene fused to a substituted or unsubstituted carbocyclylene. In certain embodiments, L comprises a substituted or unsubstituted heterocyclylene fused to a substituted or unsubstituted cyclooctylene. In certain embodiments, L comprises a substituted or unsubstituted 6-membered heterocyclylene fused to a substituted or unsubstituted cyclooctylene. In certain embodiments, L comprises a substituted or unsubstituted dihydropyridazine fused to a substituted or unsubstituted cyclooctylene. In certain embodiments, L comprises a substituted dihydropyridazine fused to an unsubstituted cyclooctylene. In certain embodiments, L comprises an octahydrocycloocta[d]pyridazine.

In certain embodiments, L comprises a substituted or unsubstituted heteroarylene fused to a substituted or unsubstituted carbocyclylene. In certain embodiments, L comprises a substituted or unsubstituted heteroarylene fused to a substituted or unsubstituted cyclooctylene. In certain embodiments, L comprises a substituted or unsubstituted 5-membered heteroarylene fused to a substituted or unsubstituted cyclooctylene. In certain embodiments, L comprises a substituted or unsubstituted triazole fused to a substituted or unsubstituted cyclooctylene.

In certain embodiments, in Formula (I), L is of formula:

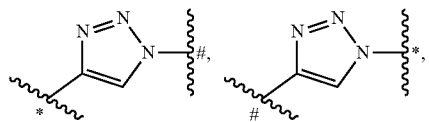

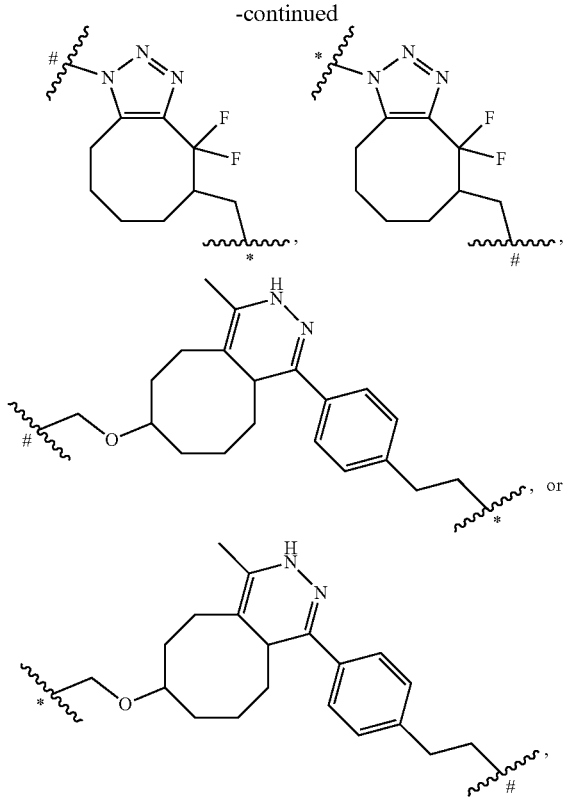

wherein * indicates the point of attachment to A, and #indicates the point of attachment to B. In certain embodiments, in Formula (I), L is of formula:

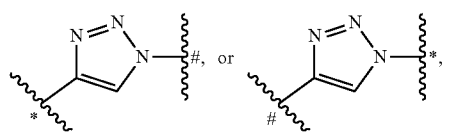 [SMILES: *c1cn(*)nn1 ; *c1cn(*)nn1]

wherein * indicates the point of attachment to A, and #indicates the point of attachment to B. In certain embodiments, L is of formula:

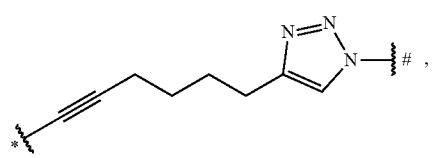

wherein * indicates the point of attachment to A, and #indicates the point of attachment to B.

In certain embodiments, in Formula (I), L is attached to a base of the nucleic acid A. In certain embodiments, in Formula (I), L is attached to the 2'OH position of a ribose, 3'OH position of a ribose or deoxyribose, or 5'OH position of a ribose or deoxyribose of the nucleic acid A. In certain embodiments, in Formula (I), L is attached to the 2'OH position of a ribose of the nucleic acid A. In certain embodiments, in Formula (I), L is attached to the 3'OH position of a ribose or deoxyribose of the nucleic acid A. In certain embodiments, in Formula (I), L is attached to an internal portion of the nucleic acid A, the 3' end of the nucleic acid A, or the 5' end of the nucleic acid A. In certain embodiments, in Formula (I), L is attached to an internal portion of the nucleic acid A. In certain embodiments, in Formula (I), A is circular RNA (circRNA), and L is attached to an internal portion of A. In certain embodiments, in Formula (I), L is attached to the 5'OH position of a ribose or deoxyribose of the nucleic acid A. In certain embodiments, in Formula (I), L is attached to the non-reducing end of N-glycan B. In certain embodiments, B is an N-glycan that is a mono-antennary N-glycan, a bi-antennary N-glycan, a tri-antennary N-glycan, or a penta-antennary N-glycan. In certain embodiments, B is an N-glycan that is a mono-antennary N-glycan. In certain embodiments, B is an N-glycan that is a bi-antennary N-glycan. In certain embodiments, B is an N-glycan that is a tri-antennary N-glycan. In certain embodiments, B is an N-glycan that is a penta-antennary N-glycan. In certain embodiments, B is an N-glycan that comprises sialic acid. In certain embodiments, B is an N-glycan of formula:

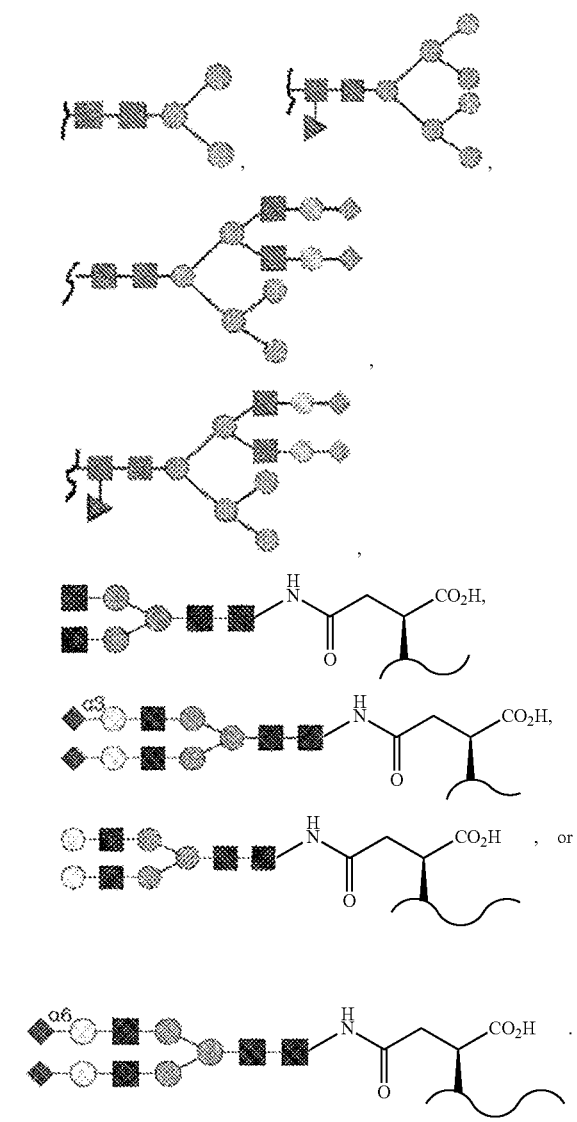

The structure of the symbols in the N-glycans B and compounds of Formula (I) are generally as designated within standard nomenclature for glycan chemistry as recognized by one of ordinary skill in the art, for example, wherein squares represent N-acetylglucosamine (GlcNAc), dark circles represent D-Mannose (Man), triangles represent L-fucose (Fuc), light circles represent D-Galactose (Gal), and diamonds represent sialic acid, and as further example, as designated in Symbol Nomenclature for Glycans (SNFG), Glycans, available at the NCBI website.

Figure 9:
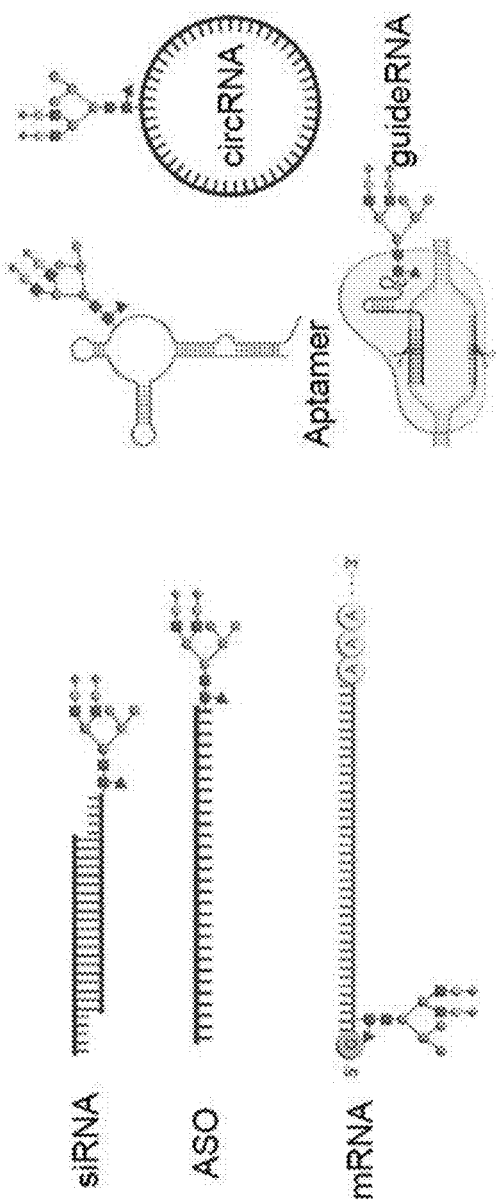
FIG. 9 shows examples of nucleic acids on which a glycan moiety may be placed. Nucleic acids can range in sugar composition (RNA or DNA), length, and include non-natural compositions such as LNAs, phosphonothioates, or other modifications. Exemplary nucleic acids shown in FIG. 9 include siRNA, ASO, mRNA, aptamer, circRNA, and guideRNA, each attached to a glycan.
Figure 10A:
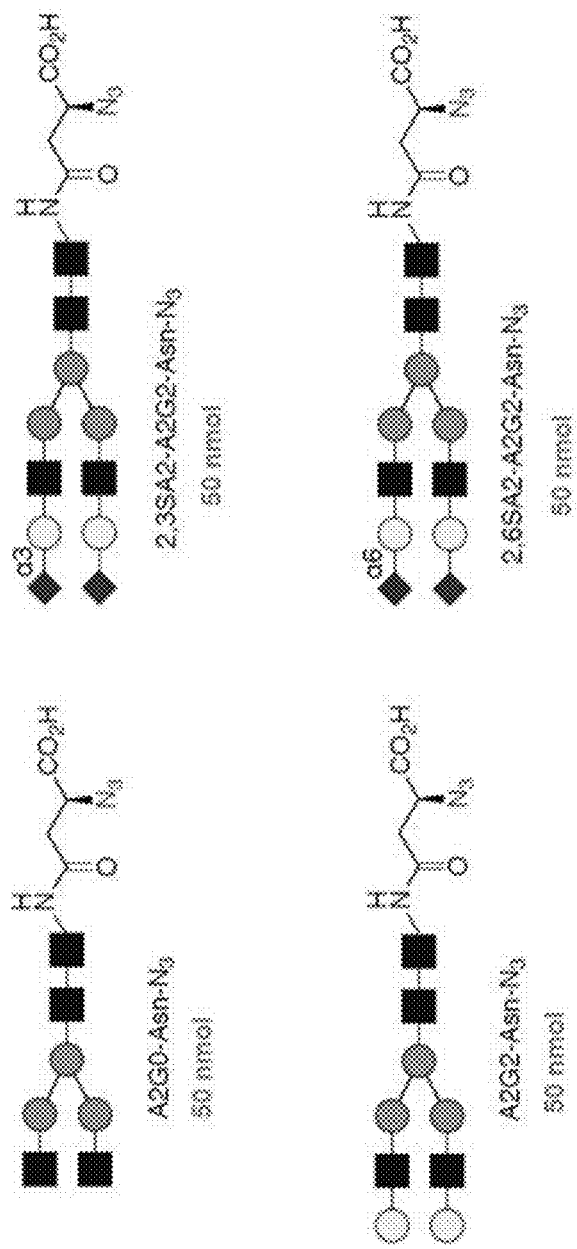
FIGS. 10A-10E show the azido-N-glycans used for preparing the nucleic acid-N-glycan conjugates in Example 10.
Figure 10B:
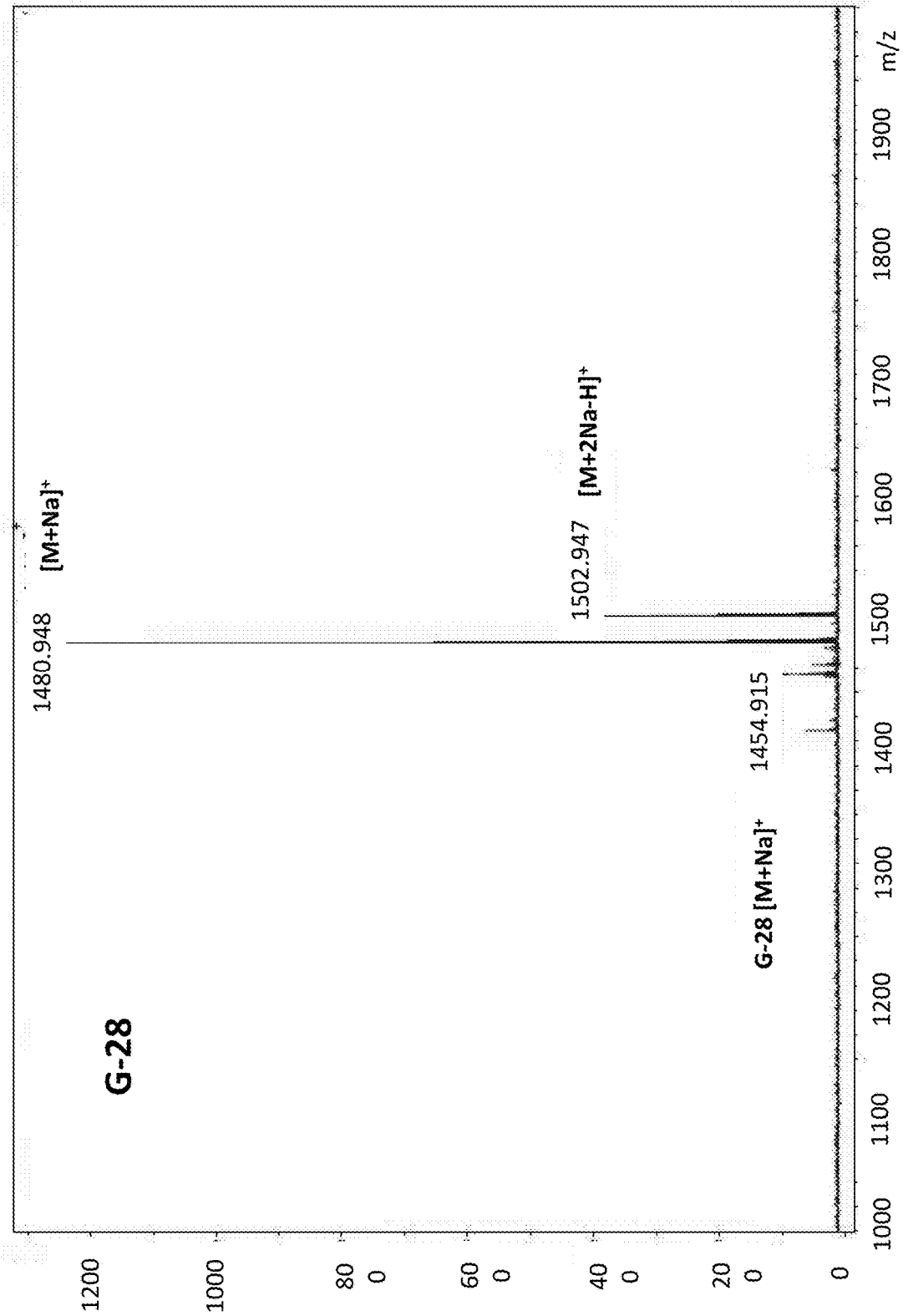
Figure 10C:
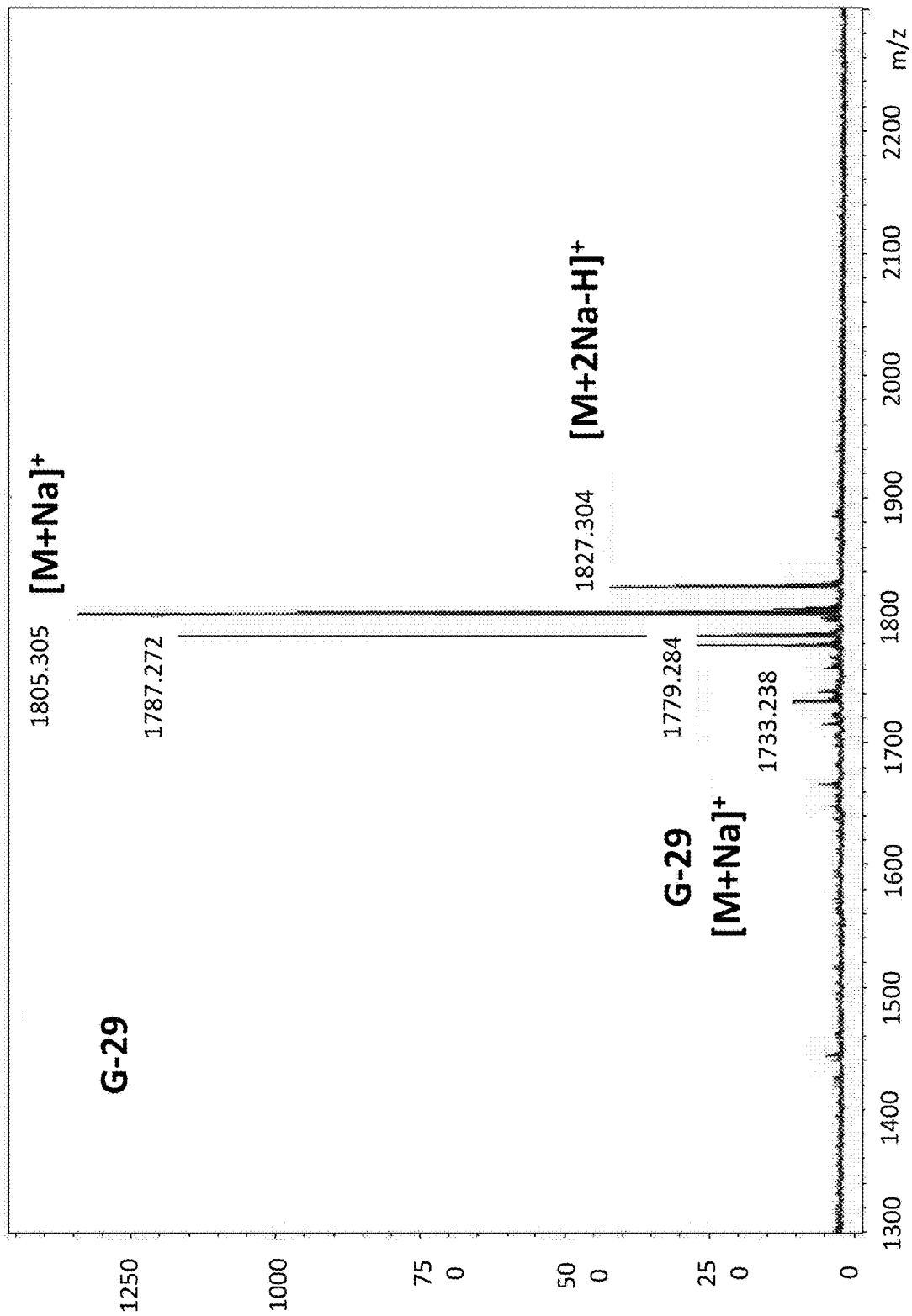
Figure 10D:
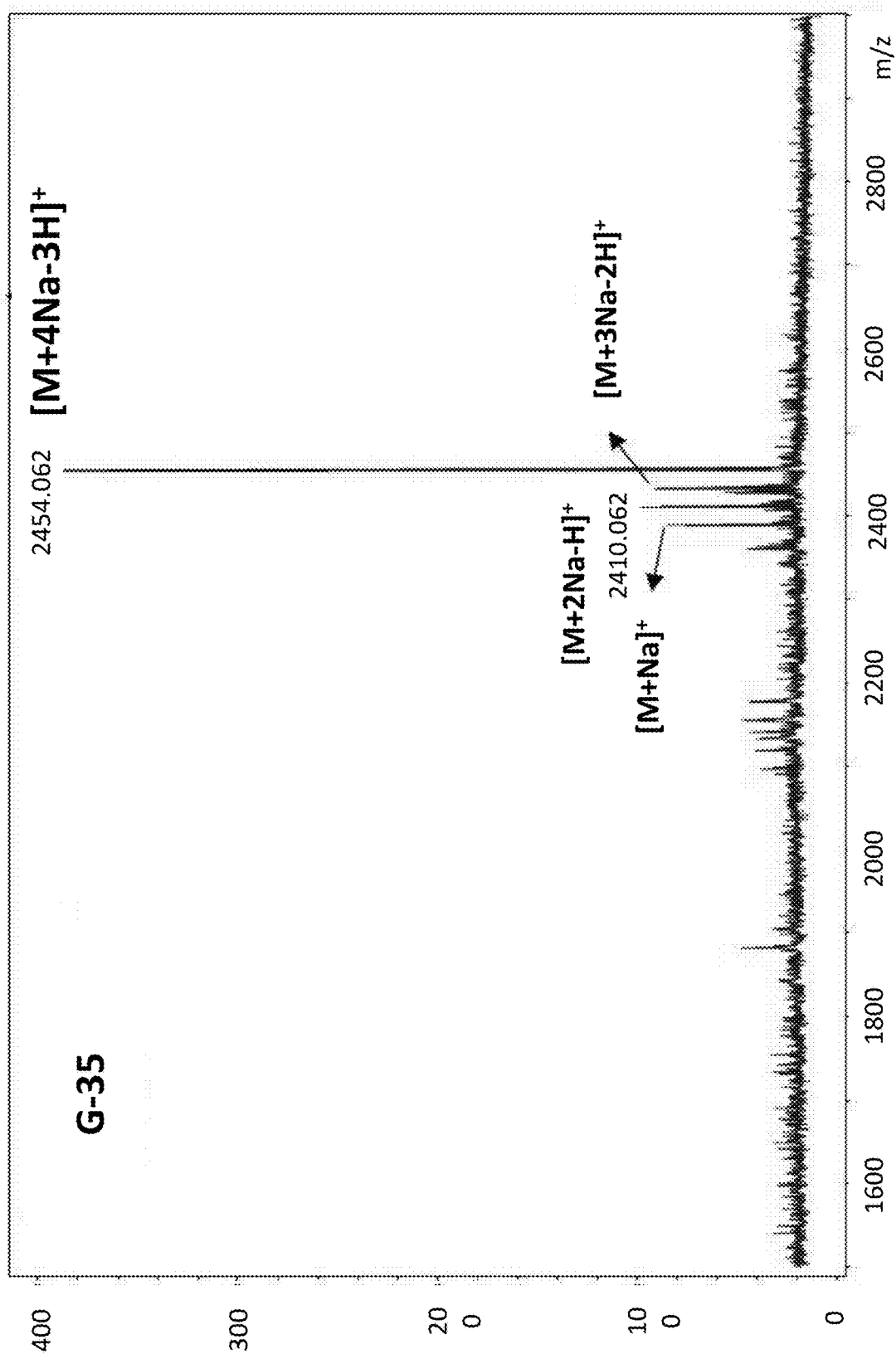
Figure 10E:
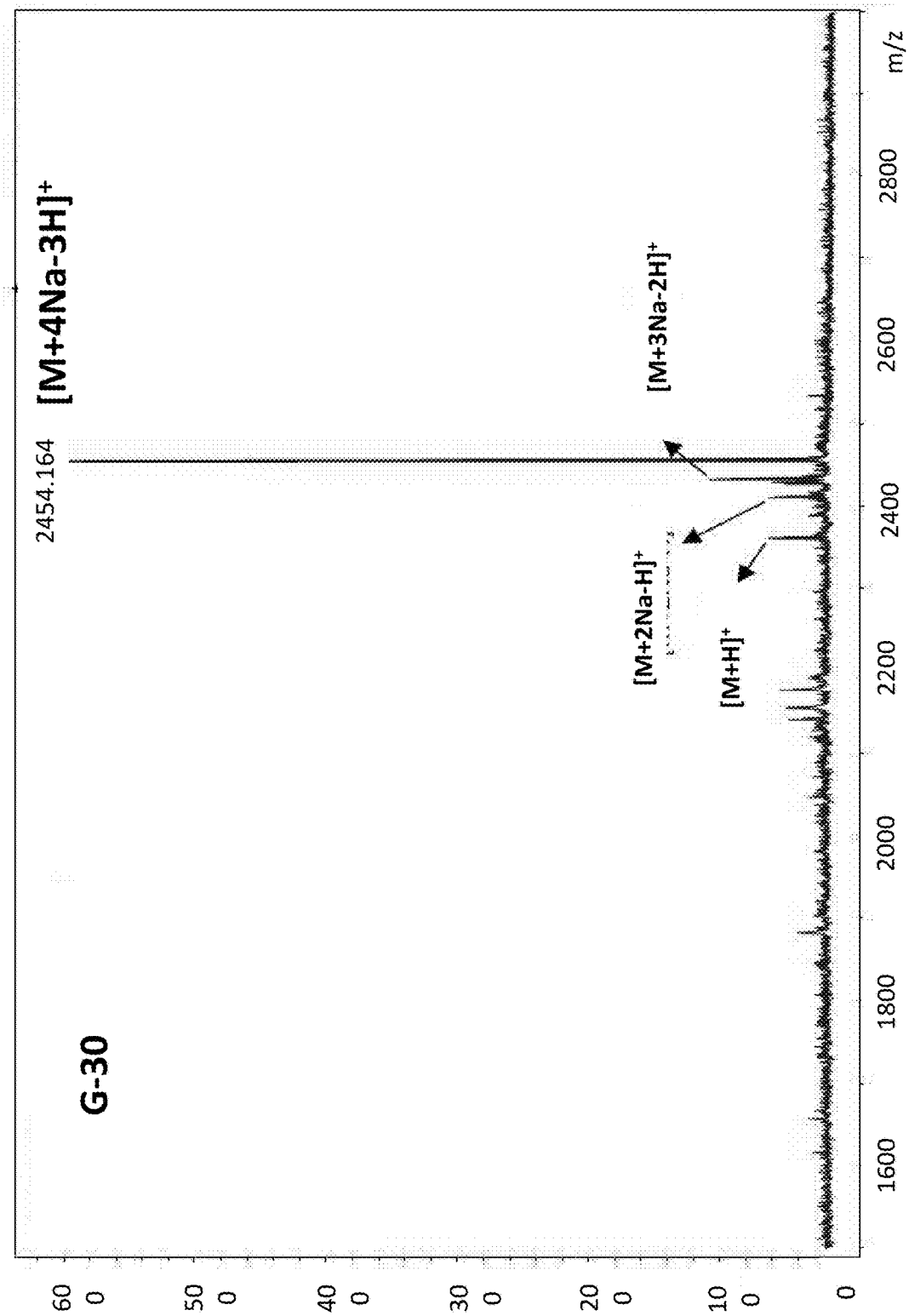
Figure 11:
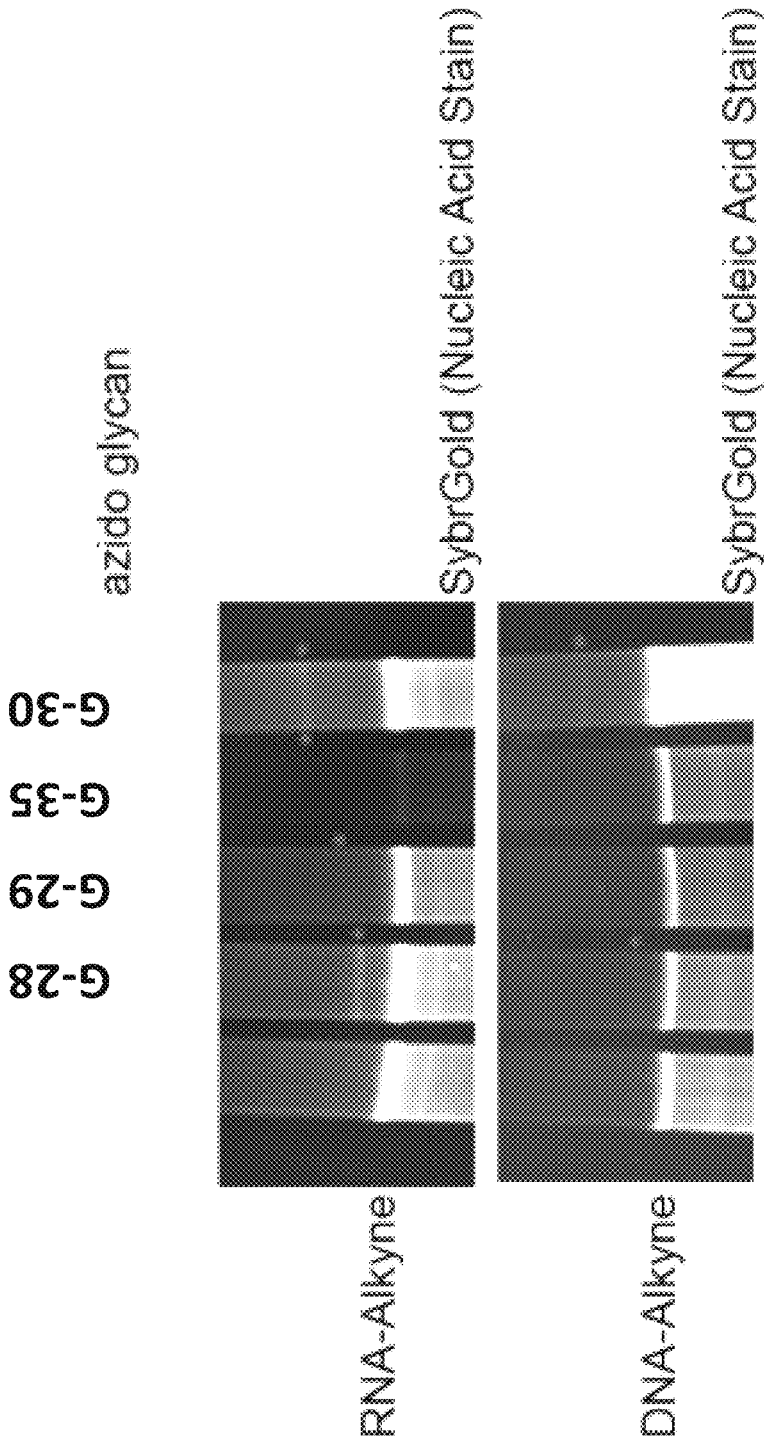
FIG. 11 shows a SybrGold nucleic acid stain showing the respective products after reacting a alkyne-RNA or alkyne-DNA with specified N-glycans G-28 (50 nmol); G-35 (50 nmol), G-29 (50 nmol), and G-30 (50 nmol), in Example 10.

In certain embodiments, the compound of Formula (I) is one shown in FIG. 9. In some embodiments, the compound of Formula (I) is one shown in FIG. 9 wherein A is siRNA. In some embodiments, the compound of Formula (I) is one shown in FIG. 9 wherein A is an ASO. In some embodiments, the compound of Formula (I) is one shown in FIG. 9 wherein A is an mRNA. In some embodiments, the compound of Formula (I) is one shown in FIG. 9 wherein A is an aptamer. In some embodiments, the compound of Formula (I) is one shown in FIG. 9 wherein A is circular RNA (circRNA). In some embodiments, the compound of Formula (I) is one shown in FIG. 9 wherein A is guideRNA.

In certain embodiments, the compound of Formula (I) comprises SEQ ID NO: 1 or SEQ ID NO: 2, wherein i5OctdU is conjugated to G-28 to form:

In certain embodiments, the compound of Formula (I) comprises SEQ ID NO: 1 or SEQ ID NO: 2, wherein i5OctdU is conjugated to G-35 to form:

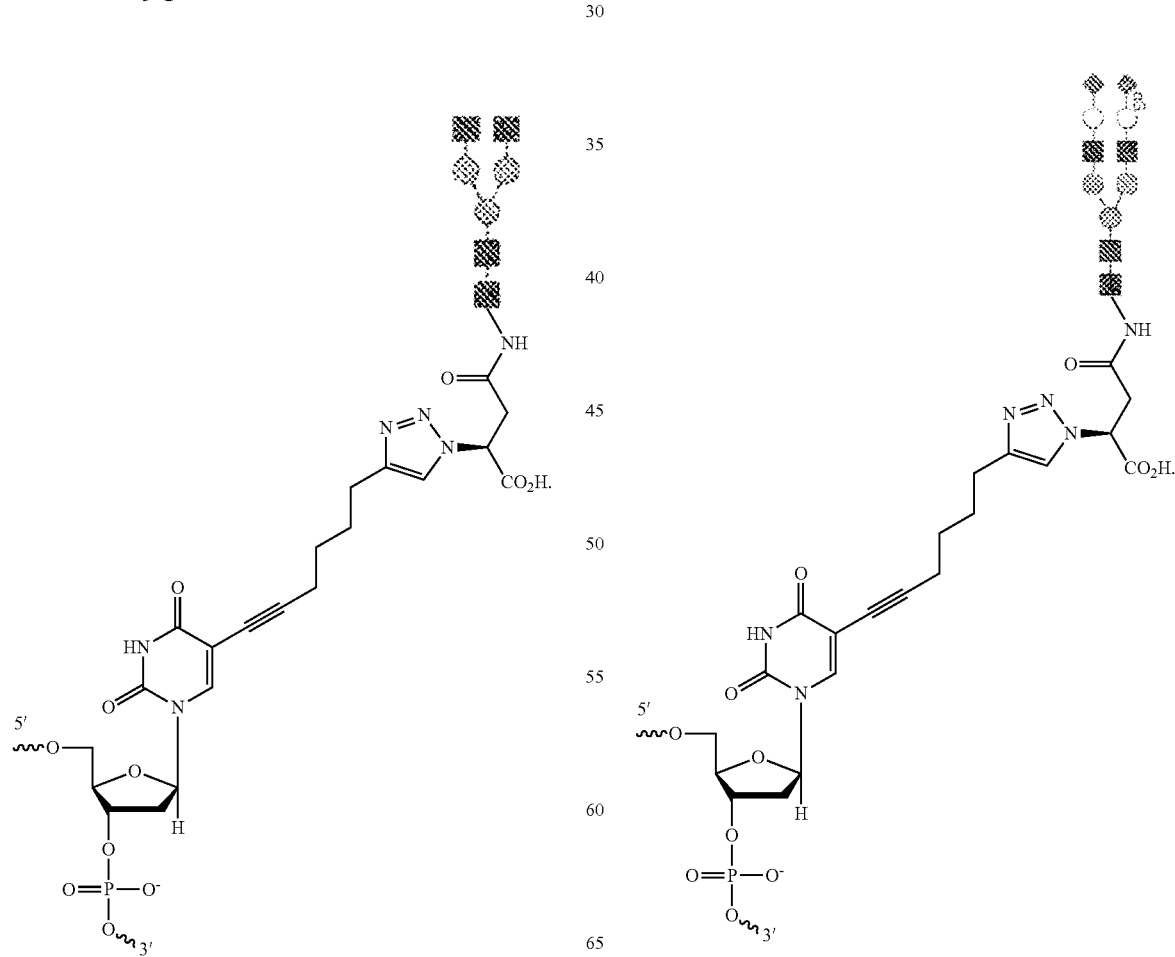

In certain embodiments, the compound of Formula (I) comprises SEQ ID NO: 1 or SEQ ID NO: 2, wherein i5OctdU is conjugated to G-29 to form:

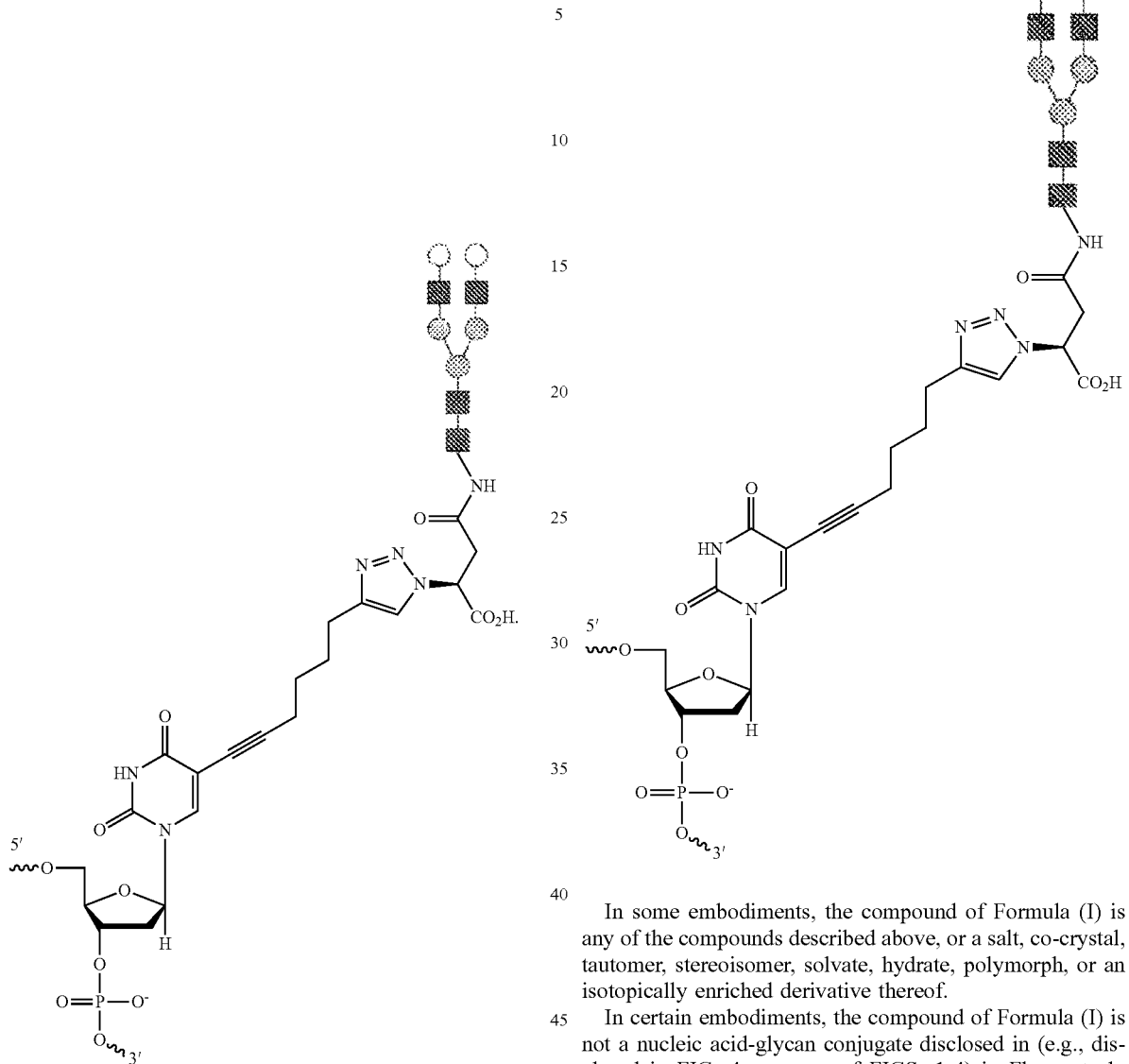

In certain embodiments, the compound of Formula (I) comprises SEQ ID NO: 1 or SEQ ID NO: 2, wherein i5OctdU is conjugated to G-30 to form:

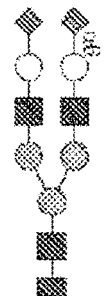

In some embodiments, the compound of Formula (I) is any of the compounds described above, or a salt, co-crystal, tautomer, stereoisomer, solvate, hydrate, polymorph, or an isotopically enriched derivative thereof.

In certain embodiments, the compound of Formula (I) is not a nucleic acid-glycan conjugate disclosed in (e.g., disclosed in FIG. 4, any one of FIGS. 1-4) in Flynn et al., Mammalian Y RNAs are modified at discrete guanosine residues with N-glycans, bioRxiv, Sep. 30, 2019.

Exemplary Methods of Making Glycan—Nucleic Acid Conjugates

The present disclosure provides methods for preparing a compound of Formula (I):

A-L-B (I), or a salt, co-crystal, tautomer, stereoisomer, solvate, hydrate, polymorph, or an isotopically enriched derivative thereof, wherein:

A is a nucleic acid of deoxyribonucleic acid (DNA) or ribonucleic acid (RNA) comprising a first click-chemistry handle;

B is an asparagine-linked glycan (N-glycan) comprising a second click-chemistry handle; and L comprises a linker formed by a biorthogonal click chemistry reaction between the first click-chemistry handle and the second click-chemistry handle;

the method comprising a first step of reacting: the nucleic acid A of ribonucleic acid (RNA) or deoxyribonucleic acid (DNA), comprising the first click-chemistry handle, with the compound B, which is an asparagine-linked glycan (N-glycan) comprising the second click-chemistry handle; wherein the reaction of the first step is carried out under biorthogonal click chemistry conditions.

In certain embodiments, in a method of preparing a compound of Formula (I), substituents A, B, and linker L are as described herein. In certain embodiments, in a method of preparing a compound of Formula (I), A is DNA or RNA, for example, ASO, siRNA, mRNA, guideRNA, circRNA, or aptamer RNA. In certain embodiments, in a method of preparing a compound of Formula (I), A is DNA (e.g., comprising a first click-chemistry handle). In certain embodiments, in Formula (I), A is an antisense oligonucleotide (ASO). In certain embodiments, in Formula (I), A is an antisense oligonucleotide (ASO) (e.g., comprising a first click-chemistry handle). In certain embodiments, in Formula (I), A is siRNA, mRNA, guideRNA, circRNA, or aptamer RNA. In certain embodiments, in Formula (I), A is single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, in Formula (I), A is single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA; comprising a first click-chemistry handle. In certain embodiments, in a method of preparing a compound of Formula (I), A is DNA which comprises SEQ ID NO: 1. In certain embodiments, A has a sequence with at least 70% sequence identity, at least 75% sequence identity, at least 80% sequence identity, at least 85% sequence identity, at least 90% sequence identity, at least 92% sequence identity, at least 95% sequence identity, or at least 98% sequence identity to the full-length sequence of SEQ ID NO: 1. In certain embodiments, in a method of preparing a compound of Formula (I), A has a sequence with at least 80% sequence identity to the full-length sequence of SEQ ID NO: 1. In certain embodiments, in a method of preparing a compound of Formula (I), A is DNA, where the DNA comprises SEQ ID NO: 1.

In certain embodiments, in a method of preparing a compound of Formula (I), A is RNA, comprising a first click-chemistry handle. In certain embodiments, in Formula (I), A is small interfering RNA (siRNA). In certain embodiments, in Formula (I), A is small interfering RNA (siRNA), comprising a first click-chemistry handle. In certain embodiments, in Formula (I), A is siRNA comprising a modification selected from the group consisting of a 2'OMe modification, a fluorine modification, a phosphorothioate modification. In certain embodiments, in Formula (I), A is siRNA comprising a modification selected from the group consisting of a 2'OMe modification, a fluorine modification, a phosphorothioate modification, comprising a first click-chemistry handle. In certain embodiments, in Formula (I), A is mRNA. In certain embodiments, in Formula (I), A is mRNA, comprising a first click-chemistry handle. In certain embodiments, in Formula (I), A is guideRNA. In certain embodiments, in Formula (I), A is guideRNA, comprising a first click-chemistry handle. In certain embodiments, in Formula (I), A is circular RNA (circRNA). In certain embodiments, in Formula (I), A is circular RNA (circRNA), comprising a first click-chemistry handle. In certain embodiments, in Formula (I), A is aptamer RNA. In certain embodiments, in Formula (I), A is aptamer RNA, comprising a first click-chemistry handle. In certain embodiments, in Formula (I), A is single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, in Formula (I), A is single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA, comprising a first click-chemistry handle. In certain embodiments, A has a sequence with at least 70% sequence identity, at least 75% sequence identity, at least 80% sequence identity, at least 85% sequence identity, at least 90% sequence identity, at least 92% sequence identity, at least 95% sequence identity, or at least 98% sequence identity to the full-length sequence of SEQ ID NO: 2. In certain embodiments, A has a sequence with at least 80% sequence identity to the full-length sequence of SEQ ID NO: 2. In certain embodiments, in a method of preparing a compound of Formula (I), A is RNA which comprises the sequence SEQ ID NO: 2. In certain embodiments, in a method of preparing a compound of Formula (I), A is RNA, where the RNA which comprises SEQ ID NO: 2.

In certain embodiments, in a method of preparing a compound of Formula (I), the first step is carried out under conditions for a biorthogonal click chemistry reaction, e.g., a click chemistry reaction of: a copper-catalyzed azide-alkyne cyclization (CuAAC), a strain-promoted azide-alkyne cycloaddition (SPAAC, for example cyclooctyne-azide cycloaddition, cyclooctene-tetrazine cycloaddition), a tetracyclooctyne (TCO)-tetrazine ligation, or an azide-Staudinger ligation. In certain embodiments, the first step is carried out under conditions for a reaction shown in Tables 3 or 4 above. In certain embodiments, the first step is carried out under conditions for the CuAAC, comprising diluting the alkyne-modified nucleic acid A in water and optionally denaturing at a temperature between 90-100° C. for approximately 1-5 minutes to produce a reactant mixture. In certain embodiments, the first step is carried out under conditions for a copper-free click chemistry reaction (e.g., one of reactions 1-13 in Table 4), comprising diluting the modified nucleic acid A (e.g., alkene-modified DNA, alkyne-modified RNA, alkene-modified DNA, alkyne-modified RNA) in water to produce a reactant mixture. In certain embodiments, the first step is carried out under conditions for the CuAAC, comprising diluting the alkyne-modified nucleic acid A in water without denaturing at a temperature between 90-100° C. for approximately 1-5 minutes to produce a reactant mixture. In certain embodiments, the first step is carried out under conditions for the CuAAC, comprising diluting the alkyne-modified nucleic acid A in water and denaturing is conducted at a temperature between 90-100° C. (e.g., approximately 95° C.) for approximately 1-5 minutes (e.g., approximately 2 minutes) to produce a reactant mixture. In certain embodiments, the first step is carried out under conditions for the CuAAC, comprising diluting the alkyne-modified nucleic acid A in water to a final concentration of between 90 μM-125 μM or 95 μM-115 μM, for example, between 100 μM-125 μM (e.g., 100 μM). In certain embodiments, the first step is carried out under conditions for the SPAAC, for example cyclooctyne-azide cycloaddition, comprising diluting the alkyne-modified (e.g., strained alkyne-modified, for example, cyclooctyne-modified) nucleic acid A in water to a final concentration of between 1 μM-115 μM or 5-100 μM, for example, between 1 μM-100 μM. In certain embodiments, the alkyne-modified nucleic acid A is prepared by coupling an RNA or DNA modified with the internal amino modifier /iUniAmM/ at the 5'-end (e.g., with an internal amino modifier of a nucleic acid, for example, available at Integrated DNA Technologies) to DIBAC (dibenzoazacyclooctyne, or "DBCO," dibenzocyclooctyne) using conditions for a N-Hydroxysuccinimide (NHS) reaction.

In certain embodiments, the first step is followed by a step of placing the reactant mixture on ice, followed by a step of folding in MgCl (e.g., 200 μM MgCl) and neutral buffer (e.g., phosphate-buffered saline (PBS) at pH 7.0). In certain embodiments, the first step is followed by a step of placing the reactant mixture on ice, followed by a step of folding in MgCl (e.g., 200 μM MgCl) and neutral buffer (e.g., phosphate-buffered saline (PBS) at pH 7.0) for approximately 5-10 minutes at 35-39° C. In certain embodiments, the method further comprises a step of adding to the reactant mixture a ligand 2-(4-((bis((1-(tert-butyl)-1H-1,2,3-triazol-4-yl)methyl)amino)methyl)-1H-1,2,3-triazol-1-yl)acetic acid (BTTAA) and incubating at room temperature, for example, approximately 18-75° C. (e.g., 18-23° C., 20-25° C., 25-40° C., 40-50° C., 50-55° C., 55-60° C., 60-70° C., 70-75° C.). In certain embodiments, the method further comprises a step of reacting A (e.g., approximately 10 μM of A, approximately 10-20 μM of A), B (e.g., approximately 20 μM or approximately 20-30 μM of B), and optionally Cu-BTTAA (e.g., approximately 100-110 μM of Cu-BTTAA). In certain embodiments, the method further comprises a step of reacting A (e.g., approximately 10 μM of A), B (e.g., approximately 20 μM B), and Cu-BTTAA (e.g., approximately 100-110 μM of Cu-BTTAA). In certain embodiments, the method further comprises a step of reacting A (e.g., approximately 10 μM of A), B (e.g., approximately 20 μM of B), optionally Cu-BTTAA (e.g., approximately 100-110 μM of Cu-BTTAA), and sodium ascorbate with buffer (e.g., PBS) for at least approximately 6-48 hours at approximately 18-75° C. (e.g., 18-23° C., 20-25° C., 25-40° C., 40-50° C., 50-55° C., 55-60° C., 60-70° C., 70-75° C.). In certain embodiments, the method further comprises a step of reacting A (e.g., approximately 10-20 μM of A), B (e.g., approximately 20-30 μM of B), optionally Cu-BTTAA (e.g., approximately 100-110 μM of Cu-BTTAA), and sodium ascorbate with buffer (e.g., PBS) for at least approximately 6-48 hours at approximately 18-75° C. (e.g., 18-23° C., 20-25° C., 25-40° C., 40-50° C., 50-55° C., 55-60° C., 60-70° C., 70-75° C.). In certain embodiments, the method further comprises a step of reacting A (e.g., approximately 1-100 μM of A) comprising cyclooctyne (e.g., DIBAC/DBCO) as a first click-chemistry handle, B (e.g., approximately 100-1000 μM of B, for example, comprising azide as a second click-chemistry handle), optionally Cu-BTTAA (e.g., approximately 100-110 μM of Cu-BTTAA), sodium ascorbate with buffer (e.g., PBS) and solvent (e.g., acetonitrile, DMSO) of 0-50% (e.g., 25-50%) of either buffer or solvent in the reaction, for at least approximately 6-48 hours at approximately 18-75° C. (e.g., 18-23° C., 20-25° C., 25-40° C., 40-50° C., 50-55° C., 55-60° C., 60-70° C., 70-75° C.).

In certain embodiments, the method further comprises a step of reacting A (e.g., approximately 1-100 μM of A) comprising cyclooctyne (e.g., DIBAC/DBCO) as a first click-chemistry handle, B (e.g., approximately 100-1000 μM of B, for example, comprising azide as a second click-chemistry handle), buffer (e.g., PBS) and solvent (e.g., acetonitrile, DMSO) of up to a final concentration of 0-50% (e.g., 25-50%) of either buffer or solvent in the reaction, for at least approximately 6-48 hours at approximately 18-75° C. (e.g., 18-23° C., 20-25° C., 25-40° C., 40-50° C., 50-55° C., 55-60° C., 60-70° C., 70-75° C.).

In certain embodiments, the method further comprises a step of reacting A (e.g., approximately 1-100 μM of A) comprising alkene as a first click-chemistry handle, B (e.g., approximately 100-1000 μM of B), optionally Cu-BTTAA (e.g., approximately 100-110 μM of Cu-BTTAA), buffer (e.g., PBS) and solvent (e.g., acetonitrile, DMSO) of up to a final concentration of 0-50% (e.g., 25-50%) of either buffer or solvent in the reaction, for at least approximately 6-48 hours at approximately 18-75° C. (e.g., 18-23° C., 20-25° C., 25-40° C., 40-50° C., 50-55° C., 55-60° C., 60-70° C., 70-75° C.). In certain embodiments, the method further comprises a step of reacting A (e.g., approximately 10-20 μM of A), B (e.g., approximately 20-30 μM of B), optionally Cu-BTTAA (e.g., approximately 100-110 μM of Cu-BTTAA), buffer (e.g., PBS) and solvent (e.g., acetonitrile, DMSO) of up to a final concentration of 0-50% (e.g., 25-50%) of either buffer or solvent in the reaction, for at least approximately 6-24 hours at approximately 18-75° C. (e.g., 18-23° C., 20-25° C., 25-40° C., 40-50° C., 50-55° C., 55-60° C., 60-70° C., 70-75° C.). In certain embodiments, the method further comprises a step of reacting A (e.g., approximately 10-20 μM of A), B (e.g., approximately 20-30 μM of B), optionally Cu-BTTAA (e.g., approximately 100-110 μM of Cu-BTTAA), buffer (e.g., PBS) and solvent (e.g., acetonitrile, DMSO) of up to a final concentration of 0-50% (e.g., 25-50%) of either buffer or solvent in the reaction for at least approximately 24-48 hours at approximately 18-75° C. (e.g., 18-23° C., 20-25° C., 25-40° C., 40-50° C., 50-55° C., 55-60° C., 60-70° C., 70-75° C.). In certain embodiments, the first step is carried out under conditions for a click chemistry reaction that is a strain-promoted azide-alkyne cycloaddition (SPAAC), a transcyclooctyne (TCO)-tetrazine ligation, transcyclooctene-tetrazine ligation, an azide-Staudinger ligation, a cross-linking between a primary amine and a N-hydroxysuccinimide ester (NHS ester), a transcyclooctyne-azide coupling, or a cyclopropane-azide coupling. In certain embodiments, the first step is carried out under conditions for a click chemistry reaction that is a strain-promoted azide-alkyne cycloaddition (SPAAC). In certain embodiments, the first step is carried out under conditions for a click chemistry reaction that is a strain-promoted azide-alkyne cycloaddition (SPAAC), which involves a reaction between a cyclooctyne (e.g., DIBAC/DBCO) as the first click-chemistry handle and azide as the second click-chemistry handle. In certain embodiments, the first step is carried out under conditions for a click chemistry reaction that is a transcyclooctyne (TCO)-tetrazine ligation or transcyclooctene-tetrazine ligation. In certain embodiments, the first step is carried out under conditions for a click chemistry reaction that is a transcyclooctyne (TCO)-tetrazine ligation. In certain embodiments, the first step is carried out under conditions for a click chemistry reaction that is transcyclooctene-tetrazine ligation. In certain embodiments, the first step is carried out under conditions for a click chemistry reaction that is an azide-Staudinger ligation, a cross-linking between a primary amine and a N-hydroxysuccinimide ester (NHS ester), a transcyclooctyne-azide coupling, or a cyclopropane-azide coupling. In certain embodiments, the first step is carried out under conditions for a click chemistry reaction that is an azide-Staudinger ligation. In certain embodiments, the first step is carried out under conditions for a click chemistry reaction that is a cross-linking between a primary amine and a N-hydroxysuccinimide ester (NHS ester). In certain embodiments, the first step is carried out under conditions for a click chemistry reaction that is a transcyclooctyne-azide coupling. In certain embodiments, the first step is carried out under conditions for a click chemistry reaction that is a cyclopropane-azide coupling. In certain embodiments, the method further comprises a step of adding approximately 10-25 mM Ethylenediaminetetraacetic Acid (EDTA) (e.g., approximately 15-20 mM EDTA, approximately 18-20 mM EDTA, approximately 20-22 mM EDTA, approximately 20 mM EDTA), for example, to quench the reaction. In certain embodiments, the method further comprises a step of enzymatic transformation of the N-glycan of the compound of Formula (I), for example, comprises addition of sugar(s) (e.g., a sugar) by a sialyltransferase or fucosyltransferase, or mannosidase cleavage (e.g., cleavage of existing sugar(s)). In certain embodiments, the method further comprises a step of precipitation and/or column purification of the compound of Formula (I), for example, via silica-based RNA or DNA desalting columns. In certain embodiments, in a method of preparing a compound of Formula (I), the first click-chemistry handle and the second click-chemistry handle are as described herein. In certain embodiments, in a method of preparing a compound of Formula (I), the first click-chemistry handle and the second click-chemistry handle are one of the pairs of click-chemistry handles shown in Table 3 or 4. In certain embodiments, in a method of preparing a compound of Formula (I), the first click-chemistry handle and the second click-chemistry handle are click-chemistry handles used in CuAAC. In certain embodiments, the first click-chemistry handle is an alkyne or azide. In certain embodiments, the first click-chemistry handle is an alkyne (e.g., unstrained alkyne, strained alkyne). In certain embodiments, the first click-chemistry handle is an alkyne that comprises the formula: In certain embodiments, the nucleic acid A comprises the first click-chemistry handle that is an alkyne attached to a base of the nucleic acid. In certain embodiments, A comprises the structure:

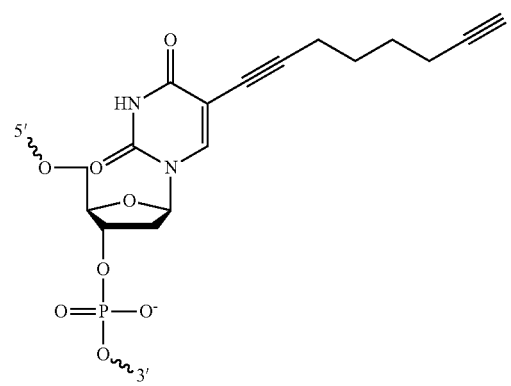

(5-Octadiynyl dU, aka i5OctdU), and A is RNA or DNA.

In certain embodiments, the nucleic acid A comprises the first click-chemistry handle that is an alkyne attached to the 2'OH position of a ribose of the nucleic acid. In certain embodiments, in a method of preparing a compound of Formula (I), the first click-chemistry handle and the second click-chemistry handle are click-chemistry handles used in a copper-free biorthogonal click chemistry reaction, for example, click-chemistry handle partners shown in reactions 1-13 of Table 4 (e.g., azide-cyclooctyne, azide-activated alkyne, tetrazine-alkene, tetrazole-alkene, thiol-alkene). In certain embodiments, in a method of preparing a compound of Formula (I), the first click-chemistry handle and the second click-chemistry handle are a cyclooctyne and azide, respectively. In certain embodiments, the first click-chemistry handle and the second click-chemistry handle are click-chemistry handles used in an alkene-tetrazine Diels-Alder retro [4+2] cycloaddition or alkene-tetrazole 1,3-dipolar cycloaddition (photoclick), shown in Table 4. In certain embodiments, the first click-chemistry handle is an alkene (e.g., transcyclooctene, norbornene, cyclopropene, 1-methylcyclopropene (MCp)). In certain embodiments, A comprises the first click-chemistry handle that is an alkene (e.g., transcyclooctene, norbornene, and 1-methylcyclopropene (MCp)). In certain embodiments, A comprises the first click-chemistry handle that is an alkene (vinyl) and B comprises a second click-chemistry handle that is a tetrazine. In certain embodiments, A comprises the first click-chemistry handle that is an alkene (vinyl) (e.g., in FIGS. 2B and/or 2C in Kubota et al.) in Kubota et al., "Expanding the Scope of RNA Metabolic Labeling with Vinyl Nucleosides and Inverse Electron-Demand Diels-Alder Chemistry." *ACS Chemical Biology* vol. 14, 8 (2019): 1698-1707, incorporated herein by reference, and B comprises a second click-chemistry handle that is an tetrazine (e.g., in FIG. 3A Kubota et al.). In certain embodiments, the nucleic acid A comprises the first click-chemistry handle that is an alkyne (e.g., unstrained alkyne, strained alkyne) attached to the 2'OH position of a ribose, 3'OH position of a ribose or deoxyribose, or 5'OH position of a ribose or deoxyribose of the nucleic acid A. In certain embodiments, in Formula (I), A comprises the first click-chemistry handle that is an alkyne (e.g., unstrained alkyne, strained alkyne) attached to the 2'OH position of a ribose of the nucleic acid A. In certain embodiments, in Formula (I), A comprises the first click-chemistry handle that is an alkyne (e.g., unstrained alkyne, strained alkyne) attached to the 3'OH position of a ribose or deoxyribose of the nucleic acid A. In certain embodiments, in Formula (I), A comprises the first click-chemistry handle that is an alkyne (e.g., unstrained alkyne, strained alkyne)

attached to an internal portion of the nucleic acid A, the 3' end of the nucleic acid A, or the 5' end of the nucleic acid A. In certain embodiments, in Formula (I), A comprises the first click-chemistry handle that is an alkyne (e.g., unstrained alkyne, strained alkyne) attached to an internal portion of the nucleic acid A. In certain embodiments, A comprises the first click-chemistry handle that is cyclooctyne (e.g., DIBAC, DBCO). In certain embodiments, A comprises the first click-chemistry handle that is cyclooctyne (e.g., DIBAC, DBCO), and B comprises the second click-chemistry handle that is an azide. In certain embodiments, A comprises the first click-chemistry handle that is an alkene. In certain embodiments, A comprises the first click-chemistry handle that is an alkene (vinyl) (e.g., in FIGS. 2B and/or 2C in Kubota et al.) in Kubota et al., "Expanding the Scope of RNA Metabolic Labeling with Vinyl Nucleosides and Inverse Electron-Demand Diels-Alder Chemistry." *ACS Chemical Biology* vol. 14, 8 (2019): 1698-1707, incorporated herein by reference. In certain embodiments, A comprises the first click-chemistry handle that is an alkene, wherein A comprises

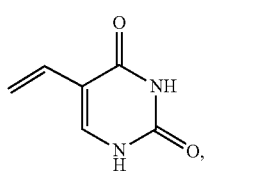
(5-VU,1)

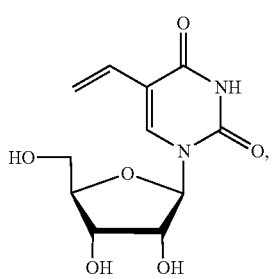
(5-VU)

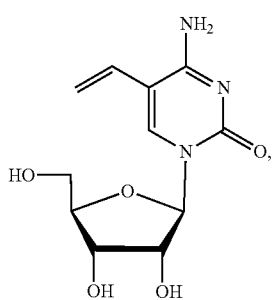
(5-VC)

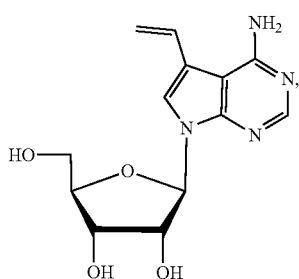
(7-dVA)

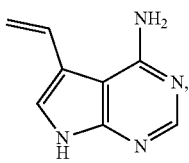
(7-dVAb)

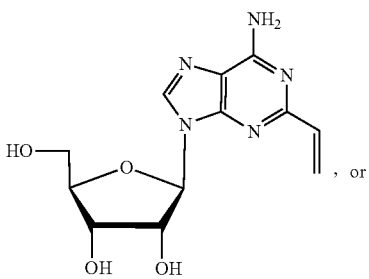
(2-VA)
, or

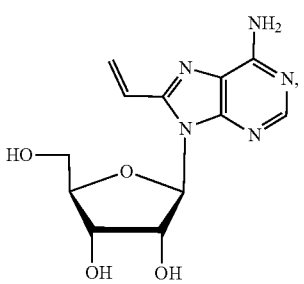
(2-VA,4)

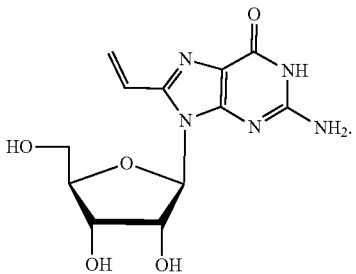
(8-VG,6)

In certain embodiments, the first click-chemistry handle is an azide. In certain embodiments, the nucleic acid A comprises the first click-chemistry handle that is an azide attached to a base of the nucleic acid. In certain embodiments, the second click-chemistry handle is an alkyne (e.g., unstrained alkyne, strained alkyne). In certain embodiments, the compound B comprises the second click-chemistry handle (e.g., a handle in Table 3 or 4) attached to the non-reducing end of the N-glycan. In certain embodiments, the compound B comprises the second click-chemistry handle that is an alkyne or azide attached to the non-reducing end of the N-glycan. In certain embodiments, the compound B comprises the second click-chemistry handle that is an alkyne attached to the non-reducing end of the N-glycan. In certain embodiments, the compound B comprises the second click-chemistry handle that is an azide attached to the non-reducing end of the N-glycan. In certain embodiments, A comprises the first click-chemistry handle that is an alkyne (e.g., unstrained alkyne, cyclooctyne) attached to DNA or RNA, and the compound B comprises the second click-chemistry handle that is an azide attached to the N-glycan. In certain embodiments, A comprises the first click-chemistry handle that is an alkyne (e.g., unstrained alkyne, cyclooctyne), and the compound B comprises the second click-chemistry handle that is an azide attached to the non-reducing end of the N-glycan.

In certain embodiments, B is an N-glycan that is a mono-antennary N-glycan, a bi-antennary N-glycan, a tri-antennary N-glycan, or a penta-antennary N-glycan. In certain embodiments, B is an N-glycan that comprises sialic acid. In certain embodiments, the compound B is of the formula:

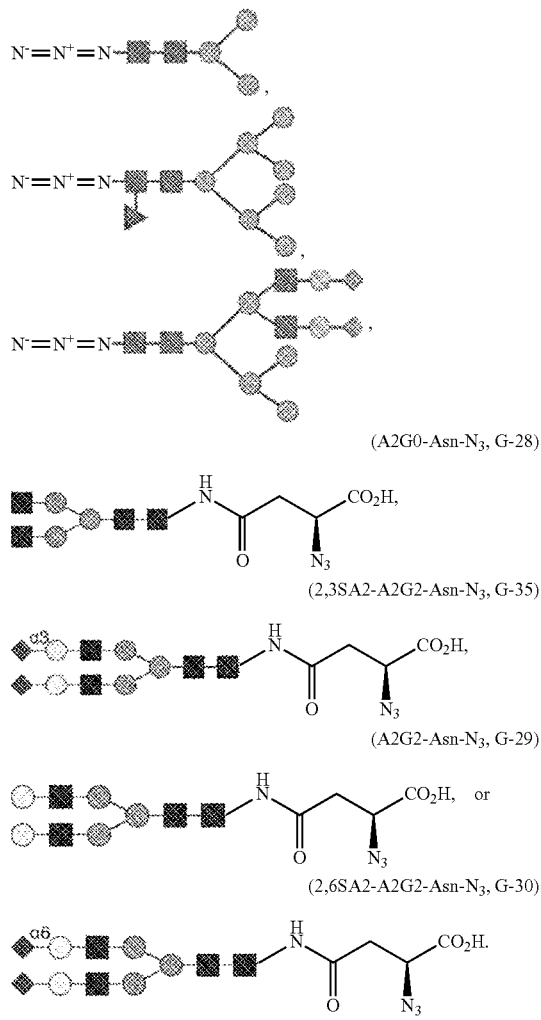

(A2G0-Asn-N₃, G-28)

(2,3SA2-A2G2-Asn-N₃, G-35)

(A2G2-Asn-N₃, G-29)

(2,6SA2-A2G2-Asn-N₃, G-30)

In certain embodiments, the compound B is G-28, G-35, G-29, or G-30.

In certain embodiments, the compound B is a compound of Table 2B.

In certain embodiments, the compound B is prepared by transforming an amino N-glycan into the corresponding azido-N-glycan, via fluorosulfuryl azide mediated diazotransfer. In certain embodiments, the compound B, which is an azido-N-glycan, is prepared by adding to an amino N-glycan of the formula

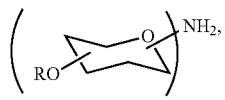

fluorosulfuryl azide, water, base (e.g., Na₂CO₃), at basic pH (e.g., approximately 8.5-9.5, approximately 9.0), at room temperature (e.g., approximately 18-23° C.) for approximately 1-2 hours (e.g., 1 hour). In certain embodiments, the compound B, which is an azido-N-glycan, is prepared via scheme 1 below:

Scheme 1. Preparation of azido-N-gylcan, an exemplary compound B

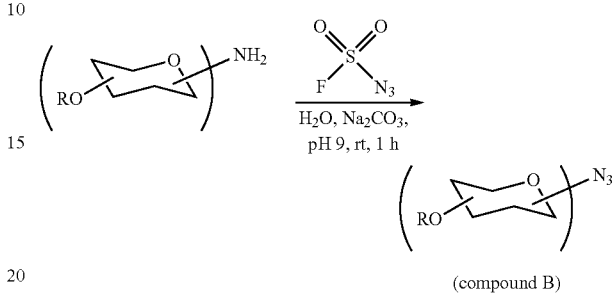

(compound B)

In certain embodiments, the compound of Formula (I) that is prepared is a compound shown in FIG. 9. In certain embodiments, the compound of Formula (I) that is prepared is a compound disclosed elsewhere herein.

Uses for Glyconucleic Acids

In one aspect, provided herein are methods and processes that utilize the modified glyconucleic acids of the present disclosure.

In one embodiment, the present disclosure provides methods whereby an isolated cell or a plurality of isolated cells are contacted with a modified glyconucleic acid of the present disclosure. In one embodiment, the present disclosure provides a method of producing a treated cell or a plurality of cells, comprising providing an isolated cell or a plurality of isolated cells, providing a modified nucleic acid comprising a glycan, as described in the present disclosure, and contacting the modified nucleic acid to the isolated cell or plurality of cells, wherein the isolated cell or plurality of cells is capable of binding the modified nucleic acid. In some embodiments, the modified nucleic acid comprising a glycan comprises a small modified RNA, such as an siRNA. In some embodiments, the modified nucleic acid comprising a glycan comprises a large modified RNA, such as an mRNA. In some embodiments, the contacting of the isolated cell or a plurality of cells further comprises electroporation.

In one embodiment, the present disclosure provides a method of generating a chimeric antigen receptor, comprising contacting an appropriate cell with a glyconucleic acid of the present disclosure, wherein the glyconucleic acid comprises a modified RNA comprising a sequence encoding a chimeric antigen receptor polypeptide. In some embodiments, the method comprises administering to a subject an effective amount of a pharmaceutical composition comprising a pharmaceutically acceptable carrier and a modified RNA of the present disclosure, wherein the modified RNA comprises a sequence encoding a chimeric antigen receptor polypeptide.

In some embodiments, the glyconucleic acids of the present disclosure internalize into cells. In some embodiments, the glyconucleic acids of the present disclosure internalize into cells with greater efficiency than analogous unmodified nucleic acids. In some embodiments, the glyconucleic acids of the present disclosure internalize into cells at least about 10% more, at least about 15% more, at least about 20% more, at least about 25% more, at least about 30% more, at least about 35% more, at least about 40% more, at least about 45% more, at least 50% more, at least 55% more, at least 60% more, at least 65% more, at least 70% more, at least 75% more, at least 80% more, at least 85% more, at least 90% more, at least 95% more, at least 100% more or at least 200% more than the analogous unmodified nucleic acids.

In some embodiments, the glyconucleic acids of the present disclosure bind to the surface of a cell. In some embodiments, the cell surface binding effects at least one change in cell signaling. In some embodiments, the binding of the glyconucleic acid to the cell surface increases at least one cell signaling pathway. In some embodiments, the binding of the glyconucleic acid to the cell surface decreases at least one cell signaling pathway.

Routes of Administration, Formulation and Pharmacodynamic Effect

Provided herein are pharmaceutical compositions comprising glyconucleic acids, such as glycoRNAs and glycoDNAs, that are suitable for administration to a subject. The pharmaceutical compositions generally comprise glyconucleic acids, such as glycoRNAs and glycoDNAs, and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions comprising glyconucleic acids, such as glycoRNAs and glycoDNAs. The pharmaceutical compositions are generally formulated as sterile, substantially isotonic and in full compliance with all Good Manufacturing Practice (GMP) regulations of the U.S. Food and Drug Administration.

Examples of suitable carriers include, but are not limited to, water, saline, Ringer's solutions, dextrose solution, and 5% human serum albumin. The use of such media and compounds for pharmaceutically active substances is well known in the art. Except insofar as any conventional media or compound is incompatible with the glyconucleic acids, such as glycoRNAs and glycoDNAs, described herein, use thereof in the compositions is contemplated. Supplementary therapeutic agents may also be incorporated into the compositions. Typically, a pharmaceutical composition is formulated to be compatible with its intended route of administration. The glyconucleic acids, such as glycoRNAs and glycoDNAs, can be administered by parenteral, topical, intravenous, oral, subcutaneous, intraarterial, intradermal, transdermal, rectal, intracranial, intraperitoneal, intranasal, intramuscular route or as inhalants. The glyconucleic acids, such as glycoRNAs and glycoDNAs, can optionally be administered in combination with other therapeutic agents that are at least partly effective in treating the disease, disorder or condition for which the glyconucleic acids, such as glycoRNAs and glycoDNAs, are intended.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens: antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition is typically sterile and should be fluid to the extent that easy syringeability exists. It should be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The desired degree of fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as mannitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the glyconucleic acids, such as glycoRNAs and glycoDNAs, in an effective amount and in an appropriate solvent with one or a combination of ingredients enumerated herein, as desired.

Generally, dispersions are prepared by incorporating the glyconucleic acids, such as glycoRNAs and glycoDNAs, into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The glyconucleic acids, such as glycoRNAs and glycoDNAs, can be administered in the form of a depot injection or implant preparation which can be formulated in such a manner to permit a sustained or pulsatile release of the glyconucleic acids.

Sterile injectable solutions can be prepared by incorporating the glyconucleic acids, such as glycoRNAs and glycoDNAs, in an effective amount and in an appropriate solvent with one or a combination of ingredients enumerated herein, as desired.

Generally, dispersions are prepared by incorporating the glyconucleic acids, such as glycoRNAs and glycoDNAs, into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The glyconucleic acids, such as glycoRNAs and glycoDNAs, can be administered in the form of a depot injection or implant preparation which can be formulated in such a manner to permit a sustained or pulsatile release of the glyconucleic acids and/or their payload(s) (e.g., encoded proteins).

For administration by inhalation, the glyconucleic acids, such as glycoRNAs and glycoDNAs, can be delivered in any suitable form using any suitable device, such as, an aerosol spray from pressured container or dispenser which contains a suitable propellant, e.g., a gas such as carbon dioxide, or a nebulizer, an aerosol using a nebulizer, or as a dry powder using a dry powder inhaler.

The glyconucleic acids, such as glycoRNAs and glycoDNAs, can also be prepared as pharmaceutical compositions in the form of suppositories (e.g., with conventional suppository bases such as cocoa butter and other glycerides) or retention enemas for rectal delivery.

In some embodiments, the glyconucleic acids, such as glycoRNAs and glycoDNAs, are prepared with carriers that will decrease the rate with which glyconucleic acids are eliminated from the body of a subject. For example, controlled release formulations are suitable, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment the pharmaceutical composition comprising glyconucleic acids, such as glycoRNAs and glycoDNAs, is administered intravenously into a subject that would benefit from the pharmaceutical composition. In other embodiments, the composition is administered to the lymphatic system, e.g., by intralymphatic injection or by intranodal injection (see e.g., Senti et al., 2008 PNAS 105(46):17908), or by intramuscular injection, by subcutaneous administration, by direct injection into the thymus, or into the liver.

Pharmaceutically acceptable carriers may be used to deliver the glyconucleic acids, such as glycoRNAs and glycoDNAs, described herein. Pharmaceutically acceptable carriers are used, in general, with a compound so as to make the compound useful for a therapy or as a product. In general, for any substance, a pharmaceutically acceptable carrier is a material that is combined with the substance for delivery to a subject.

Conventional pharmaceutical carriers, aqeuous, powder or oily bases, thickeners and the like may be necessary or desirable. In some cases, the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts.

Typically, pharmaceutically acceptable compositions are highly purified to be free of contaminants, are biocompatible and not toxic, and are suited to administration to a subject. If water is a constituent of the carrier, the water is highly purified and processed to be free of contaminants, e.g. endotoxins.

The pharmaceutically acceptable carrier may be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition may further include a lubricant, a wetting agent, a sweetener, a flavor enhancer, an emulsifying agent, a suspension agent, and/or a preservative.

In specific examples, glyconucleic acids, such as glycoRNAs and glycoDNAs, can be stored in an appropriate buffer, e.g., an FDA-approved anticoagulant preservative solution such as anticoagulant citrate-dextrose A (ACD-A), citrate-phosphate dextrose (CPD), Citratephosphate-dextrose-dextrose (CP2D), or citrate-phosphate-dextrose-adenine (CPDA-1). The compositions may be stored for up to 21 days.

In other examples, glyconucleic acids, such as glycoRNAs and glycoDNAs, can be stored in an approved additive solution, e.g., AS-1 (Adsol), AS-3 (Nutricel), AS-5 (Optisol), or AS-7 (SOLX).

Medical devices are provided that comprise a container holding a pharmaceutical composition comprising a glyconucleic acids, such as glycoRNAs and glycoDNAs, described herein and an applicator for intravenous injection of the pharmaceutical composition to a subject.

Medical kits are provided that comprise a pharmaceutical composition comprising a glyconucleic acids, such as glycoRNAs and glycoDNAs, described herein and a medical device for intravenous injection of the pharmaceutical composition to a subject.

In some embodiments, nanoparticles comprising a lipid component and a glyconucleic acid, such as glycoRNAs and glycoDNAs, can be administered, for example by parenteral or topical administration or topical application. In some embodiments, at least a portion of the protein expressed by the glyconucleic acids, such as glycoRNAs and glycoDNAs, is localized to a desired target tissue or target cell location via topical administration.

Administration of a pharmaceutical composition comprising at least one nanoparticle to a subject may involve contacting one or more cells with the pharmaceutical composition via topical administration or topical application.

In some embodiments, the methods of administration comprise providing electroporation. In some embodiments, the method comprises providing a modified RNA comprising a glycan moiety, as disclosed and described elsewhere herein, and providing electroporation to the subject.

In some embodiments, the pharmaceutical compositions disclosed herein are formulated for systemic administration to a human subject in need thereof. In some embodiments, the pharmaceutical compositions disclosed herein are formulated for systemic administration to a mammalian subject in need thereof. In some embodiments, the pharmaceutical compositions disclosed herein are formulated for multiple systemic administrations to a human subject in need thereof. In some embodiments, the pharmaceutical compositions disclosed herein are formulated for multiple systemic administrations to a mammalian subject in need thereof.

In some embodiments, the pharmaceutical composition comprising a modified nucleic acid conjugated to a glycan produces a long lasting pharmacodynamic effect when administered to a subject. In some embodiments, the pharmaceutical composition comprising a modified nucleic acid conjugated to a glycan provides a pharmacodynamic effect for at least one week after administration to the subject. In some embodiments, the pharmaceutical composition comprising a modified nucleic acid conjugated to a glycan provides a pharmacodynamic effect for at least one month after administration to the subject. In some embodiments, the pharmaceutical composition comprising a modified nucleic acid conjugated to a glycan provides a pharmacodynamic effect for at least three months after administration to the subject. In some embodiments, the pharmaceutical composition comprising a modified nucleic acid conjugated to a glycan provides a pharmacodynamic effect for at least six months after administration to the subject. In some embodiments, the pharmaceutical composition comprising a modified nucleic acid conjugated to a glycan provides a pharmacodynamic effect for at least one year after administration to the subject. In some embodiments, the pharmaceutical composition comprising a modified nucleic acid conjugated to a glycan provides a pharmacodynamic effect for at least 18 months after administration to the subject. In some embodiments, the modified nucleic acid conjugates provide increased circulation time in the body of a subject, as compared to comparable nucleic acids that are not conjugated to a glycan. In some embodiments, the modified nucleic acid conjugates have an increased half-life in the body of a subject, as compared to comparable nucleic acids that are not conjugated to a glycan. In some embodiments, the modified nucleic acid conjugates have increased stability in the body of a subject, as compared to comparable nucleic acids that are not conjugated to a glycan.

In another aspect, the present disclosure provides a pharmaceutical composition comprising a glyconucleic acid of the present disclosure, formulated as part of a nanoparticle composition. In one embodiment, the glyconucleic acid is present inside of, or within, a nanoparticle. In another embodiment, the glyconucleic acid is present on the surface of the nanoparticle. In some embodiments, the nanoparticle is a lipid nanoparticle (LNP). In some embodiments, the nanoparticle is a LNP, such as, but not limited to, those described in patent application publications WO2017049245A2, WO2019089828A1, and US20170210697A1, each of which is incorporated herein by reference, in their entirety. In another embodiment, the nanoparticle is a polymeric nanoparticle. In another embodiment, the nanoparticle is a polymeric nanoparticle, such as, but not limited to, those described by Begines, et al. (Nanomaterials 2020 July; 10(7): 1403). In another aspect, the present disclosure provides processes of making nanoparticle formulations comprising a glyconucleic acid of the present disclosure. In one embodiment, the process of producing a glyconucleic acid nanoparticle comprises providing a nucleic acid, contacting the nucleic acid with a glycan under conditions such that the nucleic acid is conjugated to the glycan to produce a modified nucleic acid comprising a glycan moiety, and then contacting the modified nucleic acid comprising a glycan moiety with a nanoparticle under conditions such that a nanoparticle comprising the glyconucleic acid is formed. In some embodiments, said nanoparticle is an LNP.

In some embodiments, the glyconucleic acids of the present disclosure are serum stable. In some embodiments, the conjugation of the glycan to the nucleic acid imparts stability to the conjugate as a whole, such that the conjugate has a longer shelf-life in serum than the same nucleic acid lacking the conjugated glycan. In one aspect, the present disclosure provides a method of producing a serum comprising a glyconucleic acid of the present disclosure, said method comprising providing a modified nucleic acid comprising a glycan moiety comprising at least ten monosaccharides, and providing a serum, wherein the glycan provides stabilization to the nucleic acid within the serum.

Dosages

The dosing and frequency of the administration of the glycoRNAs and pharmaceutical compositions thereof can be determined by the attending physician based on various factors such as the severity of disease, the patient's age, sex and diet, the severity of any inflammation, time of administration, and other clinical factors. In one example, an intravenous administration is initiated at a dose which is minimally effective, and the dose is increased over a preselected time course until a positive effect is observed. Subsequently, incremental increases in dosage are made limiting to levels that produce a corresponding increase in effect while taking into account any adverse affects that may appear.

Non-limited examples of suitable dosages can range, for example, from $1\times10^{10}$ to $1\times10^{14}$, from $1\times10^{11}$ to $1\times10^{13}$, or from $5\times10^{11}$ to $5\times10^{12}$ glycoRNAs. Specific examples include about $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, or more glycoRNAs. Each dose of glycoRNAs can be administered at intervals such as once daily, once weekly, twice weekly, once monthly, or twice monthly.

Provided are pharmaceutical compositions containing effective levels of glycoRNAs. Such compositions contain a plurality of glycoRNAs, e.g., $1\times10^3$ glycoRNAs, or $1\times10^4$, $1\times10^5$, $1\times10^6$, $1\times10^7$, $1\times10^8$, $1\times10^9$, $1\times10^{10}$, $1\times10^{11}$, $1=10^{12}$, or greater than $1\times10^{12}$ glycoRNAs. In specific examples, glycoRNAs may be administered in a saline solution at a concentration of 10%, 20%, 30%, 40%, 50%, 60%, 70%, 80%, 90%, or greater than 90% mass to volume ratio (% m/v). The time of administration to a patient may range from 10 minutes to four hours, or more.

Dosage forms are provided that comprise a pharmaceutical composition comprising a glycoRNA described herein. In some embodiments, the dosage form is formulated as a liquid suspension for intravenous injection.

A pharmaceutically acceptable suspension of glycoRNA is preferably packaged in a volume of approximately 10 to approximately 250 ml. The packaging can be a syringe or an IV bag suitable for transfusions. Administration of the suspension is carried out, e.g., by intravenous or intra-arterial injection, optionally using a drip from an IV bag or the like. The administration is typically carried out intravenously in the arm or via a central catheter. For administrations exceeding 50 ml use of a drip is preferred.

In certain embodiments, nanoparticles as disclosed herein may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of glycoRNA per subject body weight per day, one or more times a day, to obtain the desired therapeutic effect.

In some embodiments, nanoparticles as disclosed herein are administered to a subject in a single administration. In some embodiments, nanoparticles as disclosed herein are administered to the subject, at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. In each of the embodiments in this paragraph, the "multiple administrations" can be separated from each other by short (1-5 mins), medium (6-30 minutes), or long (more than 30 minutes, hours, or even days) intervals of time.

The nanoparticles may be administered to a subject using any dosage of administration effective for treating a disease, disorder, and/or condition. The exact dosage required will vary from subject to subject, depending on the age and general condition of the subject, the severity of the disease, the particular formulation, its mode of administration, its mode of activity, and the like. It will be understood, however, that the total daily usage of the compositions may be decided by the attending physician within the scope of sound medical judgment. The specific pharmaceutically effective dose level for any particular patient will depend upon a variety of factors including the severity of the disease, the specific composition employed, the age, body weight, general health, sex and diet of the patient, the time of administration, route of administration, the duration of the treatment, and like factors well-known in the medical arts.

Diseases, Disorders, and Conditions

In one aspect, provided herein are methods of modulating the concentration of a target to treat or prevent a disease, disorder or condition associated with the presence, absence, elevated or depressed concentration of the target in a subject. As used herein, the term "target" refers to a molecule or other chemical entity involved in the etiology of a disease, disorder or condition, or is diagnostic or a disease, disorder or condition. The subject may suffer from a disease, disorder or condition or may be at risk of developing the disease, disorder or condition. The methods provided herein include the administration of a suitable glyconucleic acids, such as glycoRNAs and glycoDNAs, described herein in an amount effective to substantially modulate the concentration of the target, thereby preventing or treating the disease, disorder or condition. In some embodiments, the glyconucleic acids, such as glycoRNAs and glycoDNAs, are formulated as a pharmaceutical composition. In some embodiments, the pharmaceutical composition is formulated for parenteral administration, such as intravenous injection to the subject. In some embodiments, the pharmaceutical composition is formulated for topical administration to the subject. The compositions may be administered to the subject in any desired regimen, such as by administration once to the subject or multiple administrations may be performed over a period of time. For example, two, three, four, five, or more administrations may be given to the subject. In some embodiments, administrations may be given as needed, e.g., for as long as symptoms associated with the disease, disorder or condition persist. In some embodiments, repeated administrations may be indicated for the remainder of the subject's life. Treatment periods may vary and could be, e.g., no longer than a year, six months, three months, two months, one month, two weeks, one week, three days, two days, or no longer than one day.

In some embodiments, the compositions are administered at least twice over a treatment period such that the disease, disorder or condition is treated, or a symptom thereof is decreased. In some embodiments, the compositions are administered at least twice over a treatment period such that the disease, disorder or condition is treated, or a symptom thereof is prevented. In some embodiments, the pharmaceutical composition is administered a sufficient number of times over a treatment period such that the concentration of the target is substantially decreased during the treatment period. In some embodiments wherein the target is a self-antibody, the pharmaceutical composition is administered a sufficient number of times over a treatment period such that the concentration of the target self-antibody is substantially decreased during the treatment period such that one or more symptoms of the self-antibody mediated disease, disorder or condition is prevented, decreased or delayed. In some embodiments, decreasing the concentration of the target includes decreasing the peak concentration, while in others it includes decreasing the average concentration. In some embodiments, a substantial decrease during the treatment period can be determined by comparing a pretreatment or post-treatment period in the human subject, or by comparing measurements made in a population undergoing treatment with a matched, untreated control population. In some embodiments, the concentration of the target is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period. In some embodiments, the concentration of the target is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the pharmaceutical composition is administered a sufficient number of times over a treatment period such that the concentration of the target is decreased at a rate greater than i) the endogenous clearance rate of the target by the human subject, or ii) the endogenous production rate of the target by the human subject, or iii) both i) and ii). In some embodiments, the pharmaceutical composition is administered a sufficient number of times a treatment period such that the concentration of the target is substantially decreased for at least about one week, two weeks, three weeks, four weeks, one month, two months, three months, four months, five months, six months, or greater than six months. In some embodiments, the pharmaceutical composition is administered a sufficient number of times a treatment period such that the concentration of the target is substantially decreased for a period of time at least as long as the treatment period.

In some embodiments, the pharmaceutical composition is administered at a frequency sufficient to effectively reduce the concentration of the target below a level that is associated with a symptom of the disease, disorder or condition.

In some embodiments, the time interval between administrations within a treatment period is no longer than the period in which the number of glycoRNAs is reduced to less than about 5%, 10%, 15%, 20%, 25%, 30%, 35%, 40%, 45%, 50%, 55%, 60%, 65%, 70%, 75%, 80%, 85%, 90% or 95% of the number of glycoRNAs present in the administered pharmaceutical composition.

Diseases, disorders and conditions associated with targets that may be treated or prevented by administering glyconucleic acids, such as glycoRNAs and glycoDNAs, are described herein.

Diseases, disorders and conditions associated with targets that modulated for therapeutic benefit by administering glyconucleic acids, such as glycoRNAs and glycoDNAs, include, but are not limited to: antiself-antibody-mediated diseases, complement dysregulation-associated diseases, immune complex associated diseases, amyloidoses, diseases associated with infectious agents or pathogens (e.g., bacterial, fungal, viral, parasitic infections), disease associated with toxic proteins, diseases associated with the accumulation of lipids, diseases associated with apoptotic, necrotic, aberrant or oncogenic mammalian cells, and metabolic diseases.

Provided herein, in some embodiments, are methods for the treatment or prevention of diseases or conditions that are associated with targets (e.g., molecules or entities) that can be modulated for therapeutic effect. The methods comprise, in certain embodiments, administering to a subject in need thereof a glyconucleic acids, such as glycoRNAs and glycoDNAs, or compositions, preferably pharmaceutical compositions comprising a glyconucleic acid, in an amount effective to treat or prevent the disease or condition that is associated with the molecules or entities.

Methods are provided for the treatment or prevention of inflammation and diseases associated with inflammation, including sepsis, autoimmune disease, cancer, and microbial infections, the methods comprising, administering to a subject in need thereof glyconucleic acids, such as glycoRNAs and/or glycoDNAs, in an amount effective to treat or prevent the inflammation or an associated disease. In some embodiments, the glycoRNA comprises a sequence encoding a chemokine or cytokine receptor.

Methods are provided for the modulation of chemokine homeostasis at sites of inflammation, the methods comprising, administering to a subject in need thereof glyconucleic acids, such as glycoRNAs and/or glycoDNAs, in an amount effective to modulate chemokine homeostasis at sites of inflammation. In some embodiments, the glyconucleic acid is a glycoDNA or glycoRNA that comprises a sequence encoding a chemokine receptor.

Further provided are methods of inducing toxin clearance. The methods include administering to a subject in need thereof glyconucleic acids, such as glycoRNAs and/or glycoDNAs, comprising a sequence encoding a peptide that is capable of interacting with a toxin, such as e.g., an antibody, scFv or nanobody, in an amount effective to clear toxins from circulation. Such methods may be employed to sequester the toxin and reduce the amount of tissue damage that would otherwise occur within the vasculature and dissipating its pathogenic effects in a less acute manner.

In some embodiments, provided are methods of treating diseases, including, but not limited to, metabolic diseases, cancers, clotting and anti-clotting diseases. The methods include administering to a subject in need thereof a pharmaceutical composition of glyconucleic acids, such as glycoRNAs and/or glycoDNAs, comprising a sequence encoding a peptide provided herein in an amount sufficient to treat the metabolic disease, the cancer, the clotting disease or anti-clotting disease of the subject.

In some embodiments, the disease, disorder or condition is a metabolic disease. In some embodiments, the disease, disorder or condition is a cancer. In some embodiments, the disease, disorder or condition is a clotting disease. In some embodiments, the disease, disorder or condition is an anti-clotting disease. In some embodiments, the disease, disorder or condition is an autoimmune disease. In some embodiments, the disease, disorder or condition is an IgE-mediated allergy. In some embodiments, the disease, disorder or condition is systemic lupus erythematosus. In some embodiments, the disease, disorder or condition is a viral infection.

In some embodiments, the glyconucleic acids, such as glycoRNAs and/or glycoDNAs, increase the expression of a target. In some embodiments, the glycoRNA comprises a circular RNA comprising a sequence encoding a peptide or protein.

In another aspect, provided are pharmaceutical compositions comprising glyconucleic acids of the disclosure, for use in the treatment of diseases, disorders and conditions disclosed herein. In yet another aspect, provided are pharmaceutical compositions comprising glyconucleic acids of the disclosure, for use in manufacture of a medicament for treating diseases, disorders and conditions disclosed herein.

Combination Therapies

In one embodiment, the invention is directed to a method of killing cancer cells in a subject by administering to the subject a therapeutically effective amount of glyconucleic acids, such as glycoRNAs and/or glycoDNAs. In one aspect of this embodiment, glyconucleic acids, such as glycoRNAs and glycoDNAs, are administered intravenously to the subject. In another aspect of this embodiment, glyconucleic acids, such as glycoRNAs and glycoDNAs, are administered into a tumor in the subject. In still another aspect of this embodiment, glyconucleic acids, such as glycoRNAs and glycoDNAs, are administered in proximity to the tumor or administered systemically in a vehicle that allows delivery to the tumor.

In another embodiment, the invention is directed to a method of treating a cancer in a subject by administering to the subject a therapeutically effective amount of a glyconucleic acid, such as glycoRNA and/or glycoDNA. In one aspect of this embodiment, glycoRNA is administered intravenously to the subject. In another aspect of this embodiment, glycoRNA is administered into a tumor in the subject. In still another aspect of this embodiment, glycoRNA is administered in proximity to the tumor or administered systemically in a vehicle that allows delivery to the tumor.

The cancer (and the cancer cells) are any cancer that afflicts a subject. Such cancers include liver, colon, pancreatic, lung, and bladder cancer. The liver cancer can be a primary liver cancer or a cancer that has metastasized to the liver from another tissue. Primary liver cancers include hepatocellular carcinoma and hepatoblastoma. Metastasized cancers include colon and pancreatic cancer.

In one embodiment, the invention is directed to a method of killing cancer cells in a subject by administering to the subject a therapeutically effective amount of an immune checkpoint inhibitor with the therapeutically effective amount of glyconucleic acid, such as glycoRNA and/or glycoDNA. In one aspect of this embodiment, the administration of the immune checkpoint inhibitor with the glyconucleic acid (e.g., glycoRNA) increases the efficacy of the glyconucleic acid (e.g., glycoRNA).

In another embodiment, the invention is directed to a method of treating a cancer in a subject by administering to the subject a therapeutically effective amount of an immune checkpoint inhibitor with the therapeutically effective amount of glyconucleic acid, such as glycoRNA and/or glycoDNA. In one aspect of this embodiment, the administration of the immune checkpoint inhibitor with the glyconucleic acid (e.g., glycoRNA) increases the efficacy of the glyconucleic acid (e.g., glycoRNA).

As stated above, the immune checkpoint inhibitor and the glyconucleic acid, such as glycoRNA and/or glycoDNA, are administered intravenously to the subject, into a tumor in the subject in proximity to the tumor, or systemically in a vehicle that allows delivery to the tumor.

In one aspect of this embodiment, the immune checkpoint inhibitor is a monoclonal antibody that blocks the interaction between receptors, such as PD-1, PD-L1, CTLA4, Lag3, and Tim3, and ligands for those receptors on mammalian cells, such as human cells. In a particular aspect, the monoclonal antibody is a monoclonal antibody to PD1 or PDL1.

Examples of monoclonal antibodies include Atezolizumab, Durvalumab, Nivolumab, Pembrolizumab, and Ipilimumab. In still another aspect of this embodiment, the immune checkpoint inhibitor is a small molecule that blocks the interaction between receptors, such as PD-1, PD-L1, CTLA4, Lag3, and Tim3, and ligands for those receptors on mammalian cells, such as human cells. In a particular aspect, the small molecule blocks binding between PD1 and PDL1. BMS202 and similar ligands are examples of such small molecules.

The immune checkpoint inhibitor administered with the glyconucleic acid, such as glycoRNA and/or glycoDNA, molecules is a monoclonal antibody or a small molecule as described above. It can be administered before, after, or concurrently with the combination of the glyconucleic molecules.

In another embodiment, this pharmaceutical composition is used in connection with an immune checkpoint inhibitor as described herein. Thus, this embodiment of the invention is directed to a combination of therapeutic drugs comprising an immune checkpoint inhibitor and a pharmaceutical composition comprising a glyconucleic acid, such as glycoRNA and/or glycoDNA, in a pharmaceutically acceptable carrier as described herein.

In some embodiments, the modified nucleic acid further comprises at least one therapeutic moiety operably linked to the modified nucleic acid. In some embodiments, the at least one therapeutic moiety is selected from the group consisting of an antibody, a small molecule, an isotope, an enzyme or a peptide. In some embodiments, the at least one therapeutic moiety is operably linked to the modified nucleic acid via a click-chemistry reaction. In some embodiments, the at least one therapeutic moiety is operably linked to the modified nucleic acid via high-affinity biotin/streptavidin interactions. In some embodiments, the at least one therapeutic moiety is operably linked to the modified nucleic acid via linker group covalently bound to a terminus of the modified nucleic acid. In some embodiments, the at least one therapeutic moiety is operably linked to the modified nucleic acid via a linker covalently bound to a chemically modified nucleotide in the middle of the polynucleotide. In some embodiments, the at least one therapeutic moiety is operably linked to the modified nucleic acid via a chemical handle inserted between two nucleotides in the middle of the polynucleotide.

In certain embodiments, the glyconucleic acids, such as glycoRNAs and/or glycoDNAs, is conjugated to a toxin or a radionucleotide. In some embodiments, such a glyconucleic acid conjugated to a toxin or radionucleotide binds to a receptor on a target cell and kills the cell.

If desired the glyconucleic acid, such as glycoRNA and/or glycoDNA, can be conjugated to a targeting antibody or antibody fragment. This can provide for enhanced targeting of the glyconucleic acid to a desired cell or organ, and can further stabilize (e.g, increase the serum half-life of) the glyconucleic acid.

In another embodiment, the pharmaceutical composition comprising a glyconucleic acid, such as glycoRNA and/or glycoDNA, is used in connection with a chemotherapeutic agent. Illustrative examples of chemotherapeutic agents which may be administered with the pharmaceutical composition and have a cytotoxic effect include: azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine and vincristine.

In some embodiments, the chemotherapeutic agent is selected from the group consisting of panobinostat, actinomycin, all-trans retinoic acid, azacitidine, azathioprine, bleomycin, bortezomib, carboplatin, capecitabine, cisplatin, chlorambucil, cyclophosphamide, cytosine arabinoside, daunorubicin, docetaxel, 5-fluorouracil, deoxyfluorouridine, doxorubicin, epirubicin, adriamycin, epothilone, etoposide, fluorouracil, gemcitabine, hydroxyurea, idarubicin, imatinib, irinotecan, nitrogen mustard, Mercaptopurine, methotrexate, mitoxantrone, oxaliplatin, paclitaxel, pemetrexed, teniposide, thioguanine, topotecan, valrubicin, vemurafenib, vinblastine, vincristine, vindesine, vinorelbine and hydroxycamptothecin.

In some embodiments, the chemotherapeutic agent is selected from the group consisting of docetaxel, panobinostat, 5-fluorouracil, paclitaxel, cisplatin, irinotecan, topotecan, and etoposide.

If desired, a therapeutic moiety, such as a radioisotope, ad chemotherapeutic agent or any of the therapeutic agents disclosed herein can be conjugated to the glyconucleic acid, such as glycoRNA and/or glycoDNA.

The term "chemotherapeutic agent" is a biological (macromolecule) or chemical (small molecule) compound that can be used to treat cancer. The types of chemotherapeutic drugs include, but are not limited to, histone deacetylase inhibitor (HDACI), alkylating agents, antimetabolites, alkaloids, cytotoxic/anti-cancer antibiotics, topoisomerase inhibitors, tubulin inhibitors, proteins, antibodies, kinase inhibitors, and the like. Chemotherapeutic drugs include compounds for targeted therapy and non-targeted compounds of conventional chemotherapy.

Non-limiting examples of chemotherapeutic agents include: erlotinib, afatinib, docetaxel, adriamycin, 5-FU (5-fluorouracil), panobinostat, gemcitabine, cisplatin, carboplatin, paclitaxel, bevacizumab, trastuzumab, pertuzumab, metformin, temozolomide, tamoxifen, doxorubicin, rapamycin, lapatinib, hydroxycamptothecin, trametinib. Further examples of chemotherapeutic drugs include: oxaliplatin, bortezomib, sunitinib, letrozole, imatinib, PI3K inhibitor, fulvestrant, leucovorin, lonafarnib, sorafenib, gefitinib, crizotinib, irinotecan, topotecan, valrubicin, vemurafenib, telbivinib, capecitabine, vandetanib, chloranmbucil, panitumumab, cetuximab, rituximab, tositumomab, temsirolimus, everolimus, pazopanib, canfosfamide, thiotepa, cyclophosphamide; alkyl sulfonates e.g., busulfan, improsulfan and piposulfan; ethyleneimine, benzodopa, carboquone, meturedopa, uredopa, methylmelamine, including altretamine, triethylenemelamine, triethyl phosphamide, triethyl thiophosphamide and trimethylenemelamine; bullatacin, bullatacinone; bryostatin; callystatin, CC-1065 (including its adozelesin, carzelesin, bizelesin synthetic analogue), cryptophycin (in particular, cryptophycin 1 and cryptophycin 8); dolastatin, duocarmycin (including synthetic analogue KW-2189 and CB1-TM1); eleutherobin; pancratistatin, sarcodictyin, spongistatin; nitrogen mustards, e.g., chlorambucil, chlornaphazine, cyclophosphamide, estramustine, ifosfamide, bis-chloroethyl-methylamine, Mechlorethaminoxide (melphalan, novembichin, phenesterine, prednimustine, trofosfamide, uramustine, nitrosourea, e.g., carmustine, chlorozotocin, fotemustine, lomustine, nimustine, ranimnustine, antibiotics, e.g., enediyne antibiotics (e.g., calicheamicin, calicheamicin γ1I, calicheamicin ω1I, dynemicin, dynemicin A; diphosphate, e.g, clodronate, esperamicin, and neocarzinostatin chromophore and related chromoprotein enediyne antibiotics chromophore), aclacinomycin, actinomycin, all-trans retinoic acid, anthramycin, azaserine, bleomycin, actinomycin C, carabicin, carminomycin, carzinophilin, chromomycinis, actinomycin D, daunorubicin, deoxy-fluorouridine, detorubicin, 6-dizao-5-oxo-L-norleucine, morpholino-doxorubicin, cyno-morpholino-doxorubicin, 2-pyrroline-doxorubicin, eoxy doxorubicin, epirubicin, esorubicin, idarubicin, marcellomycin, mitomycin, mycophenolic acid, nogalamycin, olivomycin, peplomycin, porfiromycin, puromycin, quelamycin, rodorubicin, streptonigrin, streptozocin, tubercidin, ubenimex, zinostatin, zorubicin; antimetabolite, e.g., methotrexate; folate analogue, e.g., dimethylfolate, methotrexate, pteropterin, trimetrexate, purine analogue, e.g., fludarabine, 6-mercaptopurine, methotrexate, thiamiprine, tioguanine; pyrimidine analogue, e.g., ancitabine, azacitidine, azathioprine, bleomycin, 6-nitrouridine, carmofur, cytarabine, dideoxyuridine, doxifluridine, enocitabine, floxuridine; androgen, calusterone, dromostanolone propionate, epitiostanol, mepitiostane, testolactone; antiadrenergic agent, e.g. aminoglutethimide, mitotane, trilostane; folate supplement, e.g. folinate; aceglatone; aldophosphamide glycoside; aminolevulinic acid; eniluracil, amsacrine, bestrabucil, bisantrene, edatraxate, defofamine, demecolcine, diaziquone, elfornithine, elliptinium acetate, epothilone, etoglucid; gallium nitrate; hydroxycarbamide; lentinan, lonidainine, maytansinoid, maytansine, ansamitocin, mitoguazone, mitoxantrone, mopidamol, nitraerine, pentostatin, phenamet, pirarubicin, losoxantrone, podophyllinic acid; 2-ethylhydrazine; procarbazine, PSK® polysaccharide complex (JHS Natural Products, Eugene, Oreg.), razoxane, rhizoxin, sizofiran, spirogermanium, tenuazonic acid, triaziquone; 2,2',2"-trichloro-triethylamine; trichothecene (in particular, T-2toxin, verracurin A, roridin A and anguidine); urethane, vindesine, dacarbazine, mannomustine; dibromomannitol; dibromodulcitol; pipobroman, gacytosine, arabinoside ("Ara-C"); cyclophosphamide; thiotepa; tioguanine; 6-mercaptopurine; methotrexate; Vinblastine; etoposide, ifosfamide, mitoxantrone, vincristine, vinorelbine, novantrone; emetrexed; teniposide, edatrexate, daunomycin; aminopterin; ibandronate; CPT-11; topoisomerase inhibitor RFS 2000; DMFO, retinoid, e.g., Retinoic acid; and a pharmaceutically acceptable salt or derivative thereof.

Methods Related to Glycan Binding Protein-Expressing Cells

Aspects of the present disclosure include methods for reducing interaction between glycan binding protein (GBP)-expressing cells and cells displaying cell surface glycosylated ribonucleic acids (glycoRNAs). The methods are based in part on the unexpected finding first described herein that cells display glycoRNAs on their surface, and that such glycoRNAs are recognized by cell surface expressed GBPs. With the benefit of the present disclosure, therefore, it will be understood that a variety of methods and agents relating to the interaction between GBPs and glycoRNAs are possible and provided herein. Such methods and agents find use in a variety of contexts including but not limited to research, therapeutic and diagnostic contexts.

According to some embodiments, provided are methods for reducing interaction between GBP-expressing cells and cells displaying cell surface glycoRNAs, the methods comprising contacting the GBP-expressing cells with soluble glycoRNAs which bind to GBP expressed on the surface of the GBP-expressing cells, in an amount effective to reduce interaction between the GBP-expressing cells and the cells displaying cell surface glycoRNAs. "Soluble" in this context means the glycoRNAs are not associated with a cell membrane when contacting with the GBP-expressing cells commences. As used herein, "reducing interaction" or "reduced interaction" is as compared to the interaction between the GBP-expressing cells and the cells displaying cell surface glycoRNAs in the absence of the contacting. The soluble glycoRNAs comprise those wherein binding of the soluble glycoRNAs to GBP expressed on the surface of the GBP-expressing cells interferes with (e.g., blocks) the ability of the GBP to bind the glycoRNAs displayed on the surface of the cells displaying cell surface glycoRNAs.

A variety of glycoRNAs may be employed. In certain embodiments, the soluble glycoRNAs comprise glycosylated (e.g., sialylated) RNAs from the Y RNA family, non-limiting examples of which include Y5 RNAs. Additional glycoRNAs that find use in the methods include glycosylated (e.g., sialylated) small nucleolar RNAs (snoRNAs), transfer RNAs (tRNAs), small nuclear RNAs (snRNAs), and any combinations thereof. The glycoRNAs may comprise a variety of glycans. In certain embodiments, the glycoRNAs comprise N-glycans. According to some embodiments, when the glycoRNAs comprise N-glycans, such glycoRNAs do not comprise O-glycans. In certain embodiments, the glycoRNAs comprise sialylated glycans, e.g., sialylated N-glycans. Sialylated glycans include, but are not limited to, glycans sialylated with Neu5Ac, Neu5Gc, or a combination thereof.

The soluble glycoRNAs may be conjugated to one or more agents. A variety of strategies for conjugating agents of interest to RNAs may be employed to conjugate agents of interest to the soluble glycoRNAs. Non-limiting examples include those described in Lau et al. (2012)*Mol. Pharm.* 9:71-8; Liu et al. (2014) *Nucleic Acids Res.* 42:11805-11817; Xia et al. (2009) *Mol. Pharm.* 6:747-751; Sugo et al. (2016) *J. Control. Release* 237:1-13; and elsewhere, the disclosures of which are incorporated herein by reference in their entireties for all purposes.

In certain embodiments, to facilitate stable association of the glycoRNA to the one or more agents of interest, the glycoRNA has, or is engineered to include, an MS2-RNA stem loop motif (MS2). Such a motif has been shown to bind to MS2-coat protein (MS2-CP) and thus would provide for non-covalent association of the glycoRNA with an agent comprising MS2-CP.

In certain embodiments, the soluble glycoRNAs are conjugated to one or more therapeutic agents. As used herein, a "therapeutic agent" is a physiologically or pharmacologically active substance that can produce a desired biological effect in a targeted site in an animal, such as a mammal or in a human. The therapeutic agent may be any inorganic or organic compound. A therapeutic agent may decrease, suppress, attenuate, diminish, arrest, or stabilize the development or progression of disease, disorder, or cell growth in an animal such as a mammal or human. Examples include, without limitation, peptides, proteins, nucleic acids (including siRNA, miRNA and DNA), polymers, and small molecules. In various embodiments, the therapeutic agents may be characterized or uncharacterized.

According to some embodiments, the soluble glycoRNAs are conjugated to one or more agents that result in killing, prevention of cell proliferation, and/or the like, of a GBP-expressing cell to which the soluble glycoRNAs bind. Such agents may vary and include cytostatic agents and cytotoxic agents, e.g., an agent capable of killing a target cell with or without being internalized into the target cell. In some embodiments, the agent is a cytotoxic agent selected from an enediyne, a lexitropsin, a duocarmycin, a taxane, a puromycin, a dolastatin, a maytansinoid, and a vinca alkaloid.

According to certain embodiments, the cytotoxic agent is paclitaxel, docetaxel, CC-1065, CPT-11 (SN-38), topotecan, doxorubicin, morpholino-doxorubicin, rhizoxin, cyanomorpholino-doxorubicin, dolastatin-10, echinomycin, combretastatin, calicheamicin, a maytansinoid, maytansine, maytansine DM1, maytansine DM4, DM-1, an auristatin or other dolastatin derivatives, such as auristatin E or auristatin F, AEB (AEB-071), AEVB (5-benzoylvaleric acid-AE ester), AEFP (antibody-endostatin fusion protein), MMAE (monomethylauristatin E), MMAF (monomethylauristatin F), pyrrolobenzodiazepines (PBDs), eleutherobin, netropsin, or any combination thereof.

In certain embodiments, the soluble glycoRNAs comprise a detectable label. Detectable labels that may be employed include, but are not limited to, fluorescent labels, colorimetric labels, chemiluminescent labels, enzyme-linked reagents, multicolor reagents, avidin-streptavidin associated detection reagents, and the like.

According to some embodiments, the detectable label is a fluorescent label. Fluorescent labels are labeling moieties that are detectable by a fluorescence detector. For example, binding of a fluorescent label to an analyte of interest (e.g., GBP of GBP-expressing cells) allows the analyte of interest to be detected by a fluorescence detector. Examples of fluorescent labels include, but are not limited to, fluorescent molecules that fluoresce upon contact with a reagent, fluorescent molecules that fluoresce when irradiated with electromagnetic radiation (e.g., UV, visible light, x-rays, etc.), fluorescent labels that are detectable by photoacoustic imaging, and the like.

According to some embodiments, the detectable label is an in vivo imaging agent. The phrase "in vivo imaging" as used herein refers to methods of detecting the glycoRNAs (and in turn, GBP and/or GBP-expressing cells to which the soluble glycoRNAs bind) in a whole, live mammal. Optically detectable agents, such as fluorescent agents (e.g., indocyanine green (ICG)), bioluminescent agents (e.g., luciferases, such as nanoluciferases), and radioactively labeled agents may be detected by in vivo imaging. In vivo imaging may be used provide 2-D as well as 3-D images of a mammal or tissues or cells therein. Charge-coupled device cameras, photodiodes, avalanche photodiodes, photomultiplier tubes, CMOS, or 3D tomographers may be used to carry out in vivo imaging. For example, Burdette J E (2008) *Journal of Mol. Endocrin.* 40: 253-261 reviews the uses of computed tomography, magnetic resonance imaging, ultrasonography, positron emission tomography, single-photon emission computed tomography, etc., for in vivo imaging. Methods for using a detectable label for real-time imaging of luciferase expression in live animals can be readily adapted for use in the subject methods disclosed herein (e.g., Greer L F et al. (2002) *Luminescence* 17: 43-74). In vivo imaging of fluorescent proteins in live animals is described in, e.g., Hoffman (2002) *Cell Death and Differentiation* 9:786-789. In some embodiments, in vivo imaging may be performed by detecting a label that emits light at a wavelength designed to penetrate living tissue. Such labels include long wavelength emitting fluorescent dyes or proteins such as infrared and near infrared dyes or proteins including but not limited to dyes or proteins that emit in the range of about 600 nm to about 800 nm, about 650 nm to about 800 nm, or about 700 nm to about 800 nm. Alternatively, labels designed to emit light that penetrates living tissue may include non-fluorescent reagents including but not limited to red-shifted luciferases.

In vivo imaging can also involve computed tomography, magnetic resonance imaging, ultrasonography, positron emission tomography, single-photon emission computed tomography (SPECT) (See Burdette J E (2008) Journal of Mol. Endocrin., 40:253-261 for details). SPECT can also be used with an integrated x-ray CAT (CT) scanner (SPECT/CT) in the subject methods. The information from many in vivo imaging methods as those described above can provide 3D distribution of the glycoRNAs (and in turn, GBP-expressing cells) in a subject.

According to some embodiments, the soluble glycoRNAs comprise an in vivo imaging agent, where the in vivo imaging agent is a photoacoustic imaging agent. Photoacoustic imaging (PAI) bridges the traditional depth limits of ballistic optical imaging and the resolution limits of diffuse optical imaging. Using the acoustic waves generated in response to the absorption of pulsed laser light, it provides noninvasive images of absorbed optical energy density at depths of several centimeters with a resolution of ~100 μm. This versatile and scalable imaging modality has proven useful for molecular imaging, which enables visualization of biological processes with systemically introduced contrast agents. Agents that find use in photoacoustic imaging include those described in Weber et al. (2016) *Nature Methods* 13:639-650. In certain embodiments, the soluble glycoRNAs comprise a photoacoustic imaging agent, and the photoacoustic imaging agent is indocyanine green (ICG), a tricarbocyanine dye that is safe for intravenous administration.

In certain embodiments, the GBP to which the soluble glycoRNAs bind comprise lectins. In some non-limiting examples, the glycoRNAs comprise sialylated glycans and the GBP to which the soluble glycoRNAs bind are sialoglycan-binding lectins. Non-limiting examples of sialoglycan-binding lectins include sialic acid-binding immunoglobulin-like lectins (Siglecs).

Siglecs are a family of immunomodulatory receptors whose functions are regulated by their glycan ligands. The Siglec family consists of 15 family members in humans that are expressed on a restricted set of cells in the hematopoietic lineage, with known exceptions including Siglec-4 (MAG) on oligodendrocytes and Schwann cells and Siglec-6 on placental trophoblasts. Through their outermost N-terminal V-set domain, Siglecs recognize sialic acid-containing glycan ligands on glycoproteins and glycolipids with unique, yet overlapping, specificities. Recognition of their ligands can affect cellular signaling through immunoreceptor tyrosine-based inhibitory motifs (ITIMs) on their cytoplasmic tails. For the majority of the Siglecs, these ITIMs have the capacity of recruiting phosphatases, therefore, these members are referred to as inhibitory-type Siglecs. Exceptions include Siglec-1 and MAG, which lack such a motif, and the activatory-type Siglecs (Siglecs-14 to -16), which are associated with immunoreceptor tyrosine-based activation motif (ITAM)-bearing adapter proteins through a positively charge amino acid in their transmembrane region.

Siglecs can be divided into two groups based on their genetic homology among mammalian species. The first group is present in all mammals and consists of Siglec-1 (Sialoadhesin), Siglec-2 (CD22), Siglec-4, and Siglec-15. The second group consists of the CD33-related Siglecs which include Siglec-3 (CD33), -5, -6, -7, -8, -9, -10, -11, -14 and -16. Monocytes, monocyte-derived macrophages, and monocyte-derived dendritic cells have largely the same Siglec profile, namely high expression of Siglec-3, -7, -9, low Siglec-10 expression and upon stimulation with IFN-α, expression of Siglec-1. In contrast, macrophages have primarily expression of Siglec-1, -3, -8, -9, -11, -15, and -16 depending on their differentiation status. Conventional dendritic cells express Siglec-3, -7, and -9, similar to monocyte-derived dendritic cells, but in addition also express low levels of Siglec-2 and Siglec-15. Plasmacytoid dendritic cells express Siglec-1 and Siglec-5. Downregulation of Siglec-7 and Siglec-9 expression on monocyte-derived dendritic cells is observed after stimulation for 48 hours with LPS, however, on monocyte-derived macrophages Siglec expression is not changed upon LPS triggering. Siglecs are also present on other immune cells, such as B cells, basophils, neutrophils, and NK cells. Further details regarding Siglecs may be found, e.g., in Angata et al. (2015) *Trends Pharmacol Sci.* 36(10): 645-660; Lubbers et al. (2018) *Front. Immunol.* 9:2807; Bochner et al. (2016) *J Allergy Clin Immunol.* 135(3):598-608; and Duan et al. (2020) *Annu. Rev. Immunol.* 38(1):365-395; the disclosures of which are incorporated herein by reference in their entireties for all purposes.

In certain embodiments, the GBP to which the soluble glycoRNAs bind comprise a CD33-related Siglec. In one non-limiting example, the CD33-related Siglec is Siglec-11. In another non-limiting example, the CD33-related Siglec is Siglec-14.

In certain embodiments, the GBP to which the soluble glycoRNAs bind comprise C-type lectins. The C-type lectins are a superfamily of proteins defined by the presence of at least one C-type lectin-like domain (CTLD) and that recognize a broad repertoire of ligands and regulate a diverse range of physiological functions. Most research attention has focused on the ability of C-type lectins to function in innate and adaptive antimicrobial immune responses, but these proteins are increasingly being recognized to have a major role in autoimmune diseases and to contribute to many other aspects of multicellular existence. The term C-type lectin was introduced to distinguish between $Ca^{2+}$-dependent and $Ca^{2+}$-independent carbohydrate-binding lectins. C-type lectins share at least one carbohydrate recognition domain, which is a compact structural module that contains conserved residue motifs and determines the carbohydrate specificity of the CLR. Of particular interest for their role in coupling both innate and adaptive immunity, are the genes of the Dectin-1 and Dectin-2 families localized on the telomeric region of the natural killer cluster of genes. These two groups of C-type lectins are expressed mostly by cells of myeloid lineage such as monocytes, macrophages, dendritic cells (DCs), and neutrophils. C-type lectins not only serve as antigen-uptake receptors for internalization and presentation to T cells but also trigger multiple signaling pathways leading to NF-κB, type I interferon (IFN), and/or inflammasome activation. This leads, in turn, to the production of pro- or anti-inflammatory cytokines and chemokines, subsequently fine tuning adaptive immune responses. Further details regarding C-type lectins may be found, e.g., in Zelensky et al. (2005) *FEBS J.* 272:6179-6217; Geijtenbeek & Grinhuis (2009) *Nature Reviews Immunology* 9:465-479; Brown et al. (2018) *Nature Reviews Immunology* 18:374-389; Dambuza & Brown (2015) *Curr. Opin. Immunol.* 32:21-7; and Chiffoleau (2018) *Front. Immunol.* 9:227; the disclosures of which are incorporated herein by reference in their entireties for all purposes. According to some embodiments, the GBP to which the soluble glycoRNAs bind comprise a C-type lectin selected from DECTIN-1, lectin-like oxidized low-density lipoprotein receptor-1 (LOX-1), C-type lectin-like receptor-1 (CLEC-1), C-type lectin-like receptor 2 (CLEC-2), myeloid inhibitory C-type lectin-like receptor (MICL), CLEC9A, DC immunoreceptor (DCIR), DECTIN-2, blood DC antigen-2 (BDCA-2), macrophage-inducible C-type lectin (MINCLE), macrophage galactose lectin (MGL), and asialoglycoprotein receptor (ASGPR).

In certain embodiments, the GBP to which the soluble glycoRNAs bind comprise selectins. Selectins are C-type transmembrane lectins that mediate leukocyte trafficking and specific adhesive interactions of leukocytes, platelets, and endothelial cells with tumor cells. These lectins are present on endothelial cells (E-Selectin), leukocytes (L-Selectin), and platelets (P-Selectin), and preferentially bind glycans containing $SLe^X$ and $SLe^A$ glycoepitopes, which are abundantly expressed in several tumor types. In the TME, selectins are functionally relevant in the context of leukocyte recruitment, tumor-promoting inflammation, and acquisition of metastatic potential. P-Selectin (CD62P) is involved in tumor growth and metastasis, as it mediates interactions between activated platelets and cancer cells contributing to tumorigenesis. E-Selectin (CD62E) also play major roles in cancer cell adhesiveness at different events of the metastatic cascade, promoting tumor cell extravasation. Finally, L-Selectin (CD62L), constitutively expressed on leukocytes, regulates tumor-leukocyte interactions and promotes cell adhesion and hematogenous metastasis by favoring emboli formation. Further details regarding selectins may be found, e.g., in Cagnoni et al. (2016) *Front Oncol.* 6:109; Barthel et al. (2007) *Expert Opin Ther Targets* 11(11):1473-91; and Chen & Geng (2006) *Arch Immunol Ther Exp* 54(2):75-84; the disclosures of which are incorporated herein by reference in their entireties for all purposes. According to some embodiments, the GBP to which the soluble glycoRNAs bind comprise a selectin selected from P-Selectin (CD62P), E-Selectin (CD62E), and L-Selectin (CD62L).

In certain embodiments, the GBP to which the soluble glycoRNAs bind comprise galectins. Galectins are a family of highly conserved glycan-binding soluble lectins, are defined by a conserved carbohydrate recognition domain (CRD) and a common structural fold. Vasta G R (2012) *Adv Exp Med Biol* 946:21-36. Based on structural features, mammalian galectins have been classified into three types: prototype galectins (Gal-1, -2, -5, -7, -10, -11, -13, -14, and -15, containing one CRD and existing as monomers or dimerizing through non-covalent interactions), tandem repeat-type galectins (Gal-4, -6, -8, -9, and -12), which exist as bivalent galectins containing two different CRDs connected by a linker peptide, and finally, Gal-3, the only chimera-type member of the galectin family. Galectins modulate different events in tumorigenesis and metastasis. Galectins contribute to immune tolerance and escape through apoptosis of effector T cells, regulation of clonal expansion, function of regulatory T cells (Tregs), and control of cytokine secretion. Expression levels for some galectins also change during malignant transformation, confirming their roles in cancer progression. Gal-1, abundantly secreted by almost all malignant tumor cells, has been characterized as a major promoter of an immunosuppressive protumorigenic microenvironment. Gal-3, another member of the family, has shown prominent protumorigenic effects in a multiplicity of tumors. Similar to Gal-1, Gal-3 signaling contributes to tilt the balance toward immunosuppressive TMEs by interacting with specific glycans, and impairing anti-tumor responses. In this regard, Gal-3 has been shown to promote anergy of tumor infiltrating lymphocytes (TILs). According to some embodiments, the glycan-binding moiety comprises the glycan-binding domain of a galectin selected from Gal-1, Gal-2, Gal-3, Gal-4, Gal-5, Gal-6, Gal-7, Gal-8, Gal-9, Gal-10, Gal-11, Gal-12, Gal-13, Gal-14, and Gal-15. In certain embodiments, the GBP to which the soluble glycoRNAs bind comprise Gal-1. According to some embodiments, the GBP to which the soluble glycoRNAs bind comprise Gal-3.

In certain aspects, provided are methods for reducing interaction between GBP-expressing cells and cells displaying cell surface glycoRNAs, the methods comprising contacting the GBP-expressing cells with an agent that binds to GBP expressed on the surface of the GBP-expressing cells and identified as binding to cell surface glycoRNAs (that is the GBP is GBP identified prior to the contacting as GBP that binds to cell surface glycoRNAs), in an amount effective to reduce interaction between the GBP-expressing cells and the cells displaying cell surface glycoRNAs. The agent is one wherein binding of the agent to GBP expressed on the surface of the GBP-expressing cells interferes with (e.g., blocks) the ability of the GBP to bind the glycoRNAs displayed on the surface of the cells displaying cell surface glycoRNAs.

According to some embodiments, the agent that binds to GBP expressed on the surface of the GBP-expressing cells is a ligand of the GBP. As used herein, a "ligand" is a substance that forms a complex with a biomolecule to serve a biological purpose. The ligand may be a substance selected from a circulating factor, a secreted factor, a cytokine, a growth factor, a hormone, a peptide, a polypeptide, a small molecule, and a nucleic acid, that forms a complex with the GBP on the surface of the GBP-expressing cell. In certain embodiments, when the agent is a ligand, the ligand is modified in such a way that complex formation with the GBP occurs, but the normal biological result of such complex formation does not occur.

In certain embodiments, the agent that binds to GBP expressed on the surface of the GBP-expressing cells is a small molecule. By "small molecule" is meant a compound having a molecular weight of 1000 atomic mass units (amu) or less. In some embodiments, the small molecule is 750 amu or less, 500 amu or less, 400 amu or less, 300 amu or less, or 200 amu or less. In certain embodiments, the small molecule is not made of repeating molecular units such as are present in a polymer.

According to some embodiments, the agent that binds to GBP expressed on the surface of the GBP-expressing cells is an antibody. By "antibody" is meant an antibody or immunoglobulin of any isotype (e.g., IgG (e.g., IgG1, IgG2, IgG3, or IgG4), IgE, IgD, IgA, IgM, etc.), whole antibodies (e.g., antibodies composed of a tetramer which in turn is composed of two dimers of a heavy and light chain polypeptide); single chain antibodies (e.g., scFv); fragments of antibodies (e.g., fragments of whole or single chain antibodies) which retain specific binding to the GBP, including, but not limited to single chain Fv (scFv), Fab, (Fab')$_2$, (scFv')$_2$, and diabodies; chimeric antibodies; monoclonal antibodies, human antibodies, humanized antibodies (e.g., humanized whole antibodies, humanized half antibodies, or humanized antibody fragments, e.g., humanized scFv); and fusion proteins comprising an antigen-binding portion of an antibody and a non-antibody protein. In certain embodiments, the antibody is selected from an IgG, Fv, single chain antibody, scFv, Fab, F(ab')$_2$, or Fab'. The antibody may be detectably labeled, e.g., with an in vivo imaging agent, a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like.

The agent that binds to GBP expressed on the surface of the GBP-expressing cells may be selected to bind one or more particular GBPs. Non-limiting examples of such agents include those that bind one or more Siglecs (e.g., Siglec-11, Siglec-14, and/or the like), one or more C-type lectins, one or more galectins, and/or one or more selectins. The agent may be selected based on the type(s) of glycoRNAs displayed on the cells displaying cell surface glycoRNAs, coupled with the identified glycoRNA binding properties of the GBP expressed on the surface of the GBP-expressing cells. In one non-limiting example, when the cells displaying cell surface glycoRNAs display glycoRNAs comprising sialylated glycans and the GBP-expressing cells express one or more Siglecs (e.g., Siglec-11, Siglec-14, and/or the like), the selected agent may be one that binds to one or more of the Siglecs and blocks interaction of the Siglecs with the glycoRNAs comprising sialylated glycans. Antibodies, ligands, and other agents capable of binding to various types of GBP and blocking GBP binding are known and may be employed when practicing the methods of the present disclosure. By way of example, Siglec blocking antibodies are available and described, e.g., in Pia Lenza et al. (2020) *Cell* 9(12):2691, the disclosure of which is incorporated herein by reference in its entirety for all purposes.

In certain aspects, provided are methods for reducing interaction between glycan GBP-expressing cells and cells displaying cell surface glycoRNAs, the methods comprising contacting the cells displaying cell surface glycoRNAs with an agent that binds to and/or edits the cell surface glycoRNAs, in an amount effective to reduce interaction between the GBP-expressing cells and the cells displaying cell surface glycoRNAs.

According to some embodiments, the agent edits the cell surface glycoRNAs. In certain embodiments, such an agent comprises an enzyme that removes glycans from the cell surface glycoRNAs. By way of example, when the cell surface glycoRNAs comprise sialylated glycans, an agent comprising a sialidase may be employed. Suitable sialidases include, but are not limited to, prokaryotic sialidases and eukaryotic sialidases. Prokaryotic sialidases that may be employed include bacterial sialidases. One example of a bacterial sialidase that finds use in the conjugates of the present disclosure is *Salmonella typhimurium* sialidase (e.g., UniProtKB—P29768). Another example of a bacterial sialidase that finds use in the conjugates of the present disclosure is *Vibrio cholera* sialidase (e.g., UniProtKB—P0C6E9). Eukaryotic sialidases that may be employed include, e.g., mammalian sialidases and non-mammalian eukaryotic sialidases. Mammalian sialidases (or mammalian neuraminidases) of interest include those from primates, e.g., human or non-human neuraminidases. In certain embodiments, the sialidase is a human sialidase. According to some embodiments, the human sialidase is selected from human neuraminidase 1 (e.g., UniProtKB—Q99519), human neuraminidase 2 (e.g., UniProtKB—Q9Y3R4), human neuraminidase 3 (e.g., UniProtKB—Q9UQ49), and human neuraminidase 4 (e.g., UniProtKB—Q8WWR8). It will be understood that the sialidase may be a derivative of a wild-type sialidase, such as truncated derivatives, derivatives that include more amino acids than the corresponding wild-type sialidase, derivatives that include one or more amino acid substitutions (e.g., one or more conservative substitutions, one or more non-conservative substitutions, a substitution of a natural amino acid with a non-natural amino acid, and/or the like), etc. The derivatives retain at least a portion of the glycoside hydrolase activity of the parental wild-type sialidase.

In certain embodiments, when an agent comprising a sialidase is employed, the sialidase may be associated with (e.g., conjugated to, fused with, etc.) a targeting moiety such as an antibody, ligand, or the like that binds to a cell surface molecule (e.g., tumor antigen, cell surface receptor, and/or the like) on the surface of the cells displaying the cell surface glycoRNAs. Non-limiting examples of such agents include those described in U.S. Patent Application Publication No. US 2019/0248919, the disclosure of which is incorporated herein by reference in its entirety for all purposes.

According to some embodiments, when an agent that edits the cell surface glycoRNAs is employed, the agent comprises a ribonuclease (RNase). Non-limiting examples of RNases that find use in practicing the methods of the present disclosure include an RNase A, a T1 RNase, a T2 RNase, and an RNase 1. In some embodiments, the RNase is a human RNase, non-limiting examples of which include human RNase 1 (UniProtKB—P07998).

In certain embodiments, the agent binds but does not edit the cell surface glycoRNAs. According to some embodiments, such an agent is an antibody that binds to the cell surface glycoRNAs. Suitable antibodies include anti-RNA antibodies, including but not limited to anti-double stranded RNA (dsRNA) antibodies. One non-limiting example of an anti-dsRNA antibody that may be employed is the J2 antibody available from Absolute Antibody and demonstrated in the Example section herein to bind glycoRNAs, or an antibody having the binding properties of the J2 antibody, e.g., an antibody that competes for binding to glycoRNAs with the J2 antibody.

According to some embodiments, when the agent binds but does not edit the cell surface glycoRNAs, the agent comprises a glycan-binding moiety that binds to the cell surface glycoRNAs. For example, the agent may be a soluble "decoy receptor" for the glycoRNAs which interfere with (e.g., block) binding of cell surface GBP to the cell surface displayed glycoRNAs. In certain embodiments, the glycan-binding moiety comprises the sialoglycan-binding domain of a sialoglycan-binding lectin. Non-limiting examples of sialoglycan-binding moieties include those that comprise the sialoglycan-binding domain of a Siglec (e.g., CD33-related Siglecs, including but not limited to, Siglec-11, Siglec-14, or the like). By "glycan-binding domain" or "sialoglycan-binding domain" of a lectin is meant the domain of a lectin or a glycan/sialoglycan-binding variant (e.g., glycan/sialoglycan-binding fragment) thereof responsible for binding to the respective glycan(s). Siglecs, for example, comprise an extracellular N-terminal V-set Ig (Ig-V) domain responsible for the binding of sialoside ligands. The amino acid sequences and domains (e.g., extracellular domains) of Siglecs and other lectins are known, and any such domains may be included in the glycan-binding moiety as desired.

Aspects of the present disclosure further include methods of targeting an agent to GBP-expressing cells, the methods comprising contacting the GBP-expressing cells with soluble glycoRNAs stably associated with the agent. In certain embodiments, "stably associated" means a physical association between two entities in which the mean half-life of association is one day or more in PBS at 4° C. In some embodiments, the physical association between the two entities has a mean half-life of one day or more, one week or more, one month or more, including six months or more, e.g., 1 year or more, in PBS at 4° C. According to some embodiments, the stable association arises from a covalent bond between the two entities, a non-covalent bond between the two entities (e.g., an ionic or metallic bond), or other forms of chemical attraction, such as hydrogen bonding, Van der Waals forces, and the like.

According to some embodiments, the agent stably associated with (e.g., conjugated to) the soluble glycoRNAs is a therapeutic agent. For example, the soluble glycoRNAs may be employed for targeted delivery of a therapeutic agent to cells that express cell surface GBPs that bind the soluble glycoRNAs. In certain embodiments, the agent is a GBP-expressing cell modulating agent. By "modulating agent" is meant the agent, upon binding of the soluble glycoRNAs to GBP of the GBP-expressing cells, modulates (e.g., induces or inhibits) one or more activities of the GBP-expressing cells. In some embodiments, the GBP-expressing cell modulating agent binds to a cell surface molecule (e.g., receptor) on the surface of the GBP-expressing cells and induces signaling (which may be activating or inhibitory signaling) through the cell surface molecule. According to some embodiments, the agent stably associated with (e.g., conjugated to) the soluble glycoRNAs is a cytostatic agent or a cytotoxic agent as described elsewhere herein, e.g., when it is desirable to halt proliferation of, or kill, the GBP-expressing cells.

In certain embodiments, the agent stably associated with (e.g., conjugated to) the soluble glycoRNAs comprises a detectable label, non-limiting examples of which are described elsewhere herein. Such methods find use, e.g., when it is desirable to detect the GBP-expressing cells in vitro and/or in vivo, e.g., by in vivo imaging.

Aspects of the present disclosure further include methods for inducing signaling through GBP expressed on the surface of GBP-expressing cells, the methods comprising contacting the GBP-expressing cells with soluble glycoRNAs, wherein binding of the soluble glycoRNAs to GBP expressed on the surface of GBP-expressing cells induces signaling through the GBP. The soluble glycoRNAs may have one or any combination of glycoRNA properties described elsewhere herein, including any of the soluble glycoRNA conjugates described elsewhere herein. In certain embodiments, the soluble glycoRNAs are selected such that they bind, and induce signaling through, a glycan-binding lectin. The glycan-binding lectin may be a sialoglycan-binding lectin, non-limiting examples of which include Siglecs. The Siglec(s) may be any of the Siglecs described elsewhere herein. In certain embodiments, soluble glycoRNAs that bind to one or more CD33-related Siglecs (e.g., Siglec-11, Siglec-14, and/or the like) are employed.

Any of the methods described herein for reducing interaction between GBP-expressing cells and cells displaying cell surface glycoRNAs, for targeting an agent to GBP-expressing cells, for inducing signaling through GBP expressed on the surface of GBP-expressing cells, etc. may be performed in vitro, in vivo, or ex vivo.

With respect to in vivo embodiments, provided in some embodiments are methods wherein the contacting comprises administering soluble glycoRNAs to an individual in need thereof (e.g., an individual in need of reduced interaction between GBP-expressing cells and cells displaying cell surface glycoRNAs), in an amount effective to reduce interaction between the GBP-expressing cells and the cells displaying cell surface glycoRNAs in the individual. Also by way of example, provided are methods wherein the contacting comprises administering an agent to an individual in need thereof (e.g., an individual in need of reduced interaction between GBP-expressing cells and cells displaying cell surface glycoRNAs), in an amount effective to reduce interaction between the GBP-expressing cells and the cells displaying cell surface glycoRNAs in the individual. In certain embodiments, provided are methods wherein the contacting comprises administering soluble glycoRNAs to an individual in need thereof (e.g., an individual in need of signaling through GBP), wherein binding of the soluble glycoRNAs to GBP expressed on the surface of GBP-expressing cells in the individual induces signaling through the GBP. Any of the soluble glycoRNAs (including conjugates thereof) and other agents described herein may be administered via an appropriate route of administration, non-limiting examples of which include oral (e.g., in tablet form, capsule form, liquid form, or the like), parenteral (e.g., by intravenous, intra-arterial, subcutaneous, intramuscular, or epidural injection), topical, intra-nasal, or intra-tumoral administration.

According to any of the in vivo embodiments described herein, the individual in need thereof may have a medical condition, non-limiting examples of which include cancer, an autoimmune disorder, an inflammatory disorder, an infectious disease, or any combination thereof.

Aspects of the present disclosure further include methods of assessing a biological sample for glycosylated ribonucleic acids (glycoRNAs), comprising performing a glycoRNA detection assay on the biological sample. In some embodiments, the sample is a cellular sample—that is, a sample comprising cells. Cellular samples may be derived from living tissues or collections of cultured cells or the like. Cellular samples may be heterogeneous, containing various (including 2 or more, 3 or more, 4 or more, 5 or more, etc.) different types of cells, or may substantially homogeneous, containing essentially one type of cell, depending on the source from which the cellular sample is derived. When the sample is a cellular sample, the assay may be a cell surface glycoRNA detection assay. With the benefit of the present disclosure, it will be appreciated that a variety of cell surface glycoRNA detection assays may be performed. In certain embodiments, the cell surface glycoRNA detection assay comprises contacting cells of the cellular sample with a glycoRNA-binding agent, and assessing for binding of the glycoRNA-binding agent to cell surface glycoRNAs in the sample. According to some embodiments, the glycoRNA-binding agent is an antibody that binds to the cell surface glycoRNAs. Suitable antibodies include anti-RNA antibodies, including but not limited to anti-double stranded RNA (dsRNA) antibodies. One non-limiting example of an anti-dsRNA antibody that may be employed is the J2 antibody available from Absolute Antibody and demonstrated in the Example section herein to bind glycoRNAs, or an antibody having the binding properties of the J2 antibody, e.g., an antibody that competes for binding to glycoRNAs with the J2 antibody.

In certain embodiments, a cell surface glycoRNA detection assay comprises contacting cells of the cellular sample with a ribonuclease (RNase) to digest cell surface glycoRNA, if present, and assessing for degradation of cell surface glycoRNA. Non-limiting examples of RNases that find use in practicing the methods of the present disclosure include an RNase A, a T1 RNase, a T2 RNase, and an RNase 1. In some embodiments, the RNase is a human RNase, non-limiting examples of which include human RNase 1 (UniProtKB—P07998).

The methods of assessing a biological sample for glycoRNAs may comprise performing a free glycoRNA detection assay on the biological sample. By "free glycoRNA" is meant RNA that has been released (e.g., secreted, shed, and/or the like) from cells. The free glycoRNA detection assay may be performed on a cellular sample or a non-cellular sample.

The methods of assessing a biological sample for glycoRNAs may performed on a variety of biological samples including a cell culture medium sample, a tissue sample, a body fluid sample, etc. In some embodiments, the sample is any solid or fluid sample obtained from any living cell or organism, including, but not limited to, human or animal tissue, organ, tissue culture, bioreactor sample, eukaryotic organism, prokaryotic organism. For example, a sample can be, or be obtained from, e.g., amniotic fluid, aqueous humour, vitreous humour, bile, blood, blood plasma, blood serum, cerebrospinal fluid, cerumen, chyle, chyme, endolymph, perilymph, exudates, feces, gastric juice, lymph, mucus, pericardial fluid, peritoneal fluid, pleural fluid, pus, rheum, saliva, sebum, serous fluid, semen, serum, smegma, sputum, synovial fluid, sweat, tears, urine, vaginal secretion, vaginal discharge, vomit, etc.

Samples used in the methods of the present disclosure may be collected by any convenient means. In some instances, useful cellular samples may be or may be derived from a biopsy. Biopsy tissues may be obtained from healthy or diseased tissues, including e.g., cancer tissues. Depending on the type of cancer and/or the type of biopsy performed the sample may be prepared from a solid tissue biopsy or a liquid biopsy.

In some instances, a sample may be prepared from a surgical biopsy. Any convenient and appropriate technique for surgical biopsy may be utilized for collection of a sample to be employed in the methods described herein including but not limited to, e.g., excisional biopsy, incisional biopsy, wire localization biopsy, and the like. In some instances, a surgical biopsy may be obtained as a part of a surgical procedure which has a primary purpose other than obtaining the sample, e.g., including but not limited to tumor resection, mastectomy, lymph node surgery, axillary lymph node dissection, sentinel lymph node surgery, and the like.

Various other biopsy techniques may be employed to obtain biopsy tissue, for use as a sample as described herein. As a non-limiting example, a sample may be obtained by a needle biopsy. Any convenient and appropriate technique for needle biopsy may be utilized for collection of a sample including but not limited to, e.g., fine needle aspiration (FNA), core needle biopsy, stereotactic core biopsy, vacuum assisted biopsy, and the like.

Aspects of the present disclosure further include methods of producing glycosylated ribonucleic acids (glycoRNAs), the methods comprising culturing glycoRNA-producing cells under conditions in which glycoRNAs are produced, and isolating the produced glycoRNAs. Such methods find use in a variety of contexts, including but not limited to, producing soluble glycoRNAs for inclusion in the conjugates and/or pharmaceutical compositions of the present disclosure. Culture conditions, isolation methods, and the like that find use in practicing the soluble glycoRNA production methods of the present disclosure are described in detail in the Example section below.

In some embodiments, producing glycoRNAs of interest may comprise production (e.g., large scale production) of cells of a given type (wild-type or glycoengineered) which are then biochemically fractionated to first isolate membranes, followed by RNA separation from proteins and other biomolecules by chemical means (e.g., precipitation). In certain embodiments, glycans are enriched using lectin or other glycan binding proteins to purify the glycoRNAs away from any other RNAs in the RNA-membrane preparation. In some embodiments, post-purification glyco-engineering is performed, non-limiting examples of which include removal or addition of sialic acids, fucose, and/or the like.

In some embodiments, during the cell culture/production phase, the methods may comprise one or any combination of the following: providing the cells with excess nucleotides to increase the flux of RNA biosynthesis as compared to the flux in the absence of excess nucleotides; providing the cells with excess sugars (e.g., excess glucose, galactose, GlcNAc, or any combination thereof) to increase the flux of glycan biosynthesis as compared to the flux in the absence of excess sugars; inhibiting one or more cell membrane turnover pathways in the cells for enhanced accumulation of cell surface glycoRNAs; and inhibiting a portion of the glycan biosynthetic pathway to favor production of RNA glycans, e.g., inhibiting O-glycan production to favor N-glycan production.

Aspects of the present disclosure further include methods of engineering display of glycosylated ribonucleic acids (glycoRNAs) on the surface of a cell. In certain embodiments, such methods comprise introducing into the cell one or more expression constructs that encode for one or more ribonucleic acid and/or glycan biosynthetic enzymes, such that the cell displays on its surface one or more types of glycoRNAs of interest. According to some embodiments, the one or more types of displayed glycoRNAs are utilized to uniquely identify the cell. For example, one or more cells could be engineered to display one or more engineered types of glycoRNAs for acting as a "barcode" which uniquely identifies the one or more cells.

Conjugates, Fusion Proteins and Compositions

Aspects of the present disclosure further include conjugates, fusion proteins and compositions. In some embodiments, the conjugates, fusion proteins and compositions find use in practicing any of the methods of the present disclosure, including any of the methods described elsewhere herein. Any of the conjugates, fusion proteins, and compositions described in the Methods sections herein are provided by the present disclosure.

In certain aspects, provided are any of the soluble glycoRNAs described elsewhere herein conjugated to any of the agents described elsewhere herein. By way of example, the agent may be a therapeutic agent, an agent comprising a detectable label, etc.

In some aspects, provided are targeting moieties (e.g., antibodies, ligands, small molecules, aptamers, and/or the like) conjugated to a ribonuclease (RNase). Non-limiting examples of RNases that may be employed in the conjugates include an RNase A, a T1 RNase, a T2 RNase, and an RNase 1. In certain embodiments, the RNase is a human RNase. According to some embodiments, the RNase is human RNase 1 (UniProtKB—P07998).

In certain aspects, provided are fusion proteins comprising a targeting moiety (e.g., antibodies, ligands, and/or any other proteinaceous targeting moiety) fused to an RNase. The targeting moiety may be selected based on its ability to specifically bind a molecule expressed on the surface of target cells that display glycoRNAs, e.g., when it is desirable to degrade the glycoRNAs on the surface of such cells.

Compositions comprising any of the soluble glycoRNAs, conjugates, and/or fusion proteins of the present disclosure are also provided. In certain embodiments, a composition of the present disclosure comprises any of the soluble glycoRNAs, conjugates, and/or fusion proteins of the present disclosure, present in a liquid medium. The liquid medium may be an aqueous liquid medium, such as water, a buffered solution, or the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, a protease inhibitor, glycerol, a chelating agent, and the like may be present in such compositions.

Aspects of the present disclosure further include pharmaceutical compositions. In some embodiments, a pharmaceutical composition of the present disclosure comprises any of the soluble glycoRNAs, conjugates, and/or fusion proteins of the present disclosure, and a pharmaceutically acceptable carrier.

The soluble glycoRNAs, conjugates, and/or fusion proteins can be incorporated into a variety of formulations for therapeutic administration. More particularly, the soluble glycoRNAs, conjugates, and/or fusion proteins can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the soluble glycoRNAs, conjugates, and/or fusion proteins for administration to an individual (e.g., suitable for human administration) are generally sterile and may further be free of detectable pyrogens or other contaminants contraindicated for administration to a patient according to a selected route of administration.

In pharmaceutical dosage forms, the soluble glycoRNAs, conjugates, and/or fusion proteins can be administered in the form of their pharmaceutically acceptable salts, or they may also be used alone or in appropriate association, as well as in combination, with other pharmaceutically active compounds. The following methods and carriers/excipients are merely examples and are in no way limiting.

For oral preparations, the soluble glycoRNAs, conjugates, and/or fusion proteins can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The soluble glycoRNAs, conjugates, and/or fusion proteins can be formulated for parenteral (e.g., intravenous, intra-arterial, intraosseous, intramuscular, intracerebral, intracerebroventricular, intrathecal, subcutaneous, etc.) administration. In certain aspects, the soluble glycoRNAs, conjugates, and/or fusion proteins are formulated for injection by dissolving, suspending or emulsifying the soluble glycoRNAs, conjugates, and/or fusion proteins in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions that include the soluble glycoRNAs, conjugates, and/or fusion proteins may be prepared by mixing the soluble glycoRNAs, conjugates, and/or fusion proteins having the desired degree of purity with optional physiologically acceptable carriers, excipients, stabilizers, surfactants, buffers and/or tonicity agents.

Acceptable carriers, excipients and/or stabilizers are non-toxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included to modulate the tonicity of the formulation. Example tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 mM.

A surfactant may also be added to the formulation to reduce aggregation and/or minimize the formation of particulates in the formulation and/or reduce adsorption. Example surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Example concentrations of surfactant may range from about 0.001% to about 1% w/v.

A lyoprotectant may also be added in order to protect the soluble glycoRNAs, conjugates, and/or fusion proteins against destabilizing conditions during a lyophilization process. For example, known lyoprotectants include sugars (including glucose and sucrose); polyols (including mannitol, sorbitol and glycerol); and amino acids (including alanine, glycine and glutamic acid). Lyoprotectants can be included, e.g., in an amount of about 10 mM to 500 nM.

In some embodiments, the pharmaceutical composition includes the soluble glycoRNAs, conjugates, and/or fusion proteins, and one or more of the above-identified components (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

Kits

Aspects of the present disclosure further include kits. In certain embodiments, the kits find use in practicing the methods of the present disclosure, e.g., in vitro, in vivo or ex vivo methods for reducing interaction between GBP-expressing cells and cells displaying cell surface glycoRNAs, methods for targeting an agent to GBP-expressing cells, methods for inducing signaling through GBP expressed on the surface of GBP-expressing cells, etc.

Accordingly, a kit of the present disclosure may comprise any of the soluble glycoRNAs, conjugates, and/or fusion proteins of the present disclosure, including any of the soluble glycoRNAs, conjugates, and/or fusion proteins described elsewhere but not reiterated herein for purposes of brevity. A kit may comprise the soluble glycoRNAs, conjugates, and/or fusion proteins present in a pharmaceutical composition. When a kit of the present disclosure comprises a pharmaceutical composition, the kit may comprise a quantity of the composition, present in unit dosages, e.g., ampoules, or a multi-dosage format. As such, in certain embodiments, the kits may include one or more (e.g., two or more) unit dosages (e.g., ampoules) of a pharmaceutical composition that includes any of the soluble glycoRNAs, conjugates, and/or fusion proteins of the present disclosure. The term "unit dosage", as used herein, refers to physically discrete units suitable as unitary dosages for human and animal subjects, each unit containing a predetermined quantity of the composition calculated in an amount sufficient to produce the desired effect. The amount of the unit dosage depends on various factors, such as the particular soluble glycoRNAs, conjugates, and/or fusion proteins employed, the effect to be achieved, and the pharmacodynamics associated with the soluble glycoRNAs, conjugates, and/or fusion proteins, in the individual. In yet other embodiments, the kits may include a single multi dosage amount of the composition.

In certain embodiments, a kit of the present disclosure includes instructions for using the contents of the kit for reducing interaction between GBP-expressing cells and cells displaying cell surface glycoRNAs, methods for targeting an agent to GBP-expressing cells, methods for inducing signaling through GBP expressed on the surface of GBP-expressing cells, and/or the like, in vitro, in vivo or ex vivo.

The instructions (e.g., instructions for use (IFU)) included in the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, the means for obtaining the instructions is recorded on a suitable substrate.

In certain embodiments, the present disclosure provides compositions comprising a compound of Formula (I) described herein, or a salt, solvate, hydrate, polymorph, co-crystal, tautomer, stereoisomer, isotopically labeled derivative, or prodrug thereof, and optionally an excipient. In certain embodiments, the composition is used in human applications (e.g., medical, industrial, research uses). In certain embodiments, the composition is used in non-human veterinary applications (e.g., used for non-human animals (e.g., farm animals, companion animals)). In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a research animal (e.g., primate, rat, mouse, dog, fish). In certain embodiments, the non-human animal is a fish, reptile, or amphibian. The non-human animal may be male or female at any stage of development. In certain embodiments, the non-human companion animal is a dog. In certain embodiments, the non-human companion animal is a cat. In certain embodiments, the non-human companion animal is a bird. Compositions described herein can be prepared by any method known in the art. In another aspect, provided are kits including a first container comprising a compound or composition described herein and instructions for use (e.g., for administering to a subject or contacting a biological sample with the compound or composition thereof). The kits may further comprise a container (e.g., a vial, ampule, bottle, syringe, and/or dispenser package, or other suitable container). In some embodiments, provided kits may optionally further include a second container comprising an excipient for dilution or suspension of a compound or composition described herein.

Exemplary Embodiments—Section A

The following descriptive embodiments are intended to be illustrative of inventions contemplated herein:

1. A pharmaceutical composition comprising:
   a) a pharmaceutically acceptable carrier; and
   b) a modified RNA comprising a glycan moiety comprising at least ten monosaccharides.
2. The pharmaceutical composition of embodiment 1 wherein the glycan moiety comprises sialic acid, fucose, or a combination thereof.
3. The pharmaceutical composition of embodiment 1 wherein the glycan moiety comprises GlcNAc, mannose, galactose, sialic acid, and fucose, or a combination thereof.
4. The pharmaceutical composition of embodiment 1, formulated for systemic administration to a human subject in need thereof.
5. The pharmaceutical composition of embodiment 1, formulated for systemic administration to a mammalian subject in need thereof.
6. The pharmaceutical composition of embodiment 1, suitable for multiple systemic administrations to a human subject in need thereof.
7. The pharmaceutical composition of embodiment 1, suitable for multiple systemic administrations to a mammalian subject in need thereof.
8. The pharmaceutical composition of embodiment 1 wherein the glycan moiety comprises a bi-antennary N-linked glycan comprises a first terminal residue and a second terminal residue, wherein at least one of the first or second terminal residue comprises sialic acid.
9. The pharmaceutical composition of embodiment 1 wherein the glycan moiety comprises a tri-antennary N-linked glycan comprises a first terminal residue, a second terminal residue, and a third terminal residue, wherein at least one of the first or second or third terminal residue comprises sialic acid.
10. The pharmaceutical composition of embodiment 1 wherein the glycan moiety comprises a tri-antennary N-linked glycan comprises a first terminal residue, a second terminal residue, and a third terminal residue, wherein at least one of the first or second or third terminal residue comprises sialic acid residue comprising one or more poly-sialic acid terminal modifications.
11. The pharmaceutical composition of embodiment 1 wherein the glycan moiety comprises a bi-antennary N-linked glycan comprises a fucose linked to a GlcNAc residue present in a core or a base of the glycan.
12. The pharmaceutical composition of embodiment 1 wherein the glycan moiety comprises a bi-antennary N-linked glycan comprises a fucose linked to a GlcNAc residue present in a tree or an arm.
13. The pharmaceutical composition of embodiment 1 wherein the glycan moiety comprises a bi-antennary N-linked glycan comprises more than one arm with a GlcNAc between two of the arms, creating a bisecting glycan.
14. The pharmaceutical composition of embodiment 1 wherein the glycan moiety comprises a tri-antennary N-linked glycan comprises a first terminal residue, a second terminal residue, and a third terminal residue, wherein at least one of the first and second terminal residue comprises fucose.
15. The pharmaceutical composition of embodiment 1 wherein the glycan moiety comprises a bi-antennary N-linked glycan comprises a first terminal residue and a second terminal residue, wherein at least one terminal residue comprises sialic acid and at least one terminal residue comprises fucose.
16. The pharmaceutical composition of embodiment 1 wherein the glycan moiety comprises a tri-antennary N-linked glycan comprises a first terminal residue, a second terminal residue, and a third terminal residue, wherein at least one terminal residue is sialic acid and one terminal residue is fucose.
17. The pharmaceutical composition of embodiment 1 wherein the glycan moiety comprises an N-linked glycan, and wherein the RNA comprises a modified nucleotide.
18. The pharmaceutical composition of embodiment 1 wherein the glycan moiety comprises an N-linked glycan, and wherein the nucleic acid includes a modified nucleotide, wherein the modified nucleotide may vary in nucleic acid position.

19. The pharmaceutical composition of embodiment 1 wherein the glycan moiety comprises an N-linked glycan, and wherein the nucleic acid includes a modified nucleotide, wherein the modifications are orthogonal to couple two or more glycans.
20. The pharmaceutical composition of embodiment 1, wherein the modified RNA comprises at least about 15, 20, 25, 30, 50, 100, 500, 1000, 1500, 2000, 2500, 3000, 4000, 5000, 6000, 7000, 8000, 9000, 10000 or greater than 10000 nucleotides.
21. The pharmaceutical composition of embodiment 1, wherein the modified RNA does not comprise non-natural nucleotides.
22. The pharmaceutical composition of embodiment 1, wherein the modified RNA comprises fewer than about 15, 20, 25, 30, or 50 nucleotides.
23. The pharmaceutical composition of embodiment 1, wherein the modified RNA comprises a microRNA binding moiety.
24. The pharmaceutical composition of embodiment 1, wherein the modified RNA comprises a sequence encoding a polypeptide.
25. The pharmaceutical composition of embodiment 1, further comprising a therapeutic moiety operably linked to the modified RNA wherein the therapeutic moiety is selected from antibodies, small molecules, isotopes, enzymes, and peptides.
26. The pharmaceutical composition of embodiment 1, wherein a modified RNA comprises a cleavable linker between an RNA and a glycan.
27. The pharmaceutical composition of embodiment 1, wherein a modified RNA comprises a cleavable linker between an RNA and a glycan wherein the cleavable linker is pH dependent, a disulfide bond, a peptide cleavage site, or a cit-val linker.
28. A method of producing a long pharmacodynamic effect comprising administering an RNA modified by a glycan to a subject in need thereof.
29. A method of treating cancer, comprising administering to a human subject in need thereof an effective amount of a pharmaceutical composition comprising
a) a pharmaceutically acceptable carrier; and
b) a modified RNA comprising a glycan moiety comprising at least ten monosaccharides.
30. A method of treating an autoimmune disease, comprising administering to a human subject in need thereof an effective amount of a pharmaceutical composition comprising
a) a pharmaceutically acceptable carrier; and
b) a modified RNA comprising a glycan moiety comprising at least ten monosaccharides.
31. A method of treating an IgE-mediated allergy, comprising administering to a human subject in need thereof an effective amount of a pharmaceutical composition comprising
a) a pharmaceutically acceptable carrier; and
b) a modified RNA comprising a glycan moiety comprising at least ten monosaccharides.
32. A method of treating systemic lupus erythematosus, comprising administering to a human subject in need thereof an effective amount of a pharmaceutical composition comprising
a) a pharmaceutically acceptable carrier; and
b) a modified RNA comprising a glycan moiety comprising at least ten monosaccharides.
33. A method of treating a viral infection, comprising administering to a human subject in need thereof an effective amount of a pharmaceutical composition comprising
a) a pharmaceutically acceptable carrier; and
b) a modified RNA comprising a glycan moiety comprising at least ten monosaccharides.
34. A method of delivering a chimeric antigen receptor, comprising administering to a human subject in need thereof an effective amount of a pharmaceutical composition comprising
a) a pharmaceutically acceptable carrier; and
b) a modified RNA comprising a glycan moiety comprising at least ten monosaccharides, wherein the modified RNA comprises a sequence encoding a chimeric antigen receptor polypeptide.
35. A method of producing a cell or a plurality of cells, comprising:
a) providing an isolated cell or a plurality of isolated cells;
b) providing a preparation of a modified RNA comprising a glycan; and
c) contacting the modified RNA to the isolated cell or the plurality of cells, wherein the isolated cell or the plurality of cells is capable of binding the modified RNA.
36. A method of producing a cell or a plurality of cells, comprising:
a) providing an isolated cell or a plurality of isolated cells;
b) providing a preparation of a small modified RNA comprising a glycan; and
c) contacting the small modified RNA to the isolated cell or the plurality of cells, wherein the isolated cell or the plurality of cells is capable of binding the small modified RNA.
37. A method of producing a cell or a plurality of cells, comprising:
a) providing an isolated cell or a plurality of isolated cells;
b) providing a preparation of a large modified RNA comprising a glycan; and
c) contacting the large modified RNA to the isolated cell or the plurality of cells, wherein the isolated cell or the plurality of cells is capable of binding the large modified RNA.
38. A method of producing a modified RNA, comprising:
a) providing an RNA; and
b) contacting the RNA with a glycan under conditions such that the RNA is modified by conjugation of the RNA to the glycan.
39. A method of producing a lipid nanoparticle (LNP), comprising:
a) providing an RNA;
b) contacting the RNA with a glycan, under conditions such that the RNA is modified by conjugation of the RNA to the glycan;
c) contacting the modified RNA with a lipid under conditions such that an LNP is formed.
40. A method of producing a modified RNA, comprising:
a) providing a modified RNA comprising a glycan moiety comprising at least ten monosaccharides;
b) providing an LNP; and
c) contacting the modified RNA with an LNP under conditions such that the modified RNA is present in and/or on a surface of the LNP.

41. A method of producing an RNA-nanoparticle (RNA NP), comprising:
   a) providing an RNA;
   b) contacting the RNA with a glycan, under conditions such that the RNA is modified by conjugation of the RNA to the glycan;
   c) contacting the modified RNA with a nanoparticle under conditions such that an RNA NP is formed.

42. A method of producing a modified RNA, comprising:
   a) providing a modified RNA comprising a glycan moiety comprising at least ten monosaccharides;
   b) providing a nanoparticle; and
   c) contacting the modified RNA with a nanoparticle under conditions such that the modified RNA is present in and/or on a surface of the nanoparticle.

43. A method of delivering a modified RNA, comprising:
   a) providing a modified RNA comprising a glycan moiety comprising at least ten monosaccharides; and
   b) providing electroporation.

44. A method of producing a modified RNA, comprising a modified RNA comprising a glycan moiety comprising at least ten monosaccharides wherein the modified RNA modulates a cell surface receptor comprising contacting a cell containing the receptor with a modified RNA.

45. A method of producing a modified RNA, comprising:
   a) providing a modified RNA comprising a glycan moiety comprising at least ten monosaccharides; and
   b) providing a serum, wherein the glycan provides stabilization to the RNA within the serum.

46. A method of producing a modified RNA, comprising:
   a) providing an RNA; and
   b) contacting the RNA with a glycan, wherein the glycan comprises N-Acetylgalactosamine, under conditions such that the RNA is modified by conjugation of the RNA to the glycan.

47. A pharmaceutical composition comprising a modified naked RNA comprising a glycan moiety comprising at least ten monosaccharides.

48. A pharmaceutical composition comprising:
   a) a pharmaceutically acceptable carrier; and
   b) a modified RNA comprising a glycan moiety comprising at least one monosaccharide.

49. A pharmaceutical composition comprising:
   a) a pharmaceutically acceptable carrier; and
   b) a modified RNA comprising a glycan moiety comprising at least two monosaccharides.

50. A pharmaceutical composition comprising:
   a) a pharmaceutically acceptable carrier; and
   b) a modified RNA comprising a glycan moiety comprising at least three monosaccharides.

51. A pharmaceutical composition comprising:
   a) a pharmaceutically acceptable carrier; and
   b) a modified RNA comprising a glycan moiety comprising at least four monosaccharides.

52. A pharmaceutical composition comprising:
   a) a pharmaceutically acceptable carrier; and
   b) a modified RNA comprising a glycan moiety comprising at least five monosaccharides.

53. A pharmaceutical composition comprising:
   a) a pharmaceutically acceptable carrier; and
   b) a modified RNA comprising a glycan moiety comprising at least six monosaccharides.

54. A pharmaceutical composition comprising:
   a) a pharmaceutically acceptable carrier; and
   b) a modified RNA comprising a glycan moiety comprising at least seven monosaccharides.

55. A pharmaceutical composition comprising:
   a) a pharmaceutically acceptable carrier; and
   b) a modified RNA comprising a glycan moiety comprising at least eight monosaccharides.

56. A pharmaceutical composition comprising:
   a) a pharmaceutically acceptable carrier; and
   b) a modified RNA comprising a glycan moiety comprising at least nine monosaccharides.

57. A pharmaceutical composition comprising:
   a) a pharmaceutically acceptable carrier; and
   b) a modified nucleic acid comprising a glycan moiety comprising at least ten monosaccharides.

58. The pharmaceutical composition of embodiment 57 wherein the glycan moiety comprises sialic acid, fucose, or a combination thereof.

59. The pharmaceutical composition of embodiment 57 wherein the glycan moiety comprises GlcNAc, mannose, galactose, sialic acid, and fucose, or a combination thereof.

60. The pharmaceutical composition of embodiment 57, formulated for systemic administration to a human subject in need thereof.

61. The pharmaceutical composition of embodiment 57, formulated for systemic administration to a mammalian subject in need thereof.

62. The pharmaceutical composition of embodiment 57, suitable for multiple systemic administrations to a human subject in need thereof.

63. The pharmaceutical composition of embodiment 57, suitable for multiple systemic administrations to a mammalian subject in need thereof.

64. The pharmaceutical composition of embodiment 57 wherein the glycan moiety comprises a bi-antennary N-linked glycan comprises a first terminal residue and a second terminal residue, wherein at least one of the first or second terminal residue comprises sialic acid.

65. The pharmaceutical composition of embodiment 57 wherein the glycan moiety comprises a tri-antennary N-linked glycan comprises a first terminal residue, a second terminal residue, and a third terminal residue, wherein at least one of the first or second or third terminal residue comprises sialic acid.

66. The pharmaceutical composition of embodiment 57 wherein the glycan moiety comprises a tri-antennary N-linked glycan comprises a first terminal residue, a second terminal residue, and a third terminal residue, wherein at least one of the first or second or third terminal residue comprises sialic acid residue comprising one or more poly-sialic acid terminal modifications.

67. The pharmaceutical composition of embodiment 57 wherein the glycan moiety comprises a bi-antennary N-linked glycan comprises a fucose linked to a GlcNAc residue present in a core or a base of the glycan.

68. The pharmaceutical composition of embodiment 57 wherein the glycan moiety comprises a bi-antennary N-linked glycan comprises a fucose linked to a GlcNAc residue present in a tree or an arm.

69. The pharmaceutical composition of embodiment 57 wherein the glycan moiety comprises a bi-antennary N-linked glycan comprises more than one arm with a GLcNAc between two of the arms, creating a bisecting glycan.

70. The pharmaceutical composition of embodiment 57 wherein the glycan moiety comprises a tri-antennary N-linked glycan comprises a first terminal residue, a second terminal residue, and a third terminal residue, wherein at least one of the first and second terminal residue comprises fucose.

71. The pharmaceutical composition of embodiment 57 wherein the glycan moiety comprises a bi-antennary N-linked glycan comprises a first terminal residue and a second terminal residue, wherein at least one terminal residue comprises sialic acid and at least one terminal residue comprises fucose.

72. The pharmaceutical composition of embodiment 57 wherein the glycan moiety comprises a tri-antennary N-linked glycan comprises a first terminal residue, a second terminal residue, and a third terminal residue, wherein at least one terminal residue is sialic acid and one terminal residue is fucose.

73. The pharmaceutical composition of embodiment 57 wherein the glycan moiety comprises an N-linked glycan, and wherein the nucleic acid comprises a modified nucleotide.

74. The pharmaceutical composition of embodiment 57 wherein the glycan moiety comprises an N-linked glycan, and wherein the nucleic acid includes a modified nucleotide, wherein the modified nucleotide may vary in nucleic acid position.

75. The pharmaceutical composition of embodiment 57 wherein the glycan moiety comprises an N-linked glycan, and wherein the nucleic acid includes a modified nucleotide, wherein the modifications are orthogonal to couple two or more glycans.

76. The pharmaceutical composition of embodiment 57, wherein the modified nucleic acid comprises at least about 15, 20, 25, 30, 50, 100, 500, 1000, 1500, 2000, 2500, 3000, 4000, 5000, 6000, 7000, 8000, 9000, 10000 or greater than 10000 nucleotides.

77. The pharmaceutical composition of embodiment 57, wherein the modified nucleic acid does not comprise non-natural nucleotides.

78. The pharmaceutical composition of embodiment 57, wherein the modified nucleic acid comprises fewer than about 15, 20, 25, 30, or 50 nucleotides.

79. The pharmaceutical composition of embodiment 57, wherein the modified nucleic acid comprises a micro-nucleic acid binding moiety.

80. The pharmaceutical composition of embodiment 57, wherein the modified nucleic acid comprises a sequence encoding a polypeptide.

81. The pharmaceutical composition of embodiment 57, further comprising a therapeutic moiety operably linked to the modified nucleic acid wherein the therapeutic moiety is selected from antibodies, small molecules, isotopes, enzymes, and peptides.

82. The pharmaceutical composition of embodiment 57, wherein a modified nucleic acid comprises a cleavable linker between a nucleoside and a glycan.

83. The pharmaceutical composition of embodiment 57, wherein a modified nucleic acid comprises a cleavable linker between a nucleic acid and a glycan wherein the cleavable linker is pH dependent, a disulfide bond, a peptide cleavage site, or a cit-val linker.

84. A method of producing a long lasting pharmacodynamic effect comprising administering a nucleic acid modified by a glycan to a subject in need thereof.

85. A method of treating cancer, comprising administering to a human subject in need thereof an effective amount of a pharmaceutical composition comprising
    a) a pharmaceutically acceptable carrier; and
    b) a modified nucleic acid comprising a glycan moiety comprising at least ten monosaccharides.

86. A method of treating an autoimmune disease, comprising administering to a human subject in need thereof an effective amount of a pharmaceutical composition comprising
    a) a pharmaceutically acceptable carrier; and
    b) a modified nucleic acid comprising a glycan moiety comprising at least ten monosaccharides.

87. A method of treating an IgE-mediated allergy, comprising administering to a human subject in need thereof an effective amount of a pharmaceutical composition comprising
    a) a pharmaceutically acceptable carrier; and
    b) a modified nucleic acid comprising a glycan moiety comprising at least ten monosaccharides.

88. A method of treating systemic lupus erythematosus, comprising administering to a human subject in need thereof an effective amount of a pharmaceutical composition comprising
    a) a pharmaceutically acceptable carrier; and
    b) a modified nucleic acid comprising a glycan moiety comprising at least ten monosaccharides.

89. A method of treating a viral infection, comprising administering to a human subject in need thereof an effective amount of a pharmaceutical composition comprising
    a) a pharmaceutically acceptable carrier; and
    b) a modified nucleic acid comprising a glycan moiety comprising at least ten monosaccharides.

90. A method of delivering a chimeric antigen receptor, comprising administering to a human subject in need thereof an effective amount of a pharmaceutical composition comprising
    a) a pharmaceutically acceptable carrier; and
    b) a modified nucleic acid comprising a glycan moiety comprising at least ten monosaccharides, wherein the modified nucleic acid comprises a sequence encoding a chimeric antigen receptor polypeptide.

91. A method of producing a cell or a plurality of cells, comprising:
    a) providing an isolated cell or a plurality of isolated cells;
    b) providing a preparation of a modified nucleic acid comprising a glycan; and
    c) contacting the modified nucleic acid to the isolated cell or the plurality of cells, wherein the isolated cell or the plurality of cells is capable of binding the modified nucleic acid.

92. A method of producing a cell or a plurality of cells, comprising:
    a) providing an isolated cell or a plurality of isolated cells;
    b) providing a preparation of a small modified nucleic acid comprising a glycan; and
    c) contacting the small modified nucleic acid to the isolated cell or the plurality of cells, wherein the isolated cell or the plurality of cells is capable of binding the small modified nucleic acid.

93. A method of producing a cell or a plurality of cells, comprising:
   a) providing an isolated cell or a plurality of isolated cells;
   b) providing a preparation of a large modified nucleic acid comprising a glycan; and
   c) contacting the large modified nucleic acid to the isolated cell or the plurality of cells, wherein the isolated cell or the plurality of cells is capable of binding the large modified nucleic acid.

94. A method of producing a modified nucleic acid, comprising:
   a) providing a nucleic acid; and
   b) contacting the nucleic acid with a glycan under conditions such that the nucleic acid is modified by conjugation of the nucleic acid to the glycan.

95. A method of producing a lipid nanoparticle (LNP), comprising:
   a) providing a nucleic acid;
   b) contacting the nucleic acid with a glycan, under conditions such that the nucleic acid is modified by conjugation of the nucleic acid to the glycan;
   c) contacting the modified nucleic acid with a lipid under conditions such that an LNP is formed.

96. A method of producing a modified nucleic acid, comprising:
   a) providing a modified nucleic acid comprising a glycan moiety comprising at least ten monosaccharides;
   b) providing an LNP; and
   c) contacting the modified nucleic acid with an LNP under conditions such that the modified nucleic acid is present in and/or on a surface of the LNP.

97. A method of producing a nucleic acid-nanoparticle, comprising:
   a) providing a nucleic acid;
   b) contacting the nucleic acid with a glycan, under conditions such that the nucleic acid is modified by conjugation of the nucleic acid to the glycan;
   c) contacting the modified nucleic acid with a nanoparticle under conditions such that a nucleic acid-nanoparticle is formed.

98. A method of producing a modified nucleic acid, comprising:
   a) providing a modified nucleic acid comprising a glycan moiety comprising at least ten monosaccharides;
   b) providing a nanoparticle; and
   c) contacting the modified nucleic acid with a nanoparticle under conditions such that the modified nucleic acid is present in and/or on a surface of the nanoparticle.

99. A method of delivering a modified nucleic acid, comprising:
   a) providing a modified nucleic acid comprising a glycan moiety comprising at least ten monosaccharides; and
   b) providing electroporation.

100. A method of producing a modified nucleic acid, comprising:
   a) providing a modified nucleic acid comprising a glycan moiety comprising at least ten monosaccharides; and
   b) providing a serum, wherein the glycan provides stabilization to the nucleic acid within the serum.

101. A method of producing a modified nucleic acid, comprising a modified nucleic acid comprising a glycan moiety comprising at least ten monosaccharides wherein the modified nucleic acid modulates a cell surface receptor comprising contacting a cell containing the receptor with a modified nucleic acid.

102. A method of producing a modified nucleic acid, comprising:
   a) providing a nucleic acid; and
   b) contacting the nucleic acid with a glycan, wherein the glycan comprises N-Acetylgalactosamine.

103. A pharmaceutical composition comprising a modified naked nucleic acid comprising a glycan moiety comprising at least ten monosaccharides.

104. A pharmaceutical composition comprising:
   a) a pharmaceutically acceptable carrier; and
   b) a modified nucleic acid comprising a glycan moiety comprising at least one monosaccharide.

105. A pharmaceutical composition comprising:
   a) a pharmaceutically acceptable carrier; and
   b) a modified nucleic acid comprising a glycan moiety comprising at least two monosaccharides.

106. A pharmaceutical composition comprising:
   a) a pharmaceutically acceptable carrier; and
   b) a modified nucleic acid comprising a glycan moiety comprising at least three monosaccharides.

107. A pharmaceutical composition comprising:
   a) a pharmaceutically acceptable carrier; and
   b) a modified nucleic acid comprising a glycan moiety comprising at least four monosaccharides.

108. A pharmaceutical composition comprising:
   a) a pharmaceutically acceptable carrier; and
   b) a modified nucleic acid comprising a glycan moiety comprising at least five monosaccharides.

109. A pharmaceutical composition comprising:
   a) a pharmaceutically acceptable carrier; and
   b) a modified nucleic acid comprising a glycan moiety comprising at least six monosaccharides.

110. A pharmaceutical composition comprising:
   a) a pharmaceutically acceptable carrier; and
   b) a modified nucleic acid comprising a glycan moiety comprising at least seven monosaccharides.

111. A pharmaceutical composition comprising:
   a) a pharmaceutically acceptable carrier; and
   b) a modified nucleic acid comprising a glycan moiety comprising at least eight monosaccharides.

112. A pharmaceutical composition comprising:
   a) a pharmaceutically acceptable carrier; and
   b) a modified nucleic acid comprising a glycan moiety comprising at least nine monosaccharides.

113. A pharmaceutical composition comprising:
   a) a pharmaceutically acceptable carrier; and
   b) a modified DNA comprising a glycan moiety comprising at least ten monosaccharides.

114. The pharmaceutical composition of embodiment 113 wherein the glycan moiety comprises sialic acid, fucose, or a combination thereof.

115. The pharmaceutical composition of embodiment 113 wherein the glycan moiety comprises GlcNAc, mannose, galactose, sialic acid, and fucose, or a combination thereof.

116. The pharmaceutical composition of embodiment 113, formulated for systemic administration to a human subject in need thereof.

117. The pharmaceutical composition of embodiment 113, formulated for systemic administration to a mammalian subject in need thereof.

118. The pharmaceutical composition of embodiment 113, suitable for multiple systemic administrations to a human subject in need thereof.
119. The pharmaceutical composition of embodiment 113, suitable for multiple systemic administrations to a mammalian subject in need thereof.
120. The pharmaceutical composition of embodiment 113 wherein the glycan moiety comprises a bi-antennary N-linked glycan comprises a first terminal residue and a second terminal residue, wherein at least one of the first or second terminal residue comprises sialic acid.
121. The pharmaceutical composition of embodiment 113 wherein the glycan moiety comprises a tri-antennary N-linked glycan comprises a first terminal residue, a second terminal residue, and a third terminal residue, wherein at least one of the first or second or third terminal residue comprises sialic acid.
122. The pharmaceutical composition of embodiment 113 wherein the glycan moiety comprises a tri-antennary N-linked glycan comprises a first terminal residue, a second terminal residue, and a third terminal residue, wherein at least one of the first or second or third terminal residue comprises sialic acid residue comprising one or more poly-sialic acid terminal modifications.
123. The pharmaceutical composition of embodiment 113 wherein the glycan moiety comprises a bi-antennary N-linked glycan comprises a fucose linked to a GlcNAc residue present in a core or a base of the glycan.
124. The pharmaceutical composition of embodiment 113 wherein the glycan moiety comprises a bi-antennary N-linked glycan comprises a fucose linked to a GlcNAc residue present in a tree or an arm.
125. The pharmaceutical composition of embodiment 113 wherein the glycan moiety comprises a bi-antennary N-linked glycan comprises more than one arm with a GLcNAc between two of the arms, creating a bisecting glycan.
126. The pharmaceutical composition of embodiment 113 wherein the glycan moiety comprises a tri-antennary N-linked glycan comprises a first terminal residue, a second terminal residue, and a third terminal residue, wherein at least one of the first and second terminal residue comprises fucose.
127. The pharmaceutical composition of embodiment 113 wherein the glycan moiety comprises a bi-antennary N-linked glycan comprises a first terminal residue and a second terminal residue, wherein at least one terminal residue comprises sialic acid and at least one terminal residue comprises fucose.
128. The pharmaceutical composition of embodiment 113 wherein the glycan moiety comprises a tri-antennary N-linked glycan comprises a first terminal residue, a second terminal residue, and a third terminal residue, wherein at least one terminal residue is sialic acid and one terminal residue is fucose.
129. The pharmaceutical composition of embodiment 113 wherein the glycan moiety comprises an N-linked glycan, and wherein the DNA comprises a modified nucleotide.
130. The pharmaceutical composition of embodiment 113 wherein the glycan moiety comprises an N-linked glycan, and wherein the nucleic acid includes a modified nucleotide, wherein the modified nucleotide may vary in nucleic acid position.
131. The pharmaceutical composition of embodiment 113 wherein the glycan moiety comprises an N-linked glycan, and wherein the nucleic acid includes a modified nucleotide, wherein the modifications are orthogonal to couple two or more glycans.
132. The pharmaceutical composition of embodiment 113, wherein the modified DNA comprises at least about 15, 20, 25, 30, 50, 100, 500, 1000, 1500, 2000, 2500, 3000, 4000, 5000, 6000, 7000, 8000, 9000, 10000 or greater than 10000 nucleotides.
133. The pharmaceutical composition of embodiment 113, wherein the modified DNA does not comprise non-natural nucleotides.
134. The pharmaceutical composition of embodiment 113, wherein the modified DNA comprises fewer than about 15, 20, 25, 30, or 50 nucleotides.
135. The pharmaceutical composition of embodiment 113, wherein the modified DNA comprises a microRNA binding moiety.
136. The pharmaceutical composition of embodiment 113, wherein the modified DNA comprises a sequence encoding a polypeptide.
137. The pharmaceutical composition of embodiment 113, further comprising a therapeutic moiety operably linked to the modified DNA wherein the therapeutic moiety is selected from antibodies, small molecules, isotopes, enzymes, and peptides.
138. The pharmaceutical composition of embodiment 113, wherein a modified DNA comprises a cleavable linker between a DNA and a glycan.
139. The pharmaceutical composition of embodiment 113, wherein a modified DNA comprises a cleavable linker between a DNA and a glycan wherein the cleavable linker is pH dependent, a disulfide bond, a peptide cleavage site, or a cit-val linker.
140. A method of producing a long lasting pharmacodynamic effect comprising administering a DNA modified by a glycan to a subject in need thereof.
141. A method of treating cancer, comprising administering to a human subject in need thereof an effective amount of a pharmaceutical composition comprising
    a) a pharmaceutically acceptable carrier; and
    b) a modified DNA comprising a glycan moiety comprising at least ten monosaccharides.
142. A method of treating an autoimmune disease, comprising administering to a human subject in need thereof an effective amount of a pharmaceutical composition comprising
    a) a pharmaceutically acceptable carrier; and
    b) a modified DNA comprising a glycan moiety comprising at least ten monosaccharides.
143. A method of treating an IgE-mediated allergy, comprising administering to a human subject in need thereof an effective amount of a pharmaceutical composition comprising
    a) a pharmaceutically acceptable carrier; and
    b) a modified DNA comprising a glycan moiety comprising at least ten monosaccharides.
144. A method of treating systemic lupus erythematosus, comprising administering to a human subject in need thereof an effective amount of a pharmaceutical composition comprising
    a) a pharmaceutically acceptable carrier; and
    b) a modified DNA comprising a glycan moiety comprising at least ten monosaccharides.

145. A method of treating a viral infection, comprising administering to a human subject in need thereof an effective amount of a pharmaceutical composition comprising
   a) a pharmaceutically acceptable carrier; and
   b) a modified DNA comprising a glycan moiety comprising at least ten monosaccharides.
146. A method of delivering a chimeric antigen receptor, comprising administering to a human subject in need thereof an effective amount of a pharmaceutical composition comprising
   a) a pharmaceutically acceptable carrier; and
   b) a modified DNA comprising a glycan moiety comprising at least ten monosaccharides, wherein the modified DNA comprises a sequence encoding a chimeric antigen receptor polypeptide.
147. A method of producing a cell or a plurality of cells, comprising:
   a) providing an isolated cell or a plurality of isolated cells;
   b) providing a preparation of a modified DNA comprising a glycan; and
   c) contacting the modified DNA to the isolated cell or the plurality of cells, wherein the isolated cell or the plurality of cells is capable of binding the modified DNA.
148. A method of producing a cell or a plurality of cells, comprising:
   a) providing an isolated cell or a plurality of isolated cells;
   b) providing a preparation of a small modified DNA comprising a glycan; and
   c) contacting the small modified DNA to the isolated cell or the plurality of cells, wherein the isolated cell or the plurality of cells is capable of binding the small modified DNA.
149. A method of producing a cell or a plurality of cells, comprising:
   a) providing an isolated cell or a plurality of isolated cells;
   b) providing a preparation of a large modified DNA comprising a glycan; and
   c) contacting the large modified DNA to the isolated cell or the plurality of cells, wherein the isolated cell or the plurality of cells is capable of binding the large modified DNA.
150. A method of producing a modified DNA, comprising:
   a) providing a DNA; and
   b) contacting the DNA with a glycan under conditions such that the DNA is modified by conjugation of the DNA to the glycan.
151. A method of producing a lipid nanoparticle (LNP), comprising:
   a) providing a DNA;
   b) contacting the DNA with a glycan, under conditions such that the DNA is modified by conjugation of the DNA to the glycan;
   c) contacting the modified DNA with a lipid under conditions such that an LNP is formed.
152. A method of producing a modified DNA, comprising:
   a) providing a modified DNA comprising a glycan moiety comprising at least ten monosaccharides;
   b) providing an LNP; and
   c) contacting the modified DNA with an LNP under conditions such that the modified DNA is present in and/or on a surface of the LNP.
153. A method of producing a DNA-nanoparticle (DNA NP), comprising:
   a) providing a DNA;
   b) contacting the DNA with a glycan, under conditions such that the DNA is modified by conjugation of the DNA to the glycan;
   c) contacting the modified DNA with a nanoparticle under conditions such that a DNA NP is formed.
154. A method of producing a modified DNA, comprising:
   a) providing a modified DNA comprising a glycan moiety comprising at least ten monosaccharides;
   b) providing a nanoparticle; and
   c) contacting the modified DNA with a nanoparticle under conditions such that the modified DNA is present in and/or on a surface of the nanoparticle.
155. A method of delivering a modified DNA, comprising:
   a) providing a modified DNA comprising a glycan moiety comprising at least ten monosaccharides; and
   b) providing electroporation.
156. A method of producing a modified DNA, comprising:
   a) providing a modified DNA comprising a glycan moiety comprising at least ten monosaccharides; and
   b) providing a serum, wherein the glycan provides stabilization to the DNA within the serum.
157. A method of producing a modified DNA, comprising a modified DNA comprising a glycan moiety comprising at least ten monosaccharides wherein the modified DNA modulates a cell surface receptor comprising contacting a cell containing the receptor with a modified DNA.
158. A method of producing a modified DNA, comprising:
   a) providing a DNA; and
   b) contacting the DNA with a glycan, wherein the glycan comprises N-Acetylgalactosamine.
159. A pharmaceutical composition comprising a modified naked DNA comprising a glycan moiety comprising at least ten monosaccharides.
160. A pharmaceutical composition comprising:
   a) a pharmaceutically acceptable carrier; and
   b) a modified DNA comprising a glycan moiety comprising at least one monosaccharide.
161. A pharmaceutical composition comprising:
   a) a pharmaceutically acceptable carrier; and
   b) a modified DNA comprising a glycan moiety comprising at least two monosaccharides.
162. A pharmaceutical composition comprising:
   a) a pharmaceutically acceptable carrier; and
   b) a modified DNA comprising a glycan moiety comprising at least three monosaccharides.
163. A pharmaceutical composition comprising:
   a) a pharmaceutically acceptable carrier; and
   b) a modified DNA comprising a glycan moiety comprising at least four monosaccharides.
164. A pharmaceutical composition comprising:
   a) a pharmaceutically acceptable carrier; and
   b) a modified DNA comprising a glycan moiety comprising at least five monosaccharides.

165. A pharmaceutical composition comprising:
   a) a pharmaceutically acceptable carrier; and
   b) a modified DNA comprising a glycan moiety comprising at least six monosaccharides.
166. A pharmaceutical composition comprising:
   a) a pharmaceutically acceptable carrier; and
   b) a modified DNA comprising a glycan moiety comprising at least seven monosaccharides.
167. A pharmaceutical composition comprising:
   a) a pharmaceutically acceptable carrier; and
   b) a modified DNA comprising a glycan moiety comprising at least eight monosaccharides.
168. A pharmaceutical composition comprising:
   a) a pharmaceutically acceptable carrier; and
   b) a modified DNA comprising a glycan moiety comprising at least nine monosaccharides.
169. The pharmaceutical composition of any of the preceding embodiments, with the proviso that the pharmaceutical composition does not include an LNP or other nucleic acid delivery vehicle.

Exemplary Embodiments—Section B

The following descriptive embodiments are intended to be illustrative of inventions contemplated herein:
1. A method for reducing interaction between glycan binding protein (GBP)-expressing cells and cells displaying cell surface glycosylated ribonucleic acids (glycoRNAs), comprising:
   contacting the GBP-expressing cells with soluble glycoRNAs which bind to GBP expressed on the surface of the GBP-expressing cells, in an amount effective to reduce interaction between the GBP-expressing cells and the cells displaying cell surface glycoRNAs.
2. The method according to embodiment 1, wherein the soluble glycoRNAs comprise RNAs from the Y RNA family.
3. The method according to embodiment 2, wherein the soluble glycoRNAs comprise Y5 RNAs.
4. The method according to any one of embodiments 1 to 3, wherein the soluble glycoRNAs comprise snoRNAs, tRNAs, snRNAs, rRNAs, or any combination thereof.
5. The method according to any one of embodiments 1 to 4, wherein the soluble glycoRNAs comprise soluble sialylated RNAs.
6. The method according to embodiment 5, wherein the soluble sialylated RNAs comprise Neu5Ac, Neu5Gc, or a combination thereof.
7. The method according to any one of embodiments 1 to 6, wherein the soluble glycoRNAs are conjugated to one or more agents.
8. The method according to embodiment 7, wherein the one or more agents comprise a therapeutic agent.
9. The method according to embodiment 7 or embodiment 8, wherein the one or more agents comprise a detectable label.
10. The method according to any one of embodiments 1 to 9, wherein the GBPs comprise sialic acid-binding immunoglobulin-like lectins (Siglecs).
11. The method according to embodiment 10, wherein the Siglecs comprise Siglec-11.
12. The method according to embodiment 10 or embodiment 11, wherein the Siglecs comprise Siglec-14.
13. The method according to any one of embodiments 1 to 12, wherein the GBPs comprise C-type lectins.
14. The method according to any one of embodiments 1 to 13, wherein the GBPs comprise galectins.
15. The method according to any one of embodiments 1 to 14, wherein the GBPs comprise selectins.
16. A method for reducing interaction between glycan binding protein (GBP)-expressing cells and cells displaying cell surface glycoRNAs, comprising:
   contacting the GBP-expressing cells with an agent that binds to GBP expressed on the surface of the GBP-expressing cells and identified as binding to cell surface glycoRNAs, in an amount effective to reduce interaction between the GBP-expressing cells and the cells displaying cell surface glycoRNAs.
17. The method according to embodiment 16, wherein the agent is a ligand for the GBP expressed on the surface of the GBP-expressing cells.
18. The method according to embodiment 16, wherein the agent is an antibody that binds to the GBP expressed on the surface of the GBP-expressing cells.
19. The method according to any one of embodiments 16 to 18, wherein the GBP to which the agent binds is one or more sialic acid-binding immunoglobulin-like lectins (Siglecs).
20. The method according to embodiment 19, wherein the one or more Siglecs comprise Siglec-11.
21. The method according to embodiment 19 or embodiment 20, wherein the one or more Siglecs comprise Siglec-14.
22. The method according to any one of embodiments 16 to 21, wherein the GBP to which the agent binds comprises C-type lectins.
23. The method according to any one of embodiments 16 to 22, wherein the GBP to which the agent binds comprises galectins.
24. The method according to any one of embodiments 16 to 23, wherein the GBP to which the agent binds comprises selectins.
25. A method for reducing interaction between glycan binding protein (GBP)-expressing cells and cells displaying cell surface glycoRNAs, comprising:
   contacting the cells displaying cell surface glycoRNAs with an agent that binds to and/or edits the cell surface glycoRNAs, in an amount effective to reduce interaction between the GBP-expressing cells and the cells displaying cell surface glycoRNAs.
26. The method according to embodiment 25, wherein the agent edits the cell surface glycoRNAs.
27. The method according to embodiment 26, wherein the agent is an enzyme that removes glycans from the cell surface glycoRNAs.
28. The method according to embodiment 27, wherein the cell surface glycoRNAs comprise cell surface sialylated RNAs, and wherein the agent comprises a sialidase.
29. The method according to embodiment 26, wherein the agent comprises a ribonuclease (RNase).
30. The method according to embodiment 29, wherein the RNase is RNase A, a T1 RNase, or a T2 RNase.
31. The method according to embodiment 29 or embodiment 30, wherein the RNase is a human RNase.
32. The method according to embodiment 31, wherein the human RNase is human RNase 1.
33. The method according to any one of embodiments 25 to 32, wherein the agent is stably associated with a targeting moiety that targets the agent to the cells displaying cell surface glycoRNAs.

34. The method according to embodiment 33, wherein the targeting moiety is an antibody, a ligand, an aptamer, or a small molecule.
35. The method according to embodiment 25, wherein the agent binds to the cell surface glycoRNAs.
36. The method according to embodiment 35, wherein the agent is an antibody that binds to the cell surface glycoRNAs.
37. The method according to embodiment 36, wherein the antibody is an anti-RNA antibody.
38. The method according to embodiment 37, wherein the anti-RNA antibody is an anti-double stranded RNA (dsRNA) antibody.
39. The method according to embodiment 35, wherein the agent comprises a glycan-binding moiety that binds to the cell surface glycoRNAs.
40. A method of targeting an agent to glycan binding protein (GBP)-expressing cells, comprising:
    contacting the GBP-expressing cells with soluble glycosylated ribonucleic acids (glycoRNAs) stably associated with the agent.
41. The method according to embodiment 40, wherein the soluble glycoRNAs are conjugated to the agent.
42. The method according to embodiment 40 or embodiment 41, wherein the agent is a GBP-expressing cell modulating agent.
43. The method according to embodiment 40 or embodiment 41, wherein the agent is a therapeutic agent.
44. The method according to embodiment 40 or embodiment 41, wherein the agent comprises a detectable label.
45. The method according to any one of embodiments 1 to 44, wherein the method is performed in vitro, in vivo, or ex vivo.
46. The method according to any one of embodiments 1 to 15, wherein the method is performed in vivo, and wherein the contacting comprises administering the soluble glycoRNAs to an individual in need thereof, in an amount effective to reduce interaction between the GBP-expressing cells and the cells displaying cell surface glycoRNAs in the individual.
47. The method according to any one of embodiments 16 to 39, wherein the method is performed in vivo, and wherein the contacting comprises administering the agent to an individual in need thereof, in an amount effective to reduce interaction between the GBP-expressing cells and the cells displaying cell surface glycoRNAs in the individual.
48. The method according to any one of embodiments 40 to 44, wherein the method is performed in vivo, and wherein the contacting comprises administering the soluble glycoRNAs stably associated with the agent to an individual.
49. The method according to any one of embodiments 46 to 48, wherein the administering is by parenteral or oral administration.
50. A pharmaceutical composition, comprising:
    soluble glycosylated ribonucleic acids (glycoRNAs); and
    a pharmaceutically acceptable carrier.
51. The pharmaceutical composition of embodiment 50, wherein the soluble glycoRNAs comprise RNAs from the Y RNA family.
52. The pharmaceutical composition of embodiment 51, wherein the soluble glycoRNAs comprise Y5 RNAs.
53. The pharmaceutical composition of any one of embodiments 50 to 52, wherein the soluble glycoRNAs comprise snoRNAs, tRNAs, snRNAs, or any combination thereof.
54. The pharmaceutical composition of any one of embodiments 50 to 53, wherein the soluble glycoRNAs comprise soluble sialylated RNAs.
55. The pharmaceutical composition of embodiment 54, wherein the soluble sialylated RNAs comprise Neu5Ac, Neu5Gc, or a combination thereof.
56. The pharmaceutical composition of any one of embodiments 50 to 55, wherein the soluble glycoRNAs are conjugated to one or more agents.
57. The pharmaceutical composition of embodiment 56, wherein the one or more agents comprise a therapeutic agent.
58. The pharmaceutical composition of embodiment 56 or embodiment 57, wherein the one or more agents comprise a detectable label.
59. A conjugate, comprising:
    a soluble glycosylated ribonucleic acid (glycoRNA) as defined in any one of embodiments 51 to 55 conjugated to one or more agents.
60. The conjugate of embodiment 59, wherein the one or more agents comprise a therapeutic agent.
61. The conjugate of embodiment 59 or embodiment 60, wherein the one or more agents comprise a detectable label.
62. A conjugate, comprising:
    a targeting moiety conjugated to a ribonuclease (RNase).
63. The conjugate of embodiment 62, wherein the targeting moiety is an antibody, a ligand, an aptamer, or a small molecule.
64. A fusion protein, comprising:
    a targeting moiety fused to a ribonuclease (RNase).
65. The fusion protein of embodiment 64, wherein the targeting moiety is an antibody or a ligand.
66. The conjugate of embodiment 62 or embodiment 63, or the fusion protein of embodiment 64 or embodiment 65, wherein the RNase is RNase A, a T1 RNase, or a T2 RNase.
67. The conjugate or fusion protein of any one of embodiments 62 to 66, wherein the RNase is a human RNase.
68. The conjugate or fusion protein of embodiment 67, wherein the human RNase is human RNase 1.
69. A method of assessing a biological sample for glycosylated ribonucleic acids (glycoRNAs), comprising performing a glycoRNA detection assay on the biological sample.
70. The method according to embodiment 69, wherein the biological sample is a cellular sample.
71. The method according to embodiment 70, wherein the assay is a cell surface glycoRNA detection assay.
72. The method according to embodiment 71, wherein the cell surface glycoRNA detection assay comprises contacting cells of the cellular sample with a glycoRNA-binding agent, and assessing for binding of the glycoRNA-binding agent to cell surface glycoRNAs in the sample.
73. The method according to embodiment 72, wherein the glycoRNA-binding agent is an antibody that binds to cell surface glycoRNAs.
74. The method according to embodiment 73, wherein the antibody is an anti-RNA antibody.

75. The method according to embodiment 74, wherein the anti-RNA antibody is an anti-double stranded RNA (dsRNA) antibody.
76. The method according to embodiment 71, wherein the cell surface glycoRNA detection assay comprises contacting cells of the cellular sample with a ribonuclease (RNase) to digest cell surface glycoRNA, if present, and assessing for degradation of cell surface glycoRNA.
77. The method according to embodiment 69 or embodiment 70, wherein the assay is a free glycoRNA detection assay.
78. The method according to any one of embodiments 69 to 77, wherein the biological sample is a tissue sample or a body fluid sample.
79. The method according to any one of embodiments 69 to 78, wherein the biological sample is a biopsy sample.
80. A method of producing glycosylated ribonucleic acids (glycoRNAs), comprising:
    culturing glycoRNA-producing cells under conditions in which glycoRNAs are produced; and
    isolating the produced glycoRNAs.
81. The method according to embodiment 80, wherein isolating the produced glycoRNAs comprises isolating membrane glycoRNAs produced by the cells.
82. The method according to embodiment 81, wherein isolating the produced glycoRNAs comprises isolating plasma membrane glycoRNAs produced by the cells.
83. The method according to embodiment 82, wherein isolating the plasma membrane glycoRNAs produced by the cells comprises cleaving the glycoRNAs from plasma membranes of the cells.
84. The method according to embodiment 80, wherein isolating the produced glycoRNAs comprises isolating free glycoRNAs produced by the cells.
85. The method according to embodiment 84, comprising isolating free glycoRNAs secreted by the cells.
86. The method according to any one of embodiments 80 to 85, comprising providing the cells with excess nucleotides to increase the flux of RNA biosynthesis as compared to the flux in the absence of excess nucleotides.
87. The method according to any one of embodiments 80 to 86, comprising providing the cells with excess sugars to increase the flux of glycan biosynthesis as compared to the flux in the absence of excess sugars.
88. The method according to embodiment 87, wherein the excess sugars comprise excess glucose, galactose, GlcNAc, or any combination thereof.
89. The method according to any one of embodiments 80 to 88, comprising inhibiting one or more cell membrane turnover pathways in the cells for enhanced accumulation of cell surface glycoRNAs, and isolating the accumulated cell surface glycoRNAs.
90. The method according to any one of embodiments 80 to 89, comprising inhibiting a portion of the glycan biosynthetic pathway to favor production of RNA glycans.
91. The method according to embodiment 90, comprising inhibiting O-glycan production to favor N-glycan production.
92. A method of engineering display of glycosylated ribonucleic acids (glycoRNAs) on the surface of a cell, comprising:
    introducing into the cell one or more expression constructs that encode for one or more ribonucleic acid and/or glycan biosynthetic enzymes, such that the cell displays on its surface one or more types of glycoRNAs of interest.
93. The method according to embodiment 92, wherein the one or more types of displayed glycoRNAs are utilized to uniquely identify the cell.

Exemplary Embodiments—Section C

1. A compound of Formula (I):

A-L-B     (I), or a salt, co-crystal, tautomer, stereoisomer, solvate, hydrate, polymorph, or an isotopically enriched derivative thereof, wherein:
   A is a nucleic acid of deoxyribonucleic acid (DNA) or ribonucleic acid (RNA) comprising a first click-chemistry handle;
   B is an asparagine-linked glycan (N-glycan) comprising a second click-chemistry handle; and
   L comprises a linker formed by a biorthogonal click chemistry reaction between the first click-chemistry handle and the second click-chemistry handle.
2. The compound of embodiment 1, wherein A is DNA.
3. The compound of embodiment 1, wherein A is RNA.
4. The compound of any one of embodiments 1-3, wherein A is an antisense oligonucleotide (ASO).
5. The compound of embodiment 1 or 3, wherein A is siRNA.
6. The compound of embodiment 1 or 3, wherein A is siRNA comprising a modification selected from the group consisting of a 2'OMe modification, a fluorine modification, a phosphorothioate modification.
7. The compound of embodiment 1 or 3, wherein A is mRNA.
8. The compound of embodiment 1 or 3, wherein A is guideRNA.
9. The compound of embodiment 1 or 3, wherein A is circular RNA (circRNA).
10. The compound of embodiment 1 or 3, wherein A is aptamer RNA.
11. The compound of any one of embodiments 1-10, wherein the click chemistry reaction is a copper-catalyzed azide-alkyne cyclization (CuAAC).
12. The compound of any one of embodiments 1-10, wherein the click chemistry reaction is a strain-promoted azide-alkyne cycloaddition (SPAAC).
13. The compound of any one of embodiments 1-10, wherein the click chemistry reaction is a transcyclooctyne (TCO)-tetrazine ligation or transcyclooctene-tetrazine ligation.
14. The compound of any one of embodiments 1-10, wherein the click chemistry reaction is an azide-Staudinger ligation, a cross-linking between a primary amine and a N-hydroxysuccinimide ester (NHS ester), a transcyclooctyne-azide coupling, or a cyclopropane-azide coupling.
15. The compound of any one of embodiments 1-13, wherein L is of formula:

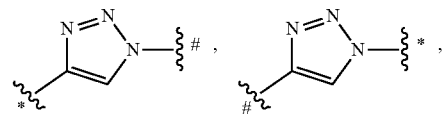

-continued

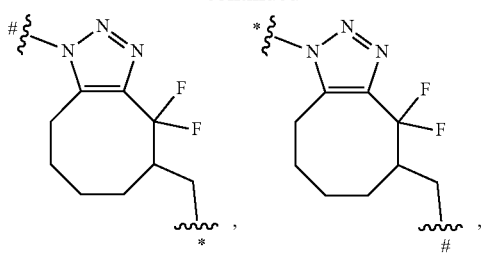

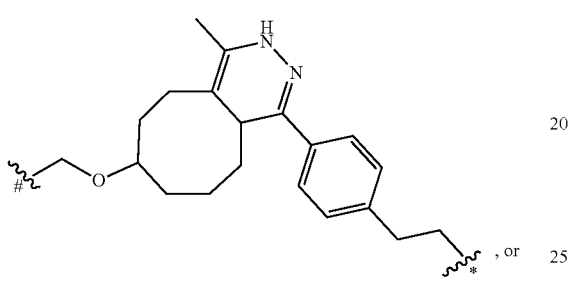

, or

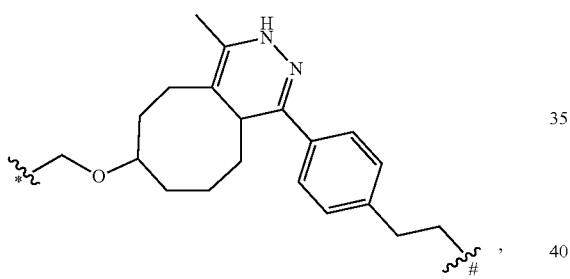

, wherein * indicates the point of attachment to A and #indicates the point of attachment to B.

16. The compound of any one of embodiments 1-11 or 15, wherein L is of formula:

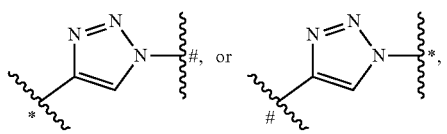 [SMILES: *c1cn(*)nn1 ; *c1cn(*)nn1]

wherein * indicates the point of attachment to A, and #indicates the point of attachment to B.

17. The compound of any one of embodiments 1-16, wherein L is attached to a base of the nucleic acid A.
18. The compound of any one of embodiments 1-16, wherein L is attached to the 2'OH position of a ribose of the nucleic acid A.
19. The compound of any one of embodiments 1-16, wherein L is attached to the 3'OH position of a deoxyribose or ribose of the nucleic acid A.
20. The compound of any one of embodiments 1-16, wherein L is attached to the 5'OH position of a deoxyribose or ribose of the nucleic acid A.
21. The compound of any one of embodiments 1-20, wherein L is attached to the non-reducing end of B.
22. The compound of any one of embodiments 1-21, wherein the N-glycan is a mono-antennary N-glycan.
23. The compound of any one of embodiments 1-21, wherein the N-glycan is a bi-antennary N-glycan.
24. The compound of any one of embodiments 1-21, wherein the N-glycan is a tri-antennary N-glycan.
25. The compound of any one of embodiments 1-21, wherein the N-glycan is a tetra-antennary N-glycan.
26. The compound of any one of embodiments 1-25, wherein the N-glycan comprises sialic acid.
27. The compound of any one of embodiments 1-26, wherein the N-glycan is of formula:

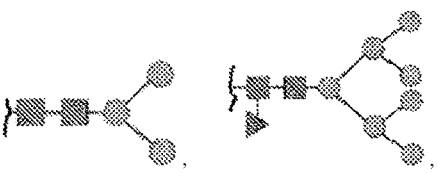

,

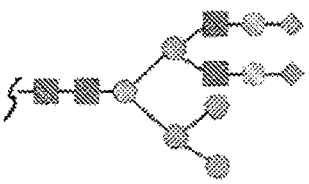

,

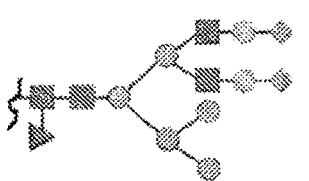

,

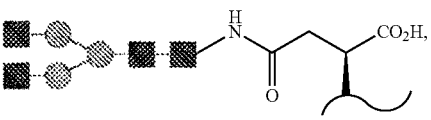

,

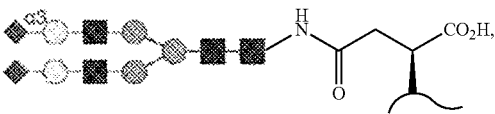

,

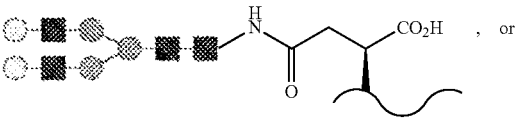

, or

-continued

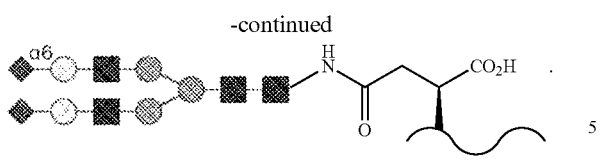

28. The compound of any one of embodiments 1, 2, 4, or 11-27, wherein A has a sequence with at least 80% sequence identity to the full-length sequence of 5'-GGC TGG TCC GAG TGC AGT GGT GTT TAC AAC TAA TTG ATC ACA ACC AGT TAC AGA TTT CT/i5OctdU/TGT TCC TTC TCC ACT CCC ACT GCT TCA CTT GAC TAG CCT T-3' (SEQ ID NO: 1).

29. The method of any one of embodiments 1 or 3-28, wherein A has a sequence with at least 80% sequence identity to the full-length sequence of:

(SEQ ID NO: 2)
AGUUGGTCCGAGUGUUGUGGGUUAUUGUUAAGUU/i5OctdU/
AUUUAACAUUGUCUCCCCCCACAACCGCGCUUGACUAGCUUGCUG.

30. The compound of any one of embodiments 1-29, wherein the compound of Formula (I) is of a formula depicted in FIG. 9 when A is siRNA, an ASO, mRNA, aptamer RNA, circRNA, or guideRNA; or SEQ ID NO: 1, wherein i5OctdU is conjugated to form structure:

SEQ ID NO: 2, wherein i5OctdU is conjugated to form structure:

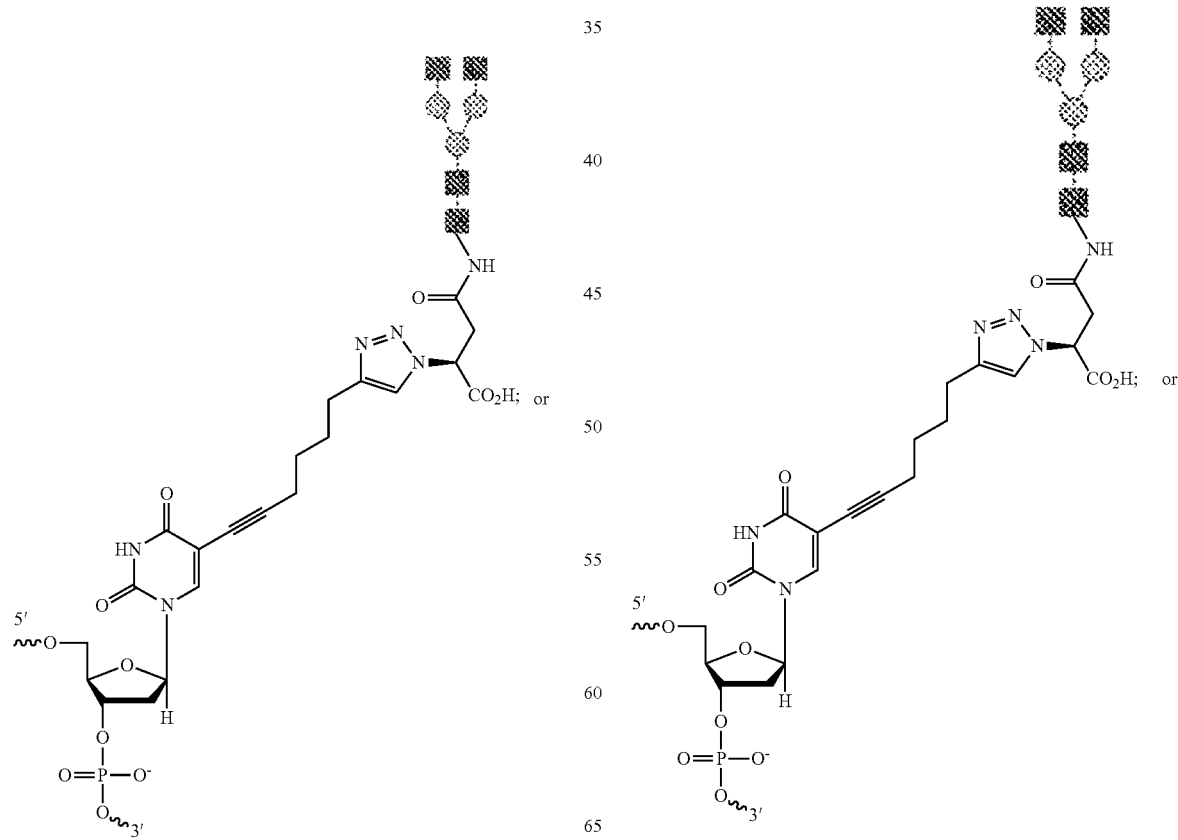

SEQ ID NO: 1, wherein i5OctdU is conjugated to form structure:
SEQ ID NO: 2, wherein i5OctdU is conjugated to form structure:
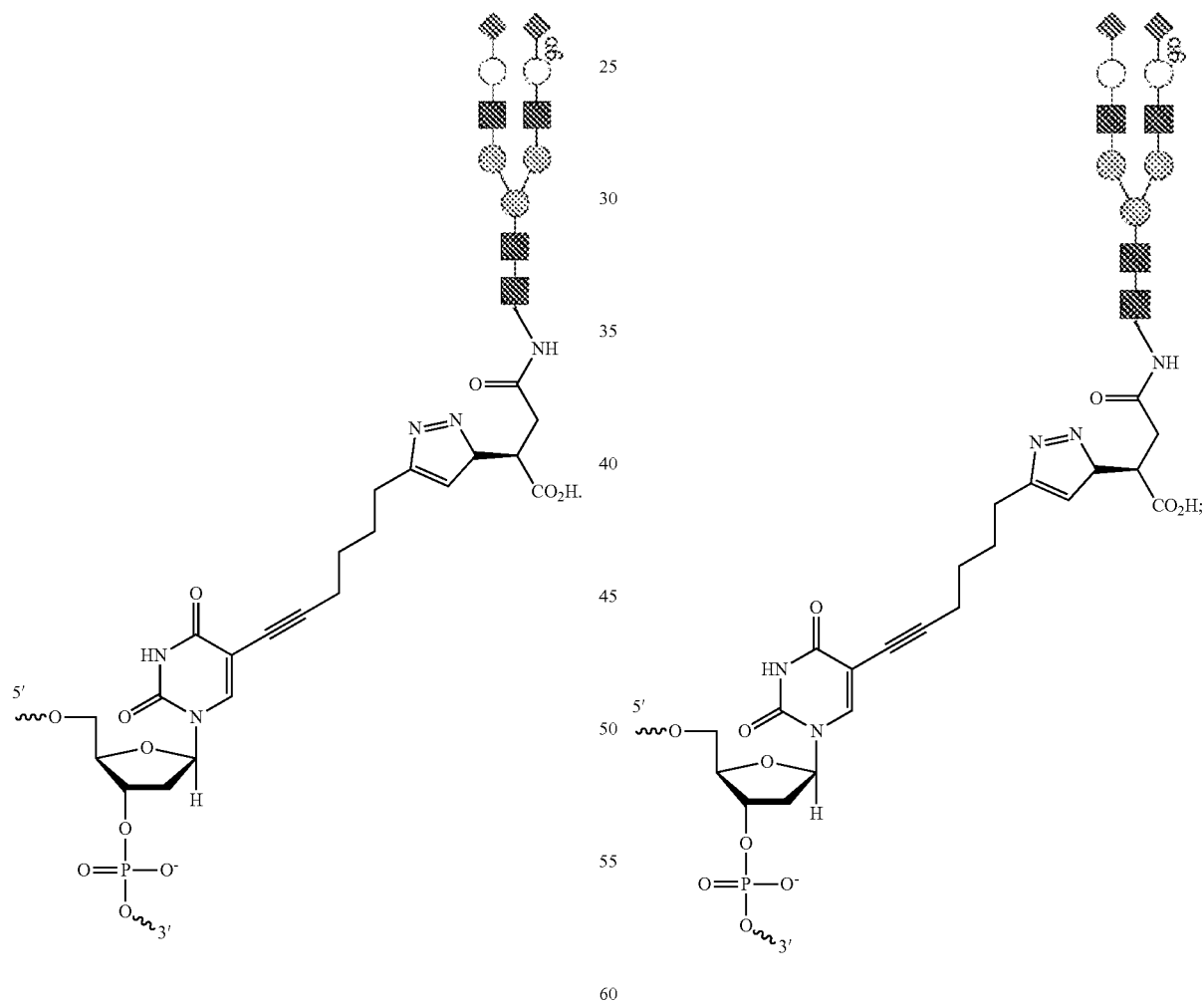

or
SEQ ID NO: 1, wherein i5OctdU is conjugated to form structure:
SEQ ID NO: 2, wherein i5OctdU is conjugated to form structure:
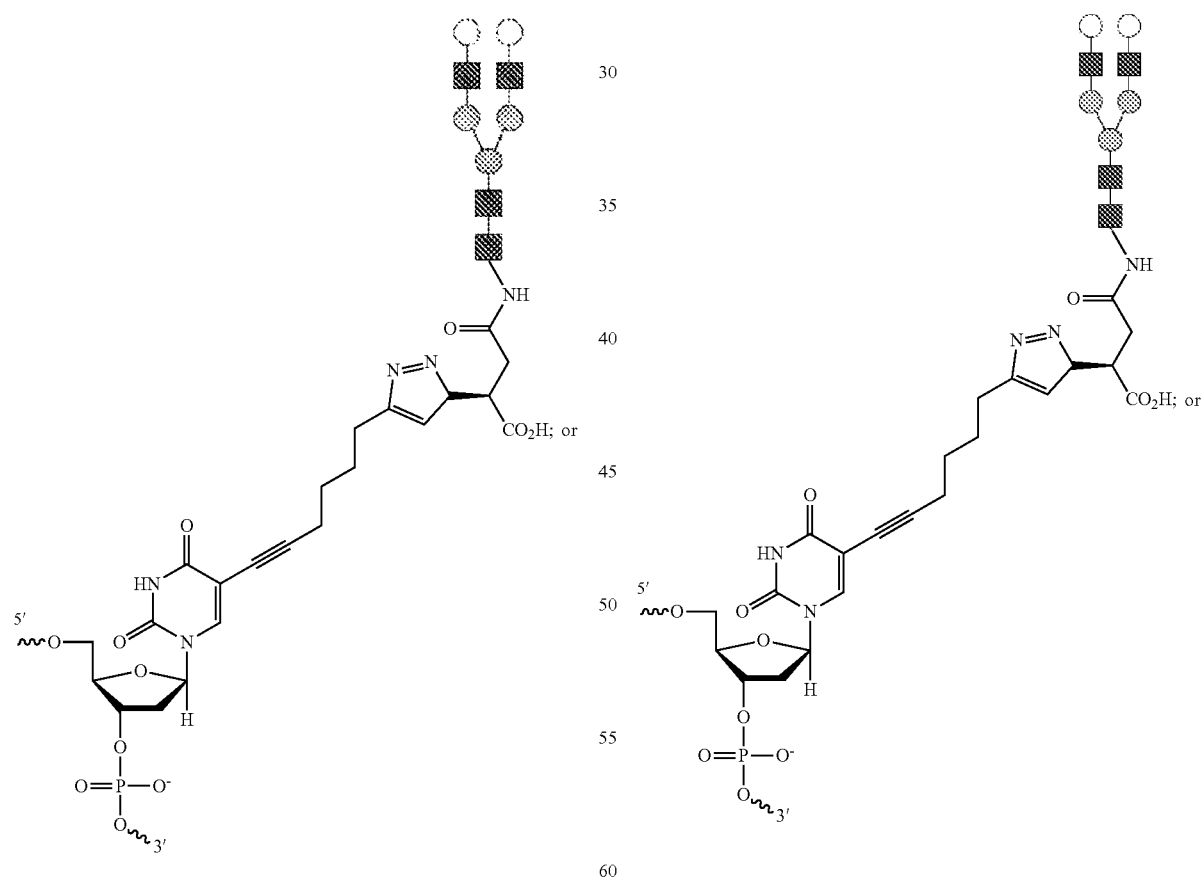

SEQ ID NO: 1, wherein i5OctdU is conjugated to form structure:

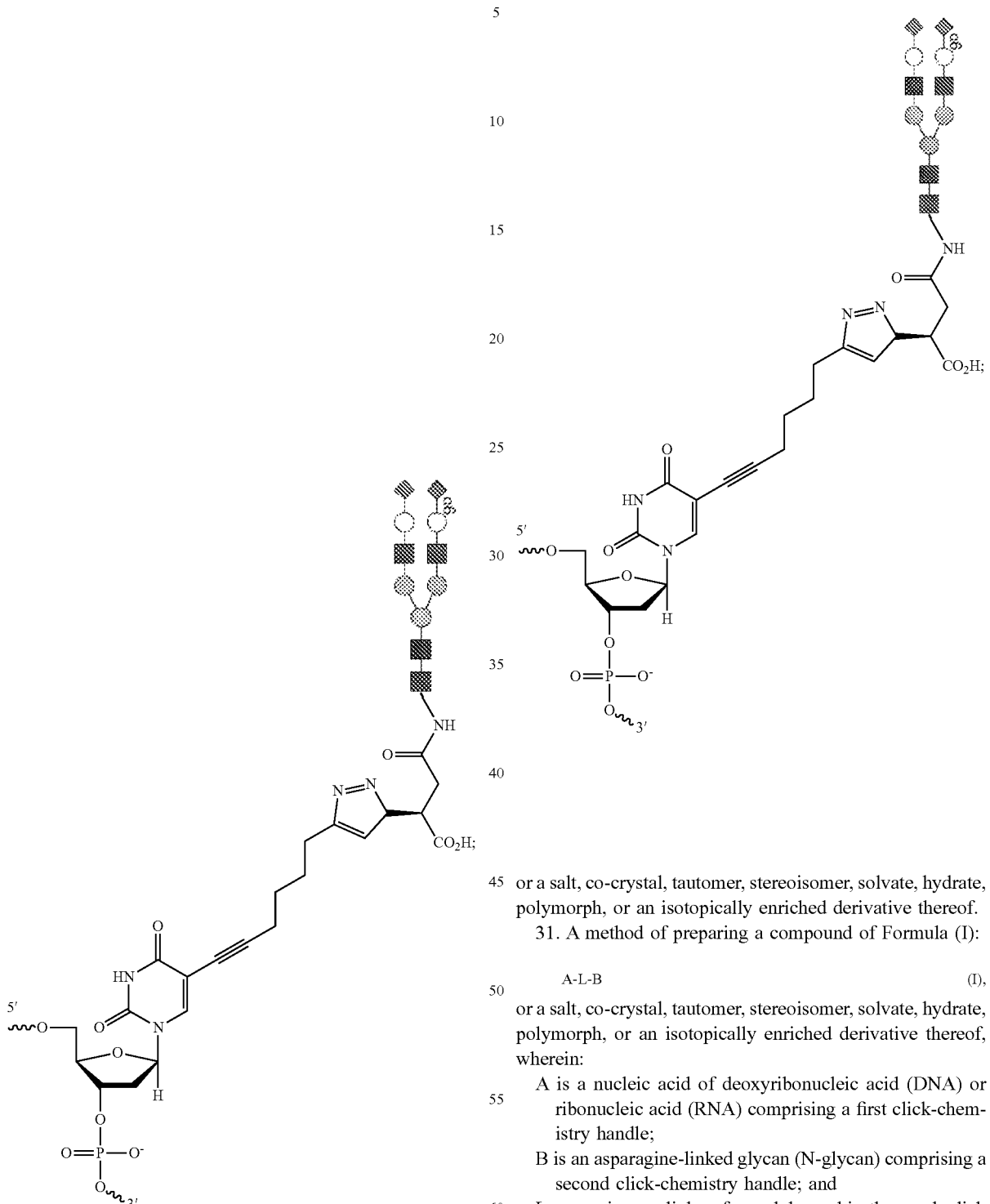

or

SEQ ID NO: 2, wherein i5OctdU is conjugated to form structure:

or a salt, co-crystal, tautomer, stereoisomer, solvate, hydrate, polymorph, or an isotopically enriched derivative thereof.

31. A method of preparing a compound of Formula (I):

A-L-B  (I), or a salt, co-crystal, tautomer, stereoisomer, solvate, hydrate, polymorph, or an isotopically enriched derivative thereof, wherein:
 A is a nucleic acid of deoxyribonucleic acid (DNA) or ribonucleic acid (RNA) comprising a first click-chemistry handle;
 B is an asparagine-linked glycan (N-glycan) comprising a second click-chemistry handle; and
 L comprises a linker formed by a biorthogonal click chemistry reaction between the first click-chemistry handle and the second click-chemistry handle; the method comprising
 a first step of reacting: the nucleic acid A of ribonucleic acid (RNA) or deoxyribonucleic acid (DNA), comprising the first click-chemistry handle;

with the compound B, which is an asparagine-linked glycan (N-glycan) comprising the second click-chemistry handle;
wherein the reaction of the first step is carried out under biorthogonal click chemistry conditions.

32. The method of embodiment 31, wherein the first step is carried out under conditions for the click chemistry reaction of: a copper-catalyzed azide-alkyne cyclization (CuAAC), a strain-promoted azide-alkyne cycloaddition (SPAAC), a tetracyclooctyne (TCO)-tetrazine ligation, or an azide-Staudinger ligation.

33. The method of embodiment 31, wherein the first step is carried out under conditions for the CuAAC, comprising diluting the alkyne-modified nucleic acid A in water and optionally denaturing at a temperature between 90-100° C. for approximately 1-5 minutes to produce a reactant mixture.

34. The method of embodiment 33, wherein the diluting alkyne-modified nucleic acid A in water is a dilution to a final concentration of between 100 uM-125 μM.

35. The method of embodiment 33 or 34, wherein the denaturing is conducted at a temperature of approximately 95° C. for two minutes.

36. The method of any one of embodiments 31-35, further comprising placing the reactant mixture on ice, followed by a step of folding in MgCl and neutral phosphate-buffered saline (PBS) for approximately 5-10 minutes at 35-39° C.

37. The method of any one of embodiments 31-36, further comprising adding to the reactant mixture a ligand 2-(4-((bis((1-(tert-butyl)-1H-1,2,3-triazol-4-yl)methyl)amino)methyl)-1H-1,2,3-triazol-1-yl)acetic acid (BT-TAA) and incubating at approximately 18-23° C.

38. The method of any one of embodiments 31-37, further comprising reacting A, B, Cu-BTTAA, and sodium ascorbate with PBS for at least approximately 6-48 hours at approximately 20-24° C.

39. The method of embodiment 38, comprising reacting approximately 10 μM of A, approximately 20 μM of B, and approximately 100-110 μM of Cu-BTTAA.

40. The method of any one of embodiments 31-39, further comprising adding approximately 15-20 mM Ethylenediaminetetraacetic Acid (EDTA).

41. The method of any one of embodiments 31-40, further comprising a step of enzymatic transformation of the N-glycan of the compound of Formula (I).

42. The method of embodiment 41, wherein the enzymatic transformation comprises addition of a sugar by a sialyltransferase or fucosyltransferase.

43. The method of embodiment 41, wherein the enzymatic transformation comprises mannosidase cleavage.

44. The method of any one of embodiments 31-43, further comprising precipitation of the compound of Formula (I).

45. The method of any one of embodiments 31-44, wherein A is DNA.

46. The method of any one of embodiments 31-44, wherein A is RNA.

47. The method of any one of embodiments 31-46, wherein A is an ASO.

48. The method of any one of embodiments 31-47, wherein A is siRNA, mRNA, guideRNA, circRNA, or aptamer RNA.

49. The method of any one of embodiments 31-48, wherein the first click-chemistry handle is an alkyne.

50. The method of embodiment 49, wherein the alkyne comprises the formula:

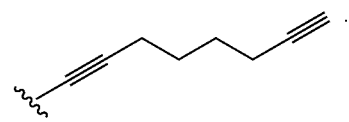

51. The method of any one of embodiments 31-50, wherein the nucleic acid A comprises the first click-chemistry handle that is an alkyne attached to a base of the nucleic acid.

52. The method of any one of embodiments 31-51, wherein A comprises the structure:

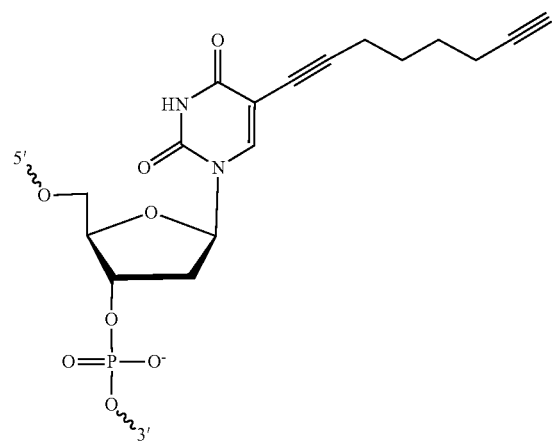

(5-Octadiynyl dU), and A is RNA or DNA.

53. The method of any one of embodiments 31-52, wherein the nucleic acid A comprises the first click-chemistry handle that is an alkyne attached to the 2'OH position of a ribose of the nucleic acid.

54. The method of any one of embodiments 31-52, wherein the nucleic acid A comprises the first click-chemistry handle that is an alkyne attached to the 3'OH position of a deoxyribose or ribose of the nucleic acid.

55. The method of any one of embodiments 31-52, wherein the nucleic acid A comprises the first click-chemistry handle that is an alkyne attached to the 5'OH position of a deoxyribose or ribose of the nucleic acid.

56. The method of any one of embodiments 31-48, wherein the first click-chemistry handle is an azide.

57. The method of embodiment 56, wherein the nucleic acid A comprises the first click-chemistry handle that is an azide attached to a base of the nucleic acid.

58. The method of any one of embodiments 31-57, wherein the second click-chemistry handle is an alkyne.

59. The method of any one of embodiments 31-58, wherein the compound B comprises the second click-chemistry handle that is an alkyne attached to the non-reducing end of the N-glycan.

60. The method of any one of embodiments 31-57, wherein the second click-chemistry handle is an azide.

61. The method of any one of embodiments 31-57 or 60, wherein the compound B comprises the second click-chemistry handle that is an azide attached to the non-reducing end of the N-glycan.

62. The method of any one of embodiments 31-61, wherein the compound B is of the formula:

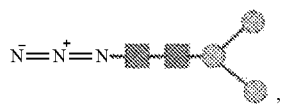

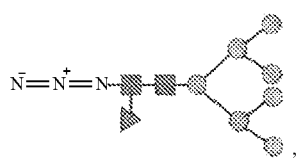

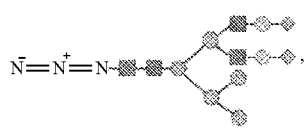

G-28, G-29, G-35 or G-30.

63. The method of any one of embodiments 31-62, wherein the compound B is G-28, G-29, G-35 or G-30.

64. The method of any one of embodiments 31-45, 47, or 49-63, wherein the DNA comprises the sequence: 5'-GGC TGG TCC GAG TGC AGT GGT GTT TAC AAC TAA TTG ATC ACA ACC AGT TAC AGA TTT CT/i5OctdU/TGT TCC TTC TCC ACT CCC ACT GCT TCA CTT GAC TAG CCT T-3' (SEQ ID NO: 1).

65. The method of any one of embodiments 31-44 or 46-63, wherein the RNA comprises the sequence:

(SEQ ID NO: 2)
AGUUGGUCCGAGUGUUGUGGGUUAUUGUUAAGUU/i5OctdU/
AUUUAACAUUGUCUCCCCCCACAACCGCGCUUGACUAGCUUGCUG.

66. The method of any one of embodiments 31-65, wherein the compound of Formula (I) is of a formula depicted in FIG. 9, when A is siRNA, an ASO, mRNA, aptamer RNA, circRNA, or guideRNA; or SEQ ID NO: 1, wherein i5OctdU is conjugated to form structure:

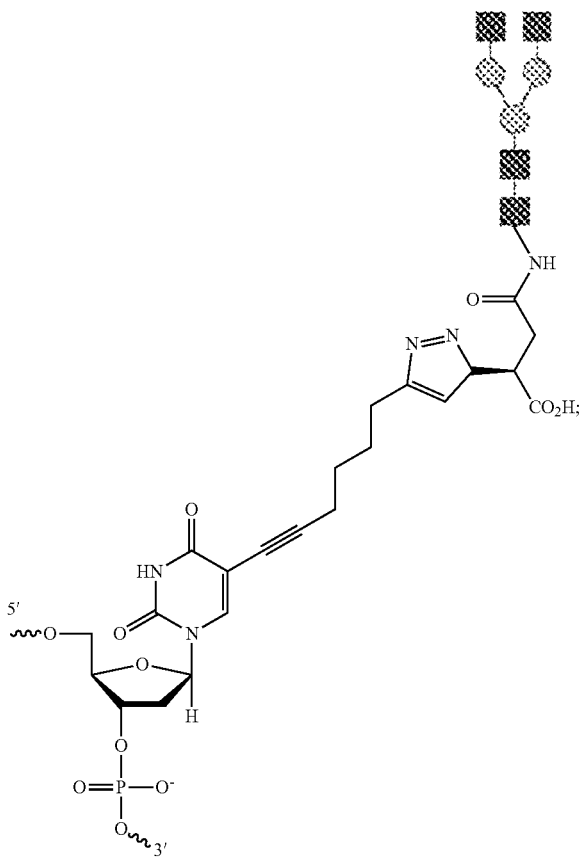

135
or
SEQ ID NO: 2, wherein i5OctdU is conjugated to form structure:
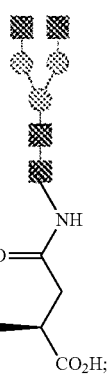
136
or
SEQ ID NO: 1, wherein i5OctdU is conjugated to form structure:

137
or
SEQ ID NO: 2, wherein i5OctdU is conjugated to form structure:
138
or
SEQ ID NO: 1, wherein i5OctdU is conjugated to form structure:
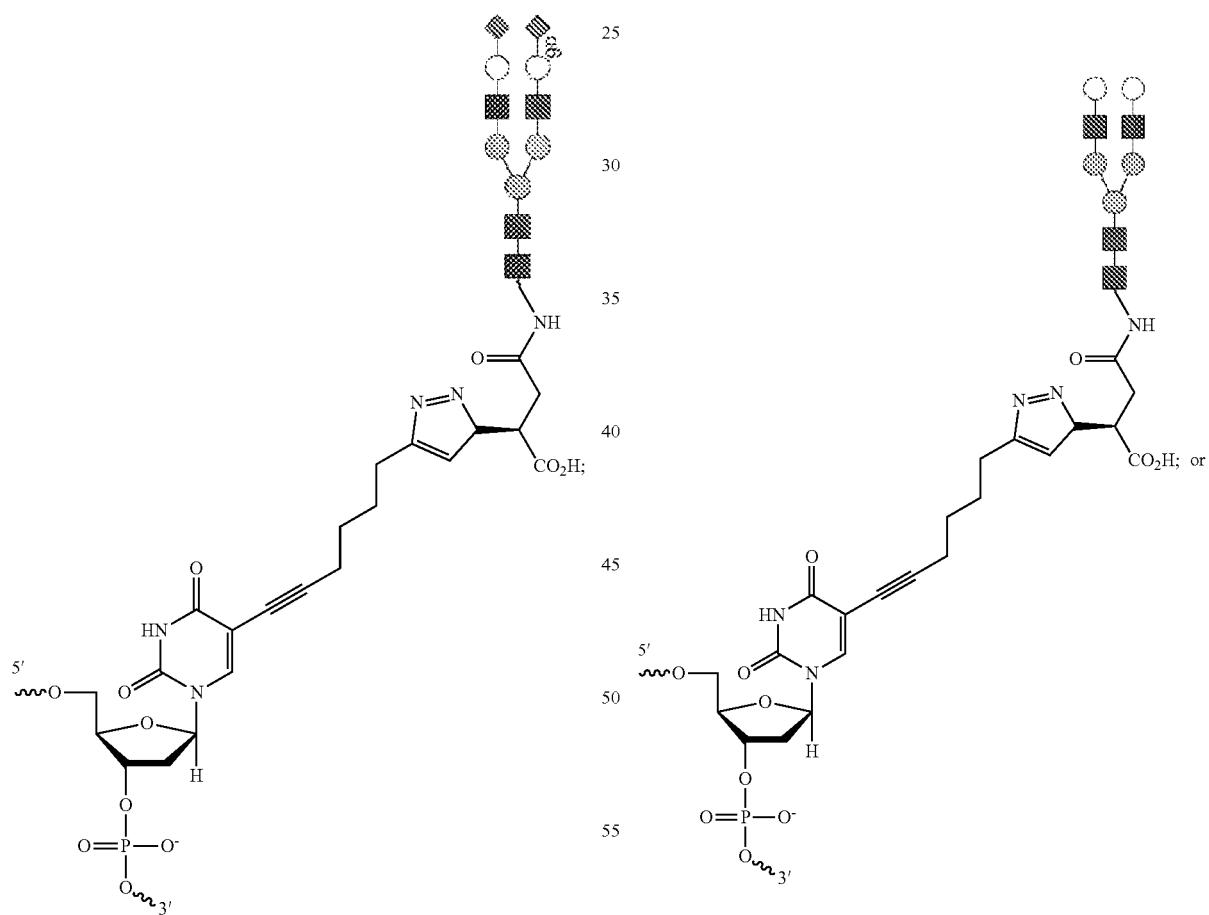

SEQ ID NO: 2, wherein i5OctdU is conjugated to form structure:
SEQ ID NO: 1, wherein i5OctdU is conjugated to form structure:
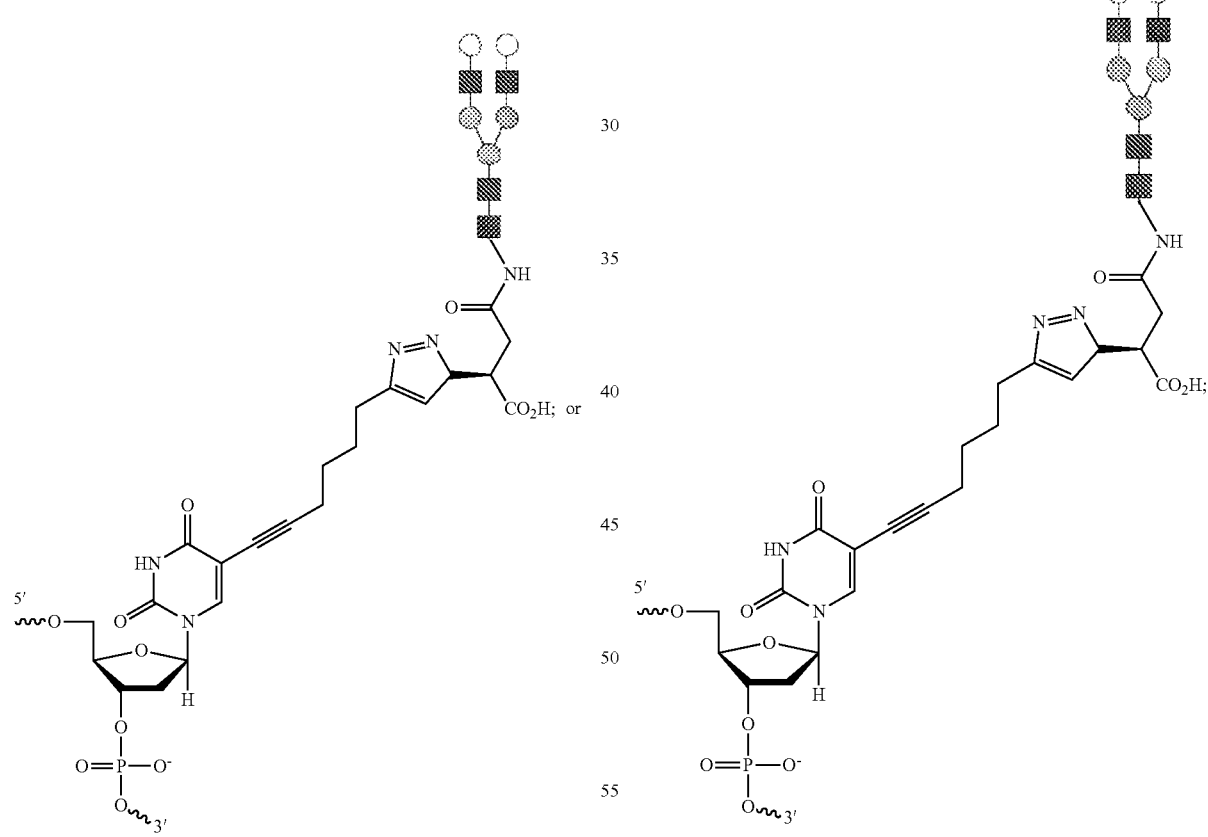

or
SEQ ID NO: 2, wherein i5OctdU is conjugated to form structure:

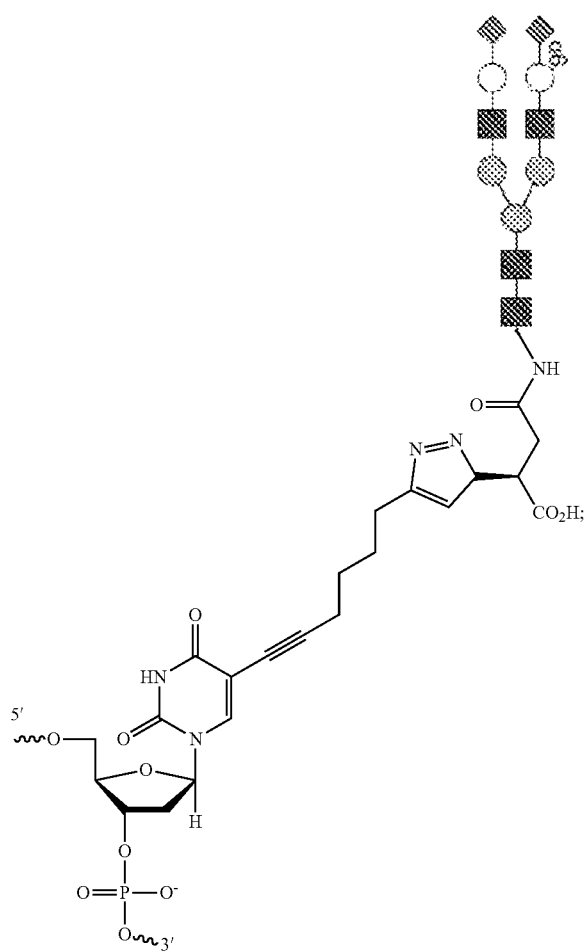

or a salt, co-crystal, tautomer, stereoisomer, solvate, hydrate, polymorph, or an isotopically enriched derivative thereof.

67. A composition comprising a compound of any one of embodiments 1-66, or a salt, solvate, hydrate, polymorph, co-crystal, tautomer, stereoisomer, isotopically labeled derivative, or prodrug thereof, and optionally an excipient.

68. A kit comprising:
   a compound of any one of embodiments 1-66, or a composition of embodiment 67; and
   instructions for administering to a subject or contacting a biological sample with the compound or composition thereof.

Exemplary Embodiments—Section D

1. A pharmaceutical composition comprising:
   a) a glyconucleic acid comprising:
      i) a nucleic acid; and
      ii) at least one glycan moiety comprising at least 6 monosaccharides, conjugated to the nucleic acid; and
   b) a pharmaceutically acceptable carrier.

2. The pharmaceutical composition of embodiment 1, wherein the at least one glycan moiety comprises at least 8 monosaccharides.

3. The pharmaceutical composition of embodiment 1, wherein the at least one glycan moiety comprises at least 10 monosaccharides.

4. The pharmaceutical composition of any one of the preceding embodiments, wherein the at least one glycan moiety comprises an N-linked glycan.

5. The pharmaceutical composition of any one of embodiments 1-3, wherein the at least one glycan moiety comprises an O-linked glycan.

6. The pharmaceutical composition of any one of the preceding embodiments, wherein the at least one glycan moiety comprises a bi-antennary glycan, wherein the bi-antennary glycan comprises a first terminal residue and a second terminal residue.

7. The pharmaceutical composition of any one of embodiments 1-5, wherein the at least one glycan moiety comprises a tri-antennary glycan, wherein the tri-antennary glycan comprises a first terminal residue, a second terminal residue and a third terminal residue.

8. The pharmaceutical composition of any one of embodiments 6 or 7, wherein at least one of the first terminal residue, the second terminal residue and the third terminal residue, if present, comprises sialic acid.

9. The pharmaceutical composition of any one of embodiments 6 or 7, wherein at least one of the first terminal residue, the second terminal residue and the third terminal residue, if present, comprises fucose.

10. The pharmaceutical composition of any one of embodiments 6 or 7, wherein at least one of the first terminal residue, the second terminal residue and the third terminal residue, if present, comprises GlcNAc.

11. The pharmaceutical composition of any one of embodiments 6 or 7, wherein at least one of the first terminal residue, the second terminal residue and the third terminal residue, if present, comprises mannose.

12. The pharmaceutical composition of any one of embodiments 6 or 7, wherein at least one of the first terminal residue, the second terminal residue and the third terminal residue, if present, comprises NeuNAc.

13. The pharmaceutical composition of any one of embodiments 6 or 7, wherein at least one of the first terminal residue, the second terminal residue and the third terminal residue, if present, comprises galactose.

14. The pharmaceutical composition of any one of the preceding embodiments, wherein the nucleic acid is an RNA.

15. The pharmaceutical composition of embodiment 14, wherein the nucleic acid is an siRNA.

16. The pharmaceutical composition of embodiment 14, wherein the nucleic acid is an mRNA.

17. The pharmaceutical composition of embodiment 14, wherein the nucleic acid is a circular RNA.

18. The pharmaceutical composition of embodiment 14, wherein the nucleic acid is a guide RNA.

19. The pharmaceutical composition of embodiment 14, wherein the nucleic acid is aptamer RNA.

20. The pharmaceutical composition of any one of embodiments 1-13, wherein the nucleic acid is a DNA.

21. The pharmaceutical composition of any one of the preceding embodiments, wherein the at least one glycan moiety comprises a compound of Table 2A or 2B.

22. The pharmaceutical composition of any one of the preceding embodiments 1-20, wherein the modified nucleic acid comprises a nucleic acid of Table 1.

23. The pharmaceutical composition of any one of the preceding embodiments, wherein the at least one glycan moiety is conjugated to the modified nucleic acid via a click-chemistry reaction.

24. The pharmaceutical composition of any one of the preceding embodiments, wherein the nucleic acid is conjugated to the glycan via a linker group covalently bound to a terminus of the nucleic acid.

25. The pharmaceutical composition of any one of embodiments 1-23, wherein the nucleic acid is conjugated to the glycan via a linker covalently bound to a chemically modified nucleotide in the middle of the nucleic acid.

26. The pharmaceutical composition of any one of embodiments 1-23, wherein the nucleic acid is conjugated to the glycan via a linker covalently bound to a chemically modified nucleotide that is not located at the 3' terminal or the 5' terminal of the nucleic acid.

27. The pharmaceutical composition of embodiment 1, wherein the nucleic acid is conjugated to the glycan via a chemical handle inserted between two nucleotides of the nucleic acid.

28. The pharmaceutical composition of embodiment 27, wherein the two nucleotides do not include nucleotides at the 3' terminal or the 5' terminal of the nucleic acid.

29. The pharmaceutical composition of embodiment 1, wherein the glyconucleic acid comprises a compound of Formula (I):

A-L-B     (I), or a salt, co-crystal, tautomer, stereoisomer, solvate, hydrate, polymorph, or an isotopically enriched derivative thereof, wherein:
A is a nucleic acid of deoxyribonucleic acid (DNA) or ribonucleic acid (RNA) comprising a first click-chemistry handle;
B is an asparagine-linked glycan (N-glycan) comprising a second click-chemistry handle; and
L comprises a linker formed by a biorthogonal click chemistry reaction between the first click-chemistry handle and the second click-chemistry handle.

30. A glyconucleic acid compound of Formula (I):

A-L-B     (I), or a salt, co-crystal, tautomer, stereoisomer, solvate, hydrate, polymorph, or an isotopically enriched derivative thereof, wherein:
A is a nucleic acid comprising a first click-chemistry handle;
B is an asparagine-linked glycan (N-glycan) comprising a second click-chemistry handle; and
L comprises a linker formed by a biorthogonal click chemistry reaction between the first click-chemistry handle and the second click-chemistry handle.

31. The glyconucleic acid of embodiment 30, wherein A is a DNA comprising a first click-chemistry handle.

32. The glyconucleic acid of embodiment 30, wherein A is an siRNA comprising a first click-chemistry handle.

33. The glyconucleic acid of embodiment 30, wherein A is an mRNA comprising a first click-chemistry handle.

34. The glyconucleic acid of embodiment 30, wherein A is a circular RNA comprising a first click-chemistry handle.

35. The glyconucleic acid of embodiment 30, wherein A is a DNA comprising a first click-chemistry handle.

36. The glyconucleic acid of embodiment 30, wherein A comprises a first click-chemistry handle selected from those listed in Table 4 under "Reagent A", and wherein B comprises a second click-chemistry handle selected from those listed in Table 4 under "Reagent B".

37. The glyconucleic acid of embodiment 30, wherein A comprises a first click-chemistry handle selected from those listed in Table 4 under "Reagent B", and wherein B comprises a second click-chemistry handle selected from those listed in Table 4 under "Reagent A"

38. The glyconucleic acid of any one of embodiments 30-37, wherein B is an asparagine linked glycan comprising a bi-antennary glycan, wherein the bi-antennary glycan comprises a first terminal residue and a second terminal residue.

39. The glyconucleic acid of any one of embodiments 30-37, wherein B is an asparagine linked glycan comprising a tri-antennary glycan, wherein the tri-antennary glycan comprises a first terminal residue, a second terminal residue and a third terminal residue.

40. The glyconucleic acid of embodiment 38 or 39, wherein at least one of the first terminal residue, the second terminal residue and the third terminal residue, if present, comprises sialic acid.

41. The glyconucleic acid of embodiment 38 or 39, wherein at least one of the first terminal residue, the second terminal residue and the third terminal residue, if present, comprises fucose.

42. The glyconucleic acid of embodiment 38 or 39, wherein at least one of the first terminal residue, the second terminal residue and the third terminal residue, if present, comprises GlcNAc.

43. The glyconucleic acid of embodiment 38 or 39, wherein at least one of the first terminal residue, the second terminal residue and the third terminal residue, if present, comprises mannose.

44. The glyconucleic acid of embodiment 38 or 39, wherein at least one of the first terminal residue, the second terminal residue and the third terminal residue, if present, comprises NeuNAc.

45. The glyconucleic acid of embodiment 38 or 39, wherein at least one of the first terminal residue, the second terminal residue and the third terminal residue, if present, comprises galactose.

46. A method of treating a disease or condition comprising administering to a subject in need thereof a therapeutically effective amount of the pharmaceutical composition of any one of embodiments 1-29 or the glyconucleic acid of any one of embodiments 30-45; wherein the disease or condition is selected from an inflammation disorder, an autoimmune disease, a cancer, a metabolic disease, a clotting disease, an anti-clotting disease, an allergy, a viral disease, and a microbial infection.

47. The method of embodiment 46, wherein the disease or condition is inflammation.

48. The method of embodiment 46, wherein the disease or condition is cancer.

49. The method of embodiment 46, wherein the disease or condition is autoimmune disease.

50. The method of embodiment 46, wherein the allergy is an IgE-mediated allergy.

51. The method of embodiment 46, wherein the autoimmune disease is systemic lupus erythematosus.

52. The method of embodiment 46, wherein the disease or condition is a microbial infection.

53. The method of embodiment 46, wherein the disease or condition is a viral infection.

54. The method of embodiment 46, wherein the disease or condition is a metabolic disease.

55. The use of the pharmaceutical composition of any one of embodiments 1-29 or the glyconucleic acid of any one of embodiments 30-45 for the manufacture of a medicament for the treatment of a disease or a condition, wherein the disease or condition is selected from an inflammation disorder, an autoimmune disease, a cancer, a metabolic disease, a clotting disease, an anti-clotting disease, an allergy, a viral disease, and a microbial infection.

56. Use of the pharmaceutical composition of any one of claims 1-29 or the glyconucleic acid of any one of embodiments 30-45 for the treatment of a disease or a condition in a subject in need thereof, wherein the disease or condition is selected from an inflammation disorder, an autoimmune disease, a cancer, a metabolic disease, a clotting disease, an anti-clotting disease, an allergy, a viral disease, and a microbial infection.

57. A method for reducing interaction between glycan binding protein (GBP)-expressing cells and cells displaying cell surface glycosylated ribonucleic acids (glycoRNAs), comprising:
    contacting the GBP-expressing cells with soluble glycoRNAs which bind to GBP expressed on the surface of the GBP-expressing cells, in an amount effective to reduce interaction between the GBP-expressing cells and the cells displaying cell surface glycoRNAs.

58. The method of embodiment 57, wherein the soluble glycoRNAs comprise RNAs from the Y RNA family.

59. The method of embodiment 58, wherein the soluble glycoRNAs comprise Y5 RNAs.

60. The method of any one of embodiments 57-59, wherein the soluble glycoRNAs comprise snoRNAs, tRNAs, snRNAs, rRNAs, or any combination thereof.

61. The method of any one of embodiments 57-59, wherein the soluble glycoRNAs comprise soluble sialylated RNAs.

62. The method of embodiments 61, wherein the soluble sialylated RNAs comprise Neu5Ac, Neu5Gc, or a combination thereof.

63. The method of any one of embodiments 57-62, wherein the soluble glycoRNAs are conjugated to one or more agents.

64. The method of embodiment 63, wherein the one or more agents comprise a therapeutic agent.

65. The method of embodiment 63 or 64, wherein the one or more agents comprise a detectable label.

66. The method according to any one of embodiments 57-65, wherein the GBPs comprise sialic acid-binding immunoglobulin-like lectins (Siglecs).

67. The method of embodiment 66, wherein the Siglecs comprise Siglec-11.

68. The method of embodiment 66, wherein the Siglecs comprise Siglec-14.

69. The method of any one of embodiments 57-65, wherein the GBPs comprise C-type lectins.

70. The method of any one of embodiments 57-65, wherein the GBPs comprise galectins.

71. The method of any one of embodiments 57-65, wherein the GBPs comprise selectins.

The following examples are offered by way of illustration and not by way of limitation.

EXAMPLES

Example 1—a Glycan Metabolic Reporter is Incorporated into Cellular RNA

Figure 1B:
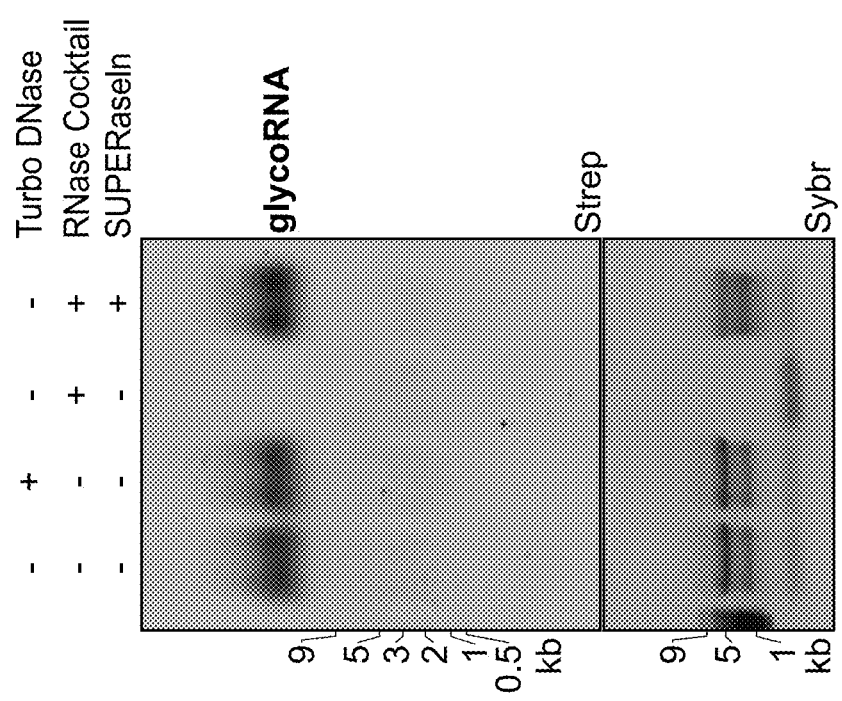
Figure 1C:
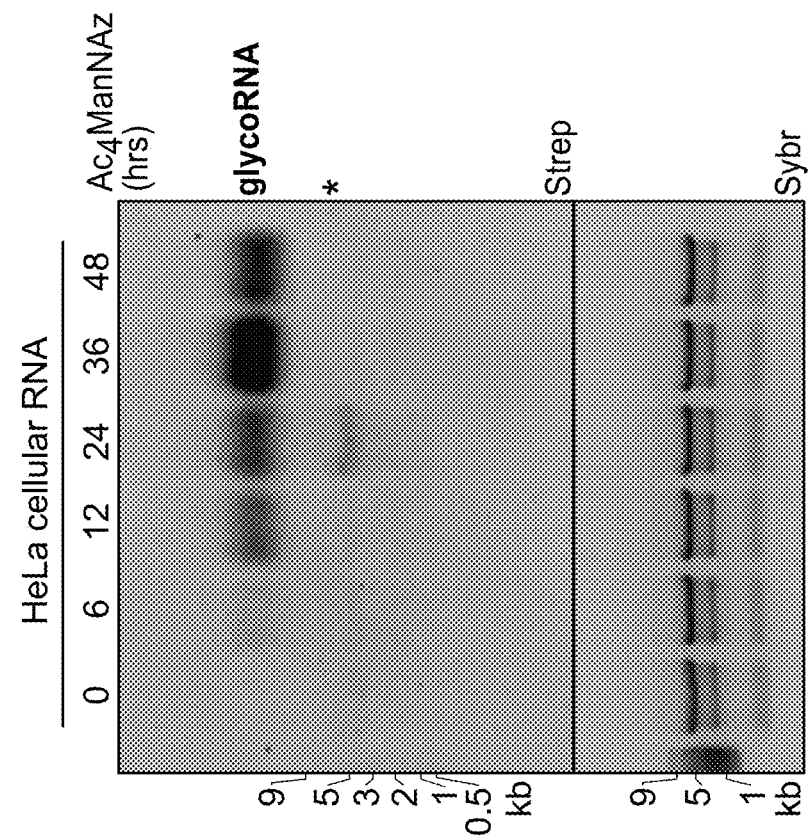

To explore the possible existence of RNA modified with sialoglycans (hereafter referred to as glycoRNA), HeLa cells were labeled with 100 µM Ac$_4$ManNAz for up to 48 hours and then used a rigorous protocol to chemically and enzymatically extract RNA with high purity: RNA is extracted with warm TRIzol (acid phenol and guanidine salts), then ethanol precipitated, desalted via silica columns, stripped of protein contamination via high concentration Proteinase K digestion, and repurified over silica columns (FIG. 1A). To visualize azide-labeled components, copper (Cu) free click chemistry was used by adding RNA samples to dibenzocyclooctyne-biotin (DBCO-biotin) in denaturing conditions (50% formamide) at 55° C., subsequently separated by denaturing gel electrophoresis and analyzed by blotting (FIG. 1B). In an Ac$_4$ManNAz- and time-dependent manner, biotinylated species in the very high (>10 kilobases) molecular weight (MW) region were observed. It has recently been reported that high doses of azidosugars can produce non-enzymatic protein labeling, however, in vitro incubation of total RNA with up to 20 mM Ac$_4$ManNAz did not produce the previously observed biotinylated species on RNAs in the high MW region. Minor background in vitro labeling was apparent on the 28S rRNA, which can also be seen more variably in some Ac$_4$ManNAz-labeled cellular RNA experiments (e.g., FIG. 1B), but no such background labeling was observed in the putative glycoRNA species. Further, treatment of RNA from Ac$_4$ManNAz-labeled HeLa cells with DNase did not affect the glycoRNA signal while treatment with an RNase cocktail (A and T1) efficiently digested the total RNA as well as the biotinylated glycoRNA (FIG. 1C). This effect required RNase enzymatic activity, as pre-blocking of the RNases with an inhibitor, SUPERaseIn, completely rescued the biotinylated glycoRNA (FIG. 1C). Thus, cells treated with Ac$_4$ManNAz incorporate the azide label into cellular RNA, which migrates on an agarose gel as a high MW species.

Figure 1D:
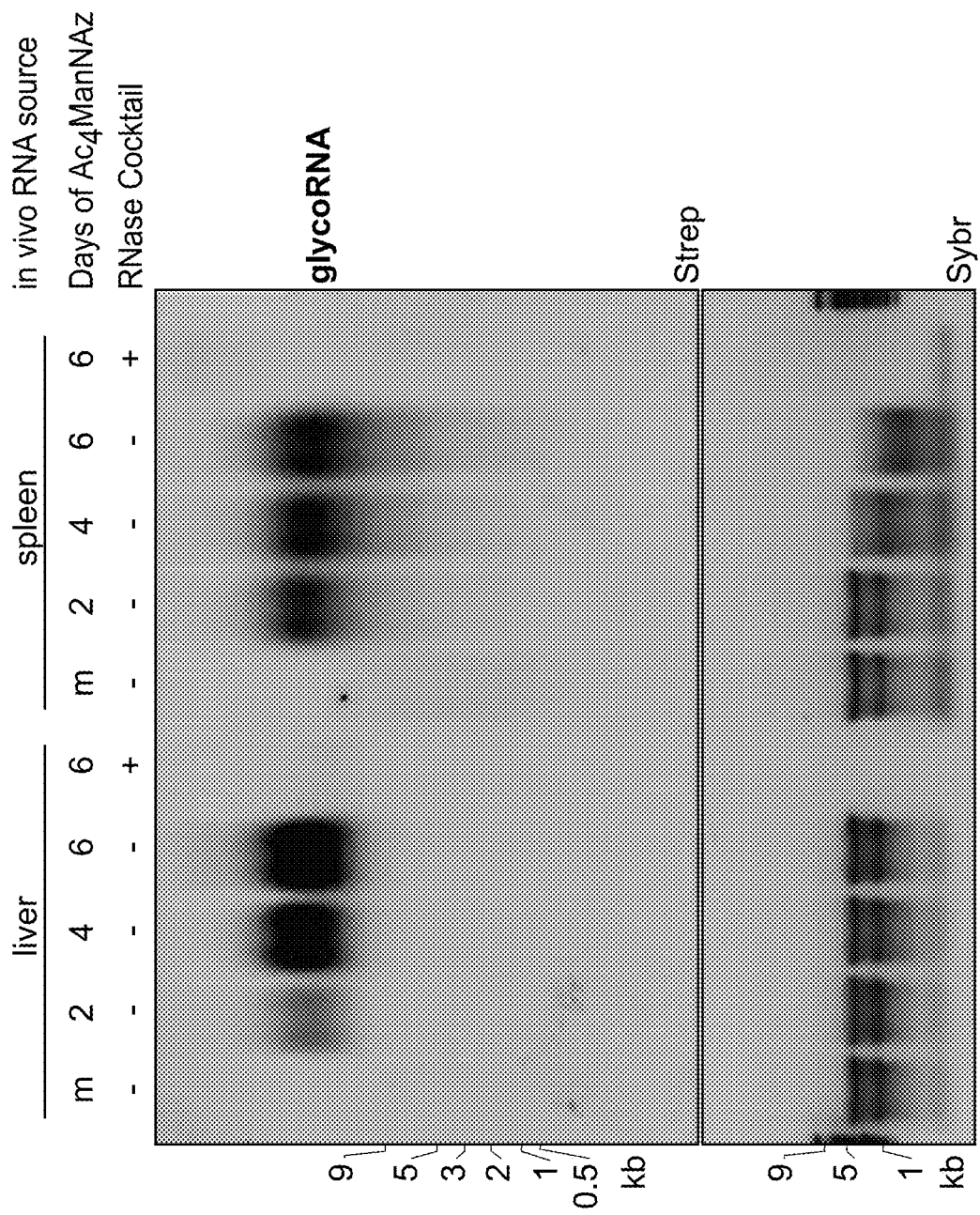

Using the same metabolic labeling approach, the presence of glycoRNA in other cell types and in animals was investigated. Human embryonic stem cells (H9), a human myelogenous leukemia line (K562), a human lymphoblastoid cell line (GM12878), a mouse T-cell acute lymphoblastic leukemia cell line (T-ALL 4188), and Chinese hamster ovary cells (CHO) all showed evidence of the presence of glycoRNA. H9 and 4188 cells showed significantly more labeling with Ac$_4$ManNAz per mass of total RNA than other cell types. Assessed next was whether this labeling could occur in vivo. To this end, intraperitoneal injections of Ac$_4$ManNAz into mice were performed for 2, 4, or 6 days. In the liver and spleen, the organs that yielded enough total RNA for analysis, dose-dependent and RNase-sensitive Ac$_4$ManNAz labeling of RNAs in the same MW region as glycoRNAs from cultured cells was observed (FIG. 1D). These data suggest that glycoRNA is not an artifact of tissue culture and occurs broadly across multiple cell and tissue types and at various abundances.

Example 2—glycoRNAs as Small Noncoding RNAs

Figure 2A:
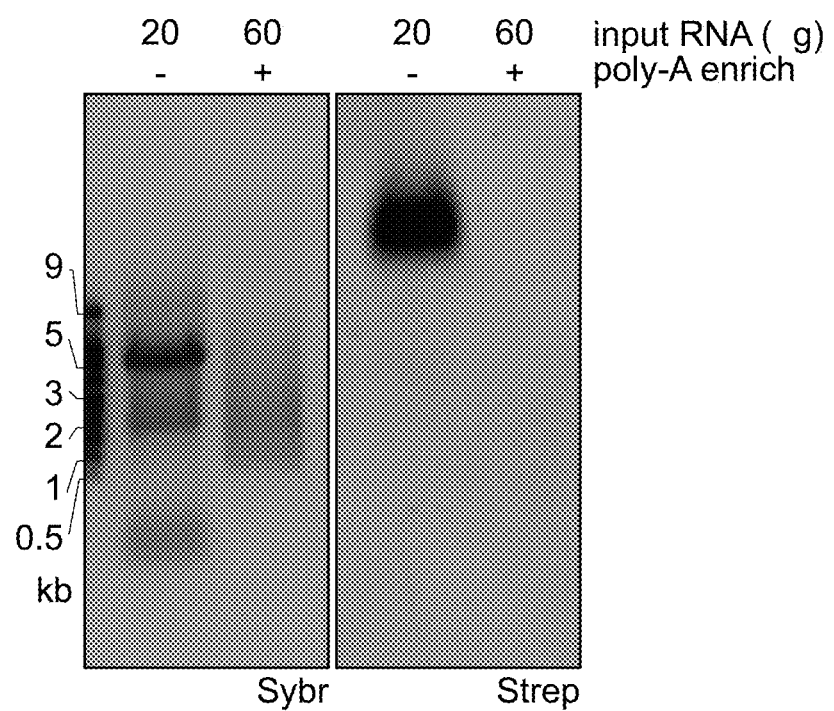
FIGS. 2A-2E are blots and a scatter plot showing that small, non-polyadenylated, and conserved transcripts comprise the pool of cellular glycoRNA.
Figure 2B:
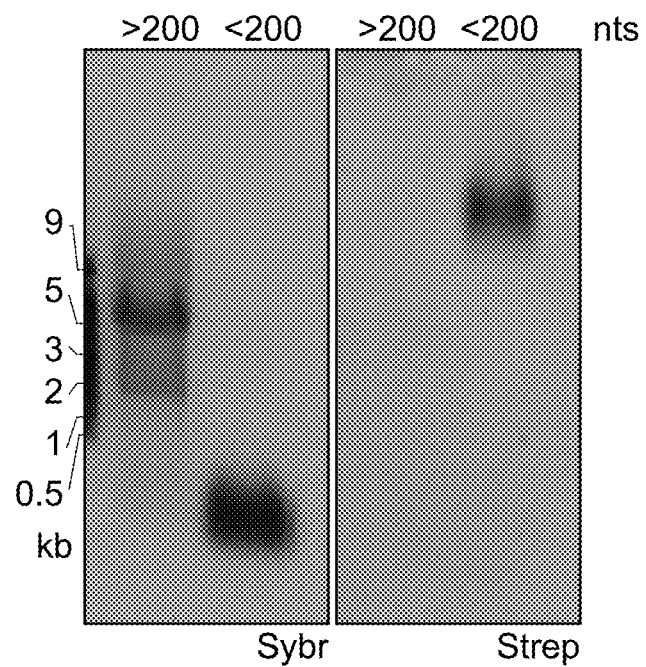
Figure 2C:
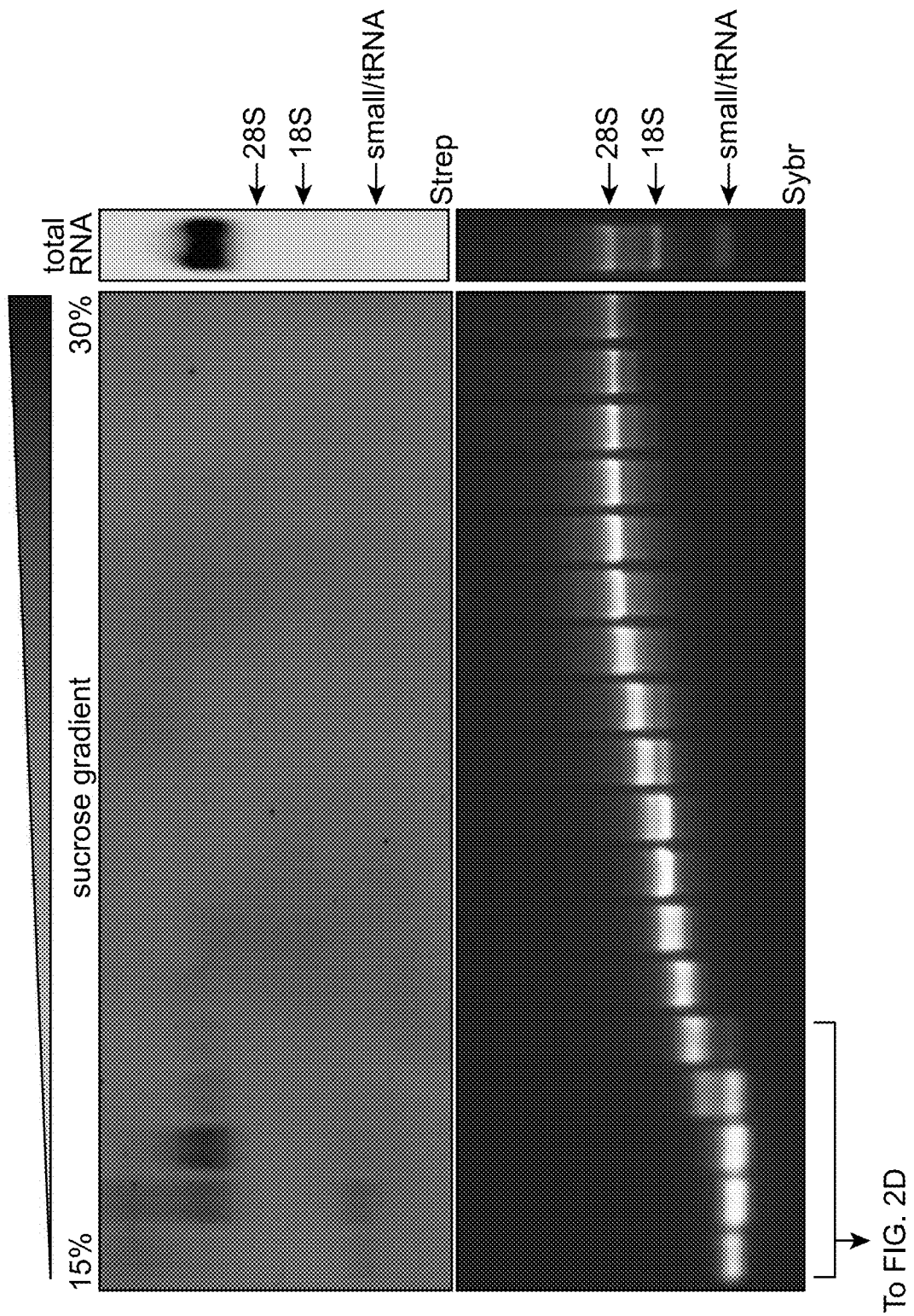

Across all cell types and organs tested, glycoRNA was found to migrate very slowly by denaturing agarose gel electrophoresis (FIGS. 1A-1D). It was hypothesized that if glycoRNAs are indeed large RNAs, they would likely be polyadenylated (poly-A). However, glycoRNA from extracted RNA via poly-A enrichment was consistently unable to be purified (FIG. 2A). This was not due to cleavage or degradation of the glycoRNA during the poly-A enrichment procedure. As an alternative enrichment strategy, a commercial fractionation method was used that leverages length-dependent RNA precipitation and binding to silica columns to separate out "large" (>200 nts) from "small" (<200 nts) transcripts (see Materials and Methods). Surprisingly, the glycoRNA fractionated exclusively with the small RNA population of total RNA (FIG. 2B). To validate this observation with an independent fractionation strategy, Ac$_4$ManNAz-labeled RNA was applied to a sucrose gradient and analyzed the distribution of total RNA via SYBR Gold staining and glycoRNA. The sucrose gradient robustly separated the major visible RNAs such as small RNAs/tRNA, 18S rRNA, and 28S rRNA (FIG. 2C). The glycoRNA fractionated with the small RNAs, but still demonstrated extremely slow migration (high apparent MW) in the agarose gel (FIG. 2C). glycoRNA's anomalous migratory behavior might be caused by its associated glycans.

Figure 2D:
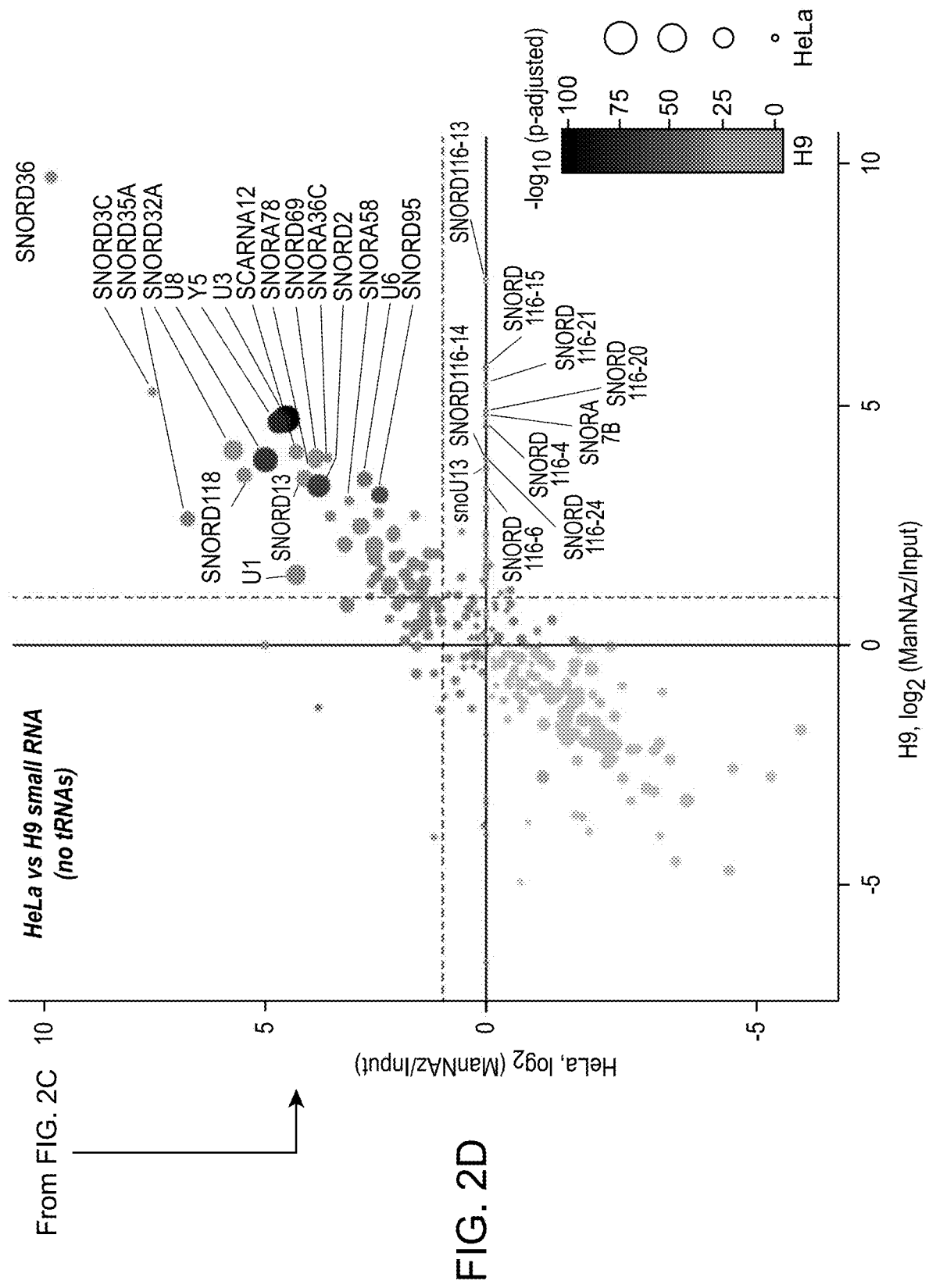

Example 3—A Common Set of Transcripts are Glycosylated Across Diverse Cell Types To identify the glycoRNA transcripts, the sucrose gradients were leveraged to isolate only the small RNA fractions from Ac$_4$ManNAz-labeled H9 and HeLa cells. RNA sequencing libraries were generated from small RNAs (input) as well as glycoRNAs that were enriched after streptavidin pulldown. Biological replicates showed high concordance across samples and the bulk of the reads mapped to small, non-polyadenylated RNAs, as expected. Assessed next was what RNAs were selectively labeled by Ac$_4$ManNAz treatment. Input expression of tRNA and non-tRNA transcripts were positively correlated between HeLa and H9 cells. Found was a set of Y RNA, snRNA, rRNA, snoRNAs, and tRNAs enriched in both H9 and HeLa cells. The enrichment values of HeLa and H9 cell glycoRNAs showed strong positive correlation, despite the different lineages of these cell types (FIG. 2D). Thus, Ac$_4$ManNAz enrichment defines 193 RNA transcripts as candidate glycoRNAs.

Figure 2E:
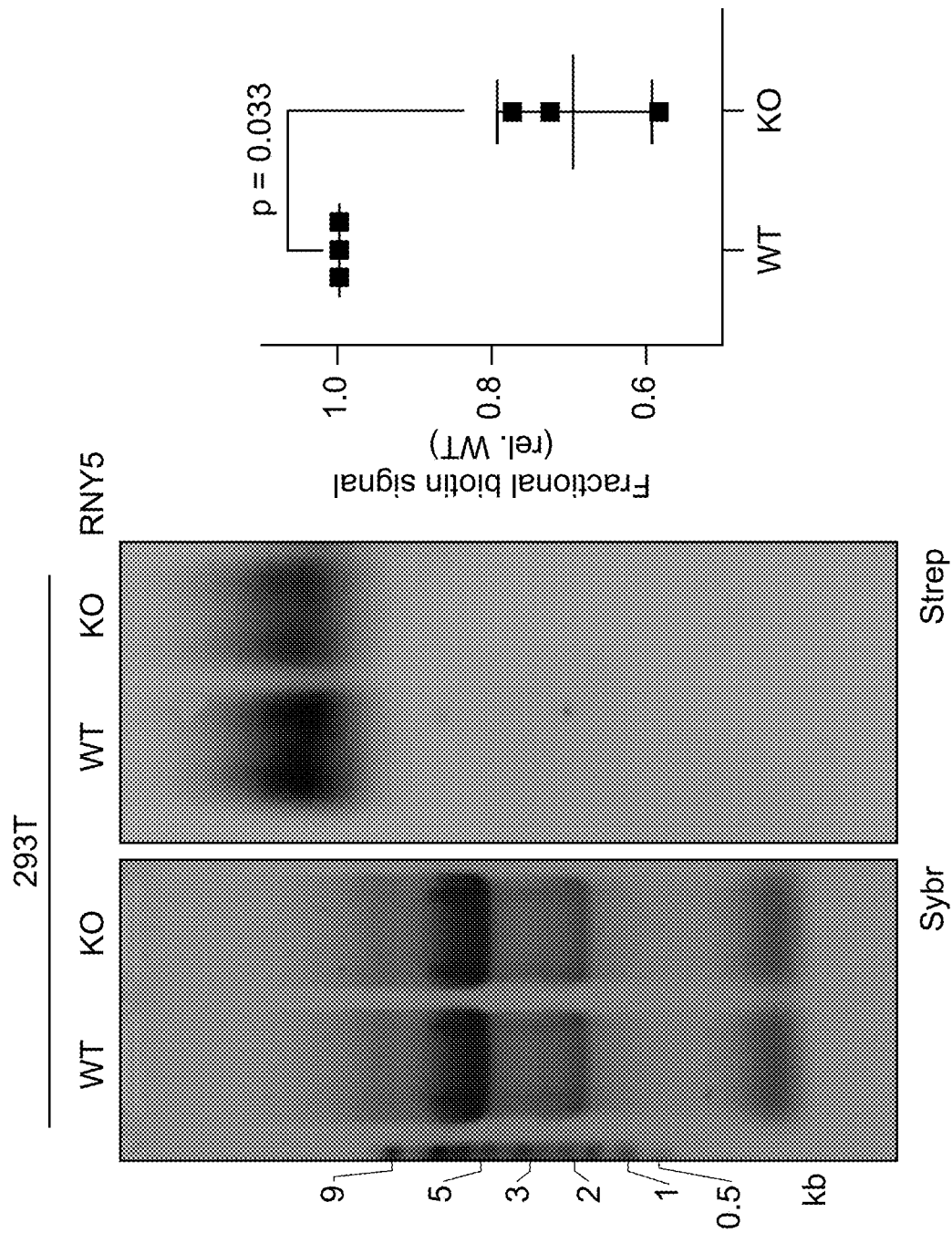

The RNAs found to be modified have many well-established and critical cellular roles. The Y RNA family stood out, as their binding proteins and ribonucleoproteins (RNPs) (among some other glycoRNAs transcripts identified) are known to be antigens associated with autoimmune diseases such as systemic lupus erythematosus (SLE). These RNAs are highly conserved in vertebrates and are thought to contribute to cytosolic RNP surveillance, particularly for the 5S rRNA. Given these features, it was desired to validate Y5 as a glycoRNA by gene knockout via CRISPR/Cas9. A 293T Y5 knockout cell line was generated using two single-guide RNAs (sgRNAs) that targeted the 5' and 3' regions of the Y5 genomic locus. Single cell clones were isolated and a KO was selected for characterization: PCR amplification of the Y5 locus yielded two amplicons corresponding to two different insertion/deletions. The KO generated no observable Y5 transcript and had no gross growth defects, consistent with previous reports of Y RNA redundancy. Ac$_4$ManNAz-labeling of the Y5 KO cells resulted in a significant (~30%, p=0.033) decrease in the amount of biotin signal compared to WT cells, without any apparent MW changes (FIG. 2E). The reduction of glycoRNA signal was consistent with the sequencing data, which identified Y5 as strongly enriched, but among a pool of other candidate glycoRNAs.

Example 4—Label and Label-Free Detection of Sialic Acid in glycoRNA

Figure 3B:
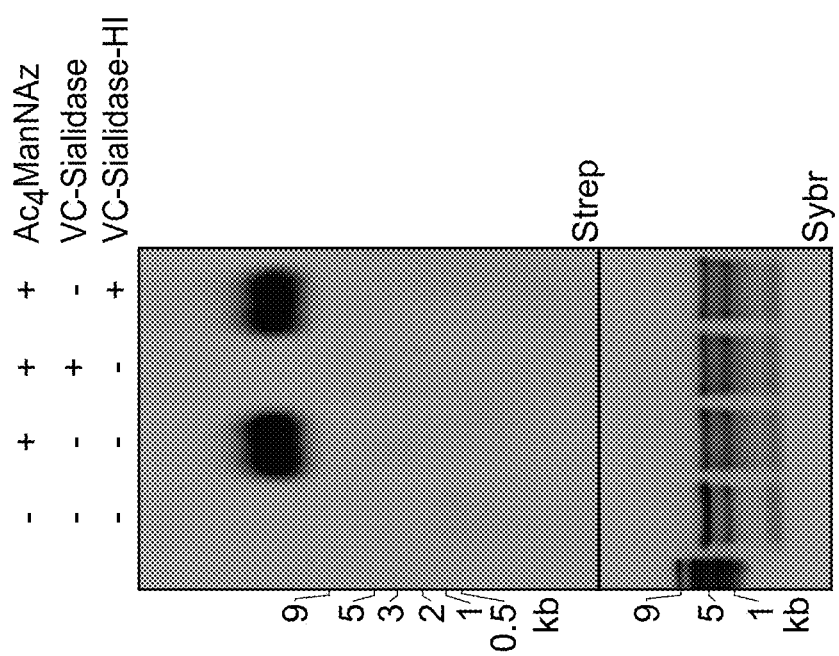
FIGS. 3A-3E are blots and graphs of glycans modifying RNA contain sialic acid.
Figure 3A:
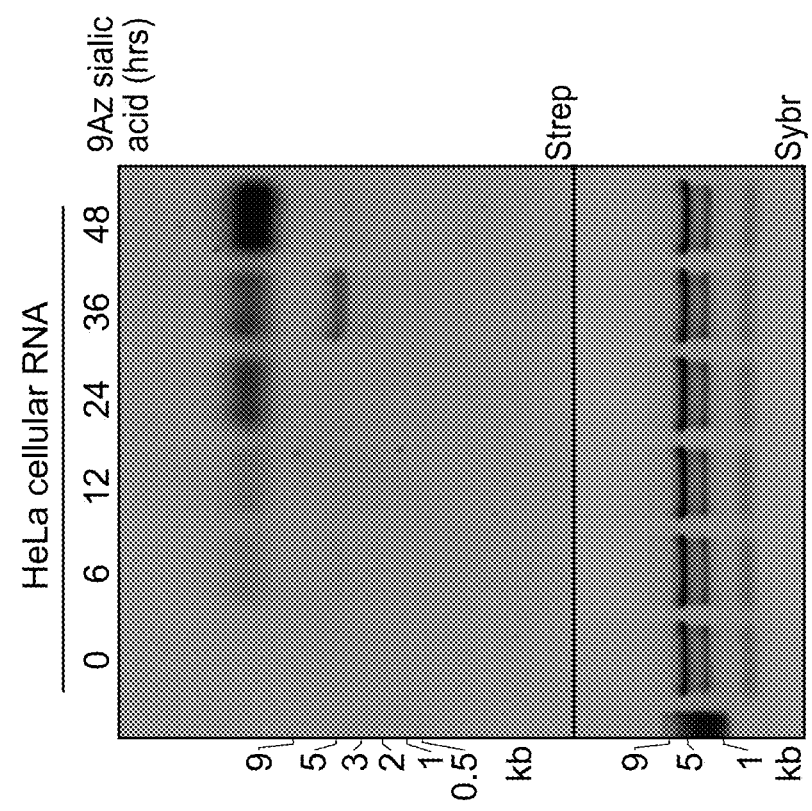
Figure 3C:
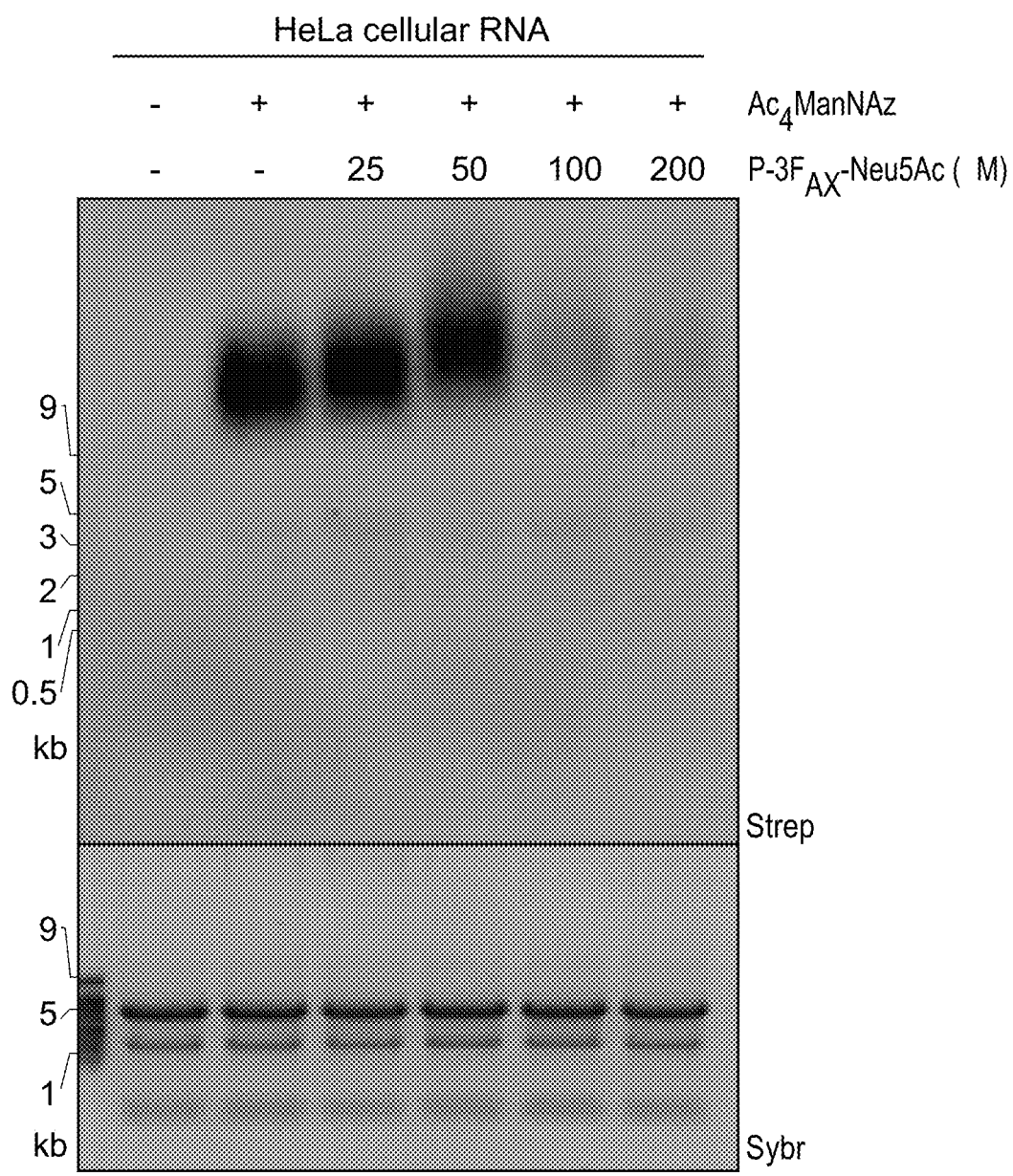

Sought next was to define the glycan structures on glycoRNAs. The major pathway for Ac$_4$ManNAz metabolism in human cells entails conversion to sialic acid, then to CMP-sialic acid, and finally addition to the termini of glycans. To exclude the possibility that Ac$_4$ManNAz is shunted into unexpected metabolic pathways, 9-azido sialic acid (9Az-sialic acid) was used, which is directly converted into CMP-sialic acid as a metabolic label. Consistent with Ac$_4$ManNAz labeling, 9Az-sialic acid produced a similar time-dependent labeling of slowly migrating cellular RNA (FIG. 3A). Treatment of Ac$_4$ManNAz-labeled cellular RNA with *Vibrio cholerae* sialidase (VC-Sia) completely abolished the biotin signal without impacting the integrity of the RNA sample, while a heat-inactivated (HI) VC-Sia was unable to reduce the signal (FIG. 3B). Assessed was the contribution of canonical sialic acid biosynthesis enzymes through the use of P-3F$_{AX}$-Neu5Ac, a cell-permeable metabolic inhibitor of sialoside biosynthesis. Treatment of HeLa cells with P-3F$_{AX}$-Neu5Ac resulted in a dose-dependent reduction in total glycoRNA signal and a concomitant shift towards higher apparent MW on the blot (FIG. 3C). This reduced mobility (appearing higher in the gel) of the glycoRNA likely results from less sialic acid, and thus less negative charge per glycoRNA molecule, as has been observed for proteins.

Figure 3D:
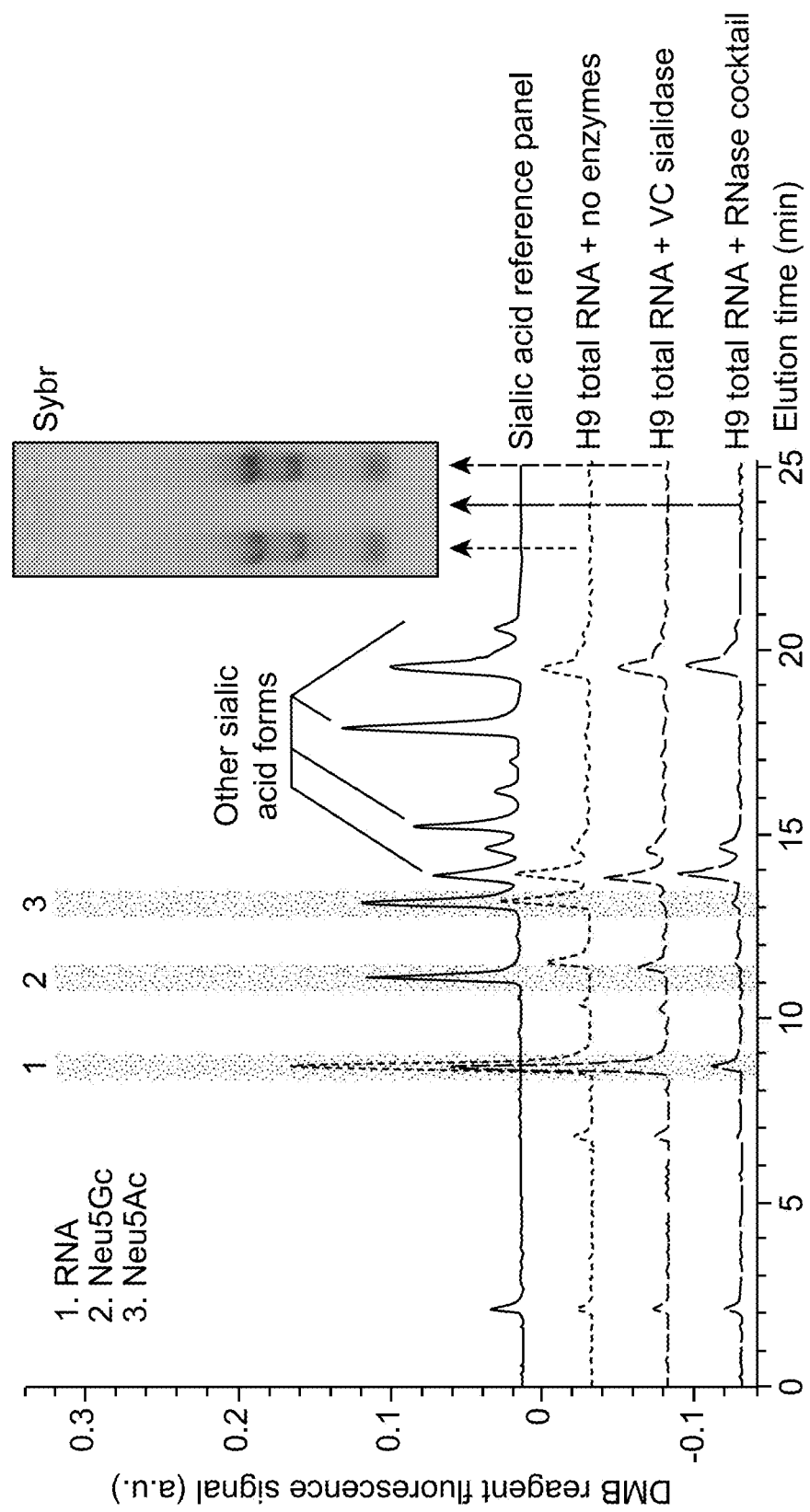

To confirm that glycoRNAs are sialylated, an independent method not relying on metabolic reporters was used. The fluorogenic 1,2-diamino-4,5-methylenedioxybenzene (DMB) probe is used to derivatize free sialic acids for detection and quantitation by HPLC-fluorescence. Native, total RNA from HeLa, H9, and 4188 cells was subjected to the DMB labeling procedure and observed the presence of two forms of sialic acid commonly found in animals, Neu5Ac and Neu5Gc (FIG. 3D). These peaks disappeared when the samples were pretreated with VC-Sia or RNase, reinforcing the notion that glycoRNA is modified with sialic acid containing glycans. Notably, sialic acid liberated from genomic DNA was unable to be detected using the DMB assay.

Figure 3E:
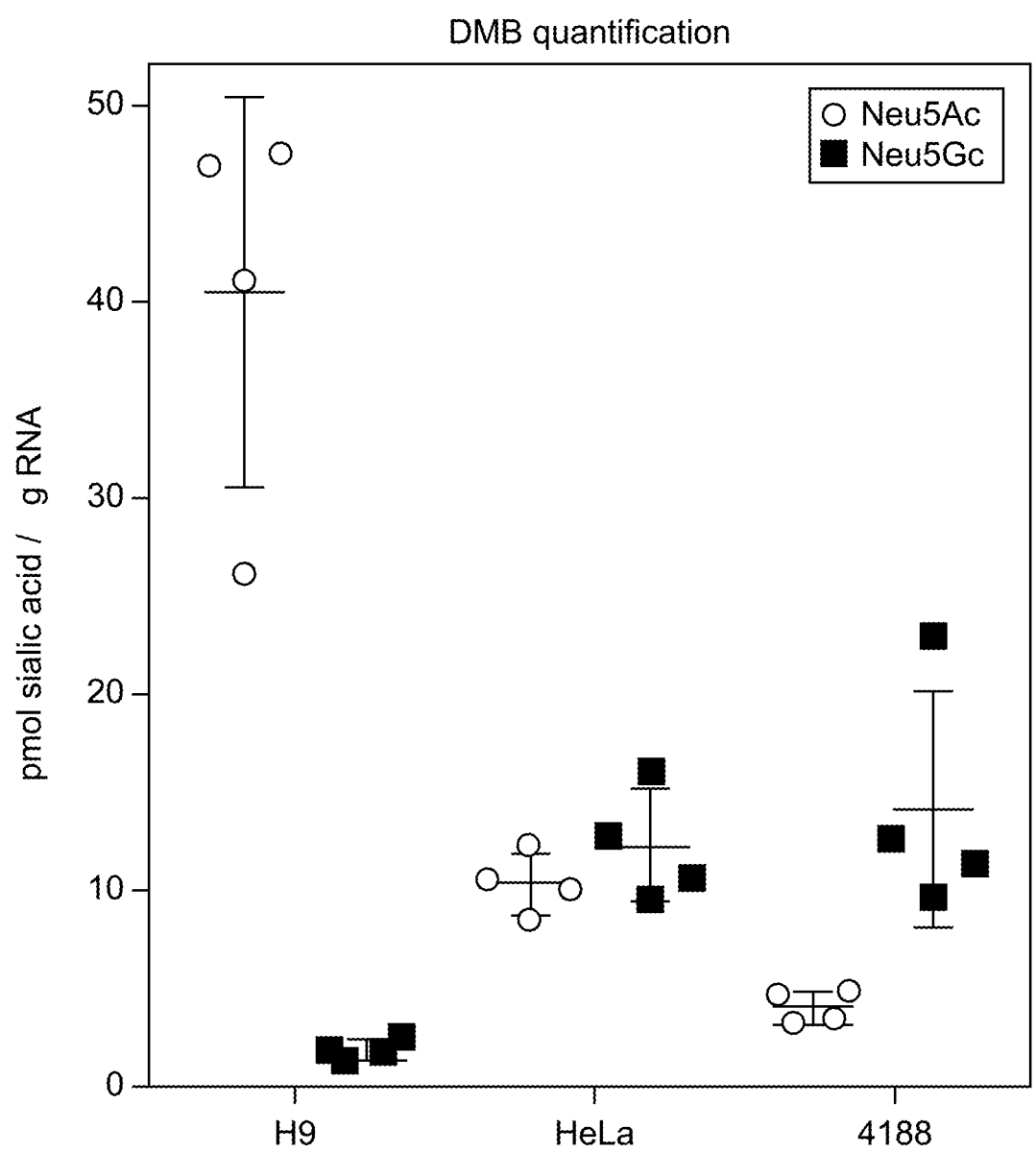

Quantitatively, H9, HeLa, and 4188 cells were found to have approximately 40, 20, and 20 picomoles (pmol) of total sialic acid per μg of total RNA, respectively (FIG. 3E). GlycoRNA from 4188 cells contained more Neu5Gc, whereas H9 cells contained mostly Neu5Ac, and HeLa cells had similar levels of Neu5Ac and Neu5Gc (FIG. 3E). Importantly, this quantitative analysis is consistent, with the observed difference in Ac$_4$ManNAz labeling intensity observed across these cell lines. Human cells lack a functional CMAH gene which is responsible for converting Neu5Ac to Neu5Gc, while this pathway exists in mouse cells. Correspondingly, higher Neu5Gc levels in glycoRNA from mouse 4188 cells were found as compared to HeLa or H9 cells (FIG. 3E). The presence of Neu5Gc in HeLa glycoRNA likely comes from bovine serum in the growth media; H9 cells were grown in serum-free media.

Figure 4B:
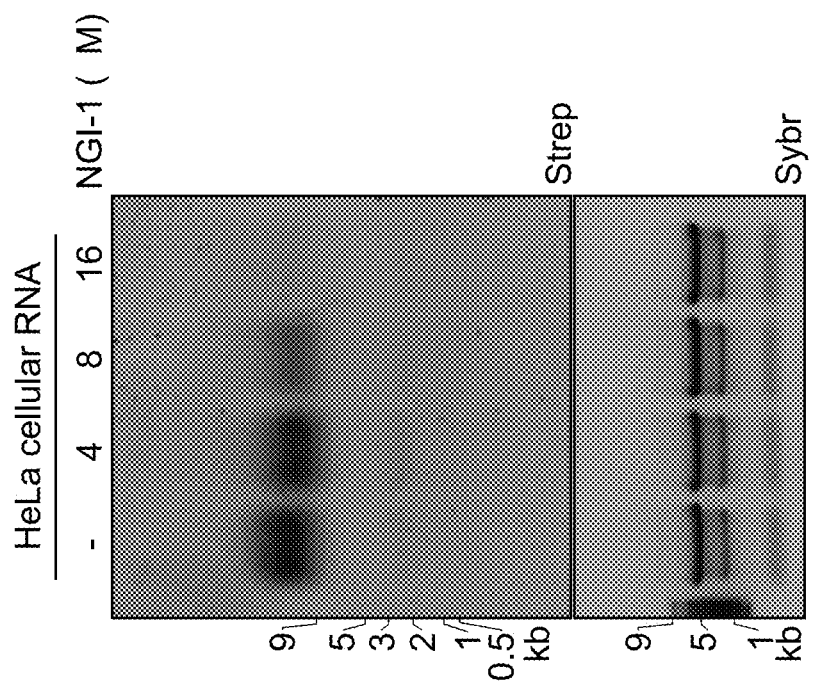
FIGS. 4A-4H are blots, graphs, and schemes showing a distinct set of N-glycans are enriched with glycoRNAs.
Figure 4A:
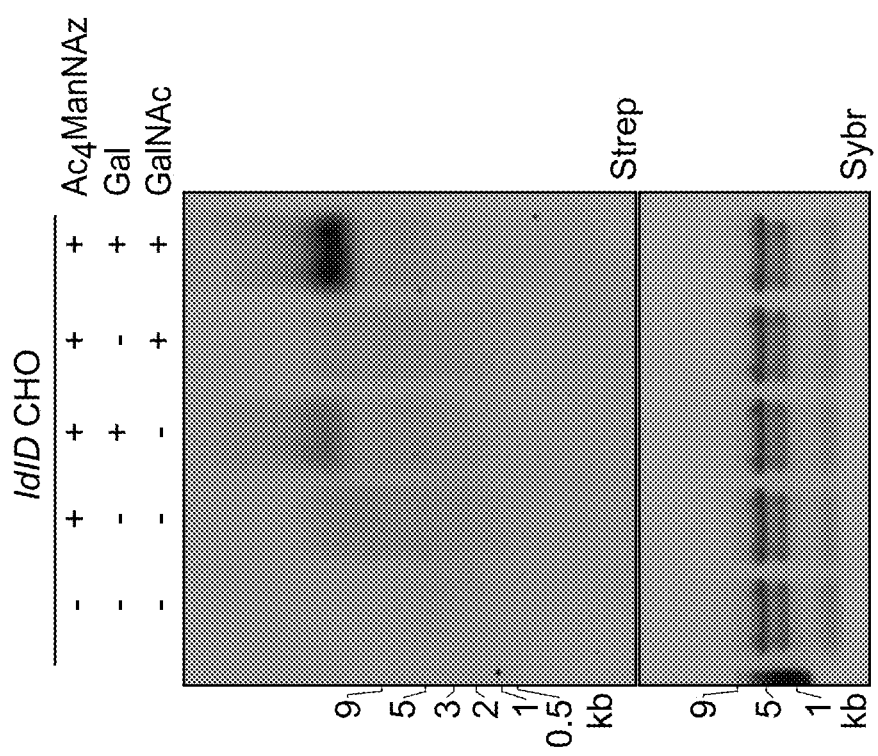

Example 5—Canonical N-Glycan Biosynthetic Machinery Contributes to glycoRNA Production There are two main classes of glycans on proteins, N- and O-glycans, and both can be sialylated. To determine whether glycoRNA structures were related to glycoprotein-associated glycan structures, a combination of genetic, pharmacological, and enzymatic methods was used. The ldlD mutant CHO cell line lacks the ability to interconvert UDP-glucose(Glc)/GlcNAc into UDP-galactose (Gal)/GalNAc. Thus, in minimal growth media, glycoproteins from ldlD CHO cells have stunted N- and O-glycans because the cells cannot produce UDP-Gal (required for N-glycan elongation) and UDP-GalNAc (required to initiate O-glycosylation). Very little glycoRNA labeling in Ac$_4$ManNAz-treated ldlD CHO cells (FIG. 4A) grown in minimal media was observed. However, supplementation of the media with galactose, but not GalNAc, restored glycoRNA labeling, and supplementation with both galactose and GalNAc further boosted labeling intensity (FIG. 4A). This result was reproduced using a human K562 cell line with a CRISPR-Cas9 targeted knockout of UDP-galactose-4-epimerase (GALE), which mimics the phenotype of the ldlD CHO cell line. The pattern of these results were similar to that observed when labeling glycoproteins in these cell types, suggesting that glycoRNA glycans are structurally related to those found on proteins.

Tested next were the effects of glycosylation inhibitors on glycoRNA biosynthesis. Oligosaccharyltransferase (OST) mediates protein N-glycosylation by transferring a 14-sugar glycan to asparagine residues on nascent polypeptides during their translocation through the Sec/translocon. Tested was the effect of NGI-1, a specific and potent small molecule inhibitor of OST, on glycoRNA production. Such treatment caused a dose-dependent loss of glycoRNA labeling with Ac$_4$ManNAz (FIG. 4B), suggesting that OST is involved in biosynthesis of glycoRNA-associated glycans. Downstream N-glycan processing steps were also perturbed with kifunensine and swainsonine, inhibitors of the N-glycan trimming enzymes α-mannosidase I and II, respectively. These treatments also caused a dose-dependent loss of azidosugar labeling (FIG. 4C) accompanied by an increase in apparent MW of the glycoRNA at higher doses, akin to the results seen with P-3F$_{AX}$-Neu5Ac. It was hypothesized that disruption of high-mannose glycan processing produces hyposialylated glycoRNAs with less net negative charge and, therefore, reduced mobility.

Figure 4D:
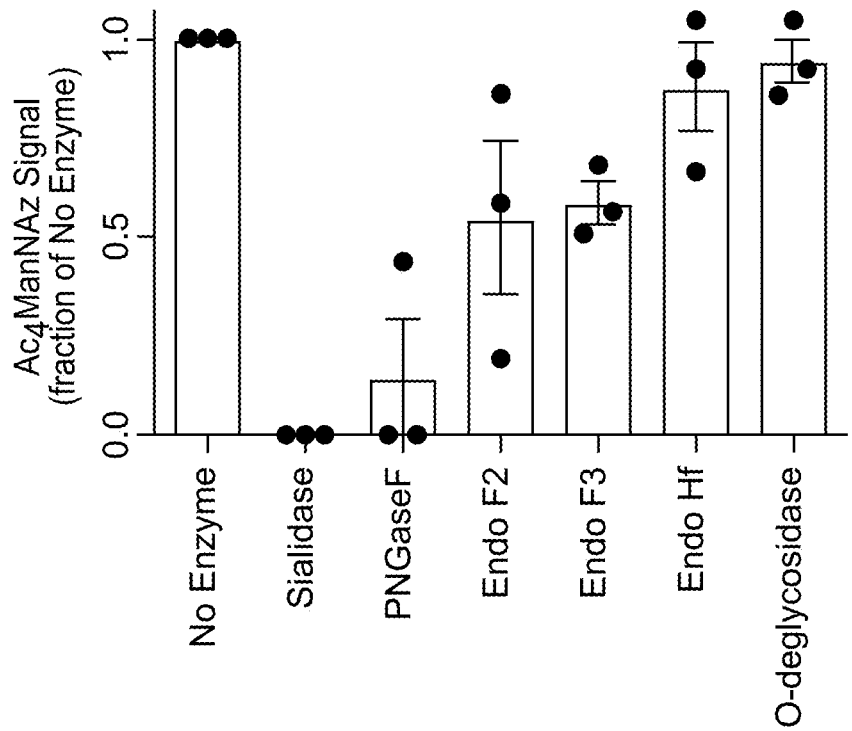
Figure 4C:
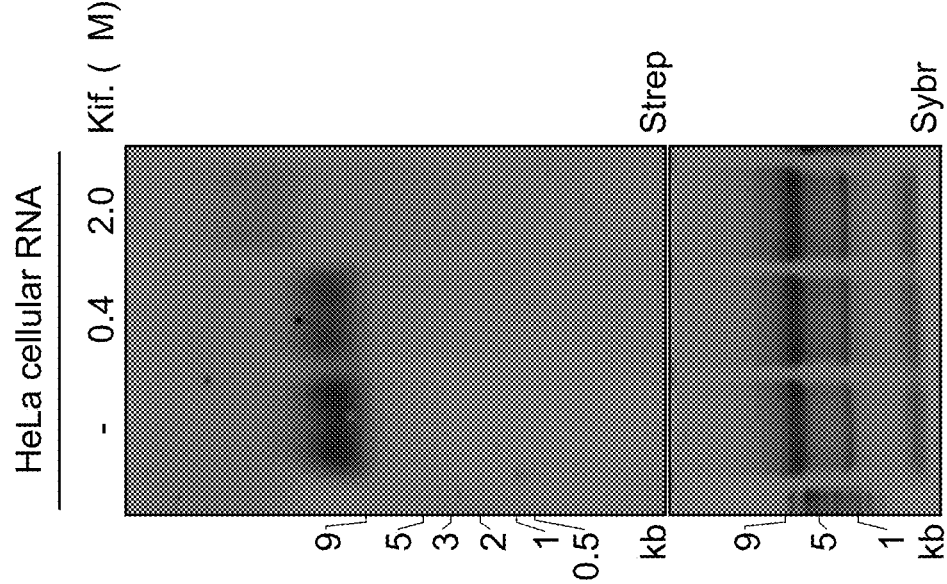

To further define the glycan structures on glycoRNA, a panel of endoglycosidases was employed. Purified RNA from Ac$_4$ManNAz-labeled HeLa cells was first exposed to each enzyme and then reacted with biotin for visualization (FIG. 4D). Treatment of glycoRNA with PNGase F, which cleaves the asparagine side chain amide bond between proteins and N-glycans, strongly abrogated signal from Ac$_4$ManNAz labeling. Endo F2 preferentially cleaves bi-antennary and high mannose structures, while Endo F3 preferentially cleaves fucosylated bi- and triantennary structures, both within the chitobiose core of the glycan. Treatment of glycoRNA with either Endo F2 or F3 resulted in a partial loss of Ac$_4$ManNAz labeling. However, Endo Hf, which is more selective for high-mannose structures, did not affect Ac$_4$ManNAz signal (FIG. 4D). In contrast to these N-glycan digesting enzymes, O-glycosidase (targeting core 1 and core 3 O-glycans) or mucinase (StcE) treatment had no effect on Ac$_4$ManNAz labeling intensity (FIG. 4D). As in previous experiments, VC-Sia completely removed the Ac$_4$ManNAz-dependent label (FIG. 4D).

Example 6—Mass Spectrometry Defines Distinct Compositions of Glycans on RNA

Figure 4E:
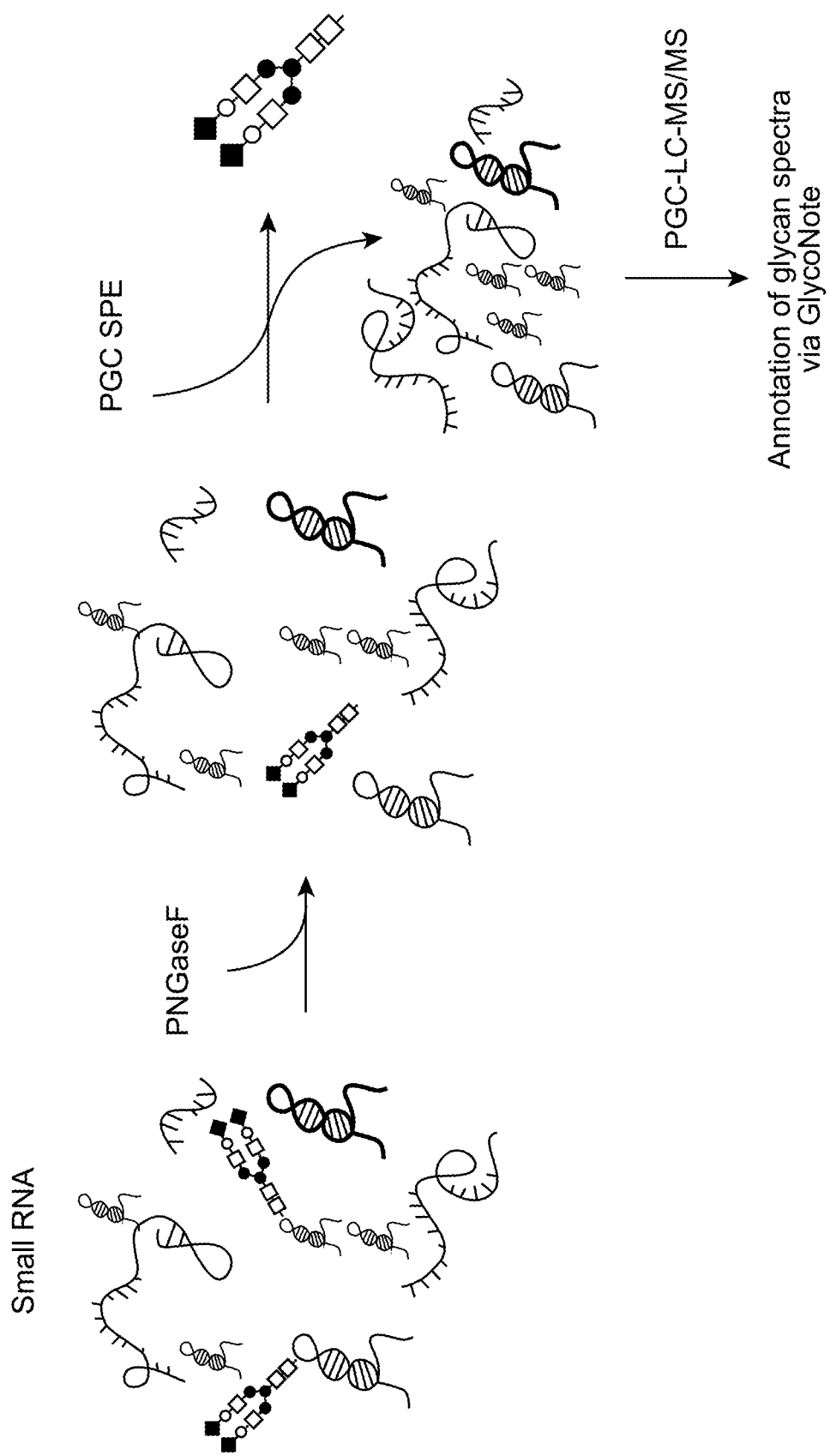
Figure 4F:
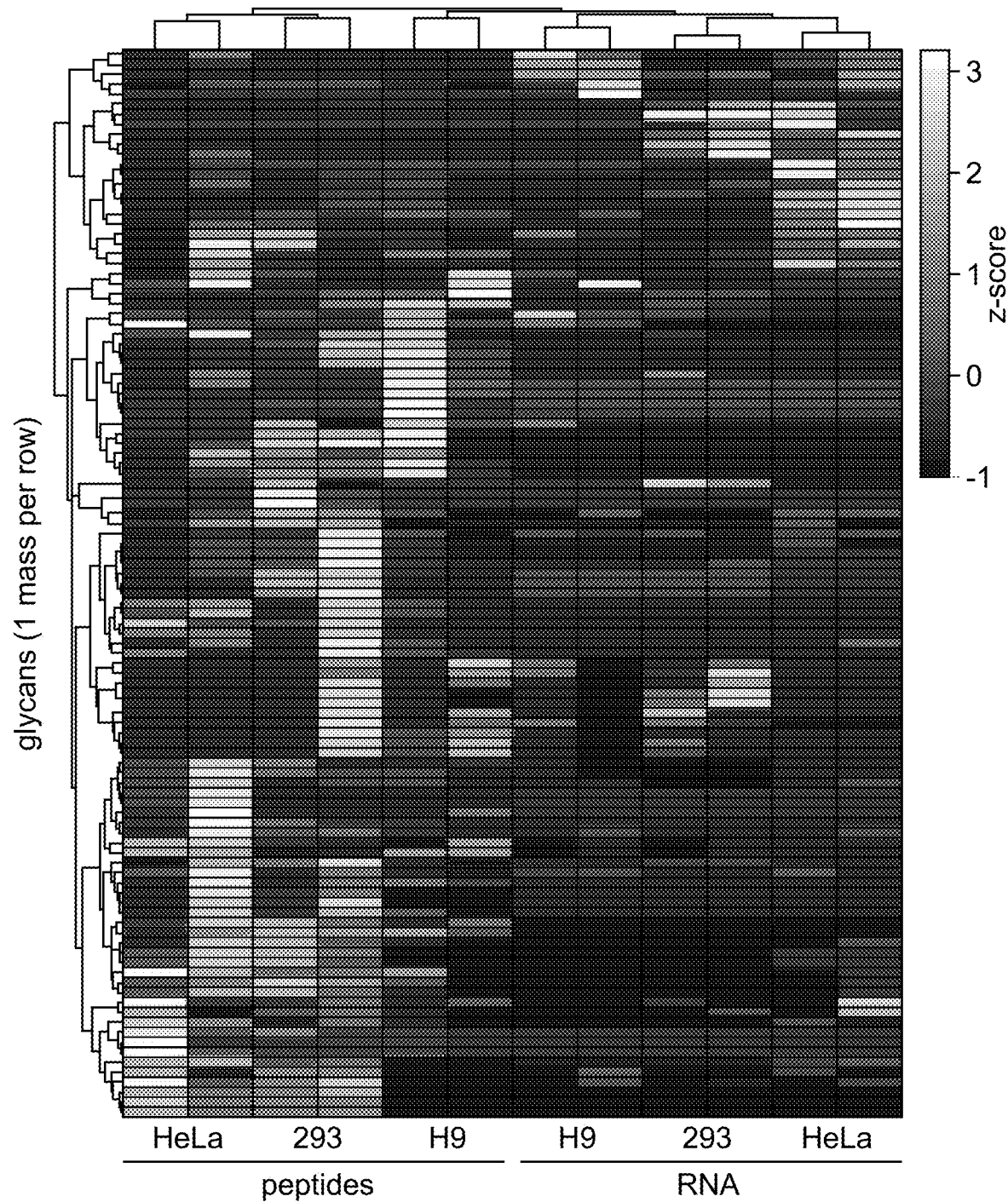
Figure 4G:
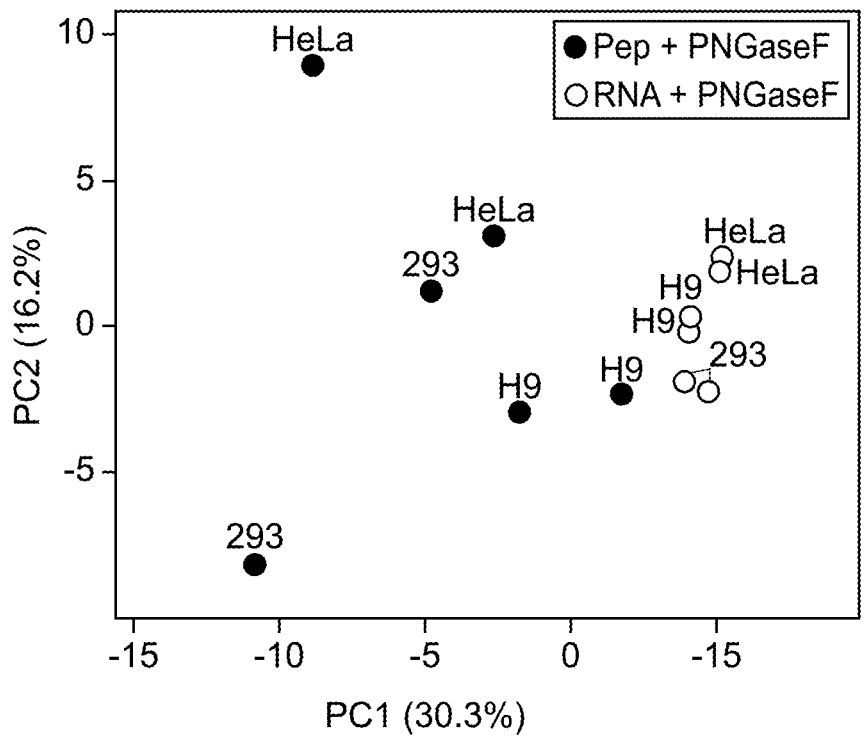
Figure 4H:
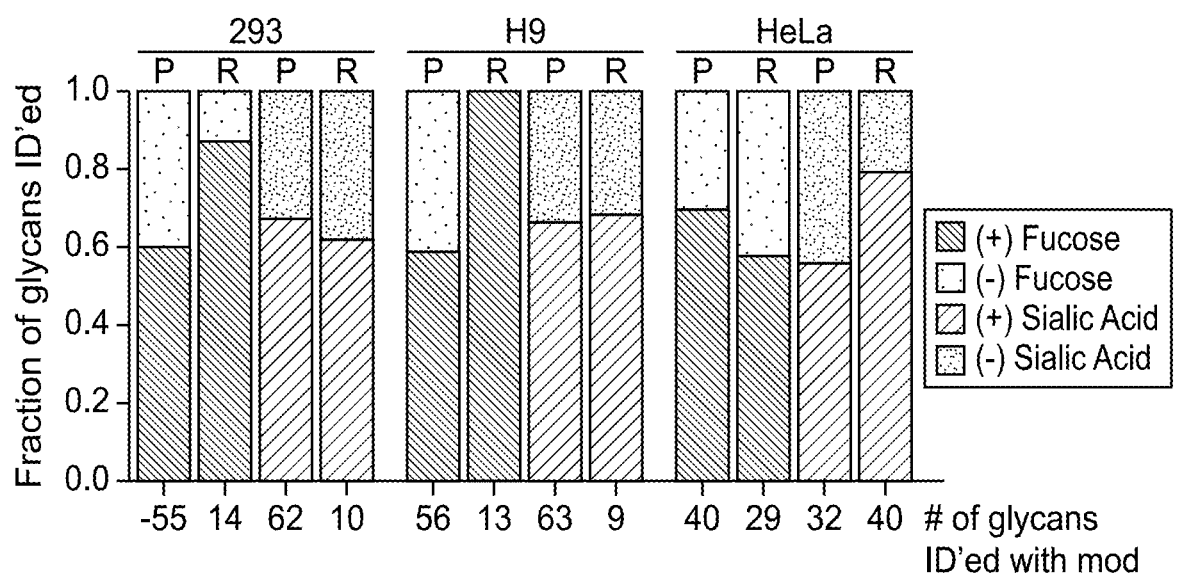

The above data suggest that glycoRNA are modified with complex-type N-glycans with at least one terminal sialic acid residue. To develop a more precise view of the glycoforms associated with RNA, a workflow based on PNGaseF-mediated release of glycans from pools of small RNAs was optimized, followed by analysis of those glycans by a porous graphitized carbon-based liquid chromatography MS strategy (PGC-LC-MS, FIG. 4D). Glycans were released from small RNA pools from 293T, H9, and HeLa cells and in parallel, peptide samples were similarly processed to compare the glycan profile on the cellular proteins. Two biological replicates were performed for each sample. 107 unique glycans present in both replicates in at least one of the six sample types were found (FIG. 4E, see Materials and Methods). Hierarchical clustering of identified glycans and principal component analysis revealed that glycans released from peptides clustered differentially when compared to those released from RNA. Further, the set of unique glycans found on RNA was smaller and more constrained relative to those on peptides (FIGS. 4F and 4G). When examining the features that distinguished RNA glycans from peptide glycans, it was noticed that both 293T and H9 cells had a higher fraction of glycans modified with fucose on RNA as compared to the peptides from these same cells. In contrast, glycoRNA glycans from HeLa cells were more likely to contain sialic acid modifications compared to the peptide glycans from HeLa cells. Overall, the PGC-LC-MS data of PNGaseF-released glycans are in line with Ac$_4$ManNAz labeling and DMB probe experiments. Importantly, since the MS-based approach does not require sialic acid for enrichment or visualization, an expanded set of glycan compositions that are often fucosylated and sometimes asialylated were able to be revealed.

Example 7—glycoRNAs are Associated with Cellular Membrane

Figure 5A:
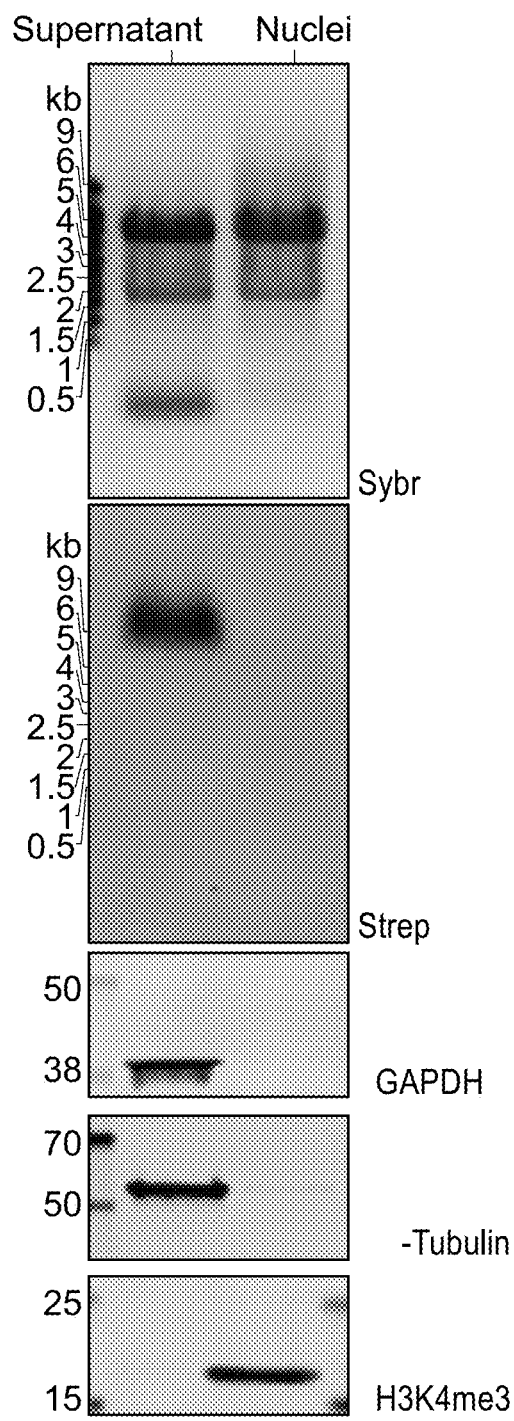
Figure 5B:
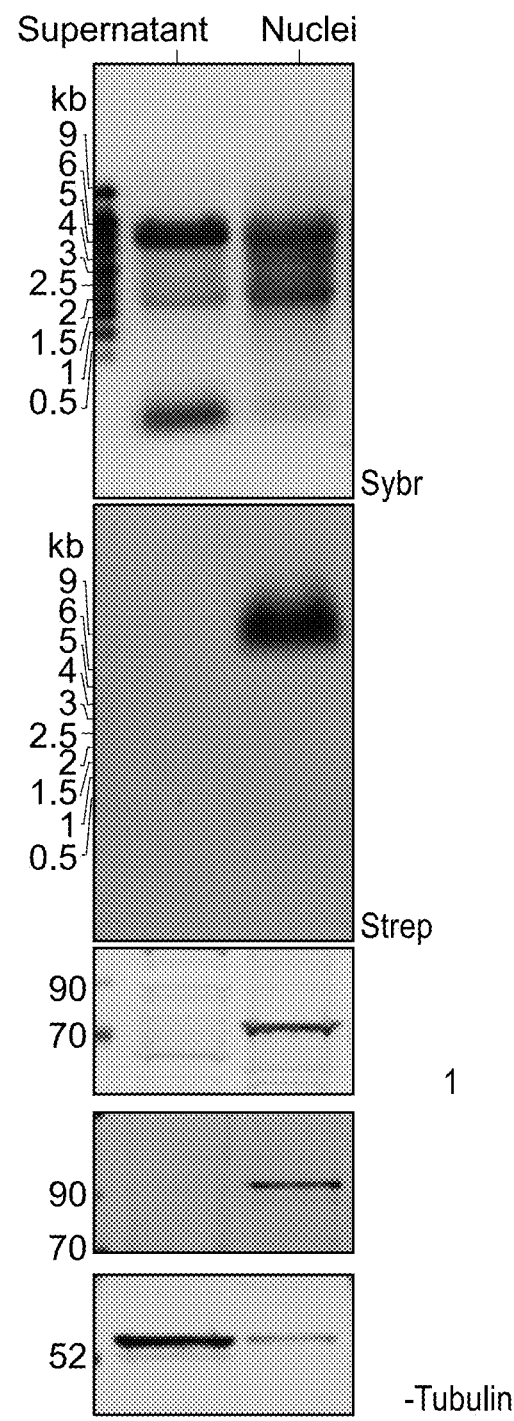

Assessed next was the subcellular localization of glycoRNA. The biogenesis of sialylated glycans occurs across many subcellular compartments including the cytosol (processing of ManNAc to Neu5Ac), the nucleus (charging of Neu5Ac with CMP), and the secretory pathway (where sialyltransferases add sialic acid to the termini of glycans). The localization of Y RNAs has been reported to be mainly cytoplasmic with a minor fraction in the nucleus. Other major classes of glycoRNA transcripts such as tRNAs and sn/snoRNAs are classically localized to the soluble cytosol and nucleus, respectively. To determine where glycoRNAs are distributed inside cells, two biochemical strategies were used: one which isolates nuclei away from membranous organelles and the cytosol and a second which separates the soluble cytosolic compartment away from membranous organelles (see Materials and Methods). Nuclear RNA from Ac$_4$ManNAz-labeled HeLa cells yielded no detectable azide-labeled species while the membrane fraction exclusively contained the glycoRNA (FIGS. 5A and 5B). This suggests that glycoRNAs are closely associated with membrane organelles.

Because membrane organelles have precise topological configurations, assessed next was whether there was a clear topological organization of glycoRNA with respect to the membranes isolated. Crude cellular membranes and membrane-bound organelles were isolated from Ac$_4$ManNAz-labeled 293T cells and subjected to VC-Sia digestion with or without pre-treatment with Triton X-100 to permeabilize membrane compartments. If glycoRNAs were topologically confined to the luminal spaces of membrane compartments, VC-Sia would only have access to these species after the addition of Triton X-100. It was found that the majority of the glycoRNA signal was sensitive to VC-Sia without Triton X-100, while a small but reproducible pool was accessible only after permeabilization. Thus, while a portion of glycoRNAs appears to reside within the luminal space of membranous organelles, the vast majority seems accessible, or on the surface of membranes in this assay.

Example 8—glycoRNAs Gain Access to the Surface of Living Cells

The accessibility to VC-Sia in the experiment above suggests that glycoRNAs do not accumulate in the lumen of intracellular vesicles or membrane organelles, however it does not precisely define on which membrane surface glycoRNAs may be present. Given the canonical trafficking and localization of glycopolymers, it was hypothesized that glycosylation of RNA may afford it the ability to be trafficked to the plasma membrane and be present on the extracellular surface of living cells. This hypothesis was addressed through two orthogonal and complementary approaches.

Figure 5C:
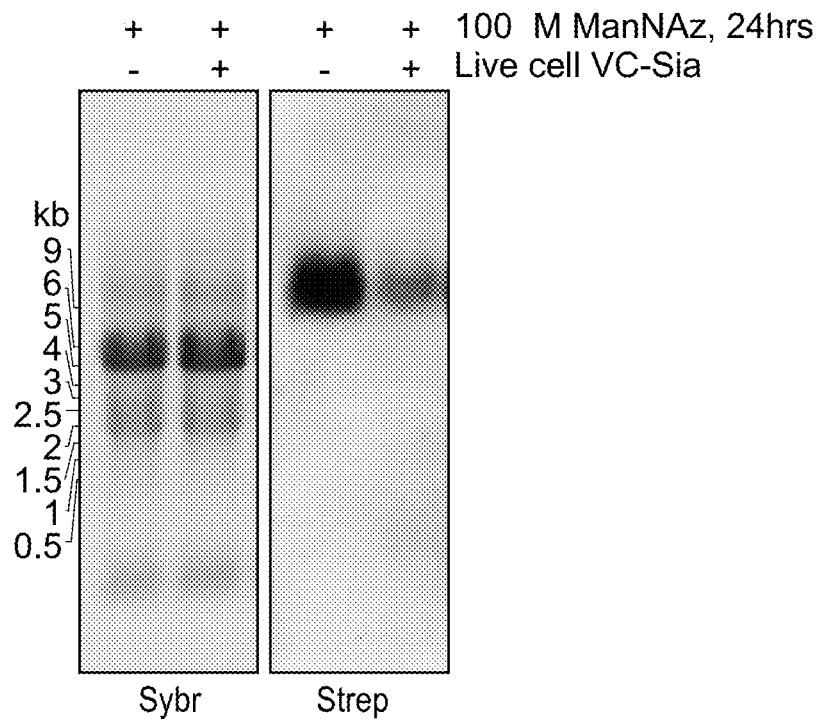
Figure 5D:
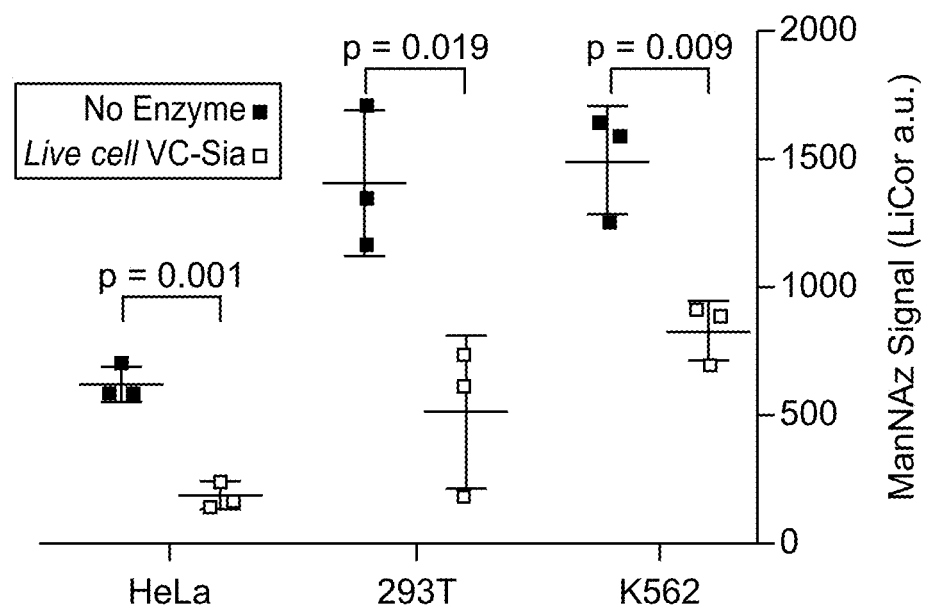

Leveraged first was the robust and specific activity of VC-Sia to cleave sialic acid (including those on glycoRNAs) and its established ability to cleave sialic acids selectively off the surface of living cells. Changes in $Ac_4ManNAz$ signal after adding VC-Sia to culture media on living HeLa cells was assayed and in as little as 20 minutes a reduction in the glycoRNA levels was seen (FIG. 5C). Replicating this experiment at 60 minutes, where the most robust difference was observed (FIG. 5D) and performing it on both adherent (HeLa and 293T) and suspension (K562) cells showed that in all cases VC-Sia was able to significantly reduce the levels of glycoRNA. These data indicate that in a short time frame and in an environment with an intact plasma membrane, VC-Sia has access to >50% of the bulk of glycoRNA purified from cells.

To validate the observation that glycoRNAs localize to live cell surfaces, required was a labeling workflow independent of $Ac_4ManNAz$ metabolic incorporation. To achieve this, a peroxidase-catalyzed proximity labeling technique was combined with the observation that biotin-aniline has significantly increased reactivity towards RNA relative to biotin phenol, which is favored for protein labeling. A non-genetic strategy was employed, leveraging lectins as cell surface affinity tools to bind live cells which could then recruit a peroxidase and deposit biotin-aniline on RNAs nearby to the bound glycan (FIG. 5E). Despite the wide use of lectins as general cell-surface binding reagents, they have specific glycoform binding features and a lectin was therefore selected which, based on the data from FIGS. 3 and 4, should not bind near glycoRNAs (ConA, specific for high mannose structures) and lectins which should bind directly to glycoRNAs (MAAII, sialic acids; WGA, N-glycans+/− sialic acid).

Figure 5F:
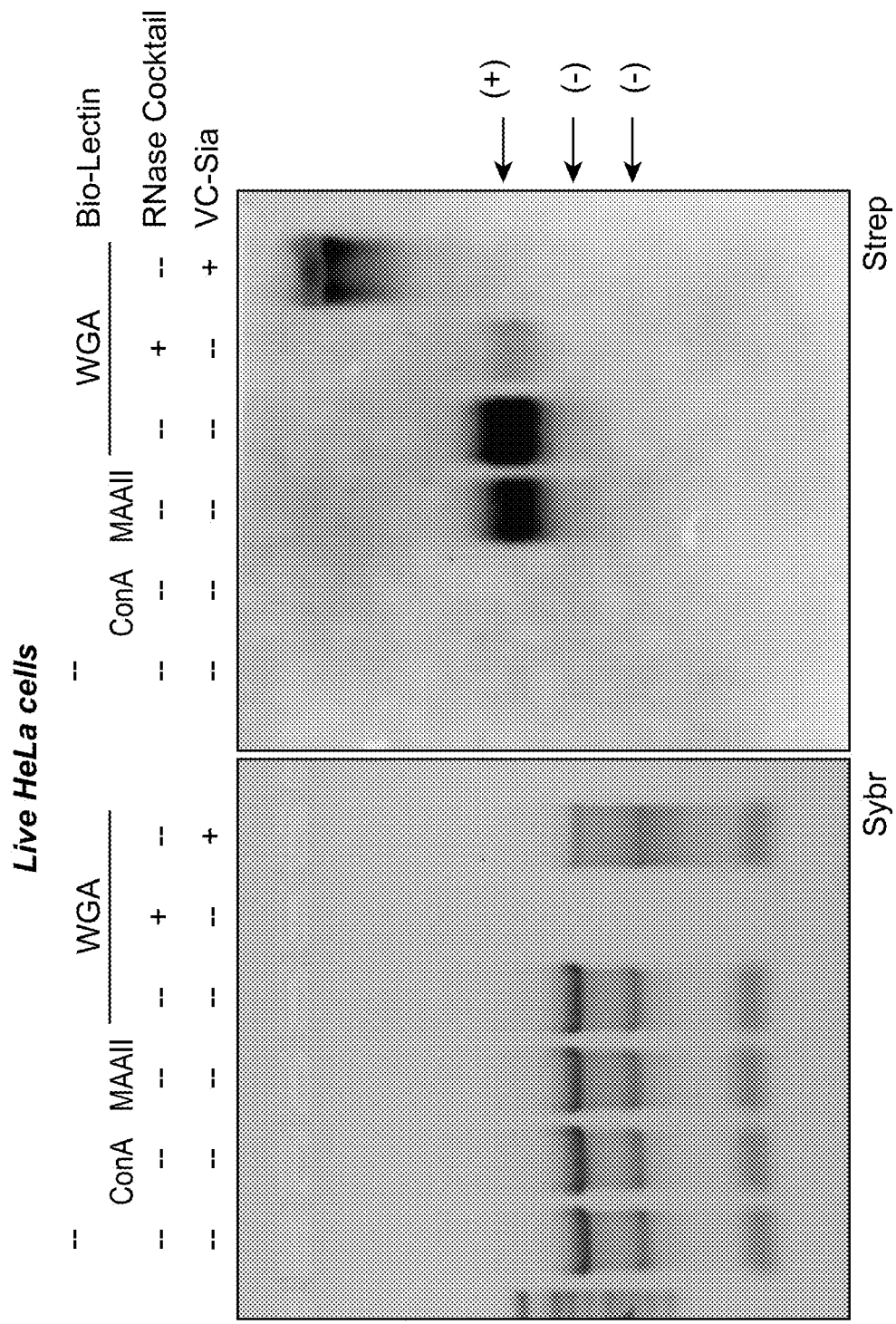

Initially this assay was benchmarked against live HeLa cell surface proteins. As expected, all three lectins were capable of recruiting streptavidin-HRP, activating biotin-aniline, and producing specific labeling patterns of cell surface proteins, while streptavidin-HRP alone was unable to generate robust labeling. This and all subsequent experiments were conducted strictly at 4° C. to reduce or eliminate vesicular trafficking, membrane recycling, or uptake of extracellular components. Assayed next was the RNA from these cells and found was specific labeling of a high molecular weight band generated when cells were stained with MAAII or WGA, but not ConA. The signal was partially RNase sensitive (89% loss, FIG. 5F). Upon treatment of the purified RNA material with sialidase, observed was a nearly quantitative shift in the biotin signal into the well of the gel without strong reduction in the amount of signal (FIG. 5F). This supports the view that biotin-aniline covalently modifies the RNA directly and that the glycan, in particular the sialic acid, contributes to glycoRNA's dramatically abnormal migration in agarose gels.

Figure 5G:
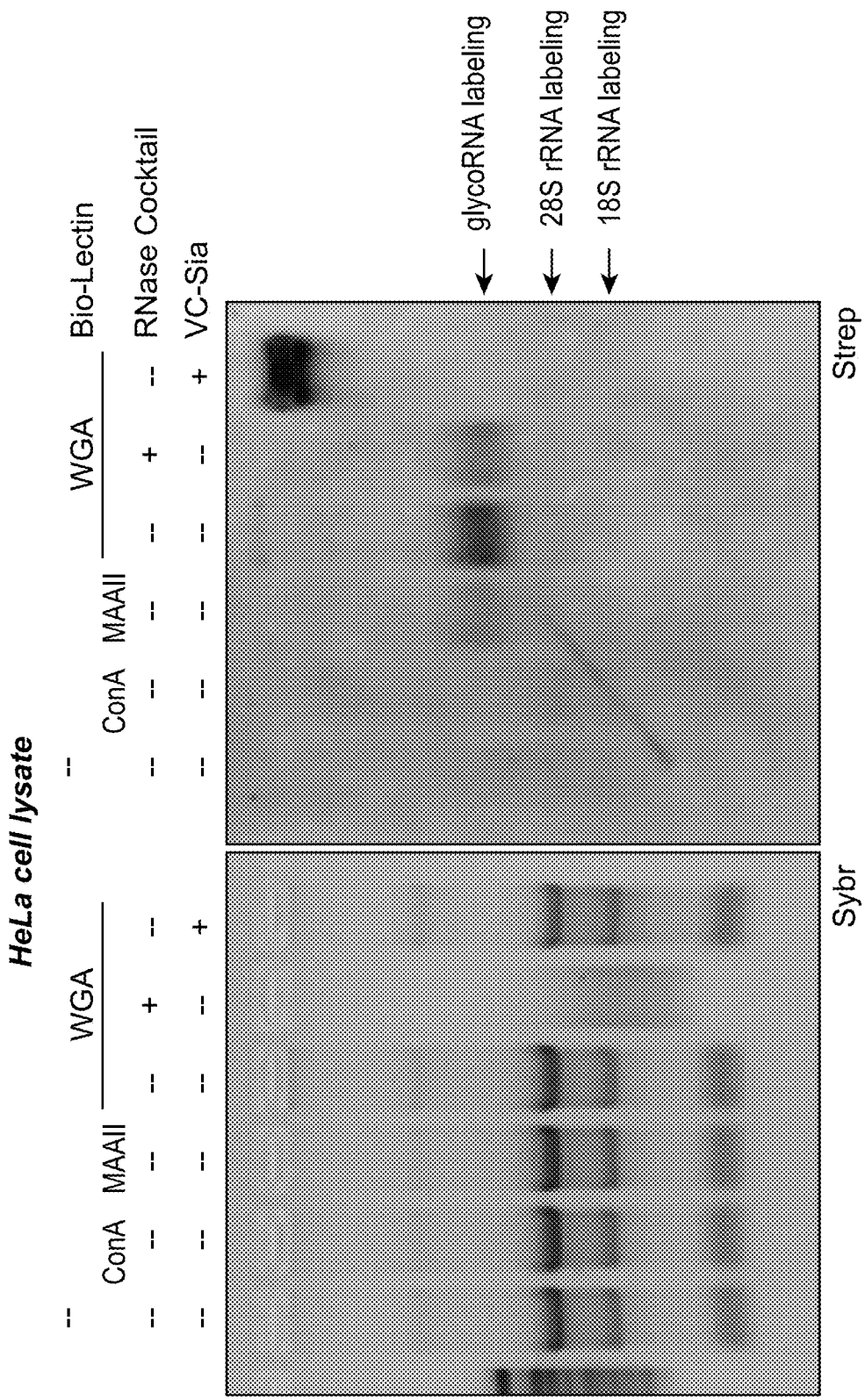

Repeating the proximity ligation assay in cell lysate rather than on live cells showed that, without an impermeable (to the activated nitrene radical of biotin-aniline) plasma membrane, MAAII and WGA still labeled glycoRNA. However, all three lectins weakly, but consistently labeled rRNA bands (FIG. 5G). The absence of these rRNA bands in the live cell experiment and their intensity relative to the high MW glycoRNA bands suggest once more that the majority of cellular glycoRNAs are on cell surfaces. Total RNA exposed to the biotin-aniline label was not fully digested with RNase (FIGS. 5F and 5G, left, 5th lanes), possibly due to covalent modification of the RNA by the aniline probe or other species. This is a possible reason that full RNase-sensitivity was not observed in these experiments. In sum, proximity-based labeling of RNAs near complex N-glycans on the surface of living cells detects glycoRNA, consistent with the chemical, genetic, and mass spectrometry results describing RNA glycans reported herein.

Figure 6A:
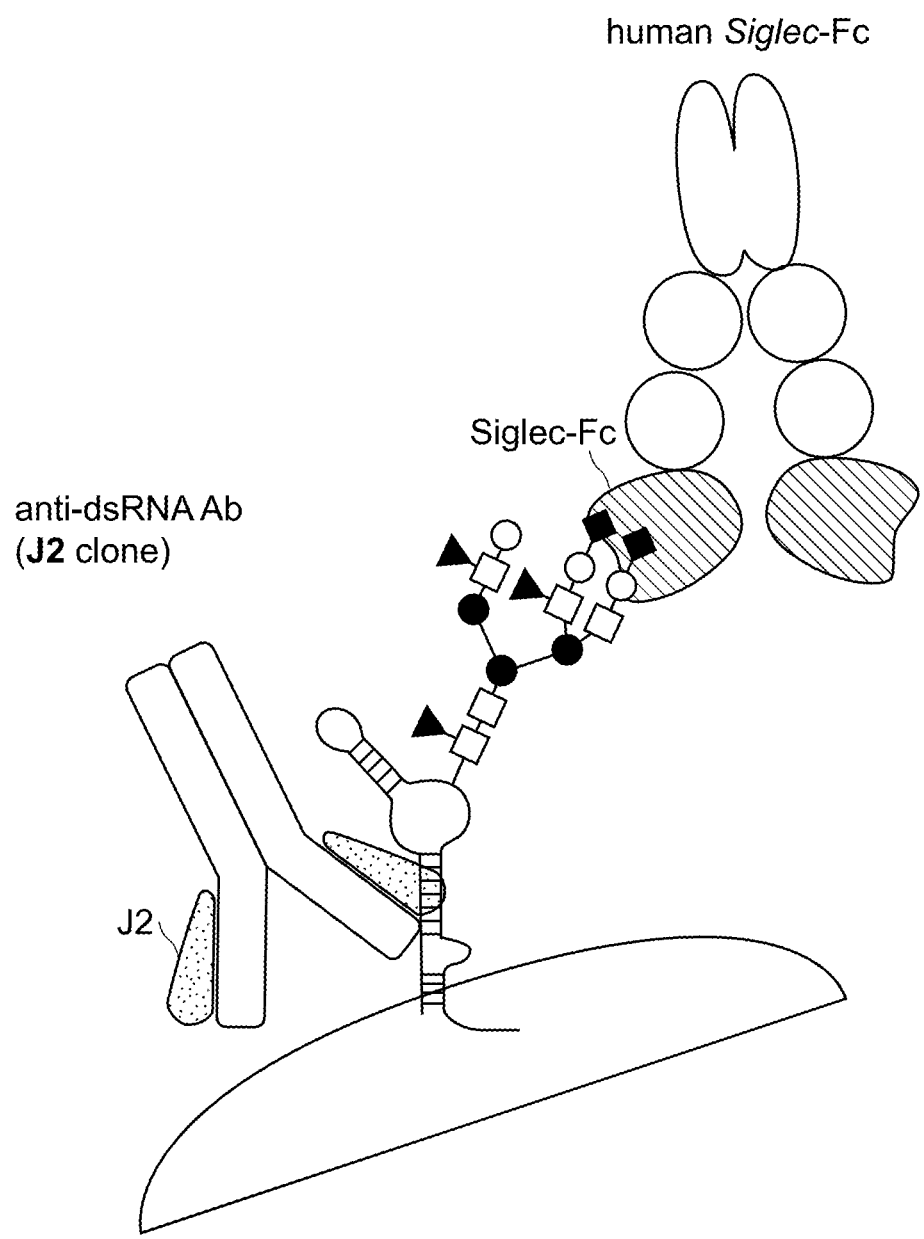
FIGS. 6A-6D are schemes and graphs showing that cell surface glycoRNAs contribute to the binding of select Siglec proteins.

Example 9—Siglec Receptors and Anti-RNA Antibodies Recognize Cell Surface glycoRNAs Biopolymers localized to the cell surface often participate in molecular interactions with binding partners in cis or in trans at cell-cell junctions. As glycoRNAs are present on cell surfaces, it was hypothesized that they too could engage in these types of interactions. Assessed was whether existing reagents to study the biology of cell surfaces, such antibody or recombinant protein-based affinity reagents, might interact with cell surface glycoRNA (FIG. 6A).

Antibodies targeting RNA have been associated with Systemic Lupus Erythematosus (SLE). Additionally, anti-RNA antibodies are used as research tools; for example, the J2 anti-double-stranded RNA (dsRNA) antibody has specificity for ds-regions of RNA (with no cross-reactivity with dsDNA) and is often used to identify cells infected with RNA viruses. The J2 antibody is reported to bind dsRNA with a minimum length of approximately 40 bp. GlycoRNAs are predicted to have duplex RNA regions, however these are generally <40 bp in length. Nonetheless, tested was whether J2 could bind a small RNA found to be enriched by $Ac_4ManNAz$ sequencing (FIGS. 2A-2E), such as the Y5 RNA, using electrophoretic mobility shift assays. The J2 antibody was able to shift free Y5 RNA in vitro. This shift was specific to J2 and was not observed using an isotype control antibody. Furthermore, the shift induced by J2 was abrogated in the presence of competing poly-(I:C), which mimics long dsRNA.

Having confirmed that J2 can bind the RNA component of glycoRNAs like Y5, a flow cytometry assay to probe cell surface RNA was established. All experiments were carried out on live cells, fixing only after antibodies were bound and background washed away for experimental workflow flexibility. It was necessary to use recombinant sources of cell dissociation enzymes. For example, commonly used crude preparations of trypsin contain significant RNase-activity and thus rapidly destroy RNA (see Materials and Methods).

Figure 6B:
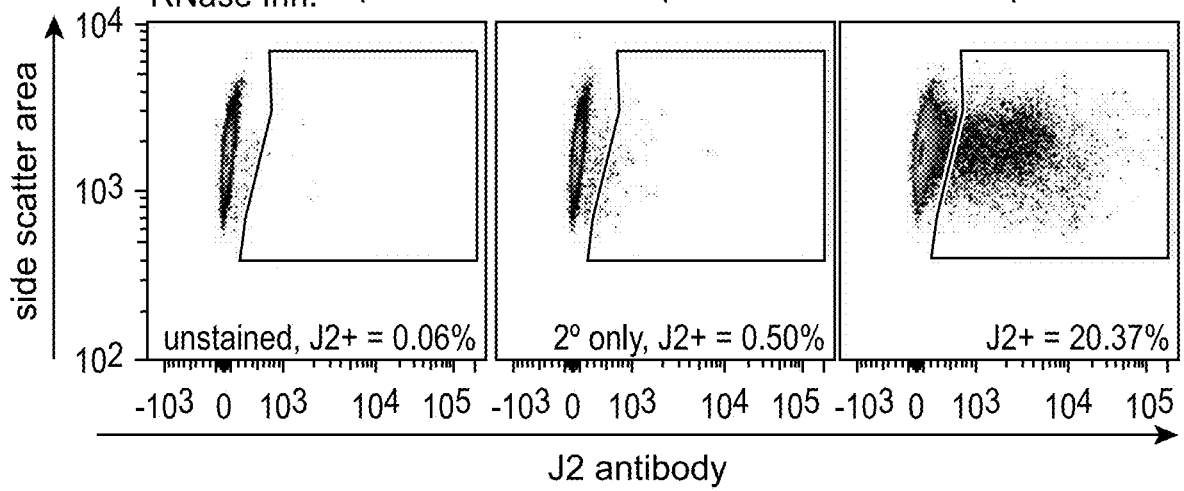
Figure 6B:
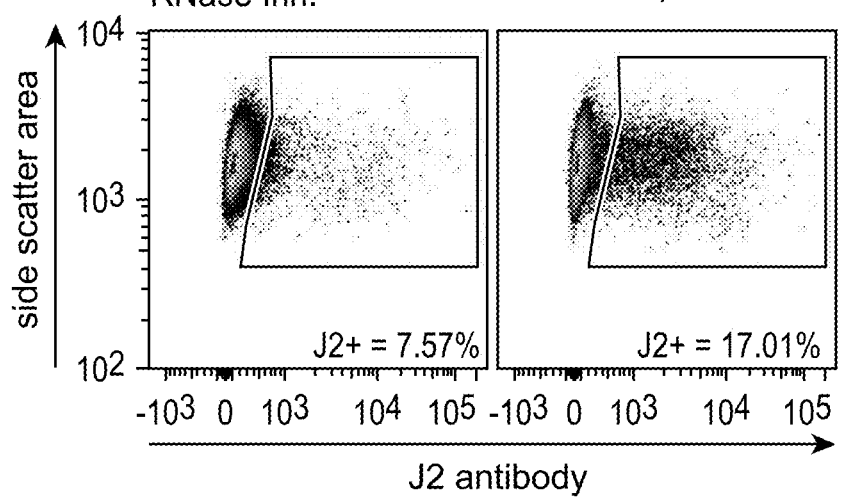
Figure 6D:
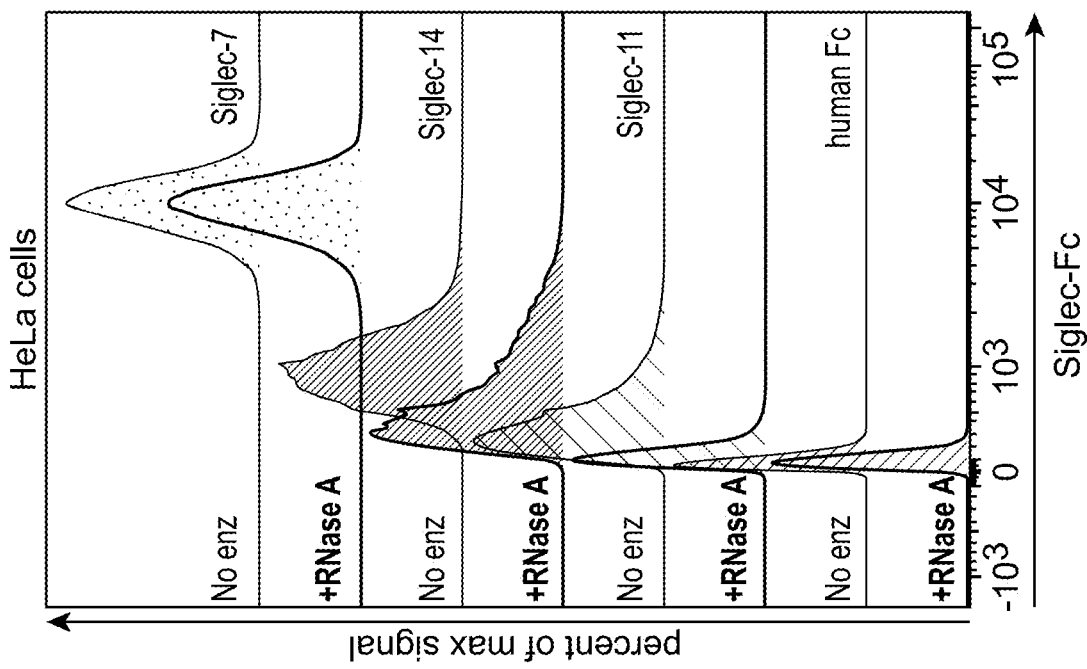
Figure 6C:
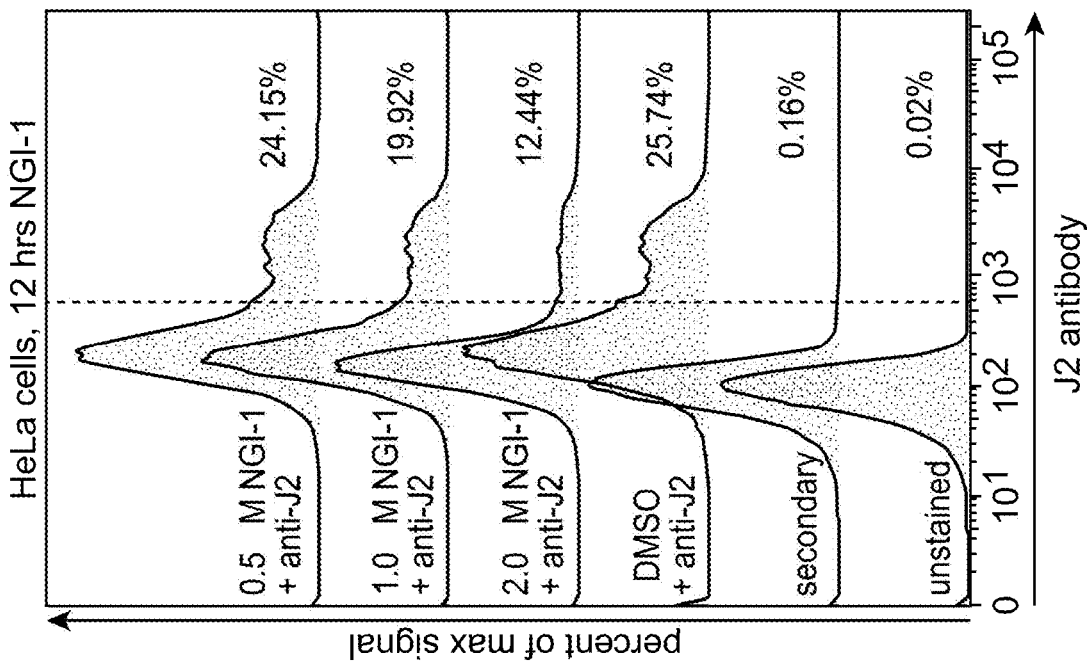

About ~20% of a population of cultured HeLa cells showed positivity with J2 staining (FIG. 6B). This binding was robustly abrogated by pre-treatment of cells with RNase A and was recovered by adding a specific protein inhibitor to the RNase A to block activity (FIG. 6B). Similar results were observed using 293T (adherent) and K562 (suspension) cells. To confirm the distribution of J2 staining the cell surface, confocal imaging of HeLa cells stained with J2 was performed, which demonstrated signal in the peripheral edges of cells that was sensitive to RNase A treatment. Asked next was whether J2 was detecting glycoRNA on the cell surface by perturbing OST as previously done in FIG. 4. HeLa cells were treated with the OST inhibitor NGI-1 for 12 hours and a dose-dependent loss of J2 binding to the cell surface was observed (FIG. 6C). This is consistent with the whole-cell RNA blotting experiments reported in FIGS. 4A-4H and suggests that much of the cell surface RNA recognized by the J2 antibody relies on N-glycosylation for its surface localization.

Finally, it was sought to determine whether glycoRNAs can interact with glycan-binding receptors whose ligands have been assumed, based on convention, to be cell-surface glycoproteins and glycolipids. As described above, the N-glycans associated with glycoRNAs are highly sialylated. Thus, asked was whether members of the sialic acid binding-immunoglobulin lectin-type (Siglec) receptor family could recognize glycoRNAs. Notably, with 14 members distributed on all classes of immune cells, the Siglecs are the largest family of sialoside-binding proteins in humans. Their roles in immune modulation are well established and include host-pathogen interactions, cancer immune evasion and genetic associations with autoimmune disease. Physiological ligands of individual Siglec family members have been identified in a few settings, but for the most part, the glycoconjugates that support Siglec binding at immune synapses are not well characterized. All efforts to do so have assumed that Siglec ligands are glycoproteins or glycolipids. To determine whether human Siglec receptors can bind cell surface glycoRNA, soluble Siglec-Fc reagents were used and their binding to cells by flow cytometry was probed. Determined first was that nine of 12 commercial Siglec-Fc reagents were able to bind above background to HeLa cells. Of these nine, the binding of two Siglec-Fc reagents, Siglec-11 and Siglec-14, was sensitive to RNase A treatment (FIG. 6D). These data suggest that cell surface glycoRNAs could be direct Siglec receptor ligands.

Materials and Methods for Examples 1-9
Metabolic Chemical Reporters and Inhibitors Stocks of azide-labeled sugars N-Acetyl-9-azido-9-deoxy-neuraminic acid (9Az sialic acid, Carbosynth) and N-azidoacetylmannosamine-tetraacylated (Ac$_4$ManNAz, Click Chemistry Tools) were made to 500 mM in sterile dimethyl sulfoxide (DMSO). Stocks of unlabeled sugars N-Acetyl-D-galactosamine (GalNAc, Sigma) and D-(+)-Galactose (Gal, Sigma) were made to 500 mM and 50 mM, respectively, in sterile water. In cell experiments ManNAz was used at a final concentration of 100 µM. In vitro experiments with ManNAz used 0, 2, or 20 mM ManNAz (up to 200× the in-cell concentrations) for 2 hours at 37° C. The in-cell experiments with 9Az sialic acid used a 1.75 mM final concentration for between 6 and 48 hours. Gal and GalNAc were used as media supplements at 10 µM and 100 µM, respectively, and were added simultaneously with ManNAz for labeling.

Working stocks of glycan-biosynthesis inhibitors were all made in DMSO at the following concentrations and stored at −80° C.: 10 mM NGI-1 (Sigma), 10 mM Kifunensine (Kif, Sigma), 10 mM Swainsonine (Swain, Sigma), 50 mM P-3F$_{AX}$-Neu5Ac (Tocris). All compounds were used on cells for 24 hours and added simultaneously with ManNAz for labeling.

Metabolic Reporters in Mouse Models

All experiments were performed according to guidelines established by the Stanford University Administrative Panel on Laboratory Animal Care. C57Bl/6 mice were crossed and bred in house. ManNAz was prepared by dissolving 100 mg ManNAz in 830 µL 70% DMSO in phosphate buffered saline (PBS), warming to 37° C. for 5 minutes, and then sterile filtering using 0.22 µm Ultrafree MC Centrifugal Filter units (Fisher Scientific); this solution was stored at −20° C. Male C57Bl/6 mice (8-12 weeks old) were injected once-daily, intraperitoneally with 100 µL of ManNAz (dosed to 300 mg ManNAz/kg/day), while control mice received the vehicle alone. At 2, 4, and 6 days, mice were euthanized, and their livers and spleens were harvested. The organs were pressed through a nylon cell strainer and resuspended with PBS to create a single cell suspension. RNA was collected as described below.

RNA Extraction and Purification Strategies

A specific series of steps were taken to ensure that RNA analyzed throughout this study was as pure as possible. First TRIzol reagent (Thermo Fisher Scientific) was used as a first step to lyse and denature cells or tissues. After homogenization in TRIzol by pipetting, samples were incubated at 37° C. to further denature non-covalent interactions. Phase separation was initiated by adding 0.2× volumes of 100% chloroform, vortexing to mix, and finally spinning at 12,000×g for 15 minutes at 4° C. The aqueous phase was carefully removed, transferred to a fresh tube and mixed with 2× volumes of 100% ethanol (EtOH). This solution was purified over a Zymo RNA clean and concentrator column (Zymo Research): sample solution was added to Zymo columns and spun at 10,000×g for 20 seconds and the flow through always discarded. Three separate washes were performed, 1×400 µL of RNA Prep Buffer (Zymo Research) and 2×400 uL RNA Wash Buffer (Zymo Research) and spun at 10,000×g for 20 seconds. To elute RNAs, two volumes of pure water were used. Next RNA was subjected to protein digestion by adding 1 µg of Proteinase K (PK, Thermo Fisher Scientific) to 25 µg of purified RNA and incubating it at 37° C. for 45 minutes. After PK digestion, RNA was purified again with a Zymo RNA clean and concentrator as described above. All RNA samples generated in this study were purified at least by these two steps first, with subsequent enzymatic or RNA fractionations occurring in addition to these first two purifications. It was found that Zymo-Spin IC and IIICG columns bind up to ~50 and 350 µg of total RNA, respectively; columns in each experiment were selected based on the amount of RNA needed to be purified.

For differential-precipitation of small vs. large RNAs, the Zymo RNA clean and concentrator protocol was used as described. Briefly, RNA in an aqueous solution was mixed with 1× volumes of 50% RNA Binding Buffer in 100% EtOH. This mix was applied to the Zymo silica column; the flow through contained small RNAs while the column retained large RNAs. The flow through was mixed with 1× volumes of 100% EtOH, bound to a new Zymo column and purified as described above.

To enrich for poly-adenylated RNA species, RNA initially purified as above was used as the input for the Poly(A)Purist MAG Kit (Thermo Fisher Scientific). Oligo(dT) MagBeads were aliquoted and washed twice in Wash Solution 1. RNA (15 µg total RNA) was brought to 600 ng/µL in 1× Binding Solution, added to washed beads, and heated to 70° C. for 5 minutes. Samples were cooled to 25° C. for 60 minutes, applied to a magnet, supernatant removed, and washed twice with Wash Solution 1 and once with Wash Solution 2. Poly-A enriched RNA was eluted by adding RNA Storage Solution to the beads and heating the samples to 70° C. The elution step was performed twice and the resulting poly-A RNA was cleaned up via the Zymo RNA clean and concentrator as described above.

Enzymatic Treatment of RNA Samples and Cells

Various endo- and exonucleases and glycosidases were used to digest RNA, DNA, or glycans. All digestions were performed on 20 µg of total RNA in a 20 µL at 37° C. for 60 minutes. To digest RNA the following was used: 1 µL of RNase cocktail (0.5 U/µL RNaseA and 20 U/µL RNase T1, Thermo Fisher Scientific) with 20 mM Tris-HCl (pH 8.0), 100 mM KCl and 0.1 mM $MgCl_2$. To block the RNase activity of the RNase Cocktail, 1 µL of RNase Cocktail was pre-mixed with 8 µL of SUPERaseIn (20 U/µL, Thermo Fisher Scientific) for 15 minutes at 25° C. before adding to the RNA solution. To digest DNA, 2 µL of TURBO DNase (2 U/µL, Thermo Fisher Scientific) with 1×TURBO DNase buffer (composition not provided by manufacture). To digest glycans: 2 µL of a2-3,6,8 Neuraminidase (50 U/µL, New England Biolabs, NEB) with GlycoBuffer 1 (NEB), or 2 µL of Endo-Hf (1,000 U/µL, NEB) with GlycoBuffer 3 (NEB), or 2 µL of PNGase F (500 U/µL, NEB) with GlycoBuffer 2 (NEB), or 2 µL of Endo-F2 (8 U/µL, NEB) with GlycoBuffer 3 (NEB), or 2 µL of Endo-F3 (8 U/µL, NEB) with GlycoBuffer 4 (NEB), or 2 µL of O-Glycosidase (40,000 U/µL, NEB) with GlycoBuffer 2 (NEB), or 1 µL of StcE at 0.5 µg/µL with or without 20 mM EDTA. For live cell treatments, VC-Sia was expressed and purified as previously described and added to cells at 150 nM final concentration in complete growth media for between 20 and 60 minutes at 37° C.

Copper-Free Click Conjugation to RNA

Copper-free conditions were used in all experiments to avoid copper in solution during the conjugate of biotin to the azido sugars (ManNAz and 9Az-Sia). All experiments used dibenzocyclooctyne-PEG4-biotin (DBCO-biotin, Sigma) as the alkyne half of the cycloaddition. To perform the SPAAC, RNA in pure water was mixed with 1× volumes of "dye-free" Gel Loading Buffer II (df-GLBII, 95% Formamide, 18 mM EDTA, and 0.025% SDS) and 500 µM DBCO-biotin. Typically, these reactions were 10 µL df-GLBII, 9 µL RNA, 1 µL 10 mM stock of the DBCO reagent. Samples were conjugated at 55° C. for 10 minutes to denature the RNA and any other possible contaminants. Reactions were stopped by adding 80 µL water, then 2× volumes (200 µL) of RNA Binding Buffer (Zymo), vortexing, and finally adding 3× volumes (300 µL) of 100% EtOH and vortexing. This binding reaction was purified over the Zymo column as described above and analyzed by gel electrophoresis as described below.

RNA Gel Electrophoresis, Blotting, and Imaging

Blotting analysis of ManNAz-labeled RNA was performed conceptually similar to a Northern Blot with the following modifications. RNA purified, enriched, or enzymatically digested and conjugated to a DBCO-biotin reagent as a described above was lyophilized dry and subsequently resuspended in 15 µL df-GLBII with 1× SybrGold (Thermo Fisher Scientific). To denature, RNA was incubated at 55° C. for 10 minutes and crashed on ice for 3 minutes. Samples were then loaded into a 1% agarose-formaldehyde denaturing gel (Northern Max Kit, Thermo Fisher Scientific) and electrophoresed at 110V for 45 minutes. Total RNA was then visualized in the gel using a UV gel imager. RNA transfer occurred as per the Northern Max protocol for 2 hours at 25° C., except 0.45 µm nitrocellulose membrane (NC, GE Life Sciences) was used. This is critical for downstream imaging as most positively charged nylon membranes have strong background in the infrared (IR) spectra. After transfer, RNA was crosslinked to the NC using UV-C light (0.18 $J/cm^2$). NC membranes were then blocked with Odyssey Blocking Buffer, PBS (Li-Cor Biosciences) for 45 minutes at 25° C. Note that the blocking buffer made with TBS or PBS, both sold from Li-Cor Biosciences, work similarly for this step. After blocking, Streptavidin-IR800 (Li-Cor Biosciences) was diluted to 1:10,000 in Odyssey Blocking Buffer and stained the NC membrane for 30 minutes at 25° C. Excess streptavidin-IR800 was washed from the membranes by three, serial washes of 0.1% Tween-20 (Sigma) in 1×PBS for 5 minutes each at 25° C. NC membranes were briefly rinsed in 1×PBS to remove the Tween-20 before scanning on an Odyssey LiCor CLx scanner (Li-Cor Biosciences) with the software set to auto-detect the signal intensity for both the 700 and 800 channels. After scanning, images were quantified with the LiCor software (when appropriate) in the 800 channel and exported.

DMB Assay for Sialic Acid Detection

Unless otherwise noted, all chemicals were supplied by Sigma. Native sialic acids on RNA or DNA were derivatized with 4,5-methylenedioxy-1,2-phenylenediamine dihydrochloride (DMB) and detected via reverse phase high-performance liquid chromatography (HPLC) according to established methods. In brief, RNA samples were lyophilized, and 100 µg (or otherwise noted in specific figures) of each sample was dissolved in 2 M acetic acid. Sialic acids were hydrolyzed by incubation at 80° C. for 2 hours, and then cooled to room temperature before the addition of DMB buffer (7 mM DMB, 0.75 M β-mercaptoethanol, 18 mM $Na_2SO_4$, 1.4 M acetic acid). Derivatization was performed at 50° C. for 2 hours. Following the addition of 0.2 M NaOH, samples were filtered through 10 kDa MWCO filters (Millipore) by centrifugation and stored in the dark at −20° C. until use. Separation was performed via reverse phase HPLC using a Poroshell 120 EC-C18 column (Agilent) with a gradient of acetonitrile in water: T(0 minutes) 2%; T(2 minutes) 2%; T(5 minutes) 5%; T(25 minutes) 10%; T(30 minutes) 50%; T(31 minutes) 100%; T(40 minutes) 100%; T(41 minutes) 2%; T(45 minutes) 2%. DMB-derivatized sialic acids were detected by excitation at 373 nm and monitoring emission at 448 nm. Sialic acids standards included N-acetylneuraminic acid (Neu5Ac; Jülich Fine Chemicals), N-glycolylneuraminic acid (Neu5Gc; Carbosynth), 3-deoxy-D-glycero-D-galacto-2-nonulosonic acid (KDN; Carbosynth), and the Glyko Sialic Acid Reference Panel (Prozyme).

Subcellular Fractionation

Isolation of Highly Pure Nuclei

Nuclei are intricately entwined with the ER, posing a challenge to biochemically separate nuclei cleanly from the ER without mixing. Gagnon et al. describe a protocol which cleanly recovers mammalian nuclei after processing without significant residual ER membrane attached. This protocol was performed on adherent ManNAz-labeled HeLa cells without modification to the step-by-step instructions published. Due to the stringent isolation of the nuclei, some fraction of nuclei themselves lyse during the process, contaminating the non-nuclear fraction. Therefore, when examining the fractionation results of this protocol, only the signal left in the nucleus is considered. Signal in the supernatant will be partially mixed ER, Golgi, cytosol, some nuclei, as well as other cellular compartments. After fractionation as per the protocol, TRIzol was used to extract and process the RNA.

Isolation of Cytosol and Crude Membrane Fractions

The ProteoExtract® Native Membrane Protein Extraction Kit (EMD Millipore) was used on adherent ManNAz-labeled HeLa cells. This kit uses serial lysis steps: first to gently release soluble cytosol proteins and RNA and second to rupture membranous organelles such as the plasma membrane, Golgi, and ER. Because the lysis buffers are gentle, residual ER/Golgi are left on the nuclear fraction and thus analysis of samples generated from this kit was limited to the efficiently separated soluble cytosolic fractions compared to the membranous fractions. Specifically, cultured HeLa cells first had growth media removed and cells were then washed twice with ice-cold Wash Buffer. Extraction Buffer I (supplemented with protease inhibitor) was added to culture plates and incubated on the cells for 10 minutes at 4° C., rocking. After the incubation, this buffer was collected as "cytoplasm". Extraction Buffer II (supplemented with protease inhibitor) was subsequently added to the cells for 30 minutes at 4° C., rocking. This buffer was collected as "ER/membrane". These fractions were then extracted with TRIzol and processed as described above.

Membrane Protection Assay

Large scale crude membranes were isolated using the Plasma Membrane Protein Extraction Kit (ab65400, Abcam): cultured cells first had growth media removed and cells were then washed twice with ice-cold 1×PBS. In the second PBS wash, cells were scraped off the plate and spun down at 400×g for 4 minutes at 4° C. Cell pellets were resuspended in 2 mL of Homogenize Buffer Mix per 3×15 cm plates of 80% confluent 293T cells. Cell suspension was Dounce Homogenized on ice for 55 strokes, and this was repeated until all the cell suspension volume was similarly processed. Homogenate was then spun at 700×g for 10 minutes at 4° C. This pellet was the nuclear fraction and supernatants were transferred to new tubes and spun again at 10,000×g for 30 minutes at 4° C. The pellets generated from this spin were crude membranes and the supernatant was soluble cytosol. For the protection assay, typically 10×15 cm plates were used for each biological replicate. Crude membranes pellets were resuspended in 800 μL KPBS (136 mM KCl, 10 mM $KH_2PO_4$, pH 7.25 was adjusted with KOH), 125 mM sucrose, and 2 mM $MgCl_2$, split into 4 reactions, and incubated at 37° C. for 1 hour with or without 0.1% Triton X-100 or 150 nM VC-Sia (homemade as per above). RNA was extracted with TRIzol and processed as described above for DMB analysis of sialic acid levels.

Protein Affinity Tools: Antibodies and Lectins

The following were used for blotting on nitrocellulose membranes at the indicated concentrations: 1:1000 GAPHD (A300-641A, Bethyl), 1:3000 β-tubulin (ab15568, Abcam), 1:5000 H3K4me3 (ab8580, Abcam), 1:1000 RPN1 (A305-026A, Bethyl), 1:1000 Sec63 (A305-084A, Bethyl). Appropriate secondary antibodies conjugated to LiCor IR dyes (Li-Cor Biosciences) and used at a final concentration of 0.1 ng/μL. All lectins were bought biotinylated from Vector labs: biotin-wheat germ agglutinin (WGA), biotin-concanavalin A (ConA), and biotin-*Maackia amurensis* Lectin II (MAAII). Pierce High Sensitivity Streptavidin-HRP (Strep-HRP, Thermo Fisher Scientific) was used for aniline labeling experiments.

Sucrose Gradient Fractionation of RNA

RNA used as input for sucrose gradient fractionation was previously extracted, PK treated, and clicked to DBCO-biotin as described above. RNA was sedimented through 15-30% sucrose gradients following McConkey's method. Typically, 250-500 μg total RNA was lyophilized and then dissolved in 500 μL buffer containing 50 mM NaCl and 100 mM sodium acetate (pH 5.5). Linear 15-30% sucrose gradients were prepared in 1×3.5 inch polypropylene tubes (Beckman) using a BioComp 107 Gradient Master. Dissolved RNA was layered on top of pre-chilled gradients, which were then centrifuged using a SW32 Ti rotor at 80,000×g (25,000 rpm) for 18 hours in a Beckman Coulter Optima L70-K Ultracentrifuge at 4° C. Gradients were fractionated using a Brandel gradient fractionation system, collecting 0.75 mL fractions. Fractionated RNA was subsequently extracted from the sucrose solution using TRIzol as described above and analyzed by agarose gel electrophoresis or deep sequencing.

Enrichment, Deep Sequencing, and Analysis of ManNAz-Labeled RNA

Two rounds of selection performed on RNA samples before sequence analysis to identify transcripts modified with ManNAz-containing glycans. Total RNA from ManNAz-labeled H9 or HeLa cells was extracted, purified, and conjugated to DBCO-biotin as described above. Biological duplicates, at the cell culture level (different passage number), were generated for the purposes of the sequencing experiments. The first enrichment was achieved by sucrose gradient fractionation; after centrifugation fractions containing small RNAs were pooled and TRIzol extracted. The second enrichment was achieved by selective affinity to streptavidin beads as previously published with the following specific steps: 10 L of MyOne C1 Streptavidin beads (Thermo Fisher Scientific), per reaction were blocked with 50 ng/μL glycogen (Thermo Fisher Scientific) in Biotin Wash Buffer (10 mM Tris HCl pH 7.5, 1 mM EDTA, 100 mM NaCl, 0.05% Tween-20) for 1 hour at 25° C. Biotinylated small RNAs from H9 and HeLa cells were thawed and 150 ng of each were saved for input library construction. Next, 25 μg of the biotinylated small RNAs were diluted in 750 μL Biotin Wash Buffer (final concentration of ~33 ng/μL) and mixed with the blocked MyOne C1 beads for 2 hours at 4° C. Beads were washed to remove non-bound RNAs: twice with 1 mL of ChIRP Wash Buffer (2×SSC, 0.5% SDS), twice with 1 mL of Biotin Wash Buffer, and twice with NT2 Buffer (50 mM Tris HCl, pH 7.5, 150 mM NaCl, 1 mM $MgCl_2$, 0.005% NP-40), all at 25° C. for 3 minutes each.

To construct deep sequencing libraries two approaches were taken using the same enzymes with different steps for the input vs. bead-enriched samples given that the latter were already conjugated to a bead-support.

Input Libraries

The 150 ng of small RNAs isolated before MyOne C1 capture were lyophilized dry and then T4 PNK mix (2 μL 5× buffer (500 mM Tris HCl pH 6.8, 50 mM $MgCl_2$, 50 mM DTT), 1 μL T4 PNK (NEB), 1 μL FastAP (Thermo Fisher Scientific), 0.5 μL SUPERaseIn, and 5.5 μL water) was added for 45 minutes at 37° C. Next, a pre-adenylated-3'linker was ligated by adding 3'Ligation Mix (1 μL of 3 μM L3-Bio_Linker, 1 μL RNA Ligase I (NEB), 1 μL 100 mM DTT, 1 μL 10×RNA Ligase Buffer (NEB) and 6 μL 50% PEG8000 (NEB)) to the T4 PNK reaction and incubating for 4 hours at 25° C. Unligated L3-Bio_Linker was digested by adding 2 μL of RecJ (NEB), 1.5 μL 5' Deadenylase (NEB), 3 μL of 10× NEBuffer 1 (NEB) and incubating the reaction at 37° C. for 60 minutes. Ligated RNA was purified with Zymo columns as described above and lyophilized dry. cDNA synthesis, enrichment of cDNA:RNA hybrids, cDNA elution, cDNA circularization, cDNA cleanup, first-step PCR, PAGE purification, and second-step PCR took place as previously described.

Bead-Enriched Libraries

Washed MyOne C1 beads bounded to ManNAz-labeled small RNAs were processed as described before with the following modifications. For the on-bead ligation step, a non-biotinylated 3'linker oligo was used (L3-Linker) such that all RNAs captured on the beads would be included in the sequencing library. After completing the second-step PCR for both the input and bead-enriched samples, the dsDNA libraries were quantified on a High Sensitivity DNA Bioanalyzer chip (Agilent) and sequenced on a NextSeq 500 instrument (Illumina).

Data Analysis

Sequencing data were processed largely as described previously with a pipeline designed to analyze infrared CLIP data. The specific version of the pipeline used in this work can be found here online. Specifically, the raw reads were removed of PCR duplicates and adaptor sequences trimmed. Next, to address reads mapping to tRNA loci reads were first mapped to a mature tRNA reference using bowtie2. Mature tRNA reference were obtained from GtRNAdb and converted to DNA sequenced in FASTA format. Identical sequences were removed and CCA was added to the 3' end of each tRNA sequence. Uniquely-mapped reads were extracted using the values of the NM and XS fields of the resulting SAM file (grep -E "@|NM:" *.sam|grep -v "XS:"). Next, reads were mapped to custom sequence indexes of human repetitive RNAs (such as snRNAs and rRNAs) and finally to the human genome reference (GCRh38). The number of unique reads for each RNA transcript (e.g. tRNAs, snRNAs, Y RNAs, etc) from each of the two biological replicates was used to calculate fold change between input and enriched samples (ManNAz or EDC capture methods) with the DESeq2 tool. Statistical analysis was performed using R, and plots generated using ggplot.

CRISPR Cas9 Knockout of Y5 and Characterization

CRISPR gRNA sequences were designed using the CHOPCHOP online webtool. Guides that flank the Y5 locus were selected. Corresponding oligos were ordered from IDT. Oligos were cloned into the Zhang lab generated Cas9 expressing pX458 guide RNA plasmid (Addgene) as previously described using Gibson assembly reaction (NEB). Two sgRNAs flanking the human Y5 locus encoded in the pX458 plasmids were co-transfected using Lipofectamine 3000 (Thermo Fisher Scientific) in a 6-well format. Transfected cells were single cell sorted based on GFP expression into 96-well plates using BD influx cell sorter (Stanford FACS facility). Clonal cell lines were allowed to expand, and genomic DNA was isolated for sequenced based genotyping of targeted allele. For this, a 300-500 base-pair region that encompassed the gRNA-targeted site was amplified and the PCR product was Sanger sequenced. Clones with editing events causing large deletions were selected for subsequent experiments and KO loss of expression was confirmed by Northern blotting (below). To evaluate doubling time, 293 WT and KO cells were cultured as described above, initially seeding 20,000 cells per 12-well plate in triplicate. At 24-hour intervals cells were trypsinized and counted using a Countess II FL Automated Cell Counter (Thermo Fisher Scientific).

Small RNA Northern Blotting

Detection of small RNAs was achieved by conventional Northern blotting and detection via radiolabeled locked-nucleic acids (LNAs). LNAs (Qiagen) complementary to the Y5 RNA or 5S rRNA were ordered and 5'end labeled: 200 pmol LNA was added to 3 µL of T4 PNK (NEB), 7 µL 10× T4 PNK buffer, and 1 µL of ATP, [γ-$^{32}$P]-3000 Ci/mmol 10 mCi/ml (γ-ATP, Perkin Elmer) in a 70 µL reaction. LNAs were incubated at 37° C. for 3 hours after which free γ-ATP was purified away using Micro Bio-Spin 6 (Bio-Rad) columns. Columns were brought to 25° C., pre-packed buffer spun out at 1000×g for 2 minutes. Samples were applied to the dried column matrix and purified by spinning at 1000×g for 4 minutes. A 12% Urea-PAGE gel (National Diagnostics) was poured and pre-run at 10 W for 15 minutes, after which 2 µg of total RNA from various cell types was separated by running the gel at 15 W. After electrophoresis, RNA was transferred to HyBond N+(GE Life Sciences) using a Semi-Dry transfer apparatus (Bio-Rad) with 0.5× Tris/Borate/EDTA (TBE, Thermo Fisher Scientific) buffer at a constant power of 18V for 90 minutes at 4° C. Next, RNA was crosslinked to the membrane, and pre-hybridized at 65° C. for 60 minutes in 2 mL of PerfectHyb Plus (Sigma) buffer. Labeled LNA probes were then added to the PerfectHyb Plus buffer (typically 25% of the labeled LNA probe was used for any single membrane hybridization) and incubated at 65° C. for 3-16 hours (no change in results with longer or shorter hybridizations). Membranes were rinsed 2×2.5 mL of Low Stringency Northern Buffer (0.1% SDS, 2×SSC (Saline-sodium citrate)) and then washed at 37° C. for 2×5 minutes in 2.5 mL of High Stringency Northern Buffer (0.1% SDS, 0.5×SSC). Wash membranes were exposed to storage phosphor screens and finally imaged with a GE Typhoon 9410 scanner.

Glycan Release from RNA Samples

Small RNAs were isolated as described above. RNA samples were sequentially digested with two glycosidases. Typically for experimental samples, 25 µg of small RNA from H9 ES, HeLa, or 293FT cells was resuspended in 10 µL of 1× GlycoBuffer 2 (NEB), 7.5 µL PNGaseF (NEB) and to a final reaction volume of 100 µL with water. PNGaseF cleavage occurred overnight at 37° C. After digestion, released glycans were desalted using PGC SPE columns (Thermo Fisher Scientific). SPE columns were first washed 5× with 80% acetonitrile (ACN)+0.1% Trifluoroacetic acid (TFA) and then 0.1% TFA. Samples were brought to 500 µL with water and passed over the column twice. SPEs were washed once with 0.1% TFA and finally eluted sequentially in 15% ACN in 0.1% TFA, 35% ACN in 0.1% TFA. ACN was pulled off with a SpeedVac (Labconco), elutions pooled, and dried by lyophilization. After drying, samples were resuspended in 5 µL LC-MS grade water (Thermo Fisher Scientific) for MS analysis.

Glycan Release from Peptide Samples

Peptides were generated from total cell lysate material from H9 ES, HeLa, or 293FT cells. Specifically, 100 µg of protein lysate was processed into tryptic peptides using an S-trap mini column (Protifi). Lysate solutions were brought to 5% SDS and 5 mM DTT final concentration, heated to 95° C. for 5 minutes, cooled to 25° C. for 5 minutes, and then added 25 mM iodoacetamide (Sigma) for alkylation at 25° C. for 30 minutes in the dark. Samples were next acidified by adding phosphoric acid (Sigma) to 1.2% final concentration and then adding 8× volumes of binding buffer (100 mM triethylammonium bicarbonate (TEAB) in 90% methanol), vortexing to mix. Protein samples were next bound the S-trap columns by centrifugation at 4000×g for 10 sections, spins were repeated until all the sample volume had passed over the column matrix. Three washes with binding buffer were performed to rinse the column. Peptides were generated by applying Trypsin (Promega) solution to the column matrix in 50 mM ammonium bicarbonate (Sigma) at a ratio of 1 µg Trypsin to 20 µg protein lysate. Digestion proceeded for 90 minutes at 47° C. Peptides were eluted by sequentially applying 0.1% formic acid in 50 mM ammonium bicarbonate and 0.1% formic acid in 50% acetonitrile. N-glycans were liberated from the peptide samples as described above for the RNA. After PNGaseF digestion, deglycosylated peptides were removed by bringing the peptide mixture to 500 µL in 0.2% formic acid and passing them over a 10 mg polymeric C-18 SPE (Strata-X) column: free glycans will flow through and were saved. The free glycans were desalted in parallel to the RNA samples with a PGC SPE and finally samples were resuspended in 5 µL LC-MS grade water (Thermo Fisher Scientific) for MS analysis.

Mass Spectrometry Chromatography

Mass spectrometric data was acquired using the following conditions. Each dried sample was reconstituted in 10 µL of 5 mM ammonium formate and 3 µL of sample were injected onto an UltiMate 3000 RSLCnano UPLC (Thermo Fisher Scientific) system equipped with a 5 µL injection loop. Separation was performed with a capillary column (100 µm ID, 18 cm length) created by hand packing a commercially available fused-silica column (IntegraFrit, New Objective, Woburn, Mass.) with 5 µm porous graphitic carbon (Hypercarb, PGC, Thermo Fisher Scientific, Waltham, Mass.) connected to stainless steel emitter (30 µM ID, Thermo Fisher Scientific). Mobile phases used were 5 mM ammonium formate (A) and 2:1 isopropanol:acetonitrile (B). The flow rate was 1000 nL/min for 5.5 min at 100% A, then decreased to 300 nL/min over 0.5 min followed by a linear gradient of 15%/min over 1 min., 1.4%/min over 25 min, 6.25%/min over 8 min then followed by a 2 min hold at 100% B, with re-equilibrated at 100% A for 5 min. at 1000 nL/min (including injection time for subsequent injection). The injection valve was switched at the 5.5 min point of the run to remove the sample loop from the flow path during the gradient.

Mass Spectrometer

All mass spectrometric data was acquired with a Lumos Orbitrap mass spectrometer (Thermo Fisher Scientific). Positive mode electrospray ionization was performed under nanospray conditions (300 nL/min) using a Thermo Fisher Scientific Nanoflex ion source with a source voltage of 2.2 kV applied to a stainless-steel emitter (30 µM ID, Thermo Fisher Scientific), and the capillary temperature was 300° C. The S-Lens RF level setting was 60%.

Free-Glycan Untargeted Screening

Data-dependent fragmentation was performed with full scan (m/z 500-2500) Orbitrap detection at a resolution setting of 120,000, normalized AGC target of 250%, and a maximum ion injection time setting of 50 ms. $MS^2$ spectra were acquired with quadrupole isolation width of m/z 1.6, HCD fragmentation of 25%, Orbitrap detection at a resolution setting of 15000, normalized AGC target of 400%, and maximum ion injection time of 22 ms. Data-dependent parameters were as follows: intensity threshold $2.5 \times 10^4$, repeat count of 3 within 30 s, exclusion duration of 20 s, and exclusion mass width of ±5 ppm with isotopes excluded. A mass exclusion list consisting of previously published endogenous RNA adducts and their $^{13}C$ isotopologues was used. A cycle time of 3 s was used, and data collection was in profile mode.

Analysis

Glycan release samples were analyzed with GlycoNote. Briefly, .raw files were converted to .mgf files and loaded into the GlycoNote GUI. The parameters were used for all glycan release files. GlycoNote output files contained glycan structures and annotated spectra, which were validated manually.

Lectin-Proximity Labeling of RNA with Biotin-Aniline

Live Cell Labeling

HeLa cells were cultured as above typically in 10 cm plates. Cells were rinsed twice in ice-cold 1×PBS, discarding after each wash, and blocked in Lectin Blocking Buffer (LBB, 20 mM HEPES, 150 mM NaCl, 1 mM $MgCl_2$, 1 mM $MnCl_2$, 1 mM $CaCl_2$, 2.5% FBS) for 15 minutes at 4° C. Blocking buffer was then discarded and replaced with LBB+Lectin+Strep-HRP. Typically, 4 mL of this was prepared at a concentration of 5 µg/mL biotinylated lectin and 6 µg/mL Strep-HRP, these components were first mixed together on ice for 30 minutes prior to the addition of LBB. LBB+Lectin+Strep-HRP staining occurred for 45 minutes at 4° C., after which the cells were rinsed twice in ice-cold 1×PBS+1 mM $CaCl_2$+1 mM $MgCl_2$ (PBS++). Immediately after this 3 mL of PBS++ with 350 µM biotin-aniline (Iris Biotech GMBH) was added to each plate and incubated on ice for 1 minute. Plates were then moved to the bench top and $H_2O_2$ was added to a final concentration of 1 mM. This reaction occurred for precisely 2 minutes, after which plates were brought back on ice, PBS++/biotin-aniline/$H_2O_2$ was aspirated, and cells were quickly but gently rinsed twice in Quenching Buffer: 5 mM Trolox, 10 mM sodium ascorbate and 10 mM sodium azide in PBS++(as described in (Fazal et al., 2019)). After removing the Quenching Buffer, TRIzol was added directly to the plate and RNA extracted and processed as described above for enzymatic digestions as well as blotting.

In Lysate Labeling

HeLa cells were grown and washed as for the Live Cell Labeling protocol. Cell lysates were generated by adding 500 µL ice-cold 50 mM Tris pH 8 with cOmplete protease inhibitor cocktail (Roche) per 10 cm plate, scraping cells, and pipetting up and down 10 times on ice. Lysate from each 10 cm plate was then incubated with the same pre-complexed ratio of biotinylated lectin and Strep-HRP for 45 minutes on ice. Lysates were subsequently warmed to 25° C. for 2 minutes, 350 µM biotin-aniline was added to each tube at 25° C. for 1 minute and then 1 mM $H_2O_2$ was added to initiate the reaction. Each reaction was allowed to proceed for exactly 2 minutes before directly adding 5 mM Trolox, 10 mM sodium ascorbate and 10 mM sodium azide. RNA was extracted from the labeled lysate samples with TRIzol LS (Thermo Fisher Scientific) and processes in parallel with the Live Cell samples.

Optimization of Cell-Lifting Reagents

In the course of establishing a FACS protocol for cell surface glycoRNAs (below), it was noticed that standard cell lifting strategies using trypsin resulted in near total destruction of cellular RNA. To understand why this was happening and find an RNA-safe strategy, the following quality control experiments were performed:

First, total protein analysis of Trypsin and TrypLE reagents used for tissue culture. Stock Trypsin products from GE Healthcare, Sigma, Stem Cell Technologies, ATCC, and Thermo Fischer Scientific were purchase, separated on an SDS-PAGE gel, stained with Acquastain Protein Gel Stain (Bulldog Bio) and scanned on a LiCor to visualize any proteinaceous components of these reagents. All Trypsin products contained a band that corresponded to the full-length trypsin protein at about 25 kDa, however every stock also contained a series of lower molecular weight bands of unknown identity.

Second, TrypLE, from the Thermo Fischer Scientific website is an "animal origin-free, recombinant enzyme" that because of its "exceptional purity increases specificity and reduces damage to cells that can be caused by other enzymes present in some trypsin extracts". It was found that TrypLE runs at a very similar molecular weight as trypsin, however it contains none of these low molecular weight bands.

Third, the relative damage these reagents cause to cellular RNA was assessed. HeLa cells were grown in 6-well plates as described above, rinsed with 1×PBS, and then incubated at 37° C. for 5 minutes in 250 μL of 1×PBS, Trypsin (GE Healthcare), or TrypLE (Thermo Fischer Scientific). After this incubation, samples were either directly lysed with 750 μL TRIzol LS or resuspended in 750 μL 1×PBS, spun at 300×g for 5 minutes, supernatant discarded, and then the cell pellet was lysed in TRIzol LS. The results of this experiment show that while PBS and TrypLE cause no RNA degradation, the Trypsin solution completely destroys the RNA if cells are not pre-washed with PBS, and if they are, there is still massive degradation of cellular RNA, even when extracted with TRIzol.

Therefore, TrypLE or other reagents that have been carefully tested for RNase contamination should be used when performing experiments to assay for cell surface glycoRNAs.

Fluorescence-Activated Cell Sorting (FACS) Analysis

Cells were grown as described above and if adherent, lifted with TrypLE (Thermo Fisher Scientific) for 4 minutes at 37° C. Cells were resuspended in FACS Buffer (0.5% bovine serum albumen (Thermo Fisher Scientific) in 1×PBS), counted, and aliquoted to 200,000 cells per 100 μL FACS Buffer, incubating on ice for 30 minutes to blocking. For RNase digestions, RNase A (Sigma) was added to the blocking buffer at indicated concentrations (typically 2 μM). After blocking, cells were brought to 25° C. for 5 minutes, then spun for 5 minutes at 4° C. and 350×g. Cells were washed once with 150 μL FACS Buffer and spun as above. Two similar approaches were taken to stain for cell surface RNA (1) or cell surface sialic acids (2). In assaying for (1), cells were resuspended in 10 μg/mL anti-J2 antibody (Scicons) in 100 μL FACS Buffer for 30 minutes on ice, spun as above and washed once as above. Cells were then stained with 8 μg/mL Goat, anti-Mouse-IR680 antibody (LiCor Bioscience) in 100 μL FACS Buffer for 30 minutes on ice and in the dark, spun as above and washed once as above. Finally, cells were fix in 100 μL of FluoroFix Buffer (BioLegend) for 30 minutes at 25° C. in the dark. Cells were finally washed once as above and stored in FACS Buffer at 4° C. for analysis. In assaying for (2), recombinant human Siglec-Fc proteins (R&D Systems) were pre-complexed to Alexa Fluor-647 AffiniPure Donkey Anti-Human IgG, Fcy fragment specific (Jackson Laboratories) both at 1.5 μg/mL in FACS Buffer on ice for 1 hour. Cells were resuspended in 100 μL of the pre-complexed Siglec-Fc-Secondary solution and incubated on ice in the dark for 30 minutes, washed once, and proceeded directly to fixation as described above. FACS data was analyzed and visualized with FloJo software.

Quantification and Statistical Analysis

RNA-seq statistics were determined by R package 'DESeq2.'

Example 10—General Procedure for Synthesis of Glyco Nucleic Acids

Nucleic acids with covalently conjugated natural glycans were made by using a classic copper click reaction (CuAAC) between azide-glycan and alkyne-nucleic acid with a copper catalyst. The RNA and DNA reactants were synthesized using an internal single modified 3' 5-Octadinyl dU (IDT). Modified nucleic acids containing an alkyne were diluted in water to a 100 μM final concentration and denatured at 95° C. for 2 minutes, placed on ice, and folded in 200 μM MgCl and PBS pH 7.0 for 5 minutes at 37° C. CuSO4 was made up in water and added to the ligand 2-(4-((bis((1-(tert-butyl)-1H-1,2,3-triazol-4-yl)methyl) amino)methyl)-1H-1,2,3-triazol-1-yl)acetic acid (BTTAA) and incubated at room temperature for 5 minutes. Then, the CuAAC reactions were assembled by sequentially adding the alkyne nucleic acid (10 μM), azide-glycan (20 μM), with the Cu BTTAA (100 uM each final concentration), and sodium ascorbate (1 mM) with 1×PBS. The click reactions were incubated for 1 hour at 35° C. The click reactions were stopped with 20 mM EDTA. The reactions were then purified using the ZYMO RESEARCH® RNA clean and concentrator kit and eluted in 10 μl. This elute was denatured using 95% formamide, 18 mM EDTA, and 0.025% SDS loading dye with 1×SYBR gold for 10 minutes at 55° C. A 1% agarose and 1.1% formaldehyde gel was used to visualize intensity and migration differences between conjugated and unconjugated glycan-nucleic acid. The azido-glycan (azide-glycan) is prepared as described below in Example 11.

The characterization of azido glycans has been accomplished with TLC and MALDI-MS. The characterization of Alkyne-DNA and Alkyne RNA was accomplished with UV-Vis and gel electrophoresis. The characterization of synthetic-N-glycan-RNAs and synthetic-N-glycan-DNAs has been accomplished by chemical labeling of sialic acid sugars, gel electrophoresis, RNA/DNA transfer, and imaging of the sialic acid sugars on the RNA/DNA transferred membrane. In Example 10, the synthetic-N-glycan-RNAs and synthetic-N-glycan-DNAs are purified away from excess reagents using standard RNA/DNA desalting columns that are silica-based.

In certain embodiments, the strained alkyne-modified nucleic acid is prepared by coupling an RNA or DNA (e.g., RNA or DNA of SEQ ID NOs. 1 or 2) modified with the internal amino modifier /iUniAmM/at the 5'-end (e.g., with an internal amino modifier of a nucleic acid, for example, available at Integrated DNA Technologies) to DIBAC (dibenzoazacyclooctyne, or "DBCO," dibenzocyclooctyne) using conditions for a N-Hydroxysuccinimide (NHS) reaction. The strained alkyne (DIBAC/DBCO)-modified RNA or strained alkyne (DIBAC/DBCO)-modified DNA is subsequently coupled to the azide-N-glycan. The azido-glycan (azide-glycan) is prepared as described below in Example 11.

Example 11—Preparation of Exemplary Azido-N-Glycans from Corresponding Exemplary Amino-N-Glycans Provided is a facile and efficient method to transform amino N-glycans to azido N-glycans via fluorosulfuryl azide mediated diazotransfer, shown in Table 5 below. This method exhibits substrate scope ranging from simple monosaccharides to oligosaccharides, N-glycans, and complex glycopeptides, which provides corresponding azido-N-glycans in nearly quantitative yields.

TABLE 5
Examples of Synthesis of Azido-N-Glycans
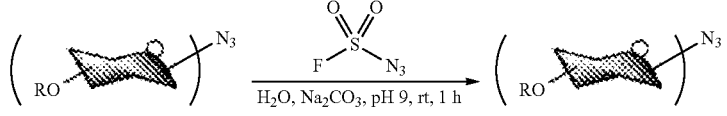
| Entry | | |
|---|---|---|
| 1 |  | |
| 2 | LNnT-MAPA | |
| 3 | LNnT-AEAB | |
| 4 | A2G0-Asn | A2G0-Asn |
| 5 | A2G2-Asn | A2G2-Asn |
| 6 | 2,3SA2-A2G2-Asn | 2,3SA2-A2G2-Asn |
| 7 | | |

TABLE 5-continued

Examples of Synthesis of Azido-N-Glycans

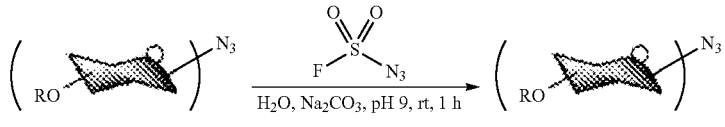

2,6SA2-A2G2-Asn    2,6SA2-A2G2-Asn

● Glc
○ Gal
◈ Man
■ GlcNAc
◆ Neu5Ac

Example 12—General Procedure for Synthesis of Azido Glycans

Materials and Methods

Free reducing end glycans were obtained from Glycobia, Inc., Ithaca, N.Y., and were made according to literature procedures known in the art.

Aminooxy-PEG3-Azide Addition

Glycans having free reducing ends were incubated with a 10-fold molar excess of aminooxy-PEG3-azide linker. Reactions were performed in 1×PBS, pH 4.0 at 65° C. for 30 h. Reactions were desalted using PGC SPE columns (Thermo Fisher Scientific®). The column was preconditioned with 1 mL acetonitrile followed by 1 mL $H_2O$. Reaction mixtures were diluted up to 500 μL with water and passed through the column. After reaction mixture loading, the column was eluted with 800 μL of 10 mM $NH_4HCO_3$ in 50/50 acetonitrile and $H_2O$. The acetonitrile was removed under vacuum and dried by lyophilization.

TABLE 6A

Exemplified Aminooxy-PEG3-azide functionalized glycans

| Ref # | Modified Glycan |
| --- | --- |
| G-12 | Man(a1-3)[Man(a1-6)]Man(b1-4)GlcNAc(b1-4)GlcNAc(b1-Aminooxy-PEG3-Azide |
| G-13 | Gal(b1-4)GlcNAc(b1-2)Man(a1-3)[Gal(b1-4)GlcNAc(b1-2)Man(a1-6)][GlcNAc(b1-4)]Man(b1-4)GlcNAc(b1-4)GlcNAc(b1-Aminooxy-PEG3-Azide |
| G-14 | NeuNAc(a2-3)Gal(b1-4)GlcNAc(b1-2)Man(a1-3)[NeuNAc(a2-3)Gal(b1-4)GlcNAc(b1-2)Man(a1-6)]Man(b1-4)GlcNAc(b1-4)GlcNAc(b1-Aminooxy-PEG3-Azide |
| G-15 | Man(b1-4)GlcNAc(b1-4)GlcNAc(b1-Aminooxy-PEG3-Azide |
| G-16 | Man(a1-6)[Man(a1-3)]Man(a1-6)[Man(a1-3)]Man(b1-4)GlcNAc(b1-4)GlcNAc(b1-Aminooxy-PEG3-Azide |
| G-17 | GlcNAc(b1-2)Man(a1-3)[GlcNAc(b1-2)Man(a1-6)]Man(b1-4)GlcNAc(b1-4)GlcNAc(b1-Aminooxy-PEG3-Azide |
| G-18 | Gal(b1-4)GlcNAc(b1-2)Man(a1-3)[Gal(b1-4)GlcNAc(b1-2)Man(a1-6)]Man(b1-4)GlcNAc(b1-4)GlcNAc(b1-Aminooxy-PEG3-Azide |
| G-19 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)GlcNAc(b1-Aminooxy-PEG3-Azide |
| G-20 | Gal(b1-4)GlcNAc(b1-2)Man(a1-3)[Gal(b1-4)GlcNAc(b1-2)Man(a1-6)]Man(b1-4)GlcNAc(b1-4)[Fuc(a1-6)]GlcNAc(b1-Aminooxy-PEG3-Azide |

Asparagine Azide Functionalization

To a solution of asparagine-linked N-glycan in distilled water, $Na_2CO_3$ (20 eq.) and $FSO_2N_3$ (40 eq.) were added. The mixture was rotated at rt for 1 h, and MALDI mass analysis showed complete conversion. The reaction mixture was placed in under vacuum for 30 min, then lyophilized. The residue (white powder) was reconstituted in mini-Q water, then loaded onto preconditioned Carb SPE tube. The tube was washed with distilled water (10×1.2 mL), then eluted with 50% acetonitrile with 100 mM $(NH_4)_2CO_3$ (4×1.2 mL). The eluent was combined and lyophilized to give the desired azido glycan.

TABLE 6B

Exemplified Asparagine Azide functionalized glycans

| Ref # | Modified Glycan | Yield | MS |
|---|---|---|---|
| G-28 | GlcNAc(b1-2)Man(a1-3)[GlcNAc(b1-2)Man(a1-6)]Man(b1-4)GlcNAc(b1-4)GlcNAc(b1-Asn-Azide | 93 | $[M + K]^+$ = 1495.156 |
| G-29 | Gal(b1-4)GlcNAc(b1-2)Man(a1-3)[Gal(b1-4)GlcNAc(b1-2)Man(a1-6)]Man(b1-4)GlcNAc(b1-4)GlcNAc(b1-Asn-Azide | 92 | $[M + K]^+$ = 1819.304 |
| G-30 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)GlcNAc(b1-Asn-Azide | 91 | $[M + 4K - 3H]^+$ = 2515.293 |
| G-31 | GlcNAc(b1-2)Man(a1-3)[GlcNAc(b1-2)Man(a1-6)]Man(b1-4)GlcNAc(b1-4)[Fuc(a1-6)]GlcNAc(b1-Asn-Azide | 91 | $[M + K]^+$ = 1641.453 |
| G-32 | Gal(b1-4)GlcNAc(b1-2)Man(a1-3)[Gal(b1-4)GlcNAc(b1-2)Man(a1-6)]Man(b1-4)GlcNAc(b1-4)[Fuc(a1-6)]GlcNAc(b1-Asn-Azide | 92 | $[M + K]^+$ = 1965.601 |
| G-33 | Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)[Fuc(a1-6)]GlcNAc(b1-Asn-Azide | 90 | $[M + 4K - 3H]^+$ = 2661.363 |

Example 13—General Procedure for Click-Chemistry Coupling of Azido Glycans and Modified siRNAs Glycan—siRNA siRNAs functionalized with DBCO at the 3' end were purchased from WuXi Biologics R or Axolabs R and made by methods well established in the art. siRNAs with DBCO conjugated at the 3' end were incubated with a 10-fold excess of azide functionalized glycan. Conjugation reactions were performed at 37° C. overnight. Conjugated glycoRNAs were purified by HPLC. HPLC purification of the glycoRNA conjugates was carried out using 200 mM HFIP+16 mM TEA in methanol. Instrument model: Agilent 1260 HPLC; Column: Agilent AdvanceBio Oligonucleotide, 2.1× 100 mm, 2.7 μm. The conjugated glycoRNAs were dried by lyophilization. The glycoRNAs were then resuspended in water to a concentration of 100 μM. GlycoRNAs were then annealed to the complementary sense strand in Annealing Buffer (30 mM Tris, pH 7.5, 100 mM NaCl, 1 mM EDTA). For the annealing reaction, samples heated to 95° C. and slow cooled to room temperature over ~6 hours. The annealed duplex was desalted using a Zeba Spin Desalting Column (Thermo Fisher Scientific R) by centrifugation at 1500 g for 2 min.

GlycoRNAs described in Table 6C were generated using the general procedures described above.

TABLE 6C

Exemplified GlycoRNAs

| Ref # | Glycan | siRNA | % Conjugation |
|---|---|---|---|
| R-1 | G-28 | I-2 | 76 |
| R-2 | G-29 | I-2 | 74 |
| R-3 | G-30 | I-2 | 67 |
| R-4 | G-31 | I-2 | 77 |
| R-5 | G-32 | I-2 | 75 |
| R-6 | G-33 | I-2 | 75 |
| R-7 | G-12 | I-2 | 50 |

TABLE 6C-continued

Exemplified GlycoRNAs

| Ref # | Glycan | siRNA | % Conjugation |
|---|---|---|---|
| R-8 | G-13 | I-2 | 48 |
| R-9 | G-14 | I-2 | 28 |
| R-10 | G-15 | I-2 | 39 |
| R-11 | G-16 | I-2 | 47 |
| R-12 | G-17 | I-2 | 23 |
| R-13 | G-18 | I-2 | 22 |
| R-14 | G-19 | I-2 | 29 |
| R-15 | G-20 | I-2 | 8 |
| R-16 | G-35 | I-2 |  |

Figure 12:
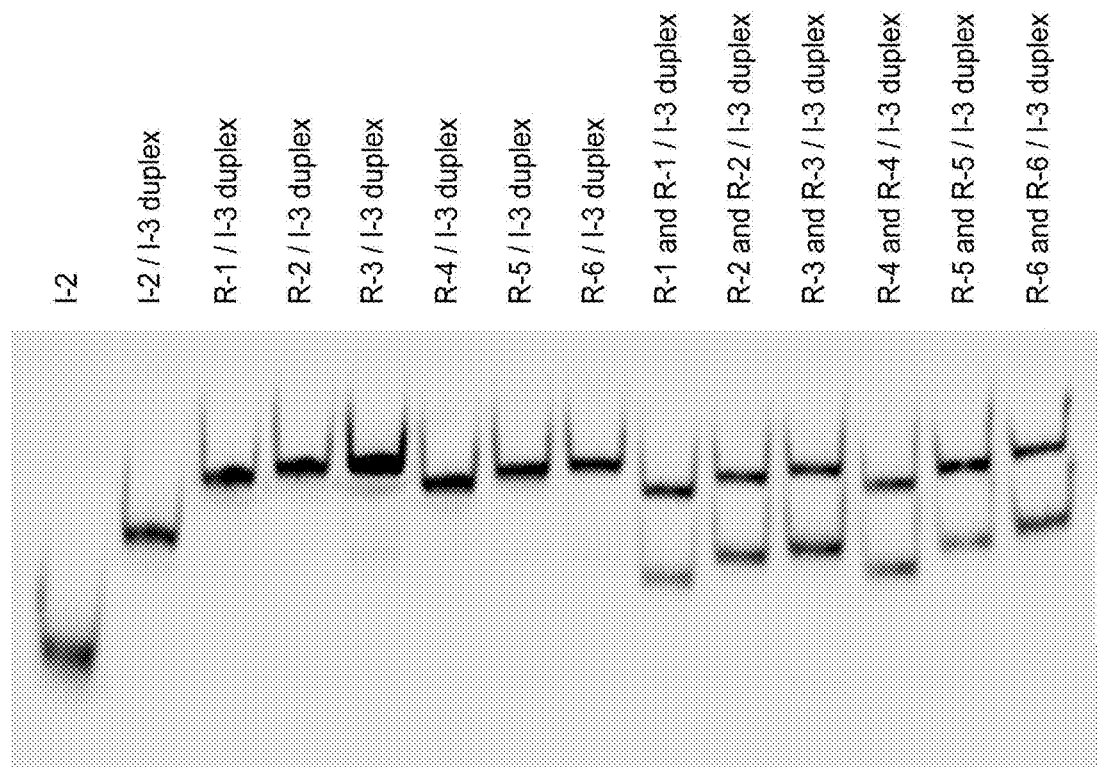
FIG. 12 is a blot showing duplexes formed between exemplary glycoRNAs R-1 through R-6 and complementary sense strand I-1.

The glycoRNAs were then annealed to I-1, using the general procedures described above. FIG. 12 is a blot showing the formation of duplexes for glycoRNAs R-1 through R-6 and unconjugated siRNA 1-2, with siRNA I-1.

Similarly, comparison compounds X-1 and X-2 were synthesized using the general procedures described above, wherein monosaccharides were used in place of the azide functionalized glycans. The conjugated monosaccharides were then annealed to I-1, using the general procedures described above.

TABLE 6D

Exemplified monosaccharide modified siRNAs

| Ref # | Monosaccharide | siRNA |
|---|---|---|
| X-1 | 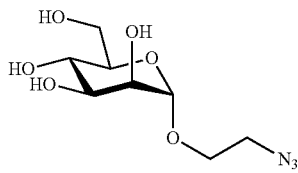<br>2-Azidoethyl α-D-mannopyranoside | I-2 |
| X-2 | 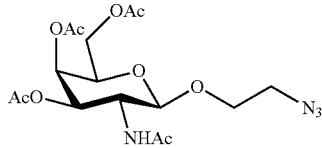<br>2-Azidoethyl 2-acetamido-3,4,6-tri-O-acetyl-2-deoxy-β-D-galactopyranoside | I-2 |

Additionally, comparison compound X-3 was synthesized using solid state synthesis procedures. The conjugated compound was then annealed to 1-4, using the general procedures described above.

TABLE 6E

Exemplified modified siRNA

| Ref # | Compound |
|---|---|
| X-3 | 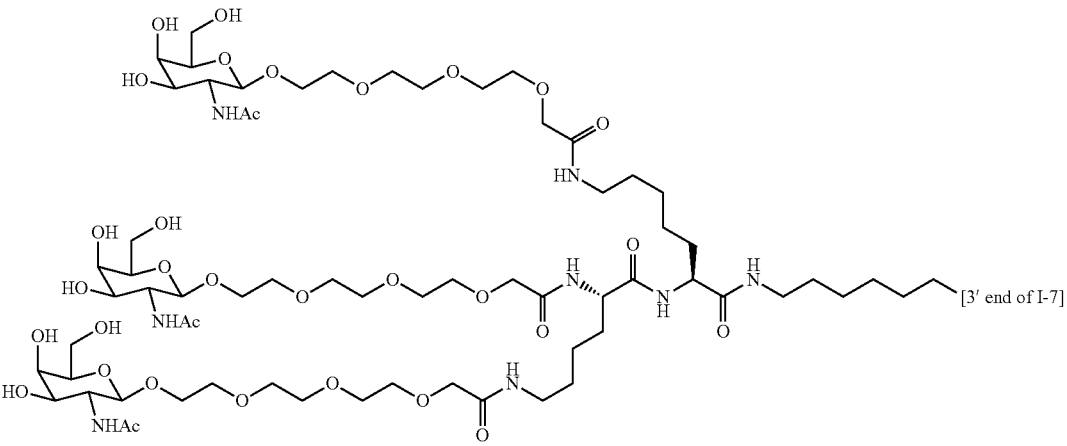 |

Figure 14:
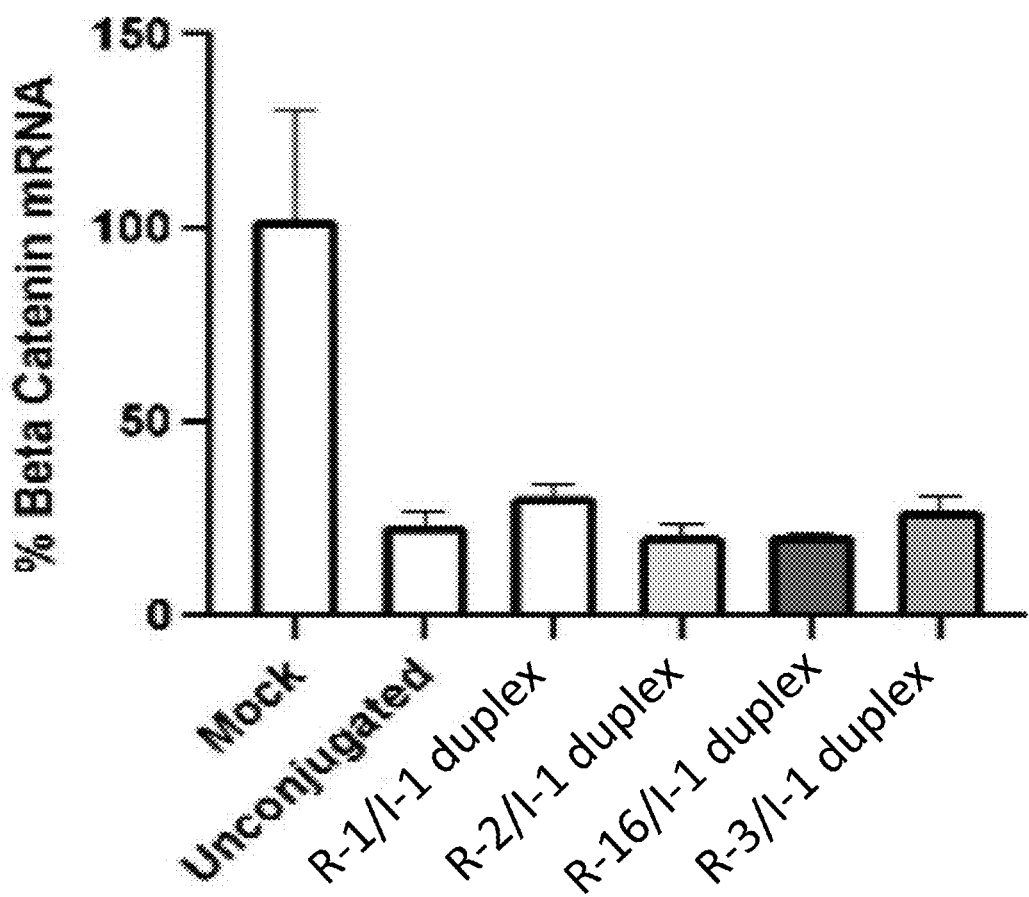
FIG. 14 is a graph showing cell signaling knockdown (the % beta catenin) using glycoRNAs (R-1/I-1 duplex, R-2/I-1 duplex, R-16/I-1 duplex, and R-3/I-1 duplex.

Example 14—Cell Signaling Knockdown Using GlycoRNAs 293T cells were plated 24 hours before the experiment at 100,000 cells in 1 mL of growth media in 24-well plates. 2 µl of lipofectamine was added to 100 µl of serum free media, and glyco-siRNA duplex was added separately to serum free media to 50 nM final concentration. These two mixtures, lipofectamine and diluted duplex, were added together at room temperature and incubated for 20 minutes. Media was aspirated from plated 293 T cells and replaced with 100 µl of fresh media. 20 µl of the lipofectamine-glyco-siRNA mixture was added to each well and incubated overnight. RNA was purified from cells using RNA lysis buffer (Zymo), followed by RNA prep, wash, and elution buffers and spins at 10,000 g for 2 min each (Zymo). After RNA was quantified it was diluted to 10 ng/µL to have 50 ng per qPCR reaction. Samples were run in duplicate and each sample had a biological replicate. qPCR primers were to the beta catenin gene and PPIB and amplified using primers at 125 nM, 1×Taq polymerase master mix, MMLV RT enzyme (0.5 units per reaction), and SYBR green at 1×. Samples were first incubated for 30 min at 50° C. then 10 min at 95° C. followed by 40 cycles of 30 s of 95° C. and 1 min at 60° C. Beta catenin Ct values were normalized by those of Ct values of PPIB to report relative abundance (% beta catenin mRNA) in FIG. 14.

Example 15—GlycoRNA Flow Assays—HepG2 Cells

Figure 15A:
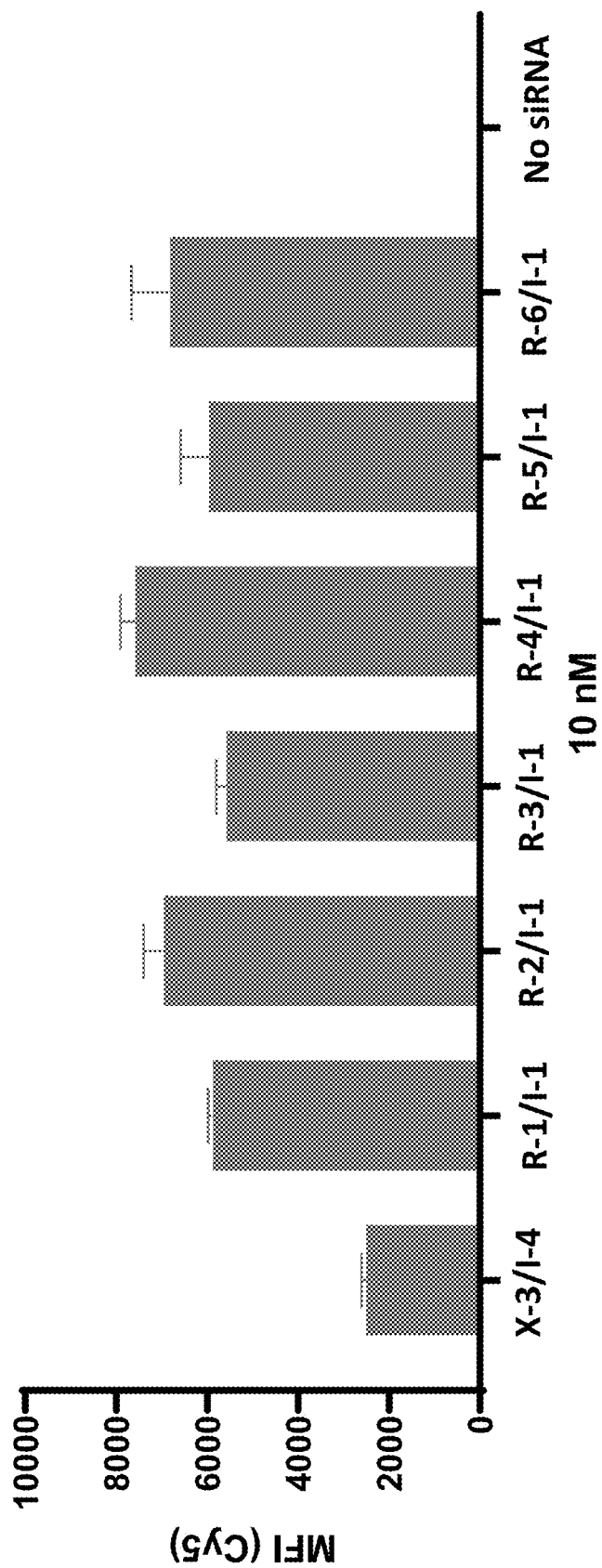
FIGS. 15A and 15B are graphs showing mean fluorescent intensity for Cy5 expression of GlycoRNAs relative to X-3/I-4 duplex in HepG2 cells.
Figure 15B:
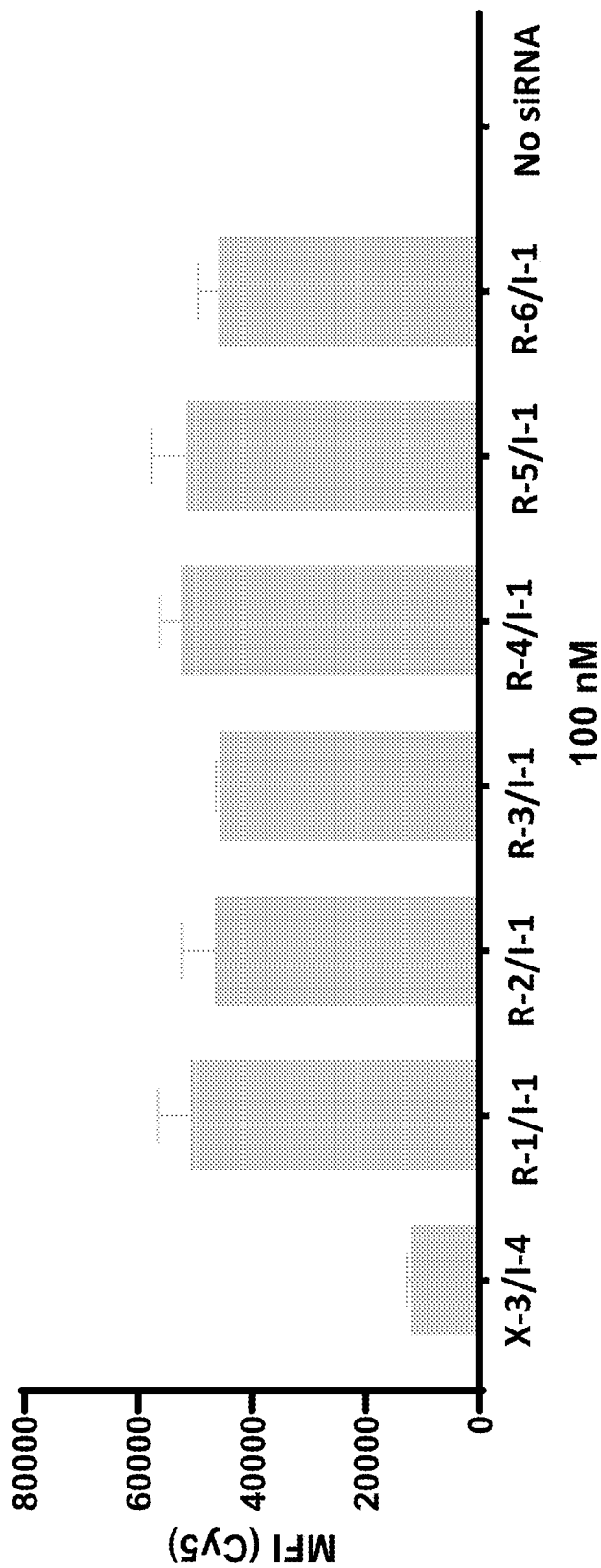

HepG2 cells were maintained in culture medias (DMEM+ 10% FBS, all reagents sourced from Gibco/Life Technologies). Cell count and viability was assessed using trypan blue exclusion on a ViCell XR cell counter (Beckman). 2×10⁵ live cells were plated per well of a 96 well v bottom plate in 100 µL total volume of assay buffer (cell culture media without additional serum or protein, Gibco/Life Technologies). Cells were washed in 1×PBS (Gibco/Life Technologies) via centrifugation and resuspended in additional PBS. 100 µL Live/dead fixable yellow cell stain (Life Technologies/Thermo Scientific) was added per the manufacturer's instructions and incubated for 15 minutes at room temperature. Samples were then washed in PBS via centrifugation as above. Cells were resuspended in blocking buffer (10% Human TruStain FcX, BioLegend, in 1×PBS+ 0.5% BSA), and incubated at room temperature for five minutes in the dark (to minimize loss of the Cy5 signal). Cy5-labelled duplexed glycoRNAs were diluted from 10 µM stocks in additional assay buffer and plated at 0.1, 1, 10, and 100 nM concentrations (in biological replicates). Cells were then incubated for four hours in the dark at 37° C., 5% CO₂ inside a standard cell culture incubator. Samples were then washed one time in assay buffer via centrifugation. Unfixed cells were then immediately acquired on an ATTUNE NxT flow cytometer with a CYTKICK 96 well high throughput attachment (Thermo Scientific). FCS files were analyzed using FlowJo® Software (BD Bioscience). Cell populations of interest were identified using both forward and side scatter properties, and doublets were excluded by comparing forward scatter height vs area. Live cells were identified based on live/dead stain exclusion. Histogram overlays and mean fluorescent intensity (MFI) for Cy5 expression for all positive cell populations of interest were compared against cells treated with X-3/I-4 duplex glycoRNA. Mean fluorescent intensity (MFI) of the tested glycoRNAs is shown in FIGS. 15A and 15B compared to X-3/I-4 duplex and graphed in Prism (GraphPad).

Example 16—siRNA-Mediated Knock Down in HepG2 Cells $1 \times 10^5$ HepG2 cells are plated per well in 96 well flat bottom plates and incubated with titrations of Cy5 labelled duplexed glycoRNAs (R-1 through R-6) for 24 hrs in serum-free DMEM media. After incubation, media is removed via aspiration and washed once in PBS. Dry pellets are frozen at −80° C. until RNA extraction. Total RNA is isolated from cells using RNeasy micro spin columns (QIAGEN) following manufacturer's instructions. Total RNA is eluted in water (14 µL total volume) and an aliquot was quantified on a NanoDrop™ (Thermo Scientific). cDNA is synthesized using 100 ng RNA per sample using the SuperScript™ IV cDNA synthesis system (Life Technologies/Thermo Scientific) with oligo(dT) primers, following manufacturer's instructions using a BioRad thermocycler. Gene expression is assessed using multiplexed TaqMan probes against β-catenin and GAPDH (Assay ID for β-catenin probe set: Hs00355045_m1, endogenous human GAPDH control: 4326317, both purchased from Applied Bio/Thermo Scientific). 10 ng of sample cDNA is plated per well in 96 well optically clear PCR plates in biological and technical replicates (Applied Bio/Thermo Scientific), and 20× TaqMan probes and 2× TaqMan gene expression master mix are added following manufacturer's instructions for 20 µL total reaction volume per well (Applied Bio/Thermo Scientific). Samples are amplified on a QuantStudio 6 Pro Real Time PCR System using the following amplification parameters: Stage 1: 50° C. for 2 min. Stage 2: 95° C. for 10 min. Stage 3: 95° C. for 15 see, 60° C. for 1 min. Repeat 40×. Gene expression of β-catenin is calculated using the ΔΔCT method relative to GAPDH expression and untreated control cells, where a value of less than 1 indicates siRNA-mediated knock down of β-catenin.

Example 17—GlycoRNA Flow Assays—PBMCs

Figure 13A:
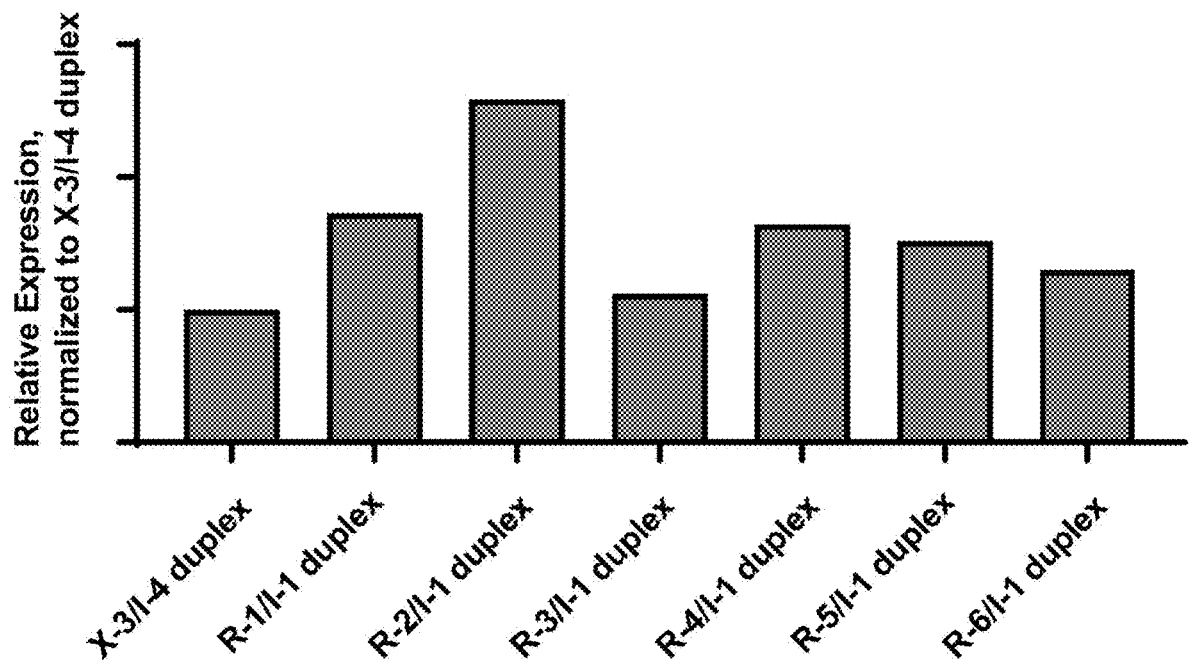
FIGS. 13A-13C are graphs depicting expression relative to X-3/I-4 duplex of GlycoRNAs.
Figure 13B:
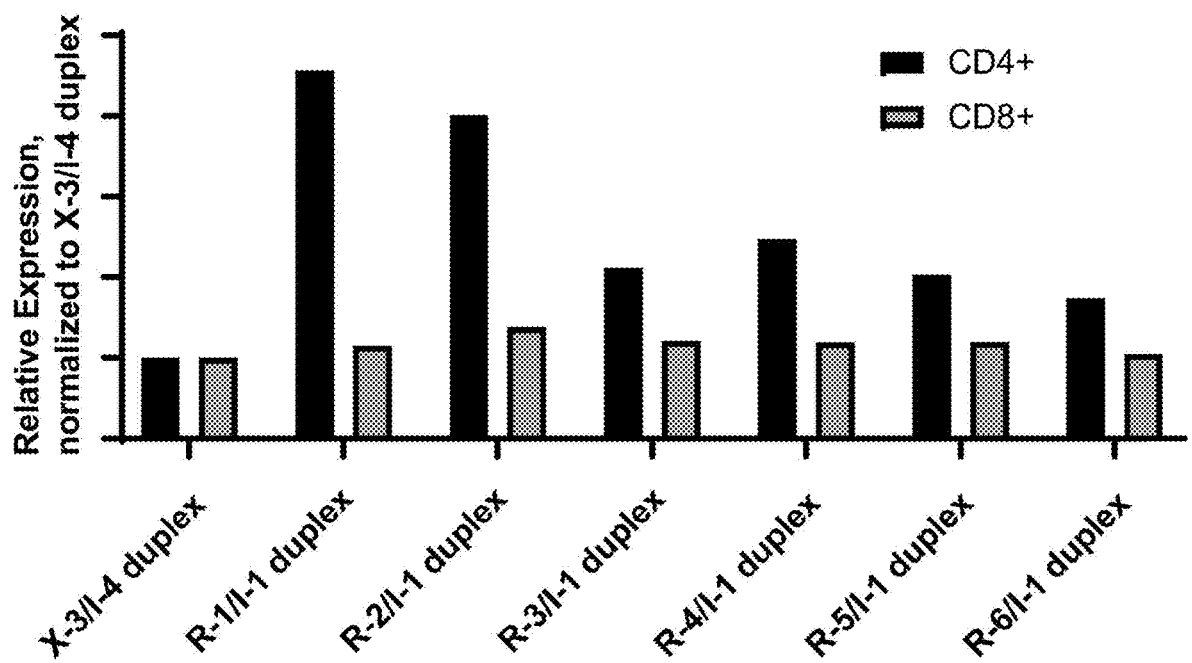
Figure 13C:
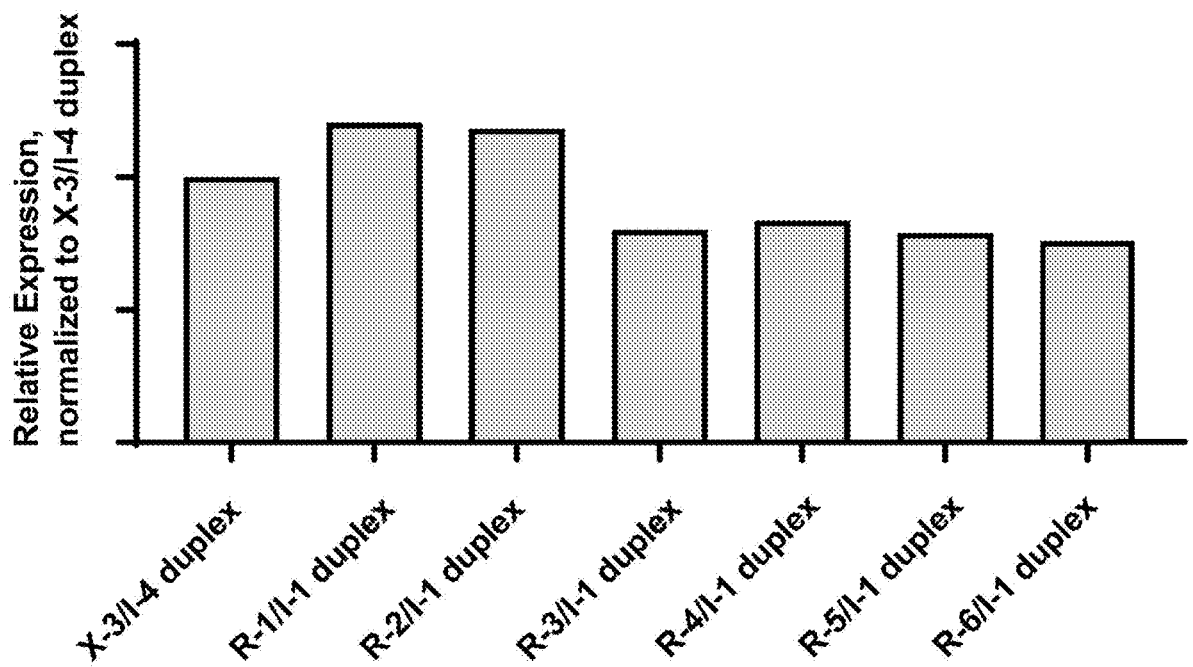

Frozen peripheral blood mononuclear cells (PBMCs) from healthy human donors were purchased from StemCell Technologies. These cells were stored in the vapor phase of a liquid nitrogen ultra-low temperature freezer until use. The vials were thawed quickly in a 37° C. water bath and washed once in PBS+10% FBS (Gibco/Life Technologies), followed by two additional washes via centrifugation (500×g, 5 min) in PBS (Gibco/Life Technologies). Cell count and viability was assessed using trypan blue exclusion on a Vi-Cell™ XR cell counter (Beckman). $4 \times 10^5$ live cells were plated per well of a 96 well round bottom plate in 100 µL total volume of assay buffer (PBS+0.5% BSA, Gibco/Life Technologies). Cy5-labelled duplexed glycoRNAs were diluted from 10 µM stocks in additional assay buffer and plated at 0.1, 1, 10, and 100 nM concentrations (in biological replicates). Cells were then incubated for four hours in the dark at 37° C., 5% $CO_2$ inside a standard cell culture incubator. Following incubation, the cells were washed once via centrifugation (as above) and resuspended in assay buffer with 10% Fc block added (Human Fc block, Miltenyi Biotech) with a total volume of 100 µL per well. The plate was incubated at room temperature for 30 minutes in the dark (to minimize loss of the Cy5 signal). Antibodies against selected immune cell markers were added following manufacturer's recommended amounts (anti CD3 clone OK3 AF 488, anti CD4 clone OKT4 Super Bright 600, anti CD8 clone OKT8 Super Bright 702, anti CD14 clone MEM-15 NovaFluor Yellow 700, and anti CD19 clone HIB19 PE-eFluor 610, all purchased from Life Technologies/Thermo Scientific) using the Super Bright staining buffer (Life Technologies/Thermo Scientific). Cells were incubated at room temperature for one hour in the dark before being washed once with assay buffer (as above). Live/dead fixable aqua cell stain (Life Technologies/Thermo Scientific) was added per the manufacturer's instructions and incubated for two minutes at room temperature. Unfixed cells were then immediately acquired on an Attune NxT flow cytometer and its CytKick 96 well high throughput attachment (Thermo Scientific). FCS files were analyzed using FlowJo software (BD Bioscience). Lymphocytes were identified using both forward and side scatter properties, and doublets were excluded by comparing forward scatter height vs area. Live cells were identified based on live/dead stain exclusion. Monocytes were identified by CD14 positive staining, and B cells were identified based on CD19 positive staining. T cells were identified first by CD3 positive staining, and then CD4 vs CD8 stains. Histogram overlays and mean fluorescent intensity (MFI) for Cy5 expression for all positive cell populations of interest were compared against cells treated with the I-4/X-3 duplex. Expression data is reported relative to X-3/I-4 duplex and graphed in Prism (GraphPad), see FIGS. 13A-13C.

Example 18—HepG2 Imaging Assays

Figure 16A:
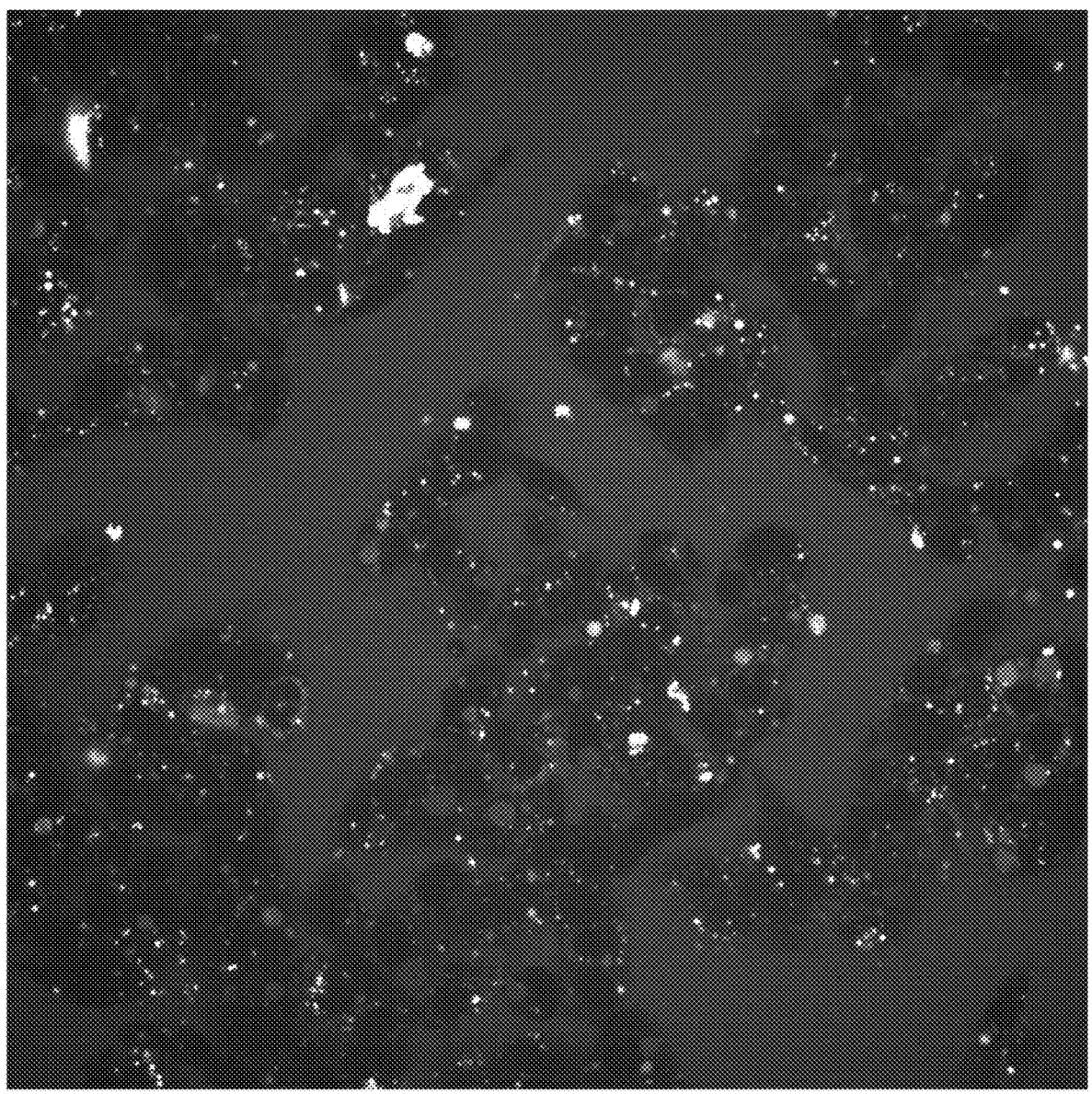
FIGS. 16A-16F are Cy5 fluorescence images captured as described in Example 18, showing internalization and/or localization of glycolRNA duplexes in and on the HepG2 cells.
Figure 16B:
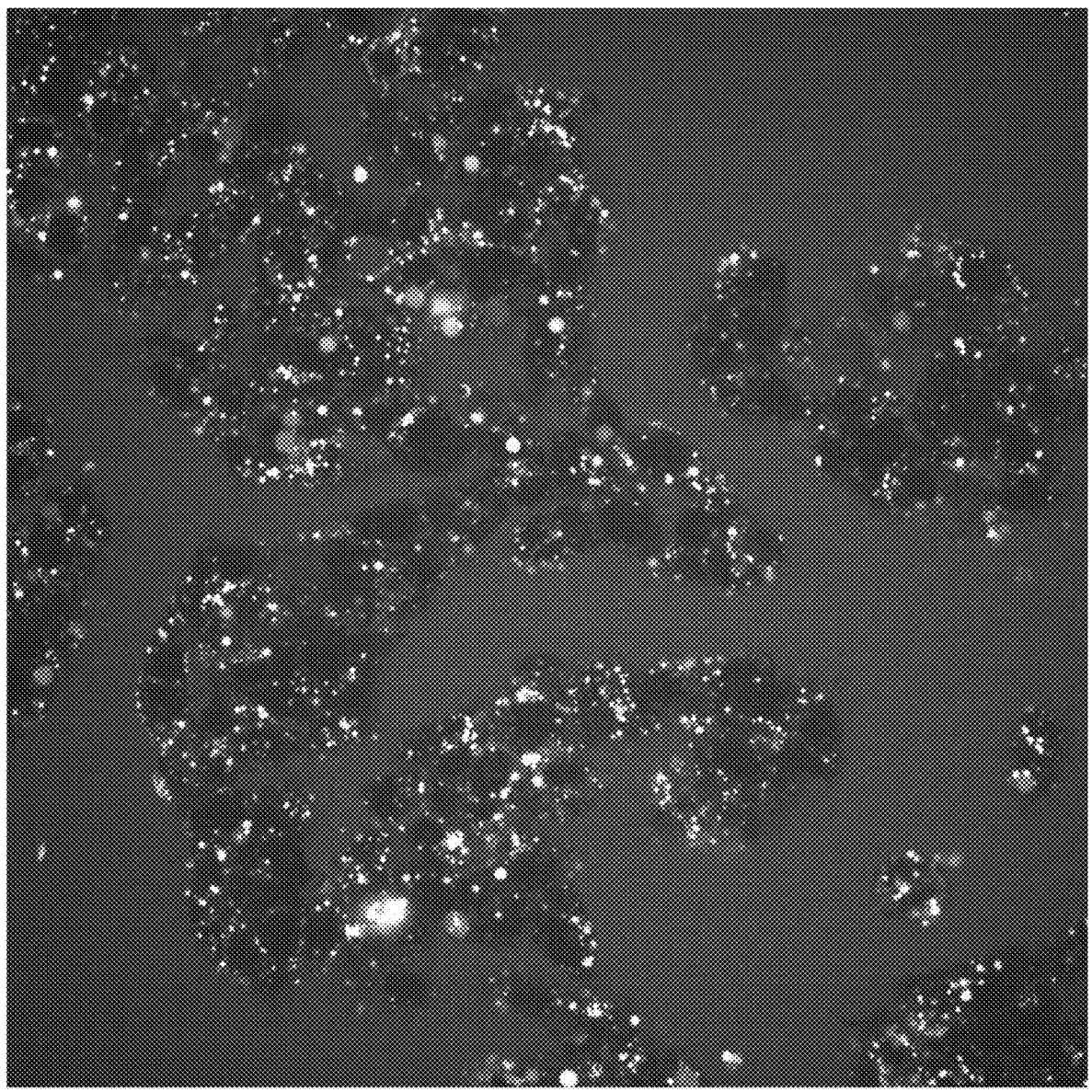
Figure 16C:
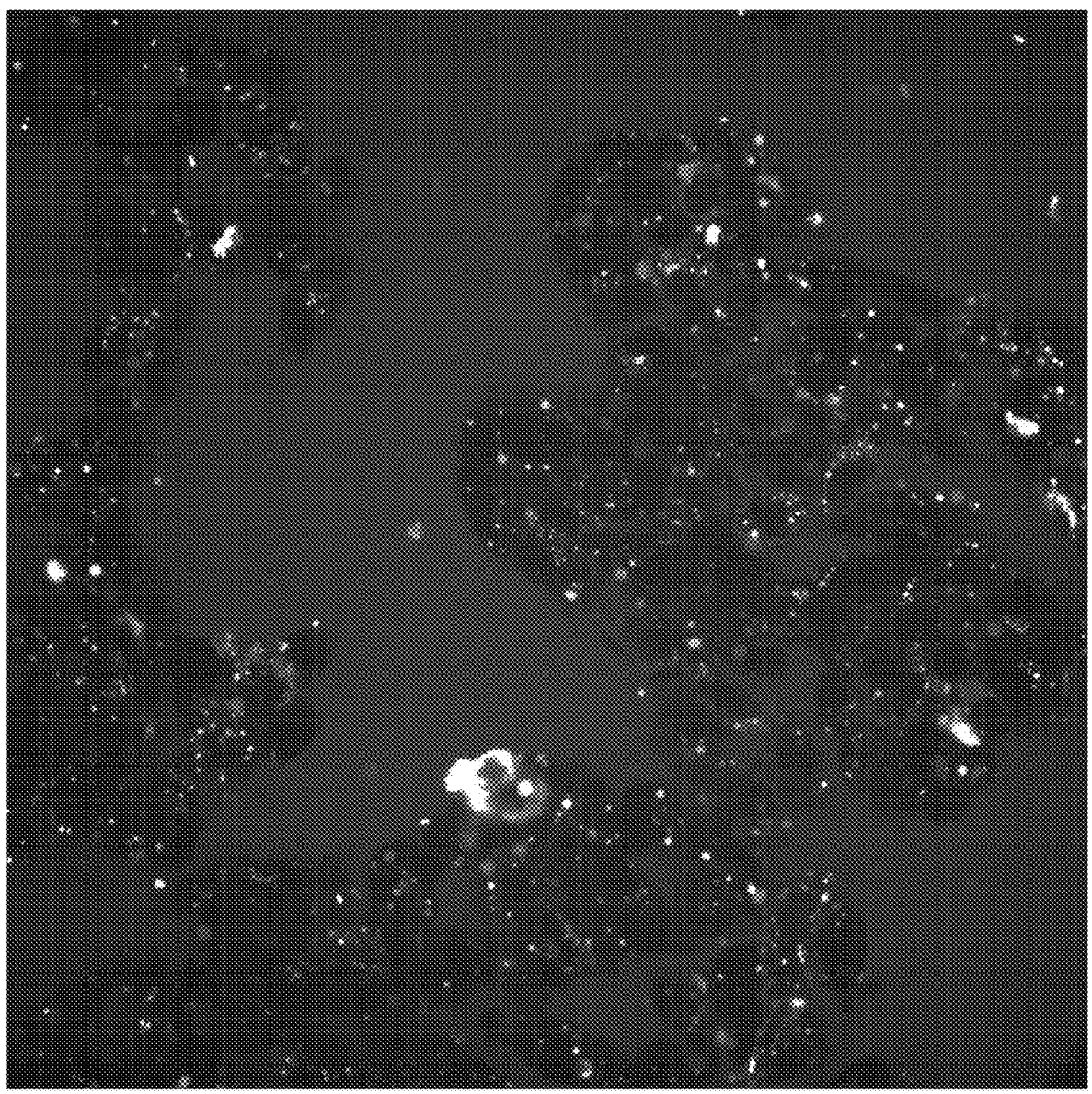
Figure 16D:
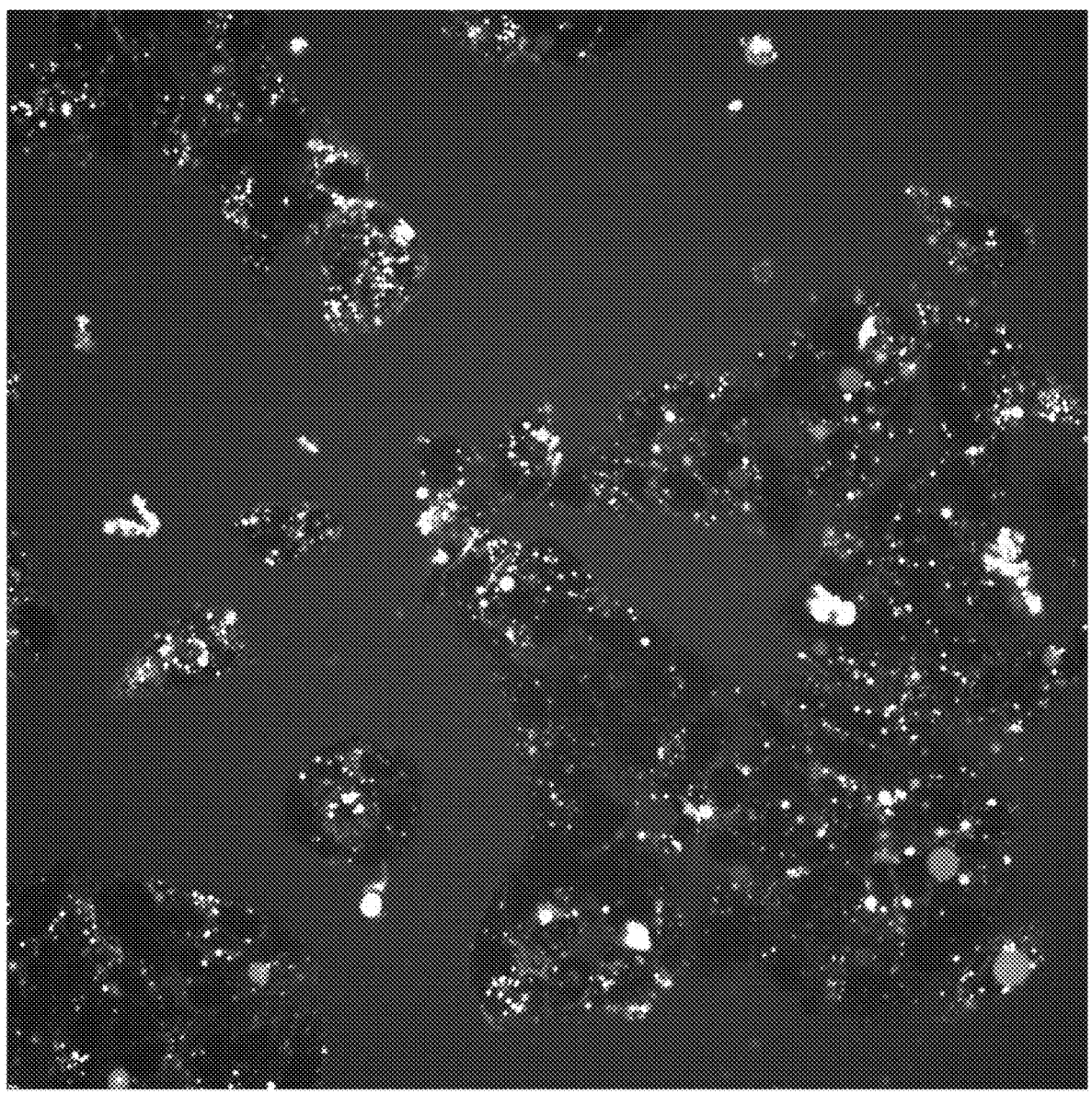
Figure 16E:
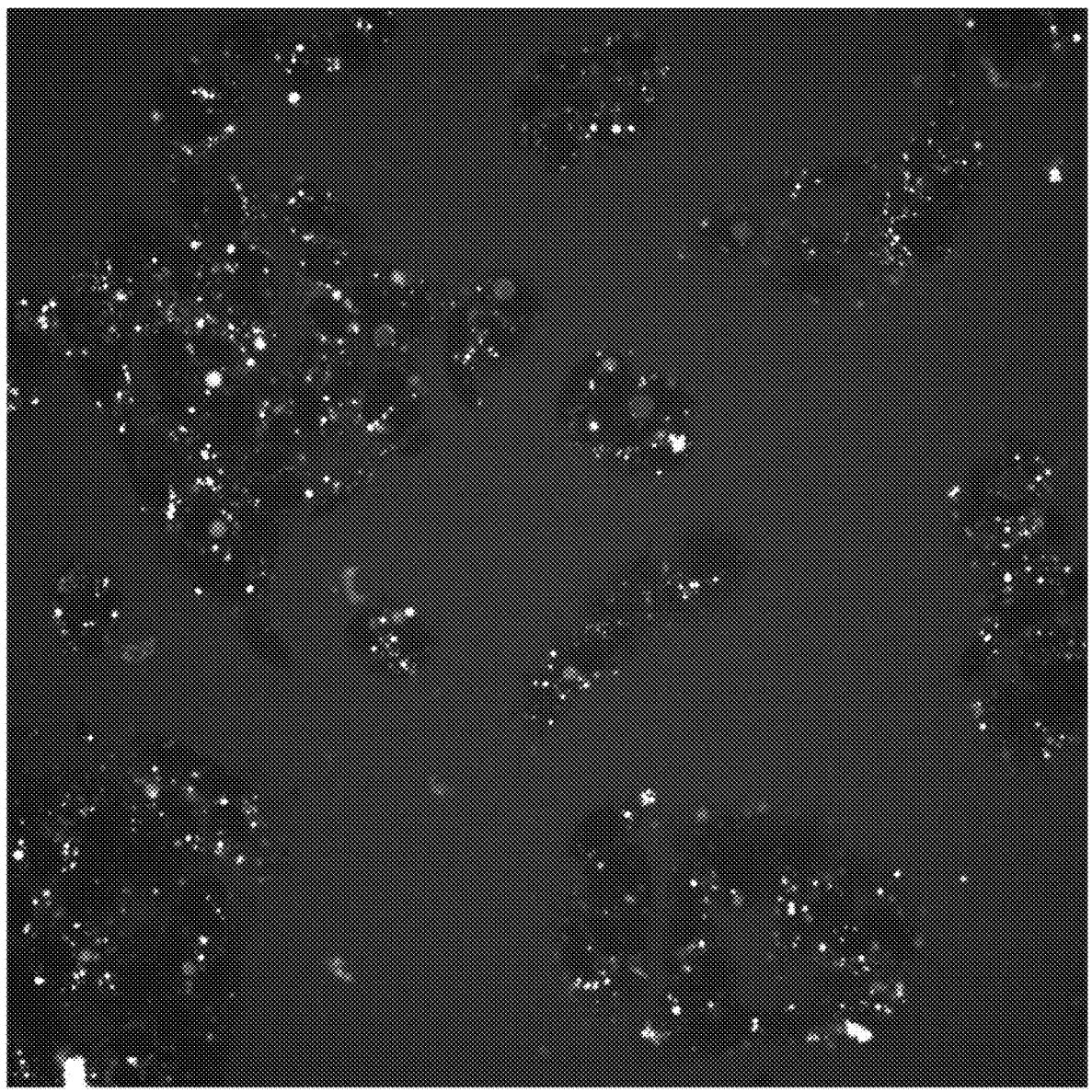
Figure 16F:
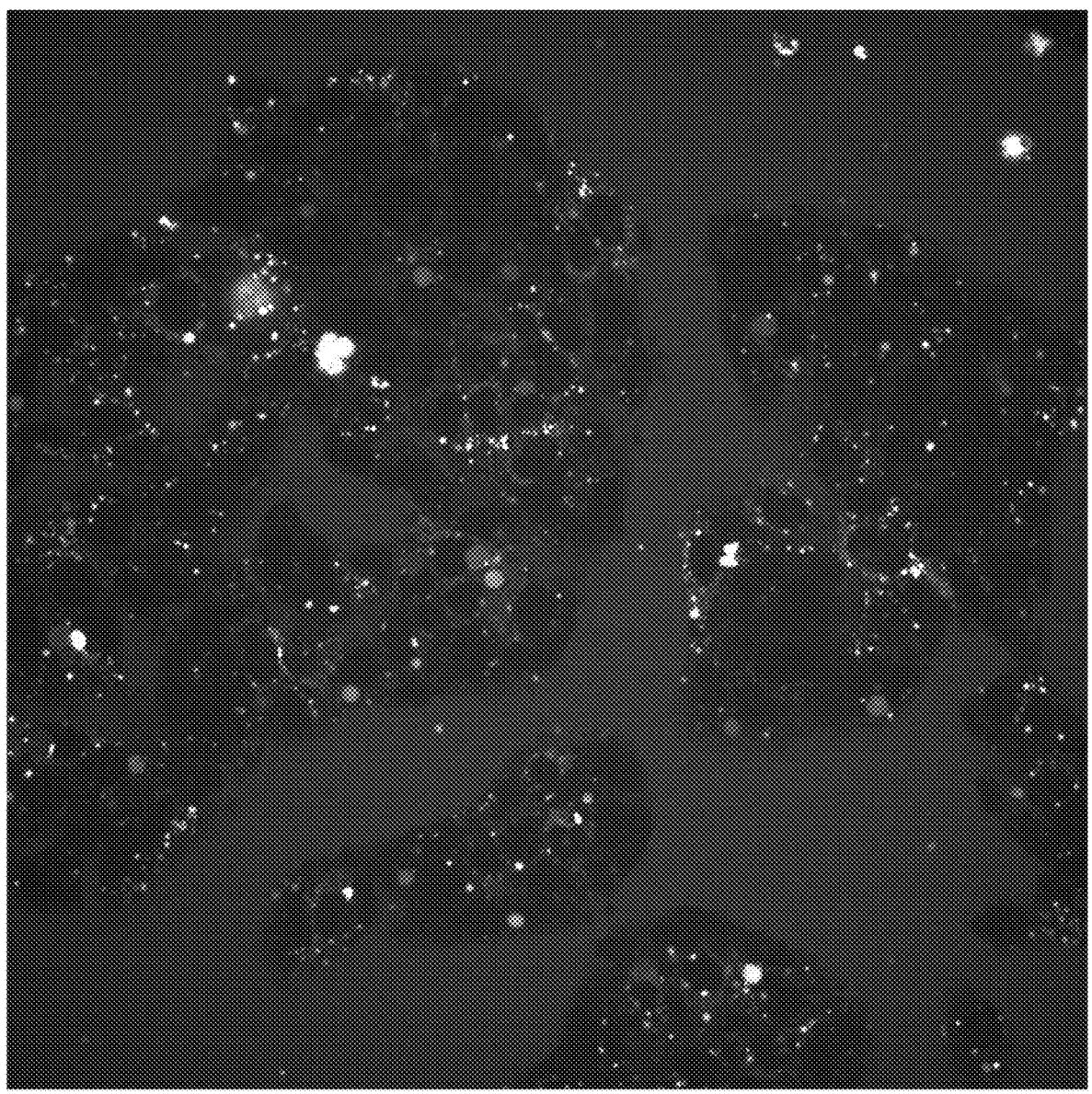

On Day 1, HepG2 cells were split using ACCUTASE® (Sigma) and counted. 2000 live cells/50 µL of complete media (DMEM+10% FBS+1% PEN/STREP, Gibco/Life Technologies) were plated into 384 well glass bottom imaging plates (CORNING®). Cells were incubated in standard tissue culture incubators at 37° C., 5% $CO_2$ overnight. On Day 2, the culture media was removed from each well and 50 µL of 1:1000 Cell Mask Green Plasma Membrane Stain (ThermoFisher) and 1:20,000 Hoechst diluted in OptiMEM was added to each well. Cells were incubated at 37° C., 5% $CO_2$ for five minutes and then gently washed with 50 µL of OptiMEM three times. OptiMEM was removed and 50 µL of 100 nM Cy5-labelled duplexed glycoRNAs was added to the cells and incubated at 37° C., 5% $CO_2$ for 16 hr. The plate was imaged on the Opera Phenix High Content Screening System with a 40× water objective in the DAPI, FITC, and Cy5 channels. FIGS. 16A-16F are Cy5 fluorescence images captured as described above, showing internalization and/or localization of the glycolRNA duplexes in and on the HepG2 cells. R-1/I-1 (FIG. 16A); R-2/I-1 (FIG. 16B); R-3/I-1 (FIG. 16C); R-4/I-1 (FIG. 16D); R-5/I-1 (FIG. 16E); and R-6/I-1 (FIG. 16F).

The preceding examples illustrate the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A pharmaceutical composition comprising:
   a) a glyconucleic acid or salt thereof, the glyconucleic acid comprising:
      i) a short interfering RNA (siRNA); and
      ii) at least one oligosaccharide moiety comprising at least 6 monosaccharides, covalently bound to the siRNA; and
   b) a pharmaceutically acceptable carrier;
   wherein the at least one oligosaccharide moiety comprises a multiple antennary complex type N-glycan comprising at least one GlcNAc residue attached to the Manα1-3 arm and at least one GlcNAc attached to the Manα1-6 arm of a trimannose core.

2. The pharmaceutical composition of claim 1, wherein the at least one oligosaccharide moiety comprises at least 8 monosaccharides.

3. The pharmaceutical composition of claim 1, wherein the at least one oligosaccharide moiety comprises at least 10 monosaccharides.

4. The pharmaceutical composition of claim 1, wherein at least one terminal residue of the multiple antennary complex type N-glycan comprises a monosaccharide selected from sialic acid, fucose, GlcNAc, mannose, and galactose.

5. The pharmaceutical composition of claim 1, wherein the at least one oligosaccharide moiety is covalently bound to the siRNA via a click-chemistry reaction.

6. The pharmaceutical composition of claim 1, wherein the siRNA is covalently bound to the oligosaccharide moiety via a linker group covalently bound to a terminus of the-siRNA.

7. The pharmaceutical composition of claim 1, wherein the siRNA is covalently bound to the oligosaccharide moiety via a linker covalently bound to a chemically modified nucleotide in the middle of the siRNA.

8. The pharmaceutical composition of claim 1, wherein the siRNA is covalently bound to the oligosaccharide moiety via a chemical handle inserted between two nucleotides of the siRNA.

9. The pharmaceutical composition of claim 1, wherein the at least one-oligosaccharide moiety comprises a tetra-antennary complex type N-glycan, comprising a first terminal residue, a second terminal residue, a third terminal residue, and a fourth terminal residue.

10. The pharmaceutical composition of claim 9, wherein at least one of the first terminal residue, the second terminal residue, the third terminal residue, and the fourth terminal residue comprises a monosaccharide selected from sialic acid, GlcNAc, and galactose.

11. The pharmaceutical composition of claim 9, wherein at least one of the first terminal residue, the second terminal residue, the third terminal residue, and the fourth terminal residue comprises galactose.

12. The pharmaceutical composition of claim 9, wherein the at least one oligosaccharide moiety comprises a fucose linked to a GlcNAc residue in a core or a base region of the complex type N-glycan.

13. The pharmaceutical composition of claim 1, wherein the at least one oligosaccharide moiety comprises a bisecting complex type N-glycan.

14. The pharmaceutical composition of claim 1, wherein the at least one oligosaccharide moiety comprises a fucose linked to a GlcNAc residue in a core or a base region of the complex type N-glycan.

15. The pharmaceutical composition of claim 9, wherein at least one of the first terminal residue, the second terminal residue, the third terminal residue, and the fourth terminal residue comprises sialic acid.

16. The pharmaceutical composition of claim 9, wherein at least one of the first terminal residue, the second terminal residue, the third terminal residue, and the fourth terminal residue comprises GlcNAc.

17. The pharmaceutical composition of claim 9, wherein at least one of the first terminal residue, the second terminal residue, the third terminal residue, and the fourth terminal residue comprises mannose.

18. The pharmaceutical composition of claim 1, wherein the at least one oligosaccharide moiety comprises a bi-antennary complex type N-glycan comprising a first terminal residue and a second terminal residue.

19. The pharmaceutical composition of claim 18, wherein at least one of the first terminal residue and the second terminal residue comprises a monosaccharide selected from sialic acid, GlcNAc and galactose.

20. The pharmaceutical composition of claim 18, wherein at least one of the first terminal residue and the second terminal residue comprises sialic acid.

21. The pharmaceutical composition of claim 18, wherein at least one of the first terminal residue and the second terminal residue comprises GlcNAc.

22. The pharmaceutical composition of claim 18, wherein at least one of the first terminal residue and the second terminal residue comprises mannose.

23. The pharmaceutical composition of claim 18, wherein the at least one oligosaccharide moiety comprises a fucose linked to a GlcNAc residue in a core or a base region of the bi-antennary N-glycan.

24. The pharmaceutical composition of claim 1, wherein the at least one oligosaccharide moiety comprises a tri-antennary complex type N-glycan comprising a first terminal residue, a second terminal residue, and a third terminal residue.

25. The pharmaceutical composition of claim 24, wherein at least one of the first terminal residue and the second terminal residue comprises a monosaccharide selected from sialic acid, GlcNAc, and galactose.

26. The pharmaceutical composition of claim 24, wherein at least one of the first terminal residue, the second terminal residue, and the third terminal residue comprises sialic acid.

27. The pharmaceutical composition of claim 24, wherein at least one of the first terminal residue, the second terminal residue, and the third terminal residue comprises GlcNAc.

28. The pharmaceutical composition of claim 24, wherein at least one of the first terminal residue, the second terminal residue, and the third terminal residue comprises mannose.

29. The pharmaceutical composition of claim 24, wherein the at least one oligosaccharide moiety comprises a fucose linked to a GlcNAc residue in a core or a base region of the tri-antennary complex type N-glycan.

30. The pharmaceutical composition of claim 1, wherein the at least one oligosaccharide moiety comprises a glycan selected from G-1 (GlcNAc(b1-2)Man(a1-3)[GlcNAc(b1-2)Man(a1-6)]Man(b1-4)GlcNAc(b1-4)[Fuc(a1-6)]GlcNAc(b1-), G-2 (Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)[Fuc(a1-6)]GlcNAc(b1-), G-4 (Gal(b1-4)GlcNAc(b1-2)Man(a1-3)[Gal(b1-4)GlcNAc(b1-2)Man(a1-6)][GlcNAc(b1-4)]Man(b1-4)GlcNAc(b1-4)GlcNAc(b1), G-5 (NeuNAc(a2-3)Gal(b1-4)GlcNAc(b1-2)Man(a1-3)[NeuNAc(a2-3)Gal(b1-4)GlcNAc(b1-2)Man(a1-6)]Man(b1-4)GlcNAc(b1-4)GlcNAc(b1-), G-8 (GlcNAc(b1-2)Man(a1-3)[GlcNAc(b1-2)Man(a1-6)]Man(b1-4)GlcNAc(b1-4)GlcNAc(b1-), G-9 (Gal(b1-4)GlcNAc(b1-2)Man(a1-3)[Gal(b1-4)GlcNAc(b1-2)Man(a1-6)]Man(b1-4)GlcNAc(b1-4)GlcNAc(b1-), G-10 (Neu5Ac(a2-6)Gal(b1-4)GlcNAc(b1-2)Man(a1-3)[Neu5Ac(a2-6)Gal(b1-4)GlcNAc(b1-2)Man(a1-6)]Man(b1-4)GlcNAc(b1-4)GlcNAc(b1-), G-11 (Gal(b1-4)GlcNAc(b1-2)Man(a1-3)[Gal(b1-4)GlcNAc(b1-2)Man(a1-6)]Man(b1-4)GlcNAc(b1-4)[Fuc(a1-6)]GlcNAc(b1-), and G-34 (Neu5Ac(a2-3)Gal(b1-4)GlcNAc(b1-2)Man(a1-3)[Neu5Ac(a2-3)Gal(b1-4)GlcNAc(b1-2)Man(a1-6)]Man(b1-4)GlcNAc(b1-4)GlcNAc(b1-).

\* \* \* \* \*

UNITED STATES PATENT AND TRADEMARK OFFICE
CERTIFICATE OF CORRECTION

PATENT NO. : 11,766,481 B2  
APPLICATION NO. : 17/825737  
DATED : September 26, 2023  
INVENTOR(S) : Flynn et al.

Page 1 of 1

It is certified that error appears in the above-identified patent and that said Letters Patent is hereby corrected as shown below:

On the Title Page

Item (73), Assignees, correct the Assignees listed from:
"GanNA Bio, Inc., Cambridge, MA (US), The Children's Medical Center, Boston, MA (US)"
To the following:
-- GanNA Bio, Inc., Cambridge, MA (US); The Children's Medical Center Corporation, Boston, MA (US); Beth Israel Deaconess Medical Center, Inc., Boston, MA (US); The Board of Trustees of the Leland Stanford Junior University, Stanford, CA (US) --

Signed and Sealed this  
Fourth Day of March, 2025

Coke Morgan Stewart  
*Acting Director of the United States Patent and Trademark Office*

SEQUENCE LISTING

```
<160> NUMBER OF SEQ ID NOS: 9

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (60)..(60)
<223> OTHER INFORMATION: i5OctdU

<400> SEQUENCE: 1
ggctggtccg agtgcagtgg tgtttacaac taattgatca caaccagtta cagatttctu    60
tgttccttct ccactcccac tgcttcactt gactagcctt                         100

<210> SEQ ID NO 2
<211> LENGTH: 80
<212> TYPE: DNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (35)..(35)
<223> OTHER INFORMATION: i5OctdU

<400> SEQUENCE: 2
aguuggtccg aguguugugg guuauuguua aguuuauuua acauugucuc cccccacaac    60
cgcgcuugac uagcuugcug                                                80

<210> SEQ ID NO 3
<211> LENGTH: 23
<212> TYPE: RNA
<213> ORGANISM: Artificial Sequence
<220> FEATURE:
<223> OTHER INFORMATION: Description of Artificial Sequence:
      Synthetic oligonucleotide
<220> FEATURE:
<221> NAME/KEY: modified_base
<222> LOCATION: (1)..(1)
<223> OTHER INFORMATION: 2-OMe Ribose nucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2-Fluororibose nucleotide
<220> FEATURE:
<221> NAME/KEY: modified_base
<222> LOCATION: (3)..(3)
```

```
<223> OTHER INFORMATION: 2-OMe Ribose nucleotide
<220> FEATURE:
<221> NAME/KEY: modified_base
<222> LOCATION: (4)..(4)
<223> OTHER INFORMATION: 2-Fluororibose nucleotide
<220> FEATURE:
<221> NAME/KEY: modified_base
<222> LOCATION: (5)..(5)
<223> OTHER INFORMATION: 2-OMe Ribose nucleotide
<220> FEATURE:
<221> NAME/KEY: modified_base
<222> LOCATION: (6)..(6)
<223> OTHER INFORMATION: 2-Fluororibose nucleotide
<220> FEATURE:
<221> NAME/KEY: modified_base
<222> LOCATION: (7)..(7)
<223> OTHER INFORMATION: 2-OMe Ribose nucleotide
<220> FEATURE:
<221> NAME/KEY: modified_base
<222> LOCATION: (8)..(8)
<223> OTHER INFORMATION: 2-Fluororibose nucleotide
<220> FEATURE:
<221> NAME/KEY: modified_base
<222> LOCATION: (9)..(9)
<223> OTHER INFORMATION: 2-OMe Ribose nucleotide
<220> FEATURE:
<221> NAME/KEY: modified_base
<222> LOCATION: (10)..(10)
<223> OTHER INFORMATION: 2-Fluororibose nucleotide
<220> FEATURE:
<221> NAME/KEY: modified_base
<222> LOCATION: (11)..(11)
<223> OTHER INFORMATION: 2-OMe Ribose nucleotide
<220> FEATURE:
<221> NAME/KEY: modified_base
<222> LOCATION: (12)..(12)
<223> OTHER INFORMATION: 2-OMe Ribose nucleotide
<220> FEATURE:
<221> NAME/KEY: modified_base
<222> LOCATION: (13)..(13)
<223> OTHER INFORMATION: 2-OMe Ribose nucleotide
<220> FEATURE:
<221> NAME/KEY: modified_base
<222> LOCATION: (14)..(14)
<223> OTHER INFORMATION: 2-Fluororibose nucleotide
<220> FEATURE:
<221> NAME/KEY: modified_base
<222> LOCATION: (15)..(15)
<223> OTHER INFORMATION: 2-OMe Ribose nucleotide
<220> FEATURE:
<221> NAME/KEY: modified_base
<222> LOCATION: (16)..(16)
<223> OTHER INFORMATION: 2-Fluororibose nucleotide
<220> FEATURE:
<221> NAME/KEY: modified_base
<222> LOCATION: (17)..(17)
<223> OTHER INFORMATION: 2-OMe Ribose nucleotide
<220> FEATURE:
<221> NAME/KEY: modified_base
<222> LOCATION: (18)..(18)
<223> OTHER INFORMATION: 2-Fluororibose nucleotide
<220> FEATURE:
<221> NAME/KEY: modified_base
<222> LOCATION: (19)..(19)
<223> OTHER INFORMATION: 2-OMe Ribose nucleotide
<220> FEATURE:
<221> NAME/KEY: modified_base
<222> LOCATION: (20)..(20)
<223> OTHER INFORMATION: 2-Fluororibose nucleotide
<220> FEATURE:
<221> NAME/KEY: modified_base
<222> LOCATION: (21)..(21)
<223> OTHER INFORMATION: 2-OMe Ribose nucleotide
<220> FEATURE:
<221> NAME/KEY: misc_feature
<222> LOCATION: (21)..(23)
<223> OTHER INFORMATION: Phosphorothioate linkage
<220> FEATURE:
<221> NAME/KEY: modified_base
```

```
<222> LOCATION: (22)..(22)
<223> OTHER INFORMATION: 2-OMe Ribose nucleotide
<220> FEATURE:
<221> NAME/KEY: modified_base
<222> LOCATION: (23)..(23)
<223> OTHER INFORMATION: 2-OMe Ribose nucleotide

<400> SEQUENCE: 3
uuucgaauca auccaacagu agc                                              23

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: 5' Cy5
<220> FEATURE:
<221> NAME/KEY: modified_base
<222> LOCATION: (1)..(1)
<223> OTHER INFORMATION: 2-Fluororibose nucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2-OMe Ribose nucleotide
<220> FEATURE:
<221> NAME/KEY: modified_base
<222> LOCATION: (3)..(3)
<223> OTHER INFORMATION: 2-Fluororibose nucleotide
<220> FEATURE:
<221> NAME/KEY: modified_base
<222> LOCATION: (4)..(4)
<223> OTHER INFORMATION: 2-OMe Ribose nucleotide
<220> FEATURE:
<221> NAME/KEY: modified_base
<222> LOCATION: (5)..(5)
<223> OTHER INFORMATION: 2-Fluororibose nucleotide
<220> FEATURE:
<221> NAME/KEY: modified_base
<222> LOCATION: (6)..(6)
<223> OTHER INFORMATION: 2-OMe Ribose nucleotide
<220> FEATURE:
<221> NAME/KEY: modified_base
<222> LOCATION: (7)..(7)
<223> OTHER INFORMATION: 2-Fluororibose nucleotide
<220> FEATURE:
<221> NAME/KEY: modified_base
<222> LOCATION: (8)..(8)
<223> OTHER INFORMATION: 2-OMe Ribose nucleotide
<220> FEATURE:
<221> NAME/KEY: modified_base
<222> LOCATION: (9)..(9)
<223> OTHER INFORMATION: 2-Fluororibose nucleotide
<220> FEATURE:
<221> NAME/KEY: modified_base
<222> LOCATION: (10)..(10)
<223> OTHER INFORMATION: 2-Fluororibose nucleotide
<220> FEATURE:
<221> NAME/KEY: modified_base
<222> LOCATION: (11)..(11)
<223> OTHER INFORMATION: 2-Fluororibose nucleotide
<220> FEATURE:
<221> NAME/KEY: modified_base
<222> LOCATION: (12)..(12)
<223> OTHER INFORMATION: 2-OMe Ribose nucleotide
<220> FEATURE:
<221> NAME/KEY: modified_base
<222> LOCATION: (13)..(13)
<223> OTHER INFORMATION: 2-Fluororibose nucleotide
<220> FEATURE:
<221> NAME/KEY: modified_base
```

```
<222> LOCATION: (14)..(14)
<223> OTHER INFORMATION: 2-OMe Ribose nucleotide
<220> FEATURE:
<221> NAME/KEY: modified_base
<222> LOCATION: (15)..(15)
<223> OTHER INFORMATION: 2-Fluororibose nucleotide
<220> FEATURE:
<221> NAME/KEY: modified_base
<222> LOCATION: (16)..(16)
<223> OTHER INFORMATION: 2-OMe Ribose nucleotide
<220> FEATURE:
<221> NAME/KEY: modified_base
<222> LOCATION: (17)..(17)
<223> OTHER INFORMATION: 2-Fluororibose nucleotide
<220> FEATURE:
<221> NAME/KEY: modified_base
<222> LOCATION: (18)..(18)
<223> OTHER INFORMATION: 2-OMe Ribose nucleotide
<220> FEATURE:
<221> NAME/KEY: modified_base
<222> LOCATION: (19)..(19)
<223> OTHER INFORMATION: 2-Fluororibose nucleotide
<220> FEATURE:
<221> NAME/KEY: modified_base
<222> LOCATION: (20)..(20)
<223> OTHER INFORMATION: 2-OMe Ribose nucleotide
<220> FEATURE:
<221> NAME/KEY: modified_base
<222> LOCATION: (21)..(21)
<223> OTHER INFORMATION: 2-Fluororibose nucleotide
<220> FEATURE:
<223> OTHER INFORMATION: 3' DBCO

<400> SEQUENCE: 4
uacuguugga uugauucgaa a                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence:
      Synthetic oligonucleotide
<220> FEATURE:
<221> NAME/KEY: modified_base
<222> LOCATION: (1)..(1)
<223> OTHER INFORMATION: 2-Fluororibose nucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2-OMe Ribose nucleotide
<220> FEATURE:
<221> NAME/KEY: modified_base
<222> LOCATION: (3)..(3)
<223> OTHER INFORMATION: 2-Fluororibose nucleotide
<220> FEATURE:
<221> NAME/KEY: modified_base
<222> LOCATION: (4)..(4)
<223> OTHER INFORMATION: 2-OMe Ribose nucleotide
<220> FEATURE:
<221> NAME/KEY: modified_base
<222> LOCATION: (5)..(5)
<223> OTHER INFORMATION: 2-Fluororibose nucleotide
<220> FEATURE:
<221> NAME/KEY: modified_base
<222> LOCATION: (6)..(6)
<223> OTHER INFORMATION: 2-OMe Ribose nucleotide
<220> FEATURE:
<221> NAME/KEY: modified_base
<222> LOCATION: (7)..(7)
<223> OTHER INFORMATION: 2-Fluororibose nucleotide
<220> FEATURE:
<221> NAME/KEY: modified_base
```

```
<222> LOCATION: (8)..(8)
<223> OTHER INFORMATION: 2-OMe Ribose nucleotide
<220> FEATURE:
<221> NAME/KEY: modified_base
<222> LOCATION: (9)..(9)
<223> OTHER INFORMATION: 2-Fluororibose nucleotide
<220> FEATURE:
<221> NAME/KEY: modified_base
<222> LOCATION: (10)..(10)
<223> OTHER INFORMATION: 2-Fluororibose nucleotide
<220> FEATURE:
<221> NAME/KEY: modified_base
<222> LOCATION: (11)..(11)
<223> OTHER INFORMATION: 2-Fluororibose nucleotide
<220> FEATURE:
<221> NAME/KEY: modified_base
<222> LOCATION: (12)..(12)
<223> OTHER INFORMATION: 2-OMe Ribose nucleotide
<220> FEATURE:
<221> NAME/KEY: modified_base
<222> LOCATION: (13)..(13)
<223> OTHER INFORMATION: 2-Fluororibose nucleotide
<220> FEATURE:
<221> NAME/KEY: modified_base
<222> LOCATION: (14)..(14)
<223> OTHER INFORMATION: 2-OMe Ribose nucleotide
<220> FEATURE:
<221> NAME/KEY: modified_base
<222> LOCATION: (15)..(15)
<223> OTHER INFORMATION: 2-Fluororibose nucleotide
<220> FEATURE:
<221> NAME/KEY: modified_base
<222> LOCATION: (16)..(16)
<223> OTHER INFORMATION: 2-OMe Ribose nucleotide
<220> FEATURE:
<221> NAME/KEY: modified_base
<222> LOCATION: (17)..(17)
<223> OTHER INFORMATION: 2-Fluororibose nucleotide
<220> FEATURE:
<221> NAME/KEY: modified_base
<222> LOCATION: (18)..(18)
<223> OTHER INFORMATION: 2-OMe Ribose nucleotide
<220> FEATURE:
<221> NAME/KEY: modified_base
<222> LOCATION: (19)..(19)
<223> OTHER INFORMATION: 2-Fluororibose nucleotide
<220> FEATURE:
<221> NAME/KEY: modified_base
<222> LOCATION: (20)..(20)
<223> OTHER INFORMATION: 2-OMe Ribose nucleotide
<220> FEATURE:
<221> NAME/KEY: modified_base
<222> LOCATION: (21)..(21)
<223> OTHER INFORMATION: 2-Fluororibose nucleotide
<220> FEATURE:
<223> OTHER INFORMATION: 3' DBCO

<400> SEQUENCE: 5
uacuguugga uugauucgaa a                                              21

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence:
      Synthetic oligonucleotide
<220> FEATURE:
<221> NAME/KEY: modified_base
<222> LOCATION: (1)..(1)
<223> OTHER INFORMATION: 2-Fluororibose nucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
```

```
<222> LOCATION: (2)..(2)
<223> OTHER INFORMATION: 2-OMe Ribose nucleotide
<220> FEATURE:
<221> NAME/KEY: modified_base
<222> LOCATION: (3)..(3)
<223> OTHER INFORMATION: 2-Fluororibose nucleotide
<220> FEATURE:
<221> NAME/KEY: modified_base
<222> LOCATION: (4)..(4)
<223> OTHER INFORMATION: 2-OMe Ribose nucleotide
<220> FEATURE:
<221> NAME/KEY: modified_base
<222> LOCATION: (5)..(5)
<223> OTHER INFORMATION: 2-Fluororibose nucleotide
<220> FEATURE:
<221> NAME/KEY: modified_base
<222> LOCATION: (6)..(6)
<223> OTHER INFORMATION: 2-OMe Ribose nucleotide
<220> FEATURE:
<221> NAME/KEY: modified_base
<222> LOCATION: (7)..(7)
<223> OTHER INFORMATION: 2-Fluororibose nucleotide
<220> FEATURE:
<221> NAME/KEY: modified_base
<222> LOCATION: (8)..(8)
<223> OTHER INFORMATION: 2-OMe Ribose nucleotide
<220> FEATURE:
<221> NAME/KEY: modified_base
<222> LOCATION: (9)..(9)
<223> OTHER INFORMATION: 2-Fluororibose nucleotide
<220> FEATURE:
<221> NAME/KEY: modified_base
<222> LOCATION: (10)..(10)
<223> OTHER INFORMATION: 2-OMe Ribose nucleotide
<220> FEATURE:
<221> NAME/KEY: modified_base
<222> LOCATION: (11)..(11)
<223> OTHER INFORMATION: 2-OMe Ribose nucleotide
<220> FEATURE:
<221> NAME/KEY: modified_base
<222> LOCATION: (12)..(12)
<223> OTHER INFORMATION: 2-OMe Ribose nucleotide
<220> FEATURE:
<221> NAME/KEY: modified_base
<222> LOCATION: (13)..(13)
<223> OTHER INFORMATION: 2-Fluororibose nucleotide
<220> FEATURE:
<221> NAME/KEY: modified_base
<222> LOCATION: (14)..(14)
<223> OTHER INFORMATION: 2-OMe Ribose nucleotide
<220> FEATURE:
<221> NAME/KEY: modified_base
<222> LOCATION: (15)..(15)
<223> OTHER INFORMATION: 2-Fluororibose nucleotide
<220> FEATURE:
<221> NAME/KEY: modified_base
<222> LOCATION: (16)..(16)
<223> OTHER INFORMATION: 2-OMe Ribose nucleotide
<220> FEATURE:
<221> NAME/KEY: modified_base
<222> LOCATION: (17)..(17)
<223> OTHER INFORMATION: 2-Fluororibose nucleotide
<220> FEATURE:
<221> NAME/KEY: modified_base
<222> LOCATION: (18)..(18)
<223> OTHER INFORMATION: 2-OMe Ribose nucleotide
<220> FEATURE:
<221> NAME/KEY: modified_base
<222> LOCATION: (19)..(19)
<223> OTHER INFORMATION: 2-Fluororibose nucleotide
<220> FEATURE:
<221> NAME/KEY: modified_base
<222> LOCATION: (20)..(20)
<223> OTHER INFORMATION: 2-OMe Ribose nucleotide
<220> FEATURE:
<221> NAME/KEY: misc_feature
<222> LOCATION: (20)..(22)
<223> OTHER INFORMATION: Phosphorothioate linkage
<220> FEATURE:
```

```
<221> NAME/KEY: modified_base
<222> LOCATION: (21)..(21)
<223> OTHER INFORMATION: 2-OMe Ribose nucleotide
<220> FEATURE:
<221> NAME/KEY: modified_base
<222> LOCATION: (22)..(22)
<223> OTHER INFORMATION: 2-OMe Ribose nucleotide

<400> SEQUENCE: 6
uucgaaucaa uccaacagua gc                                               22

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: 5' (Cy5Lumi-Mal)(SHC6)
<220> FEATURE:
<221> NAME/KEY: modified_base
<222> LOCATION: (1)..(1)
<223> OTHER INFORMATION: 2-Fluororibose nucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2-OMe Ribose nucleotide
<220> FEATURE:
<221> NAME/KEY: modified_base
<222> LOCATION: (3)..(3)
<223> OTHER INFORMATION: 2-Fluororibose nucleotide
<220> FEATURE:
<221> NAME/KEY: modified_base
<222> LOCATION: (4)..(4)
<223> OTHER INFORMATION: 2-OMe Ribose nucleotide
<220> FEATURE:
<221> NAME/KEY: modified_base
<222> LOCATION: (5)..(5)
<223> OTHER INFORMATION: 2-Fluororibose nucleotide
<220> FEATURE:
<221> NAME/KEY: modified_base
<222> LOCATION: (6)..(6)
<223> OTHER INFORMATION: 2-OMe Ribose nucleotide
<220> FEATURE:
<221> NAME/KEY: modified_base
<222> LOCATION: (7)..(7)
<223> OTHER INFORMATION: 2-Fluororibose nucleotide
<220> FEATURE:
<221> NAME/KEY: modified_base
<222> LOCATION: (8)..(8)
<223> OTHER INFORMATION: 2-OMe Ribose nucleotide
<220> FEATURE:
<221> NAME/KEY: modified_base
<222> LOCATION: (9)..(9)
<223> OTHER INFORMATION: 2-Fluororibose nucleotide
<220> FEATURE:
<221> NAME/KEY: modified_base
<222> LOCATION: (10)..(10)
<223> OTHER INFORMATION: 2-Fluororibose nucleotide
<220> FEATURE:
<221> NAME/KEY: modified_base
<222> LOCATION: (11)..(11)
<223> OTHER INFORMATION: 2-Fluororibose nucleotide
<220> FEATURE:
<221> NAME/KEY: modified_base
<222> LOCATION: (12)..(12)
<223> OTHER INFORMATION: 2-OMe Ribose nucleotide
<220> FEATURE:
<221> NAME/KEY: modified_base
<222> LOCATION: (13)..(13)
<223> OTHER INFORMATION: 2-Fluororibose nucleotide
<220> FEATURE:
```

```
<221> NAME/KEY: modified_base
<222> LOCATION: (14)..(14)
<223> OTHER INFORMATION: 2-OMe Ribose nucleotide
<220> FEATURE:
<221> NAME/KEY: modified_base
<222> LOCATION: (15)..(15)
<223> OTHER INFORMATION: 2-Fluororibose nucleotide
<220> FEATURE:
<221> NAME/KEY: modified_base
<222> LOCATION: (16)..(16)
<223> OTHER INFORMATION: 2-OMe Ribose nucleotide
<220> FEATURE:
<221> NAME/KEY: modified_base
<222> LOCATION: (17)..(17)
<223> OTHER INFORMATION: 2-Fluororibose nucleotide
<220> FEATURE:
<221> NAME/KEY: modified_base
<222> LOCATION: (18)..(18)
<223> OTHER INFORMATION: 2-OMe Ribose nucleotide
<220> FEATURE:
<221> NAME/KEY: modified_base
<222> LOCATION: (19)..(19)
<223> OTHER INFORMATION: 2-Fluororibose nucleotide
<220> FEATURE:
<221> NAME/KEY: modified_base
<222> LOCATION: (20)..(20)
<223> OTHER INFORMATION: 2-OMe Ribose nucleotide
<220> FEATURE:
<221> NAME/KEY: modified_base
<222> LOCATION: (21)..(21)
<223> OTHER INFORMATION: 2-Fluororibose nucleotide
<220> FEATURE:
<223> OTHER INFORMATION: 3' (NHC6)(DBCO-C6NHS)

<400> SEQUENCE: 7
uacuguugga uugauucgaa a                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence:
      Synthetic oligonucleotide
<220> FEATURE:
<221> NAME/KEY: modified_base
<222> LOCATION: (1)..(1)
<223> OTHER INFORMATION: 2-Fluororibose nucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: modified_base
<222> LOCATION: (2)..(2)
<223> OTHER INFORMATION: 2-OMe Ribose nucleotide
<220> FEATURE:
<221> NAME/KEY: modified_base
<222> LOCATION: (3)..(3)
<223> OTHER INFORMATION: 2-Fluororibose nucleotide
<220> FEATURE:
<221> NAME/KEY: modified_base
<222> LOCATION: (4)..(4)
<223> OTHER INFORMATION: 2-OMe Ribose nucleotide
<220> FEATURE:
<221> NAME/KEY: modified_base
<222> LOCATION: (5)..(5)
<223> OTHER INFORMATION: 2-Fluororibose nucleotide
<220> FEATURE:
<221> NAME/KEY: modified_base
<222> LOCATION: (6)..(6)
<223> OTHER INFORMATION: 2-OMe Ribose nucleotide
<220> FEATURE:
<221> NAME/KEY: modified_base
<222> LOCATION: (7)..(7)
<223> OTHER INFORMATION: 2-Fluororibose nucleotide
<220> FEATURE:
```

```
<221> NAME/KEY: modified_base
<222> LOCATION: (8)..(8)
<223> OTHER INFORMATION: 2-OMe Ribose nucleotide
<220> FEATURE:
<221> NAME/KEY: modified_base
<222> LOCATION: (9)..(9)
<223> OTHER INFORMATION: 2-Fluororibose nucleotide
<220> FEATURE:
<221> NAME/KEY: modified_base
<222> LOCATION: (10)..(10)
<223> OTHER INFORMATION: 2-Fluororibose nucleotide
<220> FEATURE:
<221> NAME/KEY: modified_base
<222> LOCATION: (11)..(11)
<223> OTHER INFORMATION: 2-Fluororibose nucleotide
<220> FEATURE:
<221> NAME/KEY: modified_base
<222> LOCATION: (12)..(12)
<223> OTHER INFORMATION: 2-OMe Ribose nucleotide
<220> FEATURE:
<221> NAME/KEY: modified_base
<222> LOCATION: (13)..(13)
<223> OTHER INFORMATION: 2-Fluororibose nucleotide
<220> FEATURE:
<221> NAME/KEY: modified_base
<222> LOCATION: (14)..(14)
<223> OTHER INFORMATION: 2-OMe Ribose nucleotide
<220> FEATURE:
<221> NAME/KEY: modified_base
<222> LOCATION: (15)..(15)
<223> OTHER INFORMATION: 2-Fluororibose nucleotide
<220> FEATURE:
<221> NAME/KEY: modified_base
<222> LOCATION: (16)..(16)
<223> OTHER INFORMATION: 2-OMe Ribose nucleotide
<220> FEATURE:
<221> NAME/KEY: modified_base
<222> LOCATION: (17)..(17)
<223> OTHER INFORMATION: 2-Fluororibose nucleotide
<220> FEATURE:
<221> NAME/KEY: modified_base
<222> LOCATION: (18)..(18)
<223> OTHER INFORMATION: 2-OMe Ribose nucleotide
<220> FEATURE:
<221> NAME/KEY: modified_base
<222> LOCATION: (19)..(19)
<223> OTHER INFORMATION: 2-Fluororibose nucleotide
<220> FEATURE:
<221> NAME/KEY: modified_base
<222> LOCATION: (20)..(20)
<223> OTHER INFORMATION: 2-OMe Ribose nucleotide
<220> FEATURE:
<221> NAME/KEY: modified_base
<222> LOCATION: (21)..(21)
<223> OTHER INFORMATION: 2-Fluororibose nucleotide
<220> FEATURE:
<223> OTHER INFORMATION: 3' (NHC6)(DBCO-C6NHS)

<400> SEQUENCE: 8
uacuguugga uugauucgaa a                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence:
      Synthetic oligonucleotide
<220> FEATURE:
<223> OTHER INFORMATION: 5' (Cy5Lumi-Mal)(SHC6)
<220> FEATURE:
<221> NAME/KEY: modified_base
<222> LOCATION: (1)..(1)
<223> OTHER INFORMATION: 2-Fluororibose nucleotide
<220> FEATURE:
<221> NAME/KEY: misc_feature
<222> LOCATION: (1)..(3)
```

```
<223> OTHER INFORMATION: Phosphorothioate linkage
<220> FEATURE:
<221> NAME/KEY: modified_base
<222> LOCATION: (2)..(2)
<223> OTHER INFORMATION: 2-OMe Ribose nucleotide
<220> FEATURE:
<221> NAME/KEY: modified_base
<222> LOCATION: (3)..(3)
<223> OTHER INFORMATION: 2-Fluororibose nucleotide
<220> FEATURE:
<221> NAME/KEY: modified_base
<222> LOCATION: (4)..(4)
<223> OTHER INFORMATION: 2-OMe Ribose nucleotide
<220> FEATURE:
<221> NAME/KEY: modified_base
<222> LOCATION: (5)..(5)
<223> OTHER INFORMATION: 2-Fluororibose nucleotide
<220> FEATURE:
<221> NAME/KEY: modified_base
<222> LOCATION: (6)..(6)
<223> OTHER INFORMATION: 2-OMe Ribose nucleotide
<220> FEATURE:
<221> NAME/KEY: modified_base
<222> LOCATION: (7)..(7)
<223> OTHER INFORMATION: 2-Fluororibose nucleotide
<220> FEATURE:
<221> NAME/KEY: modified_base
<222> LOCATION: (8)..(8)
<223> OTHER INFORMATION: 2-OMe Ribose nucleotide
<220> FEATURE:
<221> NAME/KEY: modified_base
<222> LOCATION: (9)..(9)
<223> OTHER INFORMATION: 2-Fluororibose nucleotide
<220> FEATURE:
<221> NAME/KEY: modified_base
<222> LOCATION: (10)..(10)
<223> OTHER INFORMATION: 2-Fluororibose nucleotide
<220> FEATURE:
<221> NAME/KEY: modified_base
<222> LOCATION: (11)..(11)
<223> OTHER INFORMATION: 2-Fluororibose nucleotide
<220> FEATURE:
<221> NAME/KEY: modified_base
<222> LOCATION: (12)..(12)
<223> OTHER INFORMATION: 2-OMe Ribose nucleotide
<220> FEATURE:
<221> NAME/KEY: modified_base
<222> LOCATION: (13)..(13)
<223> OTHER INFORMATION: 2-Fluororibose nucleotide
<220> FEATURE:
<221> NAME/KEY: modified_base
<222> LOCATION: (14)..(14)
<223> OTHER INFORMATION: 2-OMe Ribose nucleotide
<220> FEATURE:
<221> NAME/KEY: modified_base
<222> LOCATION: (15)..(15)
<223> OTHER INFORMATION: 2-Fluororibose nucleotide
<220> FEATURE:
<221> NAME/KEY: modified_base
<222> LOCATION: (16)..(16)
<223> OTHER INFORMATION: 2-OMe Ribose nucleotide
<220> FEATURE:
<221> NAME/KEY: modified_base
<222> LOCATION: (17)..(17)
<223> OTHER INFORMATION: 2-Fluororibose nucleotide
<220> FEATURE:
<221> NAME/KEY: modified_base
<222> LOCATION: (18)..(18)
<223> OTHER INFORMATION: 2-OMe Ribose nucleotide
<220> FEATURE:
<221> NAME/KEY: modified_base
<222> LOCATION: (19)..(19)
<223> OTHER INFORMATION: 2-Fluororibose nucleotide
<220> FEATURE:
<221> NAME/KEY: modified_base
<222> LOCATION: (20)..(20)
<223> OTHER INFORMATION: 2-OMe Ribose nucleotide
<220> FEATURE:
<221> NAME/KEY: modified_base
```

```
<222> LOCATION: (21)..(21)
<223> OTHER INFORMATION: 2-Fluororibose nucleotide

<400> SEQUENCE: 9
uacuguugga uugauucgaa a                                              21
```